US008580257B2

(12) United States Patent
Tremblay et al.

(10) Patent No.: US 8,580,257 B2
(45) Date of Patent: Nov. 12, 2013

(54) ANTIBODIES THAT SPECIFICALLY BLOCK THE BIOLOGICAL ACTIVITY OF KIDNEY ASSOCIATED ANTIGEN 1 (KAAG1)

(75) Inventors: Gilles Bernard Tremblay, La Prairie (CA); Mario Filion, Longueuil (CA)

(73) Assignee: Alethia Biotherapeutics Inc., Montreal, Quebec (CA)

( * ) Notice: Subject to any disclaimer, the term of this patent is extended or adjusted under 35 U.S.C. 154(b) by 0 days.

(21) Appl. No.: 13/187,424

(22) Filed: Jul. 20, 2011

(65) Prior Publication Data
US 2012/0093819 A1    Apr. 19, 2012

Related U.S. Application Data

(62) Division of application No. 13/127,439, filed as application No. PCT/CA2009/001586 on Nov. 3, 2009.

(60) Provisional application No. 61/193,184, filed on Nov. 3, 2008, provisional application No. 61/213,666, filed on Jun. 30, 2009.

(51) Int. Cl.
*A61K 39/395* (2006.01)
*A61P 35/00* (2006.01)

(52) U.S. Cl.
USPC ............... 424/130.1; 424/178.1; 424/141.1; 424/172.1

(58) Field of Classification Search
None
See application file for complete search history.

(56) References Cited

U.S. PATENT DOCUMENTS

| | | | |
|---|---|---|---|
| 4,745,076 A | 5/1988 | Muller et al. | |
| 5,075,447 A | 12/1991 | Muller et al. | |
| 5,585,279 A | 12/1996 | Davidson | |
| 5,708,022 A | 1/1998 | Bastos et al. | |
| 5,712,127 A | 1/1998 | Malek et al. | |
| 6,057,098 A | 5/2000 | Buechler et al. | |
| 6,288,221 B1 | 9/2001 | Grinstaff et al. | |
| 6,358,953 B1 | 3/2002 | Moheno | |
| 6,806,089 B1 | 10/2004 | Lakowicz et al. | |
| 6,812,339 B1 | 11/2004 | Venter et al. | |
| 6,962,910 B2 | 11/2005 | Brewer et al. | |
| 7,030,236 B2 | 4/2006 | Jhaveri et al. | |
| 7,202,234 B2 | 4/2007 | Chow et al. | |
| 7,429,567 B2 | 9/2008 | Lee et al. | |
| 7,439,051 B2 | 10/2008 | Sokoloff et al. | |
| 7,494,788 B2 | 2/2009 | Dunker et al. | |
| 7,501,485 B2 | 3/2009 | Cowsar | |
| 7,521,197 B2 | 4/2009 | Savage | |
| 7,531,533 B2 | 5/2009 | Shoda et al. | |
| 7,550,501 B2 | 6/2009 | Chow et al. | |
| 7,557,213 B2 | 7/2009 | Melikian et al. | |
| 7,560,441 B2 | 7/2009 | Wolfman et al. | |
| 7,585,839 B2 | 9/2009 | Larsen et al. | |
| 7,618,636 B1 | 11/2009 | Masignani et al. | |
| 7,628,989 B2 | 12/2009 | Jakobovits et al. | |
| 7,641,905 B2 | 1/2010 | Jakobovits et al. | |
| 8,216,582 B2 * | 7/2012 | Sooknanan et al. | ....... 424/155.1 |
| 2002/0049190 A1 | 4/2002 | Bridger et al. | |
| 2002/0106678 A1 | 8/2002 | Robishaw et al. | |
| 2002/0177695 A1 | 11/2002 | Grinstaff et al. | |
| 2003/0065157 A1 | 4/2003 | Lasek | |
| 2003/0087250 A1 | 5/2003 | Monahan et al. | |
| 2003/0099974 A1 | 5/2003 | Lillie et al. | |
| 2003/0118592 A1 | 6/2003 | Ledbetter et al. | |
| 2003/0124579 A1 | 7/2003 | Mack et al. | |
| 2003/0133939 A1 | 7/2003 | Ledbetter et al. | |
| 2003/0170273 A1 | 9/2003 | O'Hagan et al. | |
| 2003/0180767 A1 | 9/2003 | Brewer et al. | |
| 2003/0219760 A1 | 11/2003 | Gordon et al. | |
| 2004/0009939 A1 | 1/2004 | Chada et al. | |
| 2004/0014081 A1 | 1/2004 | Alsobrook, II et al. | |
| 2004/0053824 A1 | 3/2004 | Tang et al. | |
| 2004/0101874 A1 | 5/2004 | Ghosh et al. | |
| 2004/0172684 A1 | 9/2004 | Kovalic et al. | |
| 2004/0214272 A1 | 10/2004 | La Rosa et al. | |
| 2004/0242606 A1 | 12/2004 | Bavetsias et al. | |
| 2005/0008649 A1 | 1/2005 | Shin et al. | |
| 2005/0009851 A1 | 1/2005 | Bavetsias et al. | |

(Continued)

FOREIGN PATENT DOCUMENTS

| | | |
|---|---|---|
| CA | 2615858 | 1/2007 |
| EP | 178450 B1 | 4/1986 |

(Continued)

OTHER PUBLICATIONS

Rudikoff et Al., Single amino acid substitution altering antigen-binding specificity, 1982, Proceedings of the National Academy of Sciences USA, vol. 79, p. 1979-1983.*

Van den Eynde et Al., A new antigen recognized by cytolytic t lymphocytes on a human kideny tumor results from reverse strand transcription, 1999, Journal of Experimental Medicine, vol. 190, No. 12, p. 1793-1799.*

Panka et Al., Variable region framwork differences result in decreased or increased affinity of variant anti-digoxin antibodies, 1988, Proceedings of the National Academy of Sciences USA, vol. 85, p. 3080-3084.*

Byers et Al., Therapeutic strategies with monoclonal antibodies and immunoconjugates, 1988, Immunology, vol. 65, p. 329-335.*

(Continued)

*Primary Examiner* — Hong Sang
*Assistant Examiner* — Michael D Allen
(74) *Attorney, Agent, or Firm* — Choate, Hall & Stewart LLP; Fangli Chen; Robert N. Sahr

(57) ABSTRACT

Novel monoclonal antibodies that specifically bind to KAAG1 are described. In some embodiments, the antibodies block the biological activity of KAAG1 and are useful in composition in certain cancers, more particularly in cancers that have increased cell surface expression of KAAG1, such as ovarian, renal, lung, colorectal, breast, brain, and prostate cancer, as well as melanoma. The invention also relates to cells expressing the monoclonal antibodies and antigen binding fragments such as humanized and chimeric antibodies. Additionally, method of detecting and treating cancer using the antibodies and fragments are also disclosed.

20 Claims, 34 Drawing Sheets

(56) References Cited

U.S. PATENT DOCUMENTS

| | | |
|---|---|---|
| 2005/0053930 A1 | 3/2005 | Anderson et al. |
| 2005/0059624 A1 | 3/2005 | Hoerr et al. |
| 2005/0064481 A1 | 3/2005 | Korfhage |
| 2005/0095592 A1 | 5/2005 | Jazaeri et al. |
| 2005/0113345 A1 | 5/2005 | Chow et al. |
| 2005/0123501 A1 | 6/2005 | Lewis |
| 2005/0147621 A1 | 7/2005 | Higgins et al. |
| 2005/0153333 A1 | 7/2005 | Sooknanan et al. |
| 2005/0170450 A1 | 8/2005 | Durocher et al. |
| 2005/0196754 A1 | 9/2005 | Drmanac et al. |
| 2005/0214826 A1 | 9/2005 | Mor et al. |
| 2005/0214831 A1 | 9/2005 | Monahan et al. |
| 2006/0014686 A1 | 1/2006 | Wonsey et al. |
| 2006/0078941 A1 | 4/2006 | Santin |
| 2006/0084594 A1 | 4/2006 | Santin et al. |
| 2006/0188490 A1 | 8/2006 | Hoerr et al. |
| 2006/0229433 A1 | 10/2006 | De Rouge et al. |
| 2007/0060590 A1 | 3/2007 | Shoda et al. |
| 2007/0093467 A1 | 4/2007 | Zhang et al. |
| 2007/0167409 A1 | 7/2007 | Chow et al. |
| 2007/0167443 A1 | 7/2007 | Melikian et al. |
| 2007/0298093 A1 | 12/2007 | Komur et al. |
| 2007/0299068 A1 | 12/2007 | Karp et al. |
| 2008/0025944 A1 | 1/2008 | Hoerr et al. |
| 2008/0070232 A1 | 3/2008 | Durocher et al. |
| 2008/0166355 A1 | 7/2008 | Moheno et al. |
| 2008/0176790 A1 | 7/2008 | DeFrees |
| 2008/0200650 A1 | 8/2008 | Emery et al. |
| 2008/0213268 A1 | 9/2008 | Watts et al. |
| 2008/0274131 A1 | 11/2008 | Kenner et al. |
| 2008/0280317 A1 | 11/2008 | Wu et al. |
| 2008/0280818 A1 | 11/2008 | DeFrees |
| 2008/0300348 A1 | 12/2008 | Haddleton et al. |
| 2008/0306007 A1 | 12/2008 | McCluskey et al. |
| 2008/0311145 A1 | 12/2008 | Campion et al. |
| 2009/0074658 A1 | 3/2009 | Lupold et al. |
| 2009/0075832 A1 | 3/2009 | Neuman et al. |
| 2009/0093621 A1 | 4/2009 | Ferrari et al. |
| 2009/0110662 A1 | 4/2009 | Breitenkamp et al. |
| 2009/0137003 A1 | 5/2009 | Tolstrup et al. |
| 2009/0169520 A1 | 7/2009 | Soreq et al. |
| 2009/0176664 A1 | 7/2009 | Chu |
| 2009/0186855 A1 | 7/2009 | Chow et al. |
| 2009/0197345 A1 | 8/2009 | Seppala |
| 2009/0203542 A1 | 8/2009 | Reichmann et al. |
| 2009/0208507 A1 | 8/2009 | Rohlff |
| 2009/0209463 A1 | 8/2009 | Nakamura et al. |
| 2009/0214467 A1 | 8/2009 | Shakhov et al. |
| 2009/0214585 A1 | 8/2009 | Ciocca et al. |
| 2009/0221032 A1 | 9/2009 | Dunker et al. |
| 2009/0226448 A1 | 9/2009 | Glucksmann et al. |
| 2009/0226451 A1 | 9/2009 | Glucksmann et al. |
| 2009/0226921 A1 | 9/2009 | Afar et al. |
| 2009/0232766 A1 | 9/2009 | Wang et al. |
| 2009/0253156 A1 | 10/2009 | Patton et al. |
| 2009/0275137 A1 | 11/2009 | Kranz et al. |
| 2009/0297401 A1 | 12/2009 | Lundstrom et al. |
| 2009/0305282 A1 | 12/2009 | Yuen et al. |
| 2009/0305962 A1 | 12/2009 | Bakker et al. |
| 2009/0311681 A1 | 12/2009 | Faure |
| 2009/0325869 A1 | 12/2009 | Theil |
| 2010/0003280 A1 | 1/2010 | O'Hagan et al. |
| 2010/0003305 A1 | 1/2010 | Pattanaik |
| 2010/0040606 A1 | 2/2010 | Lantto et al. |
| 2010/0047261 A1 | 2/2010 | Hoerr et al. |
| 2010/0055077 A1 | 3/2010 | Shakhov et al. |
| 2010/0055731 A1 | 3/2010 | Wang et al. |
| 2010/0056459 A1 | 3/2010 | Bonny |
| 2010/0086541 A1 | 4/2010 | Wu et al. |
| 2010/0105692 A1 | 4/2010 | Moheno et al. |
| 2010/0111993 A1 | 5/2010 | Tureci et al. |
| 2012/0093819 A1 | 4/2012 | Tremblay et al. |
| 2012/0128661 A1 | 5/2012 | Sooknanan et al. |
| 2012/0288498 A1 | 11/2012 | Sooknanan et al. |

FOREIGN PATENT DOCUMENTS

| | | |
|---|---|---|
| EP | 0636031 B1 | 2/1995 |
| EP | 0816377 | 1/1998 |
| EP | 1318835 B1 | 6/2003 |
| EP | 1422242 | 5/2004 |
| EP | 1458410 B1 | 9/2004 |
| EP | 1465933 B1 | 10/2004 |
| EP | 1547581 A1 | 6/2005 |
| EP | 1550458 A1 | 6/2005 |
| EP | 1646661 B1 | 4/2006 |
| EP | 1751179 | 2/2007 |
| EP | 1847533 A1 | 10/2007 |
| EP | 1905844 A2 | 4/2008 |
| EP | 1970383 | 9/2008 |
| EP | 1987356 | 11/2008 |
| EP | 2002036 | 12/2008 |
| EP | 2021467 | 2/2009 |
| EP | 2057465 | 5/2009 |
| EP | 2161291 A2 | 3/2010 |
| WO | WO8704523 A1 | 7/1987 |
| WO | WO9109849 A1 | 7/1991 |
| WO | WO9613510 A1 | 5/1996 |
| WO | WO9858079 A1 | 12/1998 |
| WO | WO9931513 A1 | 6/1999 |
| WO | WO99/58546 | 11/1999 |
| WO | WO0001702 A1 | 1/2000 |
| WO | WO0014515 A1 | 3/2000 |
| WO | WO0023448 A1 | 4/2000 |
| WO | WO0025788 A1 | 5/2000 |
| WO | WO0056743 A1 | 9/2000 |
| WO | WO0119798 A2 | 3/2001 |
| WO | WO0146209 A1 | 6/2001 |
| WO | WO0170979 | 9/2001 |
| WO | WO01/98468 | 12/2001 |
| WO | WO02/070539 | 9/2002 |
| WO | WO02/086443 | 10/2002 |
| WO | WO02/102235 | 12/2002 |
| WO | WO03043987 A2 | 5/2003 |
| WO | WO03047526 | 6/2003 |
| WO | WO03051401 A2 | 6/2003 |
| WO | WO03/068054 | 8/2003 |
| WO | WO03075952 A1 | 9/2003 |
| WO | WO03087768 | 10/2003 |
| WO | WO03099205 | 12/2003 |
| WO | WO2004/030615 | 4/2004 |
| WO | WO2004/076622 | 9/2004 |
| WO | WO2004087874 | 10/2004 |
| WO | WO2004104197 | 12/2004 |
| WO | WO2004113394 A2 | 12/2004 |
| WO | WO2005/024055 | 3/2005 |
| WO | WO2005039504 A2 | 5/2005 |
| WO | WO2005063201 A2 | 7/2005 |
| WO | WO2005063288 A1 | 7/2005 |
| WO | WO2006003352 A1 | 1/2006 |
| WO | WO2006024518 A1 | 3/2006 |
| WO | WO2006027202 A1 | 3/2006 |
| WO | WO2006029385 A2 | 3/2006 |
| WO | WO2006102097 A2 | 9/2006 |
| WO | WO 2006138380 A2 | 12/2006 |
| WO | WO 2007002559 A1 | 1/2007 |
| WO | WO 2007002563 A1 | 1/2007 |
| WO | WO 2007005249 A2 | 1/2007 |
| WO | WO 2007023287 A1 | 3/2007 |
| WO | WO 2007045876 A1 | 4/2007 |
| WO | WO 2007059108 A2 | 5/2007 |
| WO | WO 2007061853 A2 | 5/2007 |
| WO | WO 2007073432 A2 | 6/2007 |
| WO | WO 2007084413 A2 | 7/2007 |
| WO | WO 2007104948 A2 | 9/2007 |
| WO | WO 2007110755 A1 | 10/2007 |
| WO | WO 2008002267 A1 | 1/2008 |
| WO | WO 2008016356 | 2/2008 |
| WO | WO 2008021290 | 2/2008 |
| WO | WO 2008033932 A2 | 3/2008 |
| WO | WO 2008052770 A2 | 5/2008 |
| WO | WO 2008054793 A2 | 5/2008 |
| WO | WO 2008082887 A2 | 7/2008 |
| WO | WO 2008083949 A2 | 7/2008 |

(56) References Cited

FOREIGN PATENT DOCUMENTS

| | | |
|---|---|---|
| WO | WO 2008104804 | 9/2008 |
| WO | WO 2009004329 A1 | 1/2009 |
| WO | WO 2009009186 | 1/2009 |
| WO | WO 2009039854 | 4/2009 |
| WO | WO 2009044162 A1 | 4/2009 |
| WO | WO 2009059972 | 5/2009 |
| WO | WO 2009061681 A2 | 5/2009 |
| WO | WO 2009069862 | 6/2009 |
| WO | WO 2009077864 | 6/2009 |
| WO | WO 2009111088 A2 | 9/2009 |
| WO | WO 2009114942 | 9/2009 |
| WO | WO 2009134370 | 11/2009 |
| WO | WO 2009144230 A1 | 12/2009 |
| WO | WO 2010003127 A2 | 1/2010 |
| WO | WO 2010014141 A1 | 2/2010 |
| WO | WO2010017479 A1 | 2/2010 |
| WO | WO2010033207 | 3/2010 |
| WO | WO2010033220 | 3/2010 |
| WO | WO2010033240 | 3/2010 |
| WO | WO2010037408 A1 | 4/2010 |
| WO | WO2010037539 A1 | 4/2010 |
| WO | WO2010060186 | 6/2010 |
| WO | WO2011054112 | 5/2011 |
| WO | WO2012129668 | 10/2012 |

OTHER PUBLICATIONS

Polyak et Al., Alanine-170 and proline-172 are critical determinants for extracellular CD20 epitopes; heterogeneity in the fine specificity of CD20 monoclonal antibodies is defintied by additional requirements imposed by both amino acid sequence and quaternary structure, 2002, Blood, vol. 99, No. 9, p. 3256-3262.*
Munodzana et Al., Conformational dependence of Anaplasma marginale major surface protein 5 surface-exposed B-cell epitopes, 1998, Infection and Immunity, vol. 66, No. 6, p. 2619-2624.*
Abhinandan, KR and Martin, ACR. Analysis and improvements to Kabat and structurally correct numbering of antibody variable domains. 2008; Mol Immunol, 45, 3832-3839.
Agrawal et al., "RNA interference: biology, mechanism, and applications," *Microbiol Mol Biol Rev* 67(4):657-685 (2003).
Benoît MH, et al., Global analysis of chromosome X gene expression in primary cultures of normal ovarian surface epithelial cells and epithelial ovarian cancer cell lines. Int. J. Oncol. 2007; 30(1): 5-17.
Berek et al., "Neoplasms of the Female Reproductive Organs," *Cancer Medicine*, 5th Ed., London: B.C. Decker, Inc. (2000), pp. 1687-1720.
Bird et al. (1988) Science 242:423-426.
Bonome et al., "Expression Profiling of Serous Low Malignant Potential, Low-Grade, and High-Grade Tumors of the Ovary," *Cancer Res* 65(22):10602-10612 (2005).
Bowie et al., "Deciphering the message in protein sequences: Tolerance to amino acid substiutions," Science 247(4948): 1306-1310 (1990).
Bristow, "Surgical standards in the management of ovarian cancer," *Curr Opin Oncol* 12:474-480 (2000).
Brown et al., "Carcinosarcoma of the Ovary: 19 Years of Prospective Data from a Single Center," *Cancer* 100:2148-2153 (2004).
Brummelkamp et al., "A system for stable expression of short interfering RNAs in mammalian cells," Science 296(5567):550-553 (2002).
Burger RA. Experience with bevacizumab in the management of epithelial ovarian cancer. J. Clin. Oncol. 2007; 25(20): 2902-2908.
Burgess et al., "Possible dissociatinof the heparin-binding and mitogenic activities of heparin-binding (acidic fibroblast) growth factor-1 from its receptor-binding activities by site-directed mutagenesis of a single lysine residue," The J of Cell Biology, 111: 2129-2138 (1990).
Byers et al., Therapeutic strategies with monoclonal antibodies and immunoconjugates, 1988, Immunology, vol. 65, pp. 329-335.
Cannistra SA and McGuire WP. "Progress in the management of gynecologic cancer," J. Clin. Oncol.; 25(20): 2865-2866 (2007).
Chambers et al., "Ovarian Cancer Biomarkers in Urine," *Clin Cancer Res* 12(2):323-327(2006).
Clarkson et al., Nature, 352:624-628 (1991).
Cody NA, et al., "Influence of monolayer, spheroid, and tumor growth conditions on chromosome 3 gene expression in tumorigenic epithelial ovarian cancer cell lines," BMC Med. Genomics 1(1):34 (2008).
Cope N, et al., "Strong evidence that KIAA0319 on chromosome 6p is a susceptibility gene for developmental dyslexia," Am. J. Hum. Genet. 76: 581-591 (2005).
De Plaen et al., "Structure, chromosomal localization, and expression of 12 genes of the MAGE family," Immunogenetics 40:360-369 (1994).
Ebel W, et al., Preclinical evaluation of MORab-003, a humanized monoclonal antibody antagonizing folate receptor-alpha. Cancer Immun, 7: 6-13 (2007).
Elbashir et al., "Duplexes of 21-nucleotide RNAs mediate RNA interference in cultured mammalian cells," *Nature* 411(6836):494-8 (2001).
Futreal et al., "A census of human cancer genes," *Nat. Rev.* 4:177-183 (2004).
GenBank Acc. No. A1922121.1, GI:5658085, first referenced 1999, updated 2000.
GenBank Acc. No. AA744939.1, GI: 2783703, 1998.
GenBank Acc. No. AC002060.4, GI:22507090, first referenced 1997, updated 2002.
GenBank Acc. No. AC068828.6, GI:16418276, first referenced 2001, updated 2005.
GenBank Acc. No. AC104837.2, GI:18249998, first referenced 2001, updated 2002.
GenBank Acc. No. AC109350.5, GI:19526559, first referenced 1998, updated 2002.
GenBank Acc. No. AC117457.11, GI:28557825, first referenced 2002, updated 2003.
GenBank Acc. No. AK092857.1, GI:21751554, first referenced 2002, updated 2004.
GenBank Acc. No. AK092936.1, GI:21751648, first referenced 2002, updated 2004.
GenBank Acc. No. AL157931.17, GI:11493240, first referenced 2000, updated 2009.
GenBank Acc. No. AL583809.3, GI:14250883, 2001.
GenBank Acc. No. AY683003.1, GI:56384942, 2004.
GenBank Acc. No. BC009078.1, GI:14290598, first referenced 2001, updated 2008.
GenBank Acc. No. BC073793.1, GI:49258111, first referenced 2002, updated 2006.
GenBank Acc. No. BC092518.1, GI:62201665, first referenced 2002, updated 2005.
GenBank Acc. No. BC037243.1, GI:23337025, first referenced 2002, updated 2008.
GenBank Acc. No. BG213598.1, GI:13735285, 2001.
GenBank Acc. No. BU595315.1, GI:23247074, 2002.
GenBank Acc. No. NM_000077.3, GI:47132606, first referenced 1994, updated 2004.
GenBank Acc. No. NM_000096.3, GI:189458860, first referenced 1977, updated 2008.
GenBank Acc. No. NM_000170.2, GI:108773800, first referenced 1989, updated 2006.
GenBank Acc. No. NM_000802.2, GI:12056965, first referenced 1990, updated 2001.
GenBank Acc. No. NM_001007027.2, GI:91984777, first referenced 1995, updated 2006.
GenBank Acc. No. NM_001017920.2, GI:217272871, first referenced 2002, updated 2008.
GenBank Acc. No. NM_001039548.1, GI:88196793, 2004.
GenBank Acc. No. NM_001463.2, GI:38455387, first referenced 1996, updated 2003.
GenBank Acc. No. NM_001565.2, GI:149999381, first referenced 1985, updated 2007.
GenBank Acc. No. NM_001719.2, GI:187608319, first referenced 1990, updated 2008.
GenBank Acc. No. NM_001826.2, GI:206725531, first referenced 1990, updated 2008.

(56) References Cited

OTHER PUBLICATIONS

GenBank Acc. No. NM_001878.2, GI:6382069, first referenced 1991, updated 1999.
GenBank Acc. No. NM_003543.3, GI:21264599, first referenced 1997, updated 2002.
GenBank Acc. No. NM_005101.3, GI:193083170, first referenced 1987, updated 2008.
GenBank Acc. No. NM_005192.3, GI:195927023, first referenced 1993, updated 2008.
GenBank Acc. No. NM_005698.2, GI:16445418, first referenced 1997, updated 2001.
GenBank Acc. No. NM_005733.2, GI:195539383, first referenced 1998, updated 2008.
GenBank Acc. No. NM_005832.3, GI:31317293, first referenced 1999, updated 2003.
GenBank Acc. No. NM_006115.3, GI:46249365, first referenced 1997, updated 2004.
GenBank Acc. No. NM_006681.2, GI:195539393, first referenced 1995, updated 2008.
GenBank Acc. No. NM_006820.2, GI:166706908, first referenced 1997, updated 2008.
GenBank Acc. No. NM_006898.4, GI:23510372, first referenced 1989, updated 2002.
GenBank Acc. No. NM_007019.2, GI:32967292, first referenced 1997, updated 2003.
GenBank Acc. No. NM_012112.4, GI:40354199, first referenced 1997, updated 2003.
GenBank Acc. No. NM_013277.3, GI:186910298, first referenced 1997, updated 2008.
GenBank Acc. No. NM_018279.3, GI:89145418, first referenced 1997, updated 2006.
GenBank Acc. No. NM_021955.3, GI:74316012, first referenced 1984, updated 2005.
GenBank Acc. No. NM_022357.3, GI:193211607, first referenced 2003, updated 2008.
GenBank Acc. No. NM_024501.1, GI:13375631, 1989.
GenBank Acc. No. NM_024626.2, GI:99028880, first referenced 2003, updated 2006.
GenBank Acc. No. NM_033445.2, GI:28872747, first referenced 1998, updated 2003.
GenBank Acc. No. NM_152864.2, GI:42476063, first referenced 2001, updated 2004.
GenBank Acc. No. NM_178580.1, GI:30581108, 2001.
GenBank Acc. No. NM_181337.3, GI:198278499, first referenced 1999, updated 2008.
GenBank Acc. No. NM_202003.1, GI:42544160, 1994.
GenBank Acc. No. NM_001001887.1, GI:49574525, first referenced 1983, updated 2006.
Gene Bank Accession No. BCO37243, Strausberg et al., Sep. 27, 2002.
Gorelik et al., "Multiplexed Immunobead-based Cytokine Profiling for Early Detection of Ovarian Cancer," *Cancer Epidemiol Biomarkers Prev* 14(4):981-987 (2005).
Guo et al., "Protein tolerance to random amino acid change," PNAS 10(25): 9205-9210 (2004).
Hannon, "RNA interference," *Nature* 418(6894):244-251 (2002).
Huston et al. Proc. Natl. Acad. Sci. USA 85:5879-5883 (1988).
Idusogie et al., J. Immunol. 164, 4178-4184 (2000).
Jemal et al., "Cancer Statistics, 2005," CA *Cancer J Clin* 55:10-30 (2005).
Jones P.T. et al. "Replacing the complementarity-determining regions in a human antibody with those from a mouse", Nature, 321(29), 522-525 (1986).
Kozak et al., "Identification of biomarkers for ovarian cancer using strong anion-exchange ProteinChips: Potential use in diagnosis and prognosis," *PNAS* 100:12343-12348 (2003).
Larkin M.A., et al. *Bioinformatics* 2007 23(21): 2947-2948.
Lazar et al., "Transforming growth factor a: mutation of aspartic acid 47 and leucine 48 results in different biological activities," Molecular and Cellular Biology 8(3):1247-1252 (1988).

Leamon et al., "Folate-mediated targeting: from diagnostics to drug and gene delivery," *Drug Discov Today* 6:44-51 (2001).
Li Xiangzhou et al., The application of monoclonal antibody BG6 against human breast cancer to diagnosis and differential diagnosis of breast cancer, Chinese Journal of Clinical Oncology, 9(6): 415-417 (1992) (English abstract).
Li, et al., Genebank Acc. No. AY648683; Jun. 15, 2005.
Liang, et al. Genebank Acc. No. AY436928; Mar. 15, 2004.
Luque et al., "A highly conserved arginine is critical for the functional folding of inhibitor of apoptosis (IAP) BIR domains," Biochemistry 41: 13663-13671 (2002).
McIntosh et al., "Combining CAI25 and SMR serum markers for diagnosis and early detection of ovarian carcinoma," *Gynecol Oncol* 95(1):9-15 (2004).
Menon et al., "Prospective Study Using the Risk of Ovarian Cancer Algorithm to Screen for Ovarian Cancer," *J Clin Oncol* 23(31):7919-7926 (2005).
Mor et al., "Serum protein markers for early detection of ovarian cancer," *PNAS* 102:7677-7682 (2005).
Mosmann, "Rapid Colorimetric Assay for Cellular Growth and Survival: Application to Proliferation and Cytotoxicity Assays," *J Immunol Methods* 65:55-63 (1983).
Munodzana et al., Conformational dependence of Anaplasma marginale major surface protein 5 surface-exposed B-cell epitopes, 1998, Infection and Immunity vol. 66(6). pp. 2619-2624.
NCBI Accession No. M32599.1, first referenced 1990.
NCBI Accession No. NM_001238, first referenced 1991.
NCBI accession No. NM_003376, 1991.
NCBI accession No. Q9UBP8, 1999.
NCBI Accession No. X00351, first referenced 1984.
Nicodemus, et al., "Monoclonal antibody therapy of ovarian cancer," Expert Rev. Anticancer Ther. 5(1): 87-96 (2005).
Oei, "The use of monoclonal antibodies for the treatment of epithelial ovarian cancer," Int. J. Oncol. 32(6): 1145-1157 (2008).
Panka et al., Variable region framework differences result in decreased or increased affinity of variant anti-digoxin antibodies, PNAS USA, 85: 3080-3084 (1988).
Polyak et al., Alanine-170 and proline 172 are critical determinants for extracellular CD20 epitopes; heterogeneity in the fine specificity of CD20 monoclonal antibodies is defined by additional requirements imposed by both amino acid sequence and quaternary structure, Blood, 99(9): 3256-3262 (2002).
Portolano et al. The Journal of Immunology 150:880-887 (1993).
Provencher et al., "Characterization of Four Novel Epithelial Ovarian Cancer Cell Lines," In Vitro Ce//DevBiolAnim 36:357-361 (2000).
Rudikoff et al. Single Amino acid substitutions altering antigen-binding specificity, PNAS USA, 79: 1979-1983 (1982).
Rudnick, S.I. et al., Influence of affinity and antigen internalization on the uptake and penetration of anti-Her2 antibodies in solid tumors, Cancer Res., 71(6): 2250-2259 (2011).
Samouelian et al., "Chemosensitivity and radiosensitivity profiles of four new human epithelial ovarian cancer cell lines exhibiting genetic alterations in BRCA2, TGF6-RII, KRAS2, TP53 and/or CDNK2A," *Cancer Chemother Pharmaco/* 54:497-504 (2004).
Schorge et al., "Osteopontin as an Adjunct to CAI25 in Detecting Recurrent Ovarian Cancer," *Clin Cancer Res* 10:3474-3478 (2004).
Schumacher et al. Am, J. Hum Genet. Jan; 78(1): 52-62 (2006).
Seidman et al., "Surface Epithelial Tumors of the Ovary," *B/austein's Pathology of the Female Genital Tract*, Kurman, R.J. (Ed.), 5th Ed., New York: Springer-Verlag (2002), pp. 791-904.
Shih et al., "Molecular Pathogenesis of Ovarian Borderline Tumors: New Insights and Old Challenges," *Clin Cancer Res* 11(20):7273-7279 (2005).
Simon I, et al. B7-H4 is a novel membrane-bound protein and a candidate serum and tissue biomarker for ovarian cancer. Cancer Res. 2006; 66(3): 1570-1575.
Skolnick et al. "From genese to protein structure and function: novel applications of computational approaches in the genomic era," TIBTech 18:37-39 (2000).
Takada et al., "Aleration of a Single Amino Acid in Peroxisom Proliferator-Activated Receptor-a (PPARa) Generates a PPAR Phenotype," Molecular Endocrinology 14(5): 733-740 (2000).

(56) References Cited

OTHER PUBLICATIONS

Tatiana, "Blast 2 sequences—a new tool for comparing protein and nucleotide sequences", FEMS Microbiol Lett. 174:247-250 (1999).
Van Den Eynde et al., "A new antigen recognized by cytolytic T lymphocytes on a human kidney tumor results from reverse strand transcription," *J. Exp. Med.* 190(12):1793-1799 (1999).
Verhoeyen et al. (1988) "Reshaping human antibodies: Grafting an antilysozyme activity", Science, 239, 4847, 1534-1535.
Vogelstein et al., "Cancer genes and the pathways they control," *Nat. Med.* 10(8):789-799 (2004).
Vucic et al., "A mutational analysis of the baculovirus inhibitor of apoptosis Op-IAP," The Journal of Biological Chemistry 273(51): 33915-33921 (1998).
Ward et al., (1989) Nature 341:544-546.
Woolas et al., "Elevation of Multiple Serum Markers in Patients with Stage I Ovarian Cancer," *J Nat/ Cancer Inst* 85(21):1748-1751 (1993).
Zhiquiang et al. (2009) "IgG2m4, and engineered antibody isotype with reduced Fc function", mAbs 1:6, 572-579.

* cited by examiner

Figure 3B

|   | 1 | 2 | 3 | 4 | 5 | 6 | 7 | 8 | 9 | 10 | 11 | 12 |
|---|---|---|---|---|---|---|---|---|---|----|----|----|
| A | 1.36 | 3.31 | 0.04 | -0.05 | 0.01 | 0.03 | 0.04 | 0.57 | 1.53 | 0.08 | 1.79 | -0.04 |
| B | 1.74 | 1.62 | -0.08 | -0.07 | 0.01 | -0.02 | -0.05 | 1.23 | -0.10 | 0.03 | 1.17 | -0.01 |
| C | -0.01 | 0.32 | 1.04 | 0.25 | -0.08 | -0.11 | -0.05 | 0.11 | -0.06 | 0.61 | 0.05 | -0.01 |
| D | 0.15 | 0.30 | 1.21 | 0.03 | 0.96 | 0.96 | -0.09 | -0.11 | -0.05 | -0.03 | 0.07 | 0.20 |
| E | -0.01 | 0.02 | 0.58 | 0.57 | 1.26 | 1.21 | 0.40 | 0.22 | 1.78 | 0.02 | -0.04 | 1.90 |
| F | 0.36 | -0.03 | -0.06 | 1.37 | 0.22 | 0.19 | 0.41 | -0.05 | -0.03 | 2.34 | 1.28 | 0.03 |
| G | 0.03 | 1.57 | 1.07 | 0.43 | 1.65 | -0.01 | 0.43 | 1.72 | 1.55 | 2.78 | -0.03 | 1.38 |
| H | 0.00 | -0.01 | 0.23 | 0.00 | 0.27 | 0.02 | 0.00 | 0.00 | 0.85 | 0.15 | 0.10 | 0.03 |

CDRL1-alignment 1

```
KSSQSLLNSSNQKNYLA 17 (SEQID NO.:184)
KSSQSLLNSSNQKNYLA 17 (SEQID NO.:185)
KSSQSLLNSSNQKNYLA 17 (SEQID NO.:186)
KSSQSLLNSSNQKNYLA 17 (SEQID NO.:187)
KSSQSLLNSSNQKNYLA 17 (SEQID NO.:188)
KSSQSLLNSSNQKNYLA 17 (SEQID NO.:189)
KSSQSLLNSSNQKNYLA 17 (SEQID NO.:190)
KSSQSLLNSSNQKNYLA 17 (SEQID NO.:191)
KSSQSLLNSSNQKNYLA 17 (SEQID NO.:192)
KSSQSLLNSSNQKNYLA 17 (SEQID NO.:193)
KSSQSLLNRSNQKNYLA 17 (SEQID NO.:194)
KSSQSLLNNSNQKNYLA 17 (SEQID NO.:195)
KSSQSLLNTSNQLNYLA 17 (SEQID NO.:196)
KSSQSLLNTSNQKNYLA 17 (SEQID NO.:197)
KSSQSLLNSNNQLNYLA 17 (SEQID NO.:198)
KSSQSLLNSNFQKNFLA 17 (SEQID NO.:199)
KSSQSLLHS-DGKTYLN 16 (SEQID NO.:200)
KSSQSLLHS-DGKTYLN 16 (SEQID NO.:201)
KSSQSLLYS-DGKTYLN 16 (SEQID NO.:202)
RSSQSLLHS-NGNTYLE 16 (SEQID NO.:203)
RSSKSLLHS-NGNTYLY 16 (SEQID NO.:204)
 :**:***      .:*
```

CDRL1-alignment 2

```
RASQDIHNFLN 11 (SEQID NO.:205)
RASQDIHRFLN 11 (SEQID NO.:206)
RASQDIHNYLN 11 (SEQID NO.:207)
RASQDIHNYLN 11 (SEQID NO.:208)
RASQDIHTYLN 11 (SEQID NO.:209)
KASQDVGTAVA 11 (SEQID NO.:210)
*****:   :
```

Figure 9A

| CDRL2-alignment1 | CDRL2-alignment 2 |
|---|---|
| `FASTRES 7 (SEQID NO.:211)`<br>`FASTRES 7 (SEQID NO.:212)`<br>`FASTTES 7 (SEQID NO.:213)`<br>`FASTRES 7 (SEQID NO.:214)`<br>`FASTRES 7 (SEQID NO.:215)`<br>`FGSTRES 7 (SEQID NO.:216)`<br>`FGSTRES 7 (SEQID NO.:217)`<br>`FASTRES 7 (SEQID NO.:218)`<br>`FASTRES 7 (SEQID NO.:219)`<br>`FASTRES 7 (SEQID NO.:220)`<br>`FASTRES 7 (SEQID NO.:221)`<br>`FASTRES 7 (SEQID NO.:222)`<br>`FASTRES 7 (SEQID NO.:223)`<br>`FASTRES 7 (SEQID NO.:224)`<br>`FASTRES 7 (SEQID NO.:225)`<br>`FASTRAS 7 (SEQID NO.:226)`<br>`*.** *` | `LVSKLDS 7 (SEQID NO.:227)`<br>`LVSKLDS 7 (SEQID NO.:228)`<br>`LVSKLDS 7 (SEQID NO.:229)`<br>`KVSNRFS 7 (SEQID NO.:230)`<br>`**: *` |

| CDRL2-alignment 3 |
|---|
| `RANRLVD 7 (SEQID NO.:231)`<br>`RANRLVD 7 (SEQID NO.:232)`<br>`RANRLVD 7 (SEQID NO.:233)`<br>`RANRLVA 7 (SEQID NO.:234)`<br>`RANRLVA 7 (SEQID NO.:235)`<br>`:****` |

Figure 9B

| CDRL3-alignment1 | CDRL3-alignment2 |
|---|---|
| QQHYSTPLT 9 (SEQID NO.:236)<br>QQHYSTPLT 9 (SEQID NO.:237)<br>QQHYSTPLT 9 (SEQID NO.:238)<br>QQHYSTPLT 9 (SEQID NO.:239)<br>QQHYSTPLT 9 (SEQID NO.:240)<br>QQHYSTPLT 9 (SEQID NO.:241)<br>QQHYSTPLT 9 (SEQID NO.:242)<br>QQHYSTPLT 9 (SEQID NO.:243)<br>QQHYSTPLT 9 (SEQID NO.:244)<br>QQHYSTPLT 9 (SEQID NO.:245)<br>QQHYSTPLT 9 (SEQID NO.:246)<br>QQHYSIPLT 9 (SEQID NO.:247)<br>QQHYSIPLT 9 (SEQID NO.:248)<br>QQHYSIPLT 9 (SEQID NO.:249)<br>QQHYSIPLT 9 (SEQID NO.:250)<br>QQHYSIPLT 9 (SEQID NO.:251)<br>QQHFNTPLT 9 (SEQID NO.:252)<br>LQYDAFPLT 9 (SEQID NO.:253)<br>LQYDAFPLT 9 (SEQID NO.:254)<br>LQYDAFPLT 9 (SEQID NO.:255)<br>LQYDEFPLT 9 (SEQID NO.:256)<br>LQYDEIPLT 9 (SEQID NO.:257)<br>  *:  ***| QQHYSIPLT 9 (SEQID NO.:247)<br>QQHYSIPLT 9 (SEQID NO.:248)<br>QQHYSIPLT 9 (SEQID NO.:249)<br>QQHYSIPLT 9 (SEQID NO.:250)<br>QQHYSIPLT 9 (SEQID NO.:251)<br>QQHYSTPLT 9 (SEQID NO.:236)<br>QQHYSTPLT 9 (SEQID NO.:237)<br>QQHYSTPLT 9 (SEQID NO.:238)<br>QQHYSTPLT 9 (SEQID NO.:239)<br>QQHYSTPLT 9 (SEQID NO.:240)<br>QQHYSTPLT 9 (SEQID NO.:241)<br>QQHYSTPLT 9 (SEQID NO.:242)<br>QQHYSTPLT 9 (SEQID NO.:243)<br>QQHYSTPLT 9 (SEQID NO.:244)<br>QQHYSTPLT 9 (SEQID NO.:245)<br>QQHYSTPLT 9 (SEQID NO.:246)<br>QQHFNTPLT 9 (SEQID NO.:252)<br>***:. *** |

| CDRL3-alignment3 | |
|---|---|
| WQGTHFPRT 9 (SEQID NO.:258)<br>WQGTHFPRT 9 (SEQID NO.:259)<br>WQGTHFPRT 9 (SEQID NO.:260)<br>FQGSHVPLT 9 (SEQID NO.:261)<br>:**:*.* * | |

Figure 9C

| CDRH1-alignment1 | CDRH1-alignment2 |
|---|---|
| GYTFTDYEIH 10 (SEQID NO.:262)<br>GYTFTDYEIH 10 (SEQID NO.:263)<br>GYTFTDYEIH 10 (SEQID NO.:264)<br>GYTFTDYEIH 10 (SEQID NO.:265)<br>GYTFTDYEIH 10 (SEQID NO.:266)<br>GYTFTDYEIH 10 (SEQID NO.:267)<br>GYTFTDYEIH 10 (SEQID NO.:268)<br>GYTFTDYEIH 10 (SEQID NO.:269)<br>GYTFTDYEIH 10 (SEQID NO.:270)<br>GYIFTDYEIH 10 (SEQID NO.:271)<br>GYIFTDYEIH 10 (SEQID NO.:272)<br>GYIFTDYEVH 10 (SEQID NO.:273)<br>GYTFTDYEVH 10 (SEQID NO.:274)<br>GYTFTDYEVH 10 (SEQID NO.:275)<br>GYTFTDYEMH 10 (SEQID NO.:276)<br>GYTFSDYEMH 10 (SEQID NO.:277)<br>GYTFTDYEMH 10 (SEQID NO.:278)<br>GYKFTDYEMH 10 (SEQID NO.:279)<br>GYTFTDYNMH 10 (SEQID NO.:280)<br>GYIFTEYNIH 10 (SEQID NO.:281)<br>GYTFTEYNMH 10 (SEQID NO.:282)<br>\*\* \*::\*::\* | GFSITSGYGWH 11 (SEQID NO.:283)<br>GFSITSGYGWH 11 (SEQID NO.:284)<br>\*\*\*\*\*\*\*\*\*\*\* |

Figure 10A

| CDRH2-alignment1 | CDRH2-alignment2 |
|---|---|
| VIDPATGDTA 10 (SEQID NO.:285)<br>VIDPATGDTA 10 (SEQID NO.:286)<br>VIDPETGDTA 10 (SEQID NO.:287)<br>VIDPETGDTA 10 (SEQID NO.:288)<br>VIDPETGDTA 10 (SEQID NO.:289)<br>VIDPETGDTA 10 (SEQID NO.:290)<br>VIDPETGVTA 10 (SEQID NO.:291)<br>VIDPETGVTA 10 (SEQID NO.:292)<br>VIDPETGNTA 10 (SEQID NO.:293)<br>VIDPETGNTA 10 (SEQID NO.:294)<br>VIDPETGSTA 10 (SEQID NO.:295)<br>VIDPETGSTA 10 (SEQID NO.:296)<br>VIDPETGATA 10 (SEQID NO.:297)<br>VIDPETGATA 10 (SEQID NO.:298)<br>GIDPETGDTV 10 (SEQID NO.:299)<br>GIDPETGSTA 10 (SEQID NO.:300)<br>VIDPETGGTA 10 (SEQID NO.:301)<br>VLDPGTGKTA 10 (SEQID NO.:302)<br>:** ** *. | VIDPATGDTA 10 (SEQID NO.:285)<br>VIDPATGDTA 10 (SEQID NO.:286)<br>VIDPETGDTA 10 (SEQID NO.:287)<br>VIDPETGDTA 10 (SEQID NO.:288)<br>VIDPETGDTA 10 (SEQID NO.:289)<br>VIDPETGDTA 10 (SEQID NO.:290)<br>VIDPETGVTA 10 (SEQID NO.:291)<br>VIDPETGVTA 10 (SEQID NO.:292)<br>VIDPETGNTA 10 (SEQID NO.:293)<br>VIDPETGNTA 10 (SEQID NO.:294)<br>VIDPETGSTA 10 (SEQID NO.:295)<br>VIDPETGSTA 10 (SEQID NO.:296)<br>VIDPETGATA 10 (SEQID NO.:297)<br>VIDPETGATA 10 (SEQID NO.:298)<br>VIDPETGGTA 10 (SEQID NO.:301)<br>VLDPGTGPTA 10 (SEQID NO.:302)<br>* :** ** ** |
| CDRH2-alignment 3 | CDRH2-alignment 4 |
| YISFNGDYN 9 (SEQID NO.:303)<br>YISFNGDSN 9 (SEQID NO.:304)<br>YINYDGHND 9 (SEQID NO.:305)<br>**.::*. : | NINPYNDVTE 10 (SEQID NO.:306)<br>NINPYNNVTE 10 (SEQID NO.:307)<br>YINPYNDVTE 10 (SEQID NO.:308)<br>***:* |
| CDRH2-alignment 5 | |
| DINPNYGGIT 10 (SEQID NO.:309)<br>DINPYYGTTT 10 (SEQID NO.:310)<br>**** ** * | |

Figure 10B

| CDRH3-alignment1 | CDRH3-alignment2 |
|---|---|
| MGYSDY 6 (SEQID NO.:311)<br>MSYSDY 6 (SEQID NO.:312)<br>MGYSDY 6 (SEQID NO.:313)<br>MGYSDY 6 (SEQID NO.:314)<br>MGYSDY 6 (SEQID NO.:315)<br>MGYSDY 6 (SEQID NO.:316)<br>MGYSDY 6 (SEQID NO.:317)<br>MGHSDY 6 (SEQID NO.:318)<br>MGYSDY 6 (SEQID NO.:319)<br>MGYSDY 6 (SEQID NO.:320)<br>MGYSDY 6 (SEQID NO.:321)<br>MGYSDY 6 (SEQID NO.:322)<br>MGYSDY 6 (SEQID NO.:323)<br>MGYADY 6 (SEQID NO.:324)<br>MGYADY 6 (SEQID NO.:325)<br>\*,::\*\* | ISYAMDY 7 (SEQID NO.:326)<br>ISYAMDY 7 (SEQID NO.:327)<br>IGYA-DY 6 (SEQID NO.:328)<br>\*.\*\* \*\* |
| CDRH3-alignment3 | CDRH3-alignment4 |
| APWGLRN 7 (SEQID NO.:329)<br>APWGLRN 7 (SEQID NO.:330)<br>AWFGLRQ 7 (SEQID NO.:331)<br>\* :\*\*\*: | ASSYDGLFAY 10 (SEQID NO.:332)<br>ASSYDGLFAY 10 (SEQID NO.:333)<br>ASSYDGLFAY 10 (SEQID NO.:334)<br>\*\*\*\*\*\*\*\*\*\* |

Figure 10C

| Light chain variable region | % identity with SEQ.16 (% similarity with SEQ 16) | % identity with SEQ.20 (% similarity with SEQ 20) | % identity with SEQ.24 (% similarity with SEQ 24) | % identity with SEQ.105 (% similarity with SEQ 105) |
|---|---|---|---|---|
| SEQ ID NO:105 | 58% (71%) | 69% (81%) | 45% (66%) | 100% (100%) |
| SEQ ID NO:106 | 59% (72%) | 71% (83%) | 48% (68%) | 92% (96%) |
| SEQ ID NO:107 | 61% (74%) | 74% (83%) | 48% (68%) | 95% (97%) |
| SEQ ID NO:108 | 63% (77%) | 100% (100%) | 50% (73%) | N.D. |
| SEQ ID NO:109 | 57% (74%) | 68% (82%) | 49% (72%) | N.D. |
| SEQ ID NO:110 | 88% (97%) | 63% (77%) | 56% (74%) | N.D. |
| SEQ ID NO:111 | 90% (97%) | 63% (79%) | 58% (76%) | N.D. |
| SEQ ID NO:112 | 88% (97%) | 61% (79%) | 56% (76%) | N.D. |
| SEQ ID NO:113 | 91% (97%) | 64% (79%) | 57% (76%) | N.D. |
| SEQ ID NO:114 | 92% (98%) | 64% (78%) | 56% (75%) | N.D. |
| SEQ ID NO:115 | 92% (98%) | 64% (78%) | 56% (75%) | N.D. |
| SEQ ID NO:116 | 92% (98%) | 65% (78%) | 57% (75%) | N.D. |
| SEQ ID NO:117 | 90% (98%) | 62% (78%) | 54% (75%) | N.D. |
| SEQ ID NO:118 | 90% (96%) | 65% (79%) | 54% (73%) | N.D. |
| SEQ ID NO:119 | 91% (96%) | 64% (79%) | 57% (75%) | N.D. |
| SEQ ID NO:120 | 90% (97%) | 61% (77%) | 54% (73%) | N.D. |
| SEQ ID NO:121 | 88% (95%) | 61% (76%) | 56% (74%) | N.D. |
| SEQ ID NO:122 | 88% (95%) | 65% (78%) | 56% (74%) | N.D. |
| SEQ ID NO:123 | 92% (98%) | 64% (78%) | 56% (75%) | N.D. |
| SEQ ID NO:124 | 100% (100%) | 63% (77%) | 56% (73%) | N.D. |
| SEQ ID NO:125 | 90% (96%) | 65% (79%) | 54% (73%) | N.D. |
| SEQ ID NO:126 | 69% (83%) | 59% (76%) | 62% (77%) | N.D. |
| SEQ ID NO:127 | 56% (73%) | 50% (73%) | 100% (100%) | N.D. |
| SEQ ID NO:128 | 54% (72%) | 54% (73%) | 89% (96%) | N.D. |
| SEQ ID NO:129 | 56% (75%) | 53% (73%) | 89% (94%) | N.D. |
| SEQ ID NO:130 | 56% (75%) | 53% (73%) | 89% (94%) | N.D. |
| SEQ ID NO:131 | 56% (74%) | 57% (81%) | 91% (94%) | N.D. |

Figure 11

| Heavy chain variable region | % identity with SEQ.18 (% similarity with SEQ 18) | % identity with SEQ.22 (% similarity with SEQ 22) | % identity with SEQ.26 (% similarity with SEQ 26) | % identity with SEQ.132 (% similarity with SEQ 132) |
|---|---|---|---|---|
| SEQ ID NO:132 | 66% (79%) | 74% (81%) | 47% (70%) | 100% (100%) |
| SEQ ID NO:133 | 70% (80%) | 73% (81%) | 47% (66%) | 87% (94%) |
| SEQ ID NO:134 | 68% (79%) | 73% (81%) | 48% (66%) | 88% (95%) |
| SEQ ID NO:135 | 88% (96%) | 66% (77%) | 41% (64%) | N.D. |
| SEQ ID NO:136 | 92% (93%) | 70% (80%) | 41% (65%) | N.D. |
| SEQ ID NO:137 | 95% (96%) | 71% (80%) | 43% (66%) | N.D. |
| SEQ ID NO:138 | 94% (97%) | 70% (80%) | 42% (66%) | N.D. |
| SEQ ID NO:139 | 92% (96%) | 71% (80%) | 43% (66%) | N.D. |
| SEQ ID NO:140 | 92% (95%) | 69% (78%) | 42% (66%) | N.D. |
| SEQ ID NO:141 | 91% (96%) | 68% (80%) | 40% (66%) | N.D. |
| SEQ ID NO:142 | 91% (94%) | 69% (78%) | 39% (65%) | N.D. |
| SEQ ID NO:143 | 91% (95%) | 71% (79%) | 41% (64%) | N.D. |
| SEQ ID NO:144 | 100% (100%) | 67% (77%) | 41% (66%) | N.D. |
| SEQ ID NO:145 | 98% (99%) | 68% (77%) | 41% (66%) | N.D. |
| SEQ ID NO:146 | 92% (93%) | 68% (77%) | 41% (65%) | N.D. |
| SEQ ID NO:147 | 91% (95%) | 66% (78%) | 39% (66%) | N.D. |
| SEQ ID NO:148 | 91% (95%) | 66% (78%) | 39% (66%) | N.D. |
| SEQ ID NO:149 | 88% (92%) | 66% (77%) | 39% (65%) | N.D. |
| SEQ ID NO:150 | 92% (95%) | 69% (79%) | 43% (64%) | N.D. |
| SEQ ID NO:151 | 85% (93%) | 71% (79%) | 43% (66%) | N.D. |
| SEQ ID NO:152 | 83% (91%) | 70% (78%) | 42% (63%) | N.D. |
| SEQ ID NO:153 | 72% (78%) | 85% (87%) | 44% (65%) | N.D. |
| SEQ ID NO:154 | 67% (77%) | 100% (100%) | 47% (66%) | N.D. |
| SEQ ID NO:155 | 42% (63%) | 45% (66%) | 92% (98%) | N.D. |
| SEQ ID NO:156 | 40% (64%) | 44% (66%) | 91% (98%) | N.D. |
| SEQ ID NO:157 | 41% (66%) | 47% (66%) | 100% (100%) | N.D. |

Figure 12

| Antibody | Ka (1/Ms) | Kd (1/s) | $K_A$ (1/M) | $K_D$ (M) | Chi² |
|---|---|---|---|---|---|
| m3D3 | 2.91 x 10⁶ | 0.00065 | 4.5 x 10⁹ | 2.35 x 10⁻¹⁰ | 0.49 |
| CC | 1.98 x 10⁶ | 0.00073 | 2.71 x 10⁹ | 3.68 x 10⁻¹⁰ | 0.142 |
| HC | 2.36 x 10⁶ | 0.00073 | 3.24 x 10⁹ | 3.09 x 10⁻¹⁰ | 0.51 |
| CH | 2.20 x 10⁶ | 0.00111 | 1.98 x 10⁹ | 5.05 x 10⁻¹⁰ | 0.208 |
| HH | 2.53 x 10⁶ | 0.00111 | 2.28 x 10⁹ | 4.39 x 10⁻¹⁰ | 0.61 |

| Name | SEQ ID NO.: | | |
|---|---|---|---|
| 3D3VL | 16 | DIVMTQSPSSLAVSIGQKVTMNCKSSQSLLNSNFQKNFLAWYQQKPGQSPKLLIYFASTR | 60 |
| | | DIVMTQSP SLAVS+G++ T+NCKSSQSLLNSNFQKNFLAWYQQKPGQ PKLLIYFASTR | |
| h3D3VL | 178 | DIVMTQSPDSLAVSLGERATINCKSSQSLLNSNFQKNFLAWYQQKPGQPPKLLIYFASTR | 60 |
| | | | |
| 3D3VL | 16 | ESSIPDRFICSGSGTDFTLTISSVQAEDLADYFCQQHYSTPLTFGAGTKLELK | 113 |
| | | ESS+PDRF GSGSGTDFTLTISS+QAED+A Y+CQQHYSTPLTFG GTKLE+K | |
| h3D3VL | 178 | ESSVPDRFSGSGSGTDFTLTISSLQAEDVAVYYCQQHYSTPLTFGQGTKLEIK | 113 |

FIGURE 20B

| Name | SEQ ID NO.: | | |
|---|---|---|---|
| 3D3VH | 18 | EVQLQQSVAELVRPGASVTLSCKASGYIFTDYEIHWVKQTPVHGLEWIGVIDPETGNTAF | 60 |
| | | EVQL QS AE+ +PGASV +SCKASGYIFTDYEIHWV+Q P GLEW+GVIDPETGNTAF | |
| h3D3VH | 179 | EVQLVQSGAEVKKPGASVKVSCKASGYIFTDYEIHWVRQAPGQGLEWMGVIDPETGNTAF | 60 |
| | | | |
| 3D3VH | 18 | NQKFKGKATLTADISSSTAYMELSSLTSEDSAVYYCMGYSDYWGQGTTLTVSS | 113 |
| | | NQKFKG+ T+TAD S+STAYMELSSLTSED+AVYYCMGYSDYWGQGT +TVSS | |
| h3D3VH | 179 | NQKFKGRVTITADTSTSTAYMELSSLTSEDTAVYYCMGYSDYWGQGTLVTVSS | 113 |

5   ### FIGURE 21A

| Name | SEQ ID NO.: | | |
|---|---|---|---|
| 3C4VL | 24 | DIVMSQSPSSMYASLGERVTITCKASQDIHNFLNWFQQKPGKSPKTLIFRANRLVDGVPS | 60 |
| | | DIVM+QSPSS+ AS+G+RVTITCKASQDIHNFLNWFQQKPGK+PKTLIFRANRLVDGVPS | |
| H3C4VL | 182 | DIVMTQSPSSLSASVGDRVTITCKASQDIHNFLNWFQQKPGKAPKTLIFRANRLVDGVPS | 60 |
| | | | |
| 3C4VL | 24 | RFSGSGSGQDYSLTISSLEFEDLGIYSCLQYDEIPLTFGAGTKLELR | 107 |
| | | RFSGSGSG DY+LTISSL+ ED   YSCLQYDEIPLTFG GTKLE++ | |
| H3C4VL | 182 | RFSGSGSGTDYTLTISSLQPEDFATYSCLQYDEIPLTFGQGTKLEIK | 107 |

FIGURE 21B

| Name | SEQ ID NO.: | | |
|---|---|---|---|
| 3C4VH | 26 | EVQLQESGPDLVKPSQSLSLTCTVTGFSITSGYGWHWIRQFPGNKLEWMGYINYDGHNDY | 60 |
| | | EVQLQESGP LVKPSQ+LSLTCTV+GFSITSGYGWHWIRQ PG  LEW+GYINYDGHNDY | |
| H3C4VH | 183 | EVQLQESGPGLVKPSQTLSLTCTVSGFSITSGYGWHWIRQHPGKGLEWIGYINYDGHNDY | 60 |
| | | | |
| 3C4VH | 26 | NPSLKSRISITQDTSKNQFFLQLNSVTTEDTATYYCASSYDGLFAYWGQGTLVTVSA | 117 |
| | | NPSLKSR++I+QDTSKNQF L+L+SVT  DTA YYCASSYDGLFAYWGQGTLVTVS | |
| H3C4VH | 183 | NPSLKSRVTISQDTSKNQFSLKLSSVTAADTAVYYCASSYDGLFAYWGQGTLVTVS | 116 |

SEQUENCE LISTING

```
<160> NUMBER OF SEQ ID NOS: 334

<210> SEQ ID NO 1
<211> LENGTH: 885
<212> TYPE: DNA
<213> ORGANISM: Homo sapiens
<300> PUBLICATION INFORMATION:
<301> AUTHORS: Van Den Eynde,B.J. et al.,
<302> TITLE: A new antigen recognized by cytolytic T lymphocytes on a
      human kidney tumor results from reverse strand transcription
<303> JOURNAL: J. Exp. Med.
<304> VOLUME: 190
<305> ISSUE: 12
<306> PAGES: 1793-1800
<307> DATE: 1999-12-20

<400> SEQUENCE: 1 gagggcatc aatcacaccg agaagtcaca gcccctcaac cactgaggtg tggggggta      60 gggatctgca tttcttcata tcaacccac actatagggc acctaaatgg gtgggcggtg   120
```

```
ggggagaccg actcacttga gtttcttgaa ggcttcctgg cctccagcca cgtaattgcc    180
cccgctctgg atctggtcta gcttccggat tcggtggcca gtccgcgggg tgtagatgtt    240
cctgacggcc ccaaagggtg cctgaacgcc gccggtcacc tccttcagga agacttcgaa    300
gctggacacc ttcttctcat ggatgacgac gcggcgcccc gcgtagaagg ggtccccgtt    360
gcggtacaca gcacgctct tcacgacggg ctgagacagg tggctggacc tggcgctgct    420
gccgctcatc ttccccgctg gccgccgcct cagctcgctg cttcgcgtcg ggaggcacct    480
ccgctgtccc agcggcctca ccgcaccag ggcgcgggat cgcctcctga acgaacgag     540 aaactgacga atccacaggt gaaagagaag taacggccgt gcgcctaggc gtccacccag    600
aggagacact aggagcttgc aggactcgga gtagacgctc aagttttttca ccgtggcgtg    660 cacagccaat caggacccgc agtgcgcgca ccacaccagg ttcacctgct acgggcagaa    720
tcaaggtgga cagcttctga gcaggagccg gaaacgcgcg gggccttcaa acaggcacgc    780
ctagtgaggg caggagagag gaggacgcac acacacacac acacacaaat atggtgaaac    840
ccaatttctt acatcatatc tgtgctaccc tttccaaaca gccta                   885
```

<210> SEQ ID NO 2
<211> LENGTH: 84
<212> TYPE: PRT
<213> ORGANISM: Homo sapiens
<300> PUBLICATION INFORMATION:
<301> AUTHORS: Van Den Eynde,B.J., et al.,
<302> TITLE: A new antigen recognized by cytolytic T lymphocytes on a
      human kidney tumor results from reverse strand transcription
<303> JOURNAL: J. Exp. Med.
<304> VOLUME: 190
<305> ISSUE: 12
<306> PAGES: 1793-1800
<307> DATE: 1999-12-20

<400> SEQUENCE: 2

Met Asp Asp Asp Ala Ala Pro Arg Val Glu Gly Val Pro Val Ala Val
1               5                   10                  15

His Lys His Ala Leu His Asp Gly Leu Arg Gln Val Ala Gly Pro Gly
            20                  25                  30

Ala Ala Ala Ala His Leu Pro Arg Trp Pro Pro Gln Leu Ala Ala
        35                  40                  45

Ser Arg Arg Glu Ala Pro Pro Leu Ser Gln Arg Pro His Arg Thr Gln
    50                  55                  60

Gly Ala Gly Ser Pro Pro Glu Thr Asn Glu Lys Leu Thr Asn Pro Gln
65                  70                  75                  80

Val Lys Glu Lys

<210> SEQ ID NO 3
<211> LENGTH: 657
<212> TYPE: DNA
<213> ORGANISM: Artificial Sequence
<220> FEATURE:
<223> OTHER INFORMATION: Nucleotide sequence of the 3D3 antibody light
      chain

<400> SEQUENCE: 3

```
gacattgtga tgacccagtc tccatcctcc ctggctgtgt caataggaca gaaggtcact    60
atgaactgca agtccagtca gagccttttta aatagtaact ttcaaaagaa cttttttggcc    120 tggtaccagc agaaaccagg ccagtctcct aaacttctga tatactttgc atccactcgg    180
gaatctagta tccctgatcg cttcataggc agtggatctg ggacagattt cactcttacc    240
```

```
atcagcagtg tgcaggctga agacctggca gattacttct gtcagcaaca ttatagcact    300
ccgctcacgt tcggtgctgg gaccaagctg gagctgaaag ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt      657
```

<210> SEQ ID NO 4
<211> LENGTH: 219
<212> TYPE: PRT
<213> ORGANISM: Artificial Sequence
<220> FEATURE:
<223> OTHER INFORMATION: Amino acid sequence of the 3D3 antibody light chain

<400> SEQUENCE: 4

```
Asp Ile Val Met Thr Gln Ser Pro Ser Ser Leu Ala Val Ser Ile Gly
 1               5                  10                  15

Gln Lys Val Thr Met Asn Cys Lys Ser Ser Gln Ser Leu Leu Asn Ser
            20                  25                  30

Asn Phe Gln Lys Asn Phe Leu Ala Trp Tyr Gln Gln Lys Pro Gly Gln
        35                  40                  45

Ser Pro Lys Leu Leu Ile Tyr Phe Ala Ser Thr Arg Glu Ser Ser Ile
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys Ala Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 5
<211> LENGTH: 1329
<212> TYPE: DNA
<213> ORGANISM: Artificial Sequence
<220> FEATURE:
<223> OTHER INFORMATION: Nucleotide sequence of the 3D3 antibody heavy chain

<400> SEQUENCE: 5

```
gaggttcagc tgcagcagtc tgtagctgag ctggtgaggc ctggggcttc agtgacgctg     60
```

```
tcctgcaagg cttcgggcta catatttact gactatgaga tacactgggt gaagcagact      120
cctgtgcatg gcctggaatg gattggggtt attgatcctg aaactggtaa tactgccttc      180
aatcagaagt tcaagggcaa ggccacactg actgcagaca tatcctccag cacagcctac      240
atggaactca gcagtttgac atctgaggac tctgccgtct attactgtat gggttattct      300
gattattggg gccaaggcac cactctcaca gtctcctcag cctcaacgaa gggcccatct      360
gtctttcccc tggccccctc ctccaagagc acctctgggg gcacagcggc cctgggctgc      420
ctggtcaagg actacttccc cgaaccggtg acggtgtcgt ggaactcagg cgccctgacc      480
agcggcgtgc acaccttccc ggctgtccta cagtcctcag gactctactc cctcagcagc      540
gtggtgaccg tgccctccag cagcttgggc acccagacct acatctgcaa cgtgaatcac      600
aagcccagca acaccaaggt ggacaagaaa gttgagccca aatcttgtga attcactcac      660
acatgcccac cgtgcccagc acctgaactc ctggggggac cgtcagtctt cctcttcccc      720
ccaaaaccca aggacaccct catgatctcc cggacccctg aggtcacatg cgtggtggtg      780
gacgtgagcc acgaagaccc tgaggtcaag ttcaactggt acgtggacgg cgtggaggtg      840
cataatgcca agacaaagcc gcgggaggag cagtacaaca gcacgtaccg tgtggtcagc      900
gtcctcaccg tcctgcacca ggactggctg aatggcaagg agtacaagtg caaggtctcc      960
aacaaagccc tcccagcccc catcgagaaa accatctcca aagccaaagg gcagccccga     1020
gaaccacagg tgtacaccct gcccccatcc cgggatgagc tgaccaagaa ccaggtcagc     1080
ctgacctgcc tggtcaaagg cttctatccc agcgacatcg ccgtggagtg ggagagcaat     1140
gggcagccgg agaacaacta caagaccacg cctcccgtgc tggactccga cggctccttc     1200
ttcctctaca gcaagctcac cgtggacaag agcaggtggc agcaggggaa cgtcttctca     1260
tgctccgtga tgcatgaggc tctgcacaac cactacacgc agaagagcct ctccctgtct     1320
cccgggaaa                                                             1329
```

<210> SEQ ID NO 6
<211> LENGTH: 443
<212> TYPE: PRT
<213> ORGANISM: Artificial Sequence
<220> FEATURE:
<223> OTHER INFORMATION: Amino acid sequence of the 3D3 antibody heavy
      chain

<400> SEQUENCE: 6

Glu Val Gln Leu Gln Gln Ser Val Ala Glu Leu Val Arg Pro Gly Ala
1               5                   10                  15

Ser Val Thr Leu Ser Cys Lys Ala Ser Gly Tyr Ile Phe Thr Asp Tyr
            20                  25                  30

Glu Ile His Trp Val Lys Gln Thr Pro Val His Gly Leu Glu Trp Ile
        35                  40                  45

Gly Val Ile Asp Pro Glu Thr Gly Asn Thr Ala Phe Asn Gln Lys Phe
    50                  55                  60

Lys Gly Lys Ala Thr Leu Thr Ala Asp Ile Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Met Gly Tyr Ser Asp Tyr Trp Gly Gln Gly Thr Thr Leu Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp

```
            130                 135                 140
Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Glu Phe Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 7
<211> LENGTH: 654
<212> TYPE: DNA
<213> ORGANISM: Artificial Sequence
<220> FEATURE:
<223> OTHER INFORMATION: Nucleotide sequence of the 3G10 antibody light
      chain

<400> SEQUENCE: 7
gatgttttga tgacccaaac tccacgctcc ctgtctgtca gtcttggaga tcaagcctcc      60
atctcttgta gatcgagtca gagccttttta catagtaatg aaacaccta tttagaatgg    120 tatttgcaga aaccaggcca gcctccaaag gtcctgatct acaaagtttc caaccgattt    180
tctggggtcc cagacaggtt cagtggcagt ggatcaggga cagatttcac actcaagatc    240
agcggagtgg aggctgagga tctgggagtt tattactgct ttcaaggttc acatgttcct    300
```

```
ctcacgttcg gtgctgggac caagctggag ctgaaagctg tggctgcacc atctgtcttc      360
atcttcccgc catctgatga gcagttgaaa tctggaactg cctctgttgt gtgcctgctg      420
aataacttct atcccagaga ggccaaagta cagtggaagg tggataacgc cctccaatcg      480
ggtaactccc aggagagtgt cacagagcag gacagcaagg acagcaccta cagcctcagc      540
agcaccctga cgctgagcaa agcagactac gagaaacaca agtctacgc ctgcgaagtc       600 acccatcagg gcctgagctc gcccgtcaca aagagcttca caggggaga gtgt             654
```

<210> SEQ ID NO 8
<211> LENGTH: 218
<212> TYPE: PRT
<213> ORGANISM: Artificial Sequence
<220> FEATURE:
<223> OTHER INFORMATION: Amino acid sequence of the 3G10 antibody light chain

<400> SEQUENCE: 8

```
Asp Val Leu Met Thr Gln Thr Pro Arg Ser Leu Ser Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Pro
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Ala Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 9
<211> LENGTH: 1335
<212> TYPE: DNA
<213> ORGANISM: Artificial Sequence
<220> FEATURE:
<223> OTHER INFORMATION: Nucleotide sequence of the 3G10 antibody heavy chain

<400> SEQUENCE: 9

```
gagatccagc tgcagcagtc tggacctgag ttggtgaagc ctggggcttc agtgaagata      60
tcctgtaagg cttctggata caccttcact gacaactaca tgaactgggt gaagcagagc      120
```

```
catggaaaga gccttgagtg gattggagat attaatcctt actatggtac tactacctac    180
aaccagaagt tcaagggcaa ggccacattg actgtagaca gtcctcccg cacagcctac     240 atggagctcc gcggcctgac atctgaggac tctgcagtct attactgtgc aagagatgac    300
tggtttgatt attggggcca agggactctg gtcactgtct ctgcagcctc aacgaagggc    360
ccatctgtct tccccctggc cccctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagaaagttg agcccaaatc ttgtgaattc    660
actcacacat gcccaccgtg cccagcacct gaactcctgg ggggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caaagggcag    1020
ccccgagaac cacaggtgta caccctgccc ccatcccggg atgagctgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctcccg ggaaa                                                     1335
```

<210> SEQ ID NO 10
<211> LENGTH: 445
<212> TYPE: PRT
<213> ORGANISM: Artificial Sequence
<220> FEATURE:
<223> OTHER INFORMATION: Amino acid sequence of the 3G10 antibody heavy chain

<400> SEQUENCE: 10

```
Glu Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Asn
            20                  25                  30

Tyr Met Asn Trp Val Lys Gln Ser His Gly Lys Ser Leu Glu Trp Ile
        35                  40                  45

Gly Asp Ile Asn Pro Tyr Tyr Gly Thr Thr Thr Tyr Asn Gln Lys Phe
    50                  55                  60

Lys Gly Lys Ala Thr Leu Thr Val Asp Lys Ser Ser Arg Thr Ala Tyr
65                  70                  75                  80

Met Glu Leu Arg Gly Leu Thr Ser Glu Asp Ser Ala Val Tyr Tyr Cys
                85                  90                  95

Ala Arg Asp Asp Trp Phe Asp Tyr Trp Gly Gln Gly Thr Leu Val Thr
            100                 105                 110

Val Ser Ala Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140
```

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Glu Phe Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 11
<211> LENGTH: 639
<212> TYPE: DNA
<213> ORGANISM: Artificial Sequence
<220> FEATURE:
<223> OTHER INFORMATION: Nucleotide sequence of the 3C4 antibody light
      chain

<400> SEQUENCE: 11
gacatcgtta tgtctcagtc tccatcttcc atgtatgcat ctctaggaga gagagtcact      60
atcacttgca aggcgagtca ggacattcat aacttttaa actggttcca gcagaaacca     120
ggaaaatctc caaagaccct gatctttcgt gcaaacagat tggtagatgg ggtcccatca    180
aggttcagtg gcagtggatc tgggcaagat tattctctca ccatcagcag cctggagttt    240
gaagatttgg gaatttattc ttgtctacag tatgatgaga ttccgctcac gttcggtgct    300
gggaccaagc tggagctgag agctgtggct gcaccatctg tcttcatctt cccgccatct    360

```
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                          639
```

```
<210> SEQ ID NO 12
<211> LENGTH: 213
<212> TYPE: PRT
<213> ORGANISM: Artificial Sequence
<220> FEATURE:
<223> OTHER INFORMATION: Amino acid sequence of the 3C4 antibody light
      chain

<400> SEQUENCE: 12
```

```
Asp Ile Val Met Ser Gln Ser Pro Ser Ser Met Tyr Ala Ser Leu Gly
1               5                   10                  15

Glu Arg Val Thr Ile Thr Cys Lys Ala Ser Gln Asp Ile His Asn Phe
            20                  25                  30

Leu Asn Trp Phe Gln Gln Lys Pro Gly Lys Ser Pro Lys Thr Leu Ile
        35                  40                  45

Phe Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Phe
65                  70                  75                  80

Glu Asp Leu Gly Ile Tyr Ser Cys Leu Gln Tyr Asp Glu Ile Pro Leu
                85                  90                  95

Thr Phe Gly Ala Gly Thr Lys Leu Glu Leu Arg Ala Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 13
<211> LENGTH: 1341
<212> TYPE: DNA
<213> ORGANISM: Artificial Sequence
<220> FEATURE:
<223> OTHER INFORMATION: Nucleotide sequence of the 3C4 antibody heavy
      chain

<400> SEQUENCE: 13
gaggtgcagc ttcaggagtc aggacctgac ctggtgaaac cttctcagtc actttcactc     60
acctgcactg tcactggctt ctccatcacc agtggttatg ctggcactg gatccggcag    120 tttccaggaa acaaactgga gtggatgggc tacataaact acgatggtca caatgactac    180
```

```
aacccatctc tcaaaagtcg aatctctatc actcaagaca catccaagaa ccagttcttc    240
ctgcagttga attctgtgac tactgaggac acagccacat attactgtgc aagcagttac    300
gacggcttat ttgcttactg gggccaaggg actctggtca ctgtctctgc agcctcaacg    360
aagggcccat ctgtctttcc cctggccccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660 gaattcactc acacatgccc accgtgccca gcacctgaac tcctgggggg accgtcagtc    720
ttcctcttcc cccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggatga gctgaccaag   1080
aaccaggtca gcctgacctg cctggtcaaa ggcttctatc cagcgacat cgccgtggag   1140 tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctcccgggaa a                                             1341

<210> SEQ ID NO 14
<211> LENGTH: 447
<212> TYPE: PRT
<213> ORGANISM: Artificial Sequence
<220> FEATURE:
<223> OTHER INFORMATION: Amino acid sequence of the 3C4 antibody heavy
      chain

<400> SEQUENCE: 14

Glu Val Gln Leu Gln Glu Ser Gly Pro Asp Leu Val Lys Pro Ser Gln
1               5                   10                  15

Ser Leu Ser Leu Thr Cys Thr Val Thr Gly Phe Ser Ile Thr Ser Gly
            20                  25                  30

Tyr Gly Trp His Trp Ile Arg Gln Phe Pro Gly Asn Lys Leu Glu Trp
        35                  40                  45

Met Gly Tyr Ile Asn Tyr Asp Gly His Asn Asp Tyr Asn Pro Ser Leu
    50                  55                  60

Lys Ser Arg Ile Ser Ile Thr Gln Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ser Ser Tyr Asp Gly Leu Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Glu Phe Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 15
<211> LENGTH: 339
<212> TYPE: DNA
<213> ORGANISM: Artificial Sequence
<220> FEATURE:
<223> OTHER INFORMATION: Nucleotide sequence of the 3D3 antibody light
      chain variable region

<400> SEQUENCE: 15
gacattgtga tgacccagtc tccatcctcc ctggctgtgt caataggaca gaaggtcact     60
atgaactgca gtccagtca gagccttta aatagtaact ttcaaaagaa cttttttggcc    120 tggtaccagc agaaaccagg ccagtctcct aaacttctga tatactttgc atccactcgg   180
gaatctagta tccctgatcg cttcataggc agtggatctg gacagattt cactcttacc    240 atcagcagtg tgcaggctga agacctggca gattacttct gtcagcaaca ttatagcact   300
ccgctcacgt tcggtgctgg gaccaagctg gagctgaaa                          339

<210> SEQ ID NO 16

-continued

```
<211> LENGTH: 113
<212> TYPE: PRT
<213> ORGANISM: Artificial Sequence
<220> FEATURE:
<223> OTHER INFORMATION: Amino acid sequence of the 3D3 antibody light
      chain variable region

<400> SEQUENCE: 16

Asp Ile Val Met Thr Gln Ser Pro Ser Ser Leu Ala Val Ser Ile Gly
1               5                   10                  15

Gln Lys Val Thr Met Asn Cys Lys Ser Ser Gln Ser Leu Leu Asn Ser
            20                  25                  30

Asn Phe Gln Lys Asn Phe Leu Ala Trp Tyr Gln Lys Pro Gly Gln
        35                  40                  45

Ser Pro Lys Leu Leu Ile Tyr Phe Ala Ser Thr Arg Glu Ser Ser Ile
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys

<210> SEQ ID NO 17
<211> LENGTH: 339
<212> TYPE: DNA
<213> ORGANISM: Artificial Sequence
<220> FEATURE:
<223> OTHER INFORMATION: Nucleotide sequence of the 3D3 antibody heavy
      chain variable region

<400> SEQUENCE: 17
gaggttcagc tgcagcagtc tgtagctgag ctggtgaggc ctggggcttc agtgacgctg      60
tcctgcaagg cttcgggcta catatttact gactatgaga tacactgggt gaagcagact     120
cctgtgcatg gcctggaatg gattggggtt attgatcctg aaactggtaa tactgccttc     180
aatcagaagt tcaagggcaa ggccacactg actgcagaca tatcctccag cacagcctac     240
atggaactca gcagtttgac atctgaggac tctgccgtct attactgtat gggttattct     300
gattattggg gccaaggcac cactctcaca gtctcctca                            339

<210> SEQ ID NO 18
<211> LENGTH: 113
<212> TYPE: PRT
<213> ORGANISM: Artificial Sequence
<220> FEATURE:
<223> OTHER INFORMATION: Amino acid sequence of the 3D3 antibody heavy
      chain variable region

<400> SEQUENCE: 18

Glu Val Gln Leu Gln Gln Ser Val Ala Glu Leu Val Arg Pro Gly Ala
1               5                   10                  15

Ser Val Thr Leu Ser Cys Lys Ala Ser Gly Tyr Ile Phe Thr Asp Tyr
            20                  25                  30

Glu Ile His Trp Val Lys Gln Thr Pro Val His Gly Leu Glu Trp Ile
        35                  40                  45

Gly Val Ile Asp Pro Glu Thr Gly Asn Thr Ala Phe Asn Gln Lys Phe
    50                  55                  60

Lys Gly Lys Ala Thr Leu Thr Ala Asp Ile Ser Ser Ser Thr Ala Tyr
65                  70                  75                  80
```

```
Met Glu Leu Ser Ser Leu Thr Ser Glu Asp Ser Ala Val Tyr Tyr Cys
                85                  90                  95

Met Gly Tyr Ser Asp Tyr Trp Gly Gln Gly Thr Thr Leu Thr Val Ser
            100                 105                 110

Ser

<210> SEQ ID NO 19
<211> LENGTH: 336
<212> TYPE: DNA
<213> ORGANISM: Artificial Sequence
<220> FEATURE:
<223> OTHER INFORMATION: Nucleotide sequence of the 3G10 antibody light
      chain variable region

<400> SEQUENCE: 19
gatgttttga tgacccaaac tccacgctcc ctgtctgtca gtcttggaga tcaagcctcc     60
atctcttgta gatcgagtca gagccttta catagtaatg aaacacccta tttagaatgg    120
tatttgcaga aaccaggcca gcctccaaag gtcctgatct acaaagtttc caaccgattt    180
tctggggtcc cagacaggtt cagtggcagt ggatcaggga cagatttcac actcaagatc    240
agcggagtgg aggctgagga tctgggagtt tattactgct ttcaaggttc acatgttcct    300
ctcacgttcg gtgctgggac caagctggag ctgaaa                              336

<210> SEQ ID NO 20
<211> LENGTH: 112
<212> TYPE: PRT
<213> ORGANISM: Artificial Sequence
<220> FEATURE:
<223> OTHER INFORMATION: Amino acid sequence of the 3G10 antibody light
      chain variable region

<400> SEQUENCE: 20

Asp Val Leu Met Thr Gln Thr Pro Arg Ser Leu Ser Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Pro
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 21
<211> LENGTH: 345
<212> TYPE: DNA
<213> ORGANISM: Artificial Sequence
<220> FEATURE:
<223> OTHER INFORMATION: Nucleotide sequence of the 3G10 antibody heavy
      chain variable region

<400> SEQUENCE: 21
gagatccagc tgcagcagtc tggacctgag ttggtgaagc ctggggcttc agtgaagata     60
tcctgtaagg cttctggata caccttcact gacaactaca tgaactgggt gaagcagagc    120
catggaaaga gccttgagtg gattggagat attaatcctt actatggtac tactacctac    180
```

```
aaccagaagt tcaagggcaa ggccacattg actgtagaca agtcctcccg cacagcctac    240
atggagctcc gcggcctgac atctgaggac tctgcagtct attactgtgc aagagatgac    300
tggtttgatt attggggcca agggactctg gtcactgtct ctgca                   345
```

<210> SEQ ID NO 22
<211> LENGTH: 115
<212> TYPE: PRT
<213> ORGANISM: Artificial Sequence
<220> FEATURE:
<223> OTHER INFORMATION: Amino acid sequence of the 3G10 antibody heavy
      chain variable region

<400> SEQUENCE: 22

```
Glu Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Asn
            20                  25                  30

Tyr Met Asn Trp Val Lys Gln Ser His Gly Lys Ser Leu Glu Trp Ile
        35                  40                  45

Gly Asp Ile Asn Pro Tyr Tyr Gly Thr Thr Tyr Asn Gln Lys Phe
    50                  55                  60

Lys Gly Lys Ala Thr Leu Thr Val Asp Lys Ser Ser Arg Thr Ala Tyr
65                  70                  75                  80

Met Glu Leu Arg Gly Leu Thr Ser Glu Asp Ser Ala Val Tyr Tyr Cys
                85                  90                  95

Ala Arg Asp Asp Trp Phe Asp Tyr Trp Gly Gln Gly Thr Leu Val Thr
            100                 105                 110

Val Ser Ala
        115
```

<210> SEQ ID NO 23
<211> LENGTH: 321
<212> TYPE: DNA
<213> ORGANISM: Artificial Sequence
<220> FEATURE:
<223> OTHER INFORMATION: Nucleotide sequence of the 3C4 antibody light
      chain variable region

<400> SEQUENCE: 23

```
gacatcgtta tgtctcagtc tccatcttcc atgtatgcat ctctaggaga gagagtcact    60
atcacttgca aggcgagtca ggacattcat aacttttaa actggttcca gcagaaacca    120
ggaaaatctc caaagaccct gatctttcgt gcaaacagat tggtagatgg ggtcccatca    180
aggttcagtg gcagtggatc tgggcaagat tattctctca ccatcagcag cctggagttt    240
gaagatttgg gaatttattc ttgtctacag tatgatgaga ttccgctcac gttcggtgct    300
gggaccaagc tggagctgag a                                             321
```

<210> SEQ ID NO 24
<211> LENGTH: 107
<212> TYPE: PRT
<213> ORGANISM: Artificial Sequence
<220> FEATURE:
<223> OTHER INFORMATION: Amino acid sequence of the 3C4 antibody light
      chain variable region

<400> SEQUENCE: 24

```
Asp Ile Val Met Ser Gln Ser Pro Ser Ser Met Tyr Ala Ser Leu Gly
1               5                   10                  15

Glu Arg Val Thr Ile Thr Cys Lys Ala Ser Gln Asp Ile His Asn Phe
```

|       |       |       | 20    |       |       |       | 25    |       |       |       | 30    |       |
|---|---|---|---|---|---|---|---|---|---|---|---|---|

Leu Asn Trp Phe Gln Gln Lys Pro Gly Lys Ser Pro Lys Thr Leu Ile
              35                        40                        45

Phe Arg Ala Asn Arg Leu Val Asp Gly Val Pro Ser Arg Phe Ser Gly
 50                       55                        60

Ser Gly Ser Gly Gln Asp Tyr Ser Leu Thr Ile Ser Ser Leu Glu Phe
65                     70                       75                       80

Glu Asp Leu Gly Ile Tyr Ser Cys Leu Gln Tyr Asp Glu Ile Pro Leu
              85                        90                        95

Thr Phe Gly Ala Gly Thr Lys Leu Glu Leu Arg
            100                    105

<210> SEQ ID NO 25
<211> LENGTH: 351
<212> TYPE: DNA
<213> ORGANISM: Artificial Sequence
<220> FEATURE:
<223> OTHER INFORMATION: Nucleotide sequence of the 3C4 antibody heavy
     chain variable region

<400> SEQUENCE: 25
gaggtgcagc ttcaggagtc aggacctgac ctggtgaaac cttctcagtc actttcactc    60
acctgcactg tcactggctt ctccatcacc agtggttatg ctggcactg gatccggcag   120 tttccaggaa acaaactgga gtggatgggc tacataaact acgatggtca caatgactac   180
aacccatctc tcaaaagtcg aatctctatc actcaagaca catccaagaa ccagttcttc   240
ctgcagttga attctgtgac tactgaggac acagccacat attactgtgc aagcagttac   300
gacggcttat tgcttactg gggccaaggg actctggtca ctgtctctgc a   351

<210> SEQ ID NO 26
<211> LENGTH: 117
<212> TYPE: PRT
<213> ORGANISM: Artificial Sequence
<220> FEATURE:
<223> OTHER INFORMATION: Amino acid sequence of the 3C4 antibody heavy
     chain variable region

<400> SEQUENCE: 26

Glu Val Gln Leu Gln Glu Ser Gly Pro Asp Leu Val Lys Pro Ser Gln
1                  5                       10                       15

Ser Leu Ser Leu Thr Cys Thr Val Thr Gly Phe Ser Ile Thr Ser Gly
              20                       25                       30

Tyr Gly Trp His Trp Ile Arg Gln Phe Pro Gly Asn Lys Leu Glu Trp
              35                       40                       45

Met Gly Tyr Ile Asn Tyr Asp Gly His Asn Asp Tyr Asn Pro Ser Leu
 50                      55                        60

Lys Ser Arg Ile Ser Ile Thr Gln Asp Thr Ser Lys Asn Gln Phe Phe
65                     70                       75                       80

Leu Gln Leu Asn Ser Val Thr Thr Glu Asp Thr Ala Thr Tyr Tyr Cys
              85                        90                        95

Ala Ser Ser Tyr Asp Gly Leu Phe Ala Tyr Trp Gly Gln Gly Thr Leu
            100                      105                     110

Val Thr Val Ser Ala
       115

<210> SEQ ID NO 27
<211> LENGTH: 17
<212> TYPE: PRT
<213> ORGANISM: Artificial Sequence

```
<220> FEATURE:
<223> OTHER INFORMATION: Amino acid sequence of the 3D3 light chain CDR1

<400> SEQUENCE: 27

Lys Ser Ser Gln Ser Leu Leu Asn Ser Asn Phe Gln Lys Asn Phe Leu
1               5                   10                  15

Ala

<210> SEQ ID NO 28
<211> LENGTH: 7
<212> TYPE: PRT
<213> ORGANISM: Artificial Sequence
<220> FEATURE:
<223> OTHER INFORMATION: Amino acid sequence of the 3D3 light chain CDR2

<400> SEQUENCE: 28

Phe Ala Ser Thr Arg Glu Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Amino acid sequence of the 3D3 light chain CDR3

<400> SEQUENCE: 29

Gln Gln His Tyr Ser Thr Pro Leu Thr
1               5

<210> SEQ ID NO 30
<211> LENGTH: 10
<212> TYPE: PRT
<213> ORGANISM: Artificial Sequence
<220> FEATURE:
<223> OTHER INFORMATION: Amino acid sequence of the 3D3 heavy chain CDR1

<400> SEQUENCE: 30

Gly Tyr Ile Phe Thr Asp Tyr Glu Ile His
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Amino acid sequence of the 3D3 heavy chain CDR2

<400> SEQUENCE: 31

Val Ile Asp Pro Glu Thr Gly Asn Thr Ala
1               5                   10

<210> SEQ ID NO 32
<211> LENGTH: 6
<212> TYPE: PRT
<213> ORGANISM: Artificial Sequence
<220> FEATURE:
<223> OTHER INFORMATION: Amino acid sequence of the 3D3 heavy chain CDR3

<400> SEQUENCE: 32

Met Gly Tyr Ser Asp Tyr
1               5

<210> SEQ ID NO 33
<211> LENGTH: 16
<212> TYPE: PRT
<213> ORGANISM: Artificial Sequence
```

```
<220> FEATURE:
<223> OTHER INFORMATION: Amino acid sequence of the 3G10 light chain CDR1

<400> SEQUENCE: 33

Arg Ser Ser Gln Ser Leu Leu His Ser Asn Gly Asn Thr Tyr Leu Glu
1               5                   10                  15

<210> SEQ ID NO 34
<211> LENGTH: 7
<212> TYPE: PRT
<213> ORGANISM: Artificial Sequence
<220> FEATURE:
<223> OTHER INFORMATION: Amino acid sequence of the 3G10 light chain CDR2

<400> SEQUENCE: 34

Lys Val Ser Asn Arg Phe Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Amino acid sequence of the 3G10 light chain CDR3

<400> SEQUENCE: 35

Phe Gln Gly Ser His Val Pro Leu Thr
1               5

<210> SEQ ID NO 36
<211> LENGTH: 10
<212> TYPE: PRT
<213> ORGANISM: Artificial Sequence
<220> FEATURE:
<223> OTHER INFORMATION: Amino acid sequence of the 3G10 heavy chain CDR1

<400> SEQUENCE: 36

Gly Tyr Thr Phe Thr Asp Asn Tyr Met Asn
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Amino acid sequence of the 3G10 heavy chain CDR2

<400> SEQUENCE: 37

Asp Ile Asn Pro Tyr Tyr Gly Thr Thr Thr
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Amino acid sequence of the 3G10 heavy chain CDR3

<400> SEQUENCE: 38

Ala Arg Asp Asp Trp Phe Asp Tyr
1               5

<210> SEQ ID NO 39
<211> LENGTH: 11
<212> TYPE: PRT
<213> ORGANISM: Artificial Sequence
<220> FEATURE:
<223> OTHER INFORMATION: Amino acid sequence of the 3C4 light chain CDR1
```

```
<400> SEQUENCE: 39

Lys Ala Ser Gln Asp Ile His Asn Phe Leu Asn
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Amino acid sequence of the 3C4 light chain CDR2

<400> SEQUENCE: 40

Arg Ala Asn Arg Leu Val Asp
1               5

<210> SEQ ID NO 41
<211> LENGTH: 9
<212> TYPE: PRT
<213> ORGANISM: Artificial Sequence
<220> FEATURE:
<223> OTHER INFORMATION: Amino acid sequence of the 3C4 light chain CDR3

<400> SEQUENCE: 41

Leu Gln Tyr Asp Glu Ile Pro Leu Thr
1               5

<210> SEQ ID NO 42
<211> LENGTH: 11
<212> TYPE: PRT
<213> ORGANISM: Artificial Sequence
<220> FEATURE:
<223> OTHER INFORMATION: Amino acid sequence of the 3C4 heavy chain CDR1

<400> SEQUENCE: 42

Gly Phe Ser Ile Thr Ser Gly Tyr Gly Trp His
1               5                   10

<210> SEQ ID NO 43
<211> LENGTH: 9
<212> TYPE: PRT
<213> ORGANISM: Artificial Sequence
<220> FEATURE:
<223> OTHER INFORMATION: Amino acid sequence of the 3C4 heavy chain CDR2

<400> SEQUENCE: 43

Tyr Ile Asn Tyr Asp Gly His Asn Asp
1               5

<210> SEQ ID NO 44
<211> LENGTH: 10
<212> TYPE: PRT
<213> ORGANISM: Artificial Sequence
<220> FEATURE:
<223> OTHER INFORMATION: Amino acid sequence of the 3C4 heavy chain CDR3

<400> SEQUENCE: 44

Ala Ser Ser Tyr Asp Gly Leu Phe Ala Tyr
1               5                   10

<210> SEQ ID NO 45
<211> LENGTH: 24
<212> TYPE: DNA
<213> ORGANISM: Artificial Sequence
<220> FEATURE:
<223> OTHER INFORMATION: Primer to amplify KAAG1 mRNA sequence

<400> SEQUENCE: 45
```

```
gaggggcatc aatcacaccg agaa                                              24
```

<210> SEQ ID NO 46
<211> LENGTH: 22
<212> TYPE: DNA
<213> ORGANISM: Artificial Sequence
<220> FEATURE:
<223> OTHER INFORMATION: Primer to amplify KAAG1 mRNA sequence

<400> SEQUENCE: 46

```
ccccaccgcc cacccattta gg                                                22
```

<210> SEQ ID NO 47
<211> LENGTH: 26
<212> TYPE: DNA
<213> ORGANISM: Artificial Sequence
<220> FEATURE:
<223> OTHER INFORMATION: Primer to amplify GAPDH gene

<400> SEQUENCE: 47

```
tgaaggtcgg agtcaacgga tttggt                                            26
```

<210> SEQ ID NO 48
<211> LENGTH: 24
<212> TYPE: DNA
<213> ORGANISM: Artificial Sequence
<220> FEATURE:
<223> OTHER INFORMATION: Primer to amplify GAPDH gene

<400> SEQUENCE: 48

```
catgtgggcc atgaggtcca ccac                                              24
```

<210> SEQ ID NO 49
<211> LENGTH: 19
<212> TYPE: DNA
<213> ORGANISM: Artificial Sequence
<220> FEATURE:
<223> OTHER INFORMATION: 19-mer used to generate KAAG1-specific shRNA

<400> SEQUENCE: 49

```
ggcctccagc cacgtaatt                                                    19
```

<210> SEQ ID NO 50
<211> LENGTH: 19
<212> TYPE: DNA
<213> ORGANISM: Artificial Sequence
<220> FEATURE:
<223> OTHER INFORMATION: 19-mer used to generate KAAG1-specific shRNA

<400> SEQUENCE: 50

```
ggcgctgctg ccgctcatc                                                    19
```

<210> SEQ ID NO 51
<211> LENGTH: 4455
<212> TYPE: DNA
<213> ORGANISM: Artificial Sequence
<220> FEATURE:
<223> OTHER INFORMATION: pSilencer 2.0 plasmid

<400> SEQUENCE: 51

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcgggctgg cttaactatg cggcatcaga gcagattgta ctgagagtgc       180
accatatgcg gtgtgaaata ccgcacagat gcgtaaggag aaaataccgc atcaggcgcc       240
```

```
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccaa gcttttccaa aaaactaccg    420
ttgttatagg tgtctcttga cacctataa caacggtagt ggatcccgcg tccttt ccac    480 aagatatata aacccaagaa atcgaaatac tttcaagtta cggtaagcat atgatagtcc    540
attttaaaac ataattttaa aactgcaaac tacccaagaa attattactt tctacgtcac    600
gtattttgta ctaatatctt tgtgtttaca gtcaaattaa ttctaattat ctctctaaca    660
gccttgtatc gtatatgcaa atatgaagga atcatgggaa ataggccctc ttcctgcccg    720
accttggcgc gcgctcggcg cgcggtcacg ctccgtcacg tggtgcgttt tgcctgcgcg    780
tctttccact ggggaattca tgcttctcct cccttttagtg agggtaattc tctctctctc    840
cctatagtga gtcgtattaa ttccttctct tctatagtgt cacctaaatc gttgcaattc    900
gtaatcatgt catagctgtt tcctgtgtga aattgttatc cgctcacaat tccacacaac    960
atacgagccg gaagcataaa gtgtaaagcc tggggtgcct aatgagtgag ctaactcaca   1020
ttaattgcgt tgcgctcact gcccgctttc cagtcgggaa acctgtcgtg ccagctgcat   1080
taatgaatcg gccaacgcgc ggggagaggc ggtttgcgta ttgggcgctc ttccgcttcc   1140
tcgctcactg actcgctgcg ctcggtcgtt cggctgcggc gagcggtatc agctcactca   1200
aaggcggtaa tacggttatc cacagaatca ggggataacg caggaaagaa catgtgagca   1260
aaaggccagc aaaaggccag gaaccgtaaa aaggccgcgt tgctggcgtt tttccatagg   1320
ctccgccccc ctgacgagca tcacaaaaat cgacgctcaa gtcagaggtg gcgaaacccg   1380
acaggactat aaagatacca ggcgtttccc cctggaagct ccctcgtgcg ctctcctgtt   1440
ccgaccctgc cgcttaccgg atacctgtcc gcctttctcc cttcgggaag cgtggcgctt   1500
tctcatagct cacgctgtag gtatctcagt tcggtgtagg tcgttcgctc caagctgggc   1560
tgtgtgcacg aaccccccgt tcagcccgac cgctgcgcct tatccggtaa ctatcgtctt   1620
gagtccaacc cggtaagaca cgacttatcg ccactggcag cagccactgg taacaggatt   1680
agcagagcga ggtatgtagg cggtgctaca gagttcttga agtggtggcc taactacggc   1740
tacactagaa gaacagtatt tggtatctgc gctctgctga agccagttac cttcggaaaa   1800
agagttggta gctcttgatc cggcaaaaaa accaccgctg gtagcggtgg ttttttt gtt   1860 tgcaagcagc agattacgcg cagaaaaaaa ggatctcaag aagatccttt gatctttt ct   1920 acggggtctg acgctcagtg gaacgaaaac tcacgttaag ggattttggt catgagatta   1980
tcaaaaagga tcttcaccta gatccttt ta aattaaaaat gaagttttaa atcaatctaa   2040
agtatatatg agtaaacttg gtctgacagt taccaatgct taatcagtga ggcacctatc   2100
tcagcgatct gtctatttcg ttcatccata gttgcctgac tccccgtcgt gtagataact   2160
acgatacggg agggcttacc atctggcccc agtgctgcaa tgataccgcg agacccacgc   2220
tcaccggctc cagatttatc agcaataaac cagccagccg gaagggccga gcgcagaagt   2280
ggtcctgcaa ctttatccgc ctccatccag tctattaatt gttgccggga agctagagta   2340
agtagttcgc cagttaatag tttgcgcaac gttgttgcca ttgctacagg catcgtggtg   2400
tcacgctcgt cgtttggtat ggcttcattc agctccggtt cccaacgatc aaggcgagtt   2460
acatgatccc ccatgttgtg caaaaaagcg gttagctcct tcggtcctcc gatcgttgtc   2520
agaagtaagt tggccgcagt gttatcactc atggttatgg cagcactgca taattctctt   2580
actgtcatgc catccgtaag atgcttttct gtgactggtg agtactcaac caagtcattc   2640
```

```
tgagaatagt gtatgcggcg accgagttgc tcttgcccgg cgtcaatacg ggataatacc    2700
gcgccacata gcagaacttt aaaagtgctc atcattggaa aacgttcttc ggggcgaaaa    2760
ctctcaagga tcttaccgct gttgagatcc agttcgatgt aacccactcg tgcacccaac    2820
tgatcttcag catcttttac tttcaccagc gtttctgggt gagcaaaaac aggaaggcaa    2880
aatgccgcaa aaagggaat aagggcgaca cggaaatgtt gaatactcat actcttcctt     2940
tttcaatatt attgaagcat ttatcagggt tattgtctca tgagcggata catatttgaa    3000
tgtatttaga aaataaaca aataggggtt ccgcgcacat ttccccgaaa agtgccacct     3060
attggtgtgg aaagtcccca ggctccccag caggcagaag tatgcaaagc atgcatctca    3120
attagtcagc aaccaggtgt ggaaagtccc caggctcccc agcaggcaga agtatgcaaa    3180
gcatgcatct caattagtca gcaaccatag tcccgcccct aactccgccc atcccgcccc    3240
taactccgcc cagttccgcc cattctccgc cccatggctg actaattttt tttatttatg    3300
cagaggccga ggccgcctcg gcctctgagc tattccagaa gtagtgagga ggcttttttg    3360
gaggcctagg cttttgcaaa aagctagctt gcatgcctgc aggtcggccg ccacgaccgg    3420
tgccgccacc atcccctgac ccacgcccct gacccctcac aaggagacga ccttccatga    3480
ccgagtacaa gcccacggtg cgcctcgcca cccgcgacga cgtccccggg gccgtacgca    3540
ccctcgccgc cgcgttcgcc gactaccccg ccacgcgcca ccgtcgac ccggaccgcc     3600 acatcgagcg ggtcaccgag ctgcaagaac tcttcctcac gcgcgtcggg ctcgacatcg    3660
gcaaggtgtg ggtcgcggac gacggcgccg cggtggcggt ctggaccacg ccggagagcg    3720
tcgaagcggg ggcggtgttc gccgagatcg gcccgcgcat ggccgagttg agcggttccc    3780
ggctggccgc gcagcaacag atggaaggcc tcctggcgcc gcaccggccc aaggagcccg    3840
cgtggttcct ggccaccgtc ggcgtctcgc ccgaccacca gggcaagggt ctgggcagcg    3900
ccgtcgtgct cccccggagtg gaggcggccg agcgcgccgg ggtgcccgcc ttcctggaga    3960
cctccgcgcc ccgcaacctc cccttctacg agcggctcgg cttcaccgtc accgccgacg    4020
tcgaggtgcc cgaaggaccg cgcacctggt gcatgacccg caagcccggt gcctgacgcc    4080
cgccccacga cccgcagcgc ccgaccgaaa ggagcgcacg accccatggc tccgaccgaa    4140
gccaccgggg gcgccccgc cgaccccgca cccgccccg aggcccaccg actctagagg       4200
atcataatca gccataccac atttgtagag gttttacttg ctttaaaaaa cctcccacac    4260
ctccccctga acctgaaaca taaaatgaat gcaattgttg ttgttaactt gtttattgca    4320
gcttataatg gttacaaata aagcaatagc atcacaaatt tcacaaataa agcatttttt    4380
tcactgcaat ctaagaaacc attattatca tgacattaac ctataaaat aggcgtatca     4440 cgaggccctt tcgtc                                                     4455
```

<210> SEQ ID NO 52
<211> LENGTH: 33
<212> TYPE: DNA
<213> ORGANISM: Artificial Sequence
<220> FEATURE:
<223> OTHER INFORMATION: forward primer containing BamHI site to amplify
      KAAG1 cDNA

<400> SEQUENCE: 52
gtaagcggat ccatggatga cgacgcggcg ccc                                33

<210> SEQ ID NO 53
<211> LENGTH: 33
<212> TYPE: DNA

```
<213> ORGANISM: Artificial Sequence
<220> FEATURE:
<223> OTHER INFORMATION: reverse primer containing HindIII site to
      amplify KAAG1 cDNA

<400> SEQUENCE: 53
gtaagcaagc ttcttctctt tcacctgtgg att                                    33

<210> SEQ ID NO 54
<211> LENGTH: 5138
<212> TYPE: DNA
<213> ORGANISM: Artificial Sequence
<220> FEATURE:
<223> OTHER INFORMATION: pYD5 vector

<400> SEQUENCE: 54
gtacatttat attggctcat gtccaatatg accgccatgt tgacattgat tattgactag       60
ttattaatag taatcaatta cggggtcatt agttcatagc ccatatatgg agttccgcgt      120
tacataactt acggtaaatg gcccgcctgg ctgaccgccc aacgacccccc gcccattgac     180 gtcaataatg acgtatgttc ccatagtaac gccaataggg actttccatt gacgtcaatg      240
ggtggagtat ttacggtaaa ctgcccactt ggcagtacat caagtgtatc atatgccaag      300
tccgccccct attgacgtca atgacggtaa atggcccgcc tggcattatg cccagtacat      360
gaccttacgg gactttccta cttggcagta catctacgta ttagtcatcg ctattaccat      420
ggtgatgcgg ttttggcagt acaccaatgg gcgtggatag cggtttgact cacggggatt      480
tccaagtctc cacccccattg acgtcaatgg gagtttgttt tggcaccaaa atcaacggga     540 cttttccaaaa tgtcgtaata accccgcccc gttgacgcaa atgggcggta ggcgtgtacg     600
gtgggaggtc tatataagca gagctcgttt agtgaaccgt cagatcctca ctctcttccg      660
catcgctgtc tgcgagggcc agctgttggg ctcgcggttg aggacaaaact cttcgcggtc    720 tttccagtac tcttggatcg aaacccgtc ggcctccgaa cggtactccg ccaccgaggg      780
acctgagcca gtccgcatcg accggatcgg aaaacctctc gagaaaggcg tctaaccagt     840
cacagtcgca aggtaggctg agcaccgtgg cgggcggcag cgggtggcgg tcggggttgt      900
ttctggcgga ggtgctgctg atgatgtaat taaagtaggc ggtcttgagc cggcggatgg      960
tcgaggtgag gtgtggcagg cttgagatcc agctgttggg gtgagtactc cctctcaaaa     1020
gcgggcatga cttctgcgct aagattgtca gtttccaaaa acgaggagga tttgatattc     1080
acctggcccg atctgccat acacttgagt gacaatgaca tccactttgc ctttctctcc       1140
acaggtgtcc actcccaggt ccaagtttgc cgccaccatg gagacagaca cactcctgct     1200
atgggtactg ctgctctggg ttccaggttc cactggcgcc ggatcaactc acacatgccc     1260
accgtgccca gcacctgaac tcctgggggg accgtcagtc ttcctcttcc ccccaaaacc     1320
caaggacacc ctcatgatct cccggacccc tgaggtcaca tgcgtggtgg tggacgtgag      1380
ccacgaagac cctgaggtca agttcaactg gtacgtggac ggcgtggagg tgcataatgc     1440
caagacaaag ccgcgggagg agcagtacaa cagcacgtac cgtgtggtca gcgtcctcac     1500
cgtcctgcac caggactggc tgaatggcaa ggagtacaag tgcaaggtct ccaacaaagc     1560
cctcccagcc cccatcgaga aaaccatctc caaagccaaa gggcagcccc gagaaccaca     1620
ggtgtacacc ctgcccccat cccgggatga gctgaccaag aaccaggtca gcctgacctg     1680
cctggtcaaa ggcttctatc ccagcgacat cgccgtggag tgggagagca atgggcagcc    1740
ggagaacaac tacaagacca cgcctcccgt gttggactcc gacggctcct tcttcctcta     1800
cagcaagctc accgtggaca agagcaggtg gcagcagggg aacgtcttct catgctccgt     1860
```

```
gatgcatgag gctctgcaca accactacac gcagaagagc ctctccctgt ctcccgggaa    1920
agctagcgga gccggaagca caaccgaaaa cctgtatttt cagggcggat ccgaattcaa    1980
gcttgatatc tgatccccg acctcgacct ctggctaata aaggaaattt attttcattg     2040
caatagtgtg ttggaatttt ttgtgtctct cactcggaag gacatatggg agggcaaatc    2100
atttggtcga gatccctcgg agatctctag ctagagcccc gccgccggac gaactaaacc    2160
tgactacggc atctctgccc cttcttcgcg gggcagtgca tgtaatccct tcagttggtt    2220
ggtacaactt gccaactgaa ccctaaacgg gtagcatatg cttcccgggt agtagtatat    2280
actatccaga ctaaccctaa ttcaatagca tatgttaccc aacgggaagc atatgctatc    2340
gaattagggt tagtaaaagg gtcctaagga acagcgatgt aggtgggcgg gccaagatag    2400
gggcgcgatt gctgcgatct ggaggacaaa ttacacacac ttgcgcctga gcgccaagca    2460
cagggttgtt ggtcctcata ttcacgaggt cgctgagagc acggtgggct aatgttgcca    2520
tgggtagcat atactaccca aatatctgga tagcatatgc tatcctaatc tatatctggg    2580
tagcataggc tatcctaatc tatatctggg tagcatatgc tatcctaatc tatatctggg    2640
tagtatatgc tatcctaatt tatatctggg tagcataggc tatcctaatc tatatctggg    2700
tagcatatgc tatcctaatc tatatctggg tagtatatgc tatcctaatc tgtatccggg    2760
tagcatatgc tatcctaata gagattaggg tagtatatgc tatcctaatt tatatctggg    2820
tagcatatac tacccaaata tctggatagc atatgctatc ctaatctata tctgggtagc    2880
atatgctatc ctaatctata tctgggtagc ataggctatc ctaatctata tctgggtagc    2940
atatgctatc ctaatctata tctgggtagt atatgctatc ctaatttata tctgggtagc    3000
ataggctatc ctaatctata tctgggtagc atatgctatc ctaatctata tctgggtagt    3060
atatgctatc ctaatctgta tccgggtagc atatgctatc ctcacgatga taagctgtca    3120
aacatgagaa ttaattcttg aagacgaaag ggcctcgtga tacgcctatt tttataggtt    3180
aatgtcatga taataatggt ttcttagacg tcaggtggca cttttcgggg aaatgtgcgc    3240 ggaacccta tttgtttatt tttctaaata cattcaaata tgtatccgct catgagacaa     3300
taaccctgat aaatgcttca ataatattga aaaggaaga gtatgagtat tcaacatttc     3360
cgtgtcgccc ttattccctt ttttgcggca ttttgccttc ctgttttttgc tcacccagaa   3420 acgctggtga agtaaaaga tgctgaagat cagttgggtg cacgagtggg ttacatcgaa     3480
ctggatctca acagcggtaa gatccttgag agttttcgcc ccgaagaacg ttttccaatg    3540
atgagcactt ttaaagttct gctatgtggc gcggtattat cccgtgttga cgccgggcaa    3600
gagcaactcg gtcgccgcat acactattct cagaatgact tggttgagta ctcaccagtc    3660
acagaaaagc atcttacgga tggcatgaca gtaagagaat tatgcagtgc tgccataacc    3720
atgagtgata acactgcggc caacttactt ctgacaacga tcggaggacc gaaggagcta    3780
accgcttttt tgcacaacat ggggatcat gtaactcgcc ttgatcgttg ggaaccggag     3840
ctgaatgaag ccataccaaa cgacgagcgt gacaccacga tgcctgcagc aatggcaaca    3900
acgttgcgca aactattaac tggcgaacta cttactctag cttcccggca acaattaata    3960
gactggatgg aggcggataa agttgcagga ccacttctgc gctcggccct tccggctggc    4020
tggtttattg ctgataaatc tggagccggt gagcgtgggt ctcgcggtat cattgcagca    4080
ctggggccag atggtaagcc ctcccgtatc gtagttatct acacgacggg gagtcaggca    4140
actatggatg aacgaaatag acagatcgct gagataggtg cctcactgat taagcattgg    4200
taactgtcag accaagttta ctcatatata ctttagattg atttaaaact tcattttta    4260
```

```
tttaaaagga tctaggtgaa gatccttttt gataatctca tgaccaaaat cccttaacgt    4320
gagttttcgt tccactgagc gtcagacccc gtagaaaaga tcaaaggatc ttcttgagat    4380 ccttttttc  tgcgcgtaat ctgctgcttg caaacaaaaa aaccaccgct accagcggtg    4440
gtttgtttgc cggatcaaga gctaccaact ctttttccga aggtaactgg cttcagcaga    4500
gcgcagatac caaatactgt ccttctagtg tagccgtagt taggccacca cttcaagaac    4560
tctgtagcac cgcctacata cctcgctctg ctaatcctgt taccagtggc tgctgccagt    4620
ggcgataagt cgtgtcttac cgggttggac tcaagacgat agttaccgga taaggcgcag    4680
cggtcgggct gaacggggg  ttcgtgcaca cagcccagct tggagcgaac gacctacacc    4740
gaactgagat acctacagcg tgagcattga gaaagcgcca cgcttcccga agggagaaag    4800
gcggacaggt atccggtaag cggcagggtc ggaacaggag agcgcacgag ggagcttcca    4860
gggggaaacg cctggtatct ttatagtcct gtcgggtttc gccacctctg acttgagcgt    4920
cgatttttgt gatgctcgtc aggggggcgg agcctatgga aaaacgccag caacgcggcc    4980
tttttacggt tcctggcctt ttgctggcct tttgctcaca tgttctttcc tgcgttatcc    5040
cctgattctg tggataaccg tattaccgcc tttgagtgag ctgataccgc tcgccgcagc    5100
cgaacgaccg agcgcagcga gtcagtgagc gaggaagc                            5138
```

<210> SEQ ID NO 55
<211> LENGTH: 36
<212> TYPE: DNA
<213> ORGANISM: Artificial Sequence
<220> FEATURE:
<223> OTHER INFORMATION: primer used to generate Fc-fused KAAG1 fragment

<400> SEQUENCE: 55
gtaagcaagc ttaggccgct gggacagcgg aggtgc                              36

<210> SEQ ID NO 56
<211> LENGTH: 33
<212> TYPE: DNA
<213> ORGANISM: Artificial Sequence
<220> FEATURE:
<223> OTHER INFORMATION: primer used to generate Fc-fused KAAG1 fragment

<400> SEQUENCE: 56
gtaagcaagc ttggcagcag cgccaggtcc agc                                 33

<210> SEQ ID NO 57
<211> LENGTH: 33
<212> TYPE: DNA
<213> ORGANISM: Artificial Sequence
<220> FEATURE:
<223> OTHER INFORMATION: OGS1773 primer

<400> SEQUENCE: 57
gtaagcagcg ctgtggctgc accatctgtc ttc                                 33

<210> SEQ ID NO 58
<211> LENGTH: 35
<212> TYPE: DNA
<213> ORGANISM: Artificial Sequence
<220> FEATURE:
<223> OTHER INFORMATION: OGS1774 primer

<400> SEQUENCE: 58
gtaagcgcta gcctaacact ctcccctgtt gaagc                               35

```
<210> SEQ ID NO 59
<211> LENGTH: 321
<212> TYPE: DNA
<213> ORGANISM: Homo sapiens

<400> SEQUENCE: 59
gctgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgtta g                                               321

<210> SEQ ID NO 60
<211> LENGTH: 106
<212> TYPE: PRT
<213> ORGANISM: Homo sapiens

<400> SEQUENCE: 60

Ala Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 61
<211> LENGTH: 6385
<212> TYPE: DNA
<213> ORGANISM: Artificial Sequence
<220> FEATURE:
<223> OTHER INFORMATION: pTTVK1 expression plasmid

<400> SEQUENCE: 61
cttgagccgg cggatggtcg aggtgaggtg tggcaggctt gagatccagc tgttggggtg      60
agtactccct ctcaaaagcg ggcattactt ctgcgctaag attgtcagtt tccaaaaacg     120
aggaggattt gatattcacc tggcccgatc tggccataca cttgagtgac aatgacatcc     180
actttgcctt tctctccaca ggtgtccact cccaggtcca agtttaaacg atctctagc      240 gaattcatga actttctgct gtcttgggtg cattggagcc ttgccttgct gctctacctc     300
caccatgcca gtggtccca ggcttgagac ggagcttaca gcgctgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga acacaaagt ctacgcctgc     600 gaagtcaccc atcagggcct gagctcgccc gtcacaaaga gcttcaacag gggagagtgt     660
```

```
tagggtaccg cggccgcttc gaatgagatc ccccgacctc gacctctggc taataaagga    720
aatttatttt cattgcaata gtgtgttgga atttttttgtg tctctcactc ggaaggacat    780
atgggagggc aaatcatttg gtcgagatcc ctcgagatct ctagctaga gccccgccgc    840 cggacgaact aaacctgact acggcatctc tgccccttct tcgcggggca gtgcatgtaa    900
tcccttcagt tggttggtac aacttgccaa ctgggccctg ttccacatgt gacacgggg    960 gggaccaaac acaaggggt tctctgactg tagttgacat ccttataaat ggatgtgcac   1020
atttgccaac actgagtggc tttcatcctg gagcagactt tgcagtctgt ggactgcaac   1080
acaacattgc ctttatgtgt aactcttggc tgaagctctt acaccaatgc tgggggacat   1140
gtacctccca ggggcccagg aagactacgg gaggctacac caacgtcaat cagaggggcc   1200
tgtgtagcta ccgataagcg gaccctcaag agggcattag caatagtgtt tataaggccc   1260
ccttgttaac cctaaacggg tagcatatgc ttcccgggta gtagtatata ctatccagac   1320
taaccctaat tcaatagcat atgttaccca acgggaagca tatgctatcg aattagggtt   1380
agtaaaaggg tcctaaggaa cagcgatatc tcccacccca tgagctgtca cggtttatt    1440 tacatggggt caggattcca cgagggtagt gaaccatttt agtcacaagg gcagtggctg   1500
aagatcaagg agcgggcagt gaactctcct gaatcttcgc ctgcttcttc attctccttc   1560
gtttagctaa tagaataact gctgagttgt gaacagtaag gtgtatgtga ggtgctcgaa   1620
aacaaggttt caggtgacgc ccccagaata aaatttggac ggggggttca gtggtggcat   1680
tgtgctatga caccaatata accctcacaa accccttggg caataaatac tagtgtagga   1740
atgaaacatt ctgaatatct ttaacaatag aaatccatgg ggtggggaca agccgtaaag   1800
actggatgtc catctcacac gaatttatgg ctatgggcaa cacataatcc tagtgcaata   1860
tgatactggg gttattaaga tgtgtcccag gcagggacca agacaggtga accatgttgt   1920
tacactctat ttgtaacaag gggaaagaga gtggacgccg acagcagcgg actccactgg   1980
ttgtctctaa cacccccgaa aattaaacgg ggctccacgc caatggggcc cataaacaaa   2040
gacaagtggc cactcttttt tttgaaattg tggagtgggg gcacgcgtca gcccccacac   2100
gccgccctgc ggttttggac tgtaaaataa gggtgtaata acttggctga ttgtaacccc   2160
gctaaccact gcggtcaaac cacttgccca caaaccact aatggcaccc cggggaatac   2220
ctgcataagt aggtgggcgg gccaagatag gggcgcgatt gctgcgatct ggaggacaaa   2280
ttacacacac ttgcgcctga gcgccaagca cagggttgtt ggtcctcata ttcacgaggt   2340
cgctgagagc acgtgggct aatgttgcca tgggtagcat atactaccca aatatctgga   2400
tagcatatgc tatcctaatc tatatctggg tagcataggc tatcctaatc tatatctggg   2460
tagcatatgc tatcctaatc tatatctggg tagtatatgc tatcctaatt tatatctggg   2520
tagcataggc tatcctaatc tatatctggg tagcatatgc tatcctaatc tatatctggg   2580
tagtatatgc tatcctaatc tgtatccggg tagcatatgc tatcctaata gagattaggg   2640
tagtatatgc tatcctaatt tatatctggg tagcatatac tacccaaata tctggatagc   2700
atatgctatc ctaatctata tctgggtagc atatgctatc ctaatctata tctgggtagc   2760
ataggctatc ctaatctata tctgggtagc atatgctatc ctaatctata tctgggtagt   2820
atatgctatc taatttata tctgggtagc ataggctatc ctaatctata tctgggtagc   2880
atatgctatc ctaatctata tctgggtagt atatgctatc ctaatctgta tccgggtagc   2940
atatgctatc ctcacgatga taagctgtca aacatgagaa ttaattcttg aagacgaaag   3000
ggcctcgtga tacgcctatt tttataggtt aatgtcatga taataatggt ttcttagacg   3060
```

```
tcaggtggca cttttcgggg aaatgtgcgc ggaacccta tttgtttatt tttctaaata   3120
cattcaaata tgtatccgct catgagacaa taaccctgat aaatgcttca ataatattga   3180
aaaaggaaga gtatgagtat tcaacatttc cgtgtcgccc ttattccctt ttttgcggca   3240
ttttgccttc ctgttttgc tcacccagaa acgctggtga agtaaaaga tgctgaagat    3300
cagttgggtg cacgagtggg ttacatcgaa ctggatctca acagcggtaa gatccttgag   3360
agttttcgcc ccgaagaacg ttttccaatg atgagcactt ttaaagttct gctatgtggc   3420
gcggtattat cccgtgttga cgccgggcaa gagcaactcg gtcgccgcat acactattct   3480
cagaatgact tggttgagta ctcaccagtc acagaaaagc atcttacgga tggcatgaca   3540
gtaagagaat tatgcagtgc tgccataacc atgagtgata acactgcggc caacttactt   3600
ctgacaacga tcgaggacc gaaggagcta accgcttttt tgcacaacat gggggatcat    3660
gtaactcgcc ttgatcgttg ggaaccggag ctgaatgaag ccataccaaa cgacgagcgt   3720
gacaccacga tgcctgcagc aatggcaaca acgttgcgca aactattaac tggcgaacta   3780
cttactctag cttcccggca acaattaata gactggatgg aggcggataa agttgcagga   3840
ccacttctgc gctcggccct tccggctggc tggtttattg ctgataaatc tggagccggt   3900
gagcgtgggt ctcgcggtat cattgcagca ctggggccag atggtaagcc ctcccgtatc   3960
gtagttatct acacgacggg gagtcaggca actatggatg aacgaaatag acagatcgct   4020
gagataggtg cctcactgat taagcattgg taactgtcag accaagttta ctcatatata   4080
ctttagattg atttaaaact tcatttttaa tttaaaagga tctaggtgaa gatcctttt    4140
gataatctca tgaccaaaat cccttaacgt gagttttcgt tccactgagc gtcagacccc   4200
gtagaaaaga tcaaaggatc ttcttgagat cctttttttc tgcgcgtaat ctgctgcttg   4260
caaacaaaaa aaccaccgct accagcggtg gtttgtttgc cggatcaaga gctaccaact   4320
ctttttccga aggtaactgg cttcagcaga gcgcagatac caaatactgt ccttctagtg   4380
tagccgtagt taggccacca cttcaagaac tctgtagcac cgcctacata cctcgctctg   4440
ctaatcctgt taccagtggc tgctgccagt ggcgataagt cgtgtcttac cgggttggac   4500
tcaagacgat agttaccgga taaggcgcag cggtcgggct gaacggggg ttcgtgcaca    4560
cagcccagct tggagcgaac gacctacacc gaactgagat acctacagcg tgagcattga   4620
gaaagcgcca cgcttcccga agggagaaag gcggacaggt atccggtaag cggcagggtc   4680
ggaacaggag agcgcacgag ggagcttcca gggggaaacg cctggtatct ttatagtcct   4740
gtcgggtttc gccacctctg acttgagcgt cgatttttgt gatgctcgtc agggggggcg   4800
agcctatgga aaaacgccag caacgcggcc ttttacggt tcctggcctt tgctggcct     4860
tttgctcaca tgttctttcc tgcgttatcc cctgattctg tggataaccg tattaccgcc   4920
tttgagtgag ctgataccgc tcgccgcagc cgaacgaccg agcgcagcga gtcagtgagc   4980
gaggaagcgg aagagcgccc aatacgcaaa ccgcctctcc ccgcgcgttg gccgattcat   5040
taatgcagct ggcacgacag gtttcccgac tggaaagcgg gcagtgagcg caacgcaatt   5100
aatgtgagtt agctcactca ttaggcaccc caggctttac actttatgct tccggctcgt   5160
atgttgtgtg gaattgtgag cggataacaa tttcacacag gaaacagcta tgaccatgat   5220
tacgccaagc tctagctaga gtcgaccaa ttctcatgtt tgacagctta tcatcgcaga   5280
tccgggcaac gttgttgcat tgctgcaggc gcagaactgg taggtatggc agatctatac   5340
attgaatcaa tattggcaat tagccatatt agtcattggt tatatagcat aaatcaatat   5400
tggctattgg ccattgcata cgttgtatct atatcataat atgtacattt atattggctc   5460
```

-continued

```
atgtccaata tgaccgccat gttgacattg attattgact agttattaat agtaatcaat    5520 tacgggtca ttagttcata gcccatatat ggagttccgc gttacataac ttacggtaaa    5580
tggcccgcct ggctgaccgc ccaacgaccc ccgcccattg acgtcaataa tgacgtatgt    5640
tcccatagta acgccaatag ggactttcca ttgacgtcaa tgggtggagt atttacggta    5700
aactgcccac ttggcagtac atcaagtgta tcatatgcca agtccgcccc ctattgacgt    5760
caatgacggt aaatggcccg cctggcatta tgcccagtac atgaccttac ggactttcc    5820 tacttggcag tacatctacg tattagtcat cgctattacc atggtgatgc ggttttggca    5880
gtacaccaat gggcgtggat agcggtttga ctcacgggga tttccaagtc tccaccccat    5940
tgacgtcaat gggagtttgt tttggcacca aaatcaacgg gactttccaa aatgtcgtaa    6000
taaccccgcc ccgttgacgc aaatgggcgg taggcgtgta cggtgggagg tctatataag    6060
cagagctcgt ttagtgaacc gtcagatcct cactctcttc cgcatcgctg tctgcgaggg    6120
ccagctgttg ggctcgcggt tgaggacaaa ctcttcgcgg tctttccagt actcttggat    6180
cggaaacccg tcggcctccg aacggtactc cgccaccgag ggacctgagc gagtccgcat    6240
cgaccggatc ggaaaacctc tcgagaaagg cgtctaacca gtcacagtcg caaggtaggc    6300
tgagcaccgt ggcgggcggc agcgggtggc ggtcggggtt gtttctggcg gaggtgctgc    6360
tgatgatgta attaaagtag gcggt                                         6385
```

<210> SEQ ID NO 62
<211> LENGTH: 43
<212> TYPE: DNA
<213> ORGANISM: Artificial Sequence
<220> FEATURE:
<223> OTHER INFORMATION: Primer specific for the light chain variable
      region of the 3D3 antibody

<400> SEQUENCE: 62
atgccaagtg gtcccaggct gacattgtga tgacccagtc tcc                43

<210> SEQ ID NO 63
<211> LENGTH: 43
<212> TYPE: DNA
<213> ORGANISM: Artificial Sequence
<220> FEATURE:
<223> OTHER INFORMATION: Primer specific for the light chain variable
      region of the 3G10 antibody

<400> SEQUENCE: 63
atgccaagtg gtcccaggct gatgttttga tgacccaaac tcc                43

<210> SEQ ID NO 64
<211> LENGTH: 43
<212> TYPE: DNA
<213> ORGANISM: Artificial Sequence
<220> FEATURE:
<223> OTHER INFORMATION: Primer specific for the light chain variable
      region of the 3C4 antibody

<400> SEQUENCE: 64
atgccaagtg gtcccaggct gacatcgtta tgtctcagtc tcc                43

<210> SEQ ID NO 65
<211> LENGTH: 32
<212> TYPE: DNA
<213> ORGANISM: Artificial Sequence
<220> FEATURE:
<223> OTHER INFORMATION: reverse primer to amplify the 3D3, 3G10 and 3C4
      antibody light chains

<400> SEQUENCE: 65
gggaagatga agacagatgg tgcagccaca gc					32

<210> SEQ ID NO 66
<211> LENGTH: 50
<212> TYPE: DNA
<213> ORGANISM: Artificial Sequence
<220> FEATURE:
<223> OTHER INFORMATION: OGS1769 primer

<400> SEQUENCE: 66
gtaagcgcta gcgcctcaac gaagggccca tctgtctttc ccctggcccc			50

<210> SEQ ID NO 67
<211> LENGTH: 37
<212> TYPE: DNA
<213> ORGANISM: Artificial Sequence
<220> FEATURE:
<223> OTHER INFORMATION: OGS1770 primer

<400> SEQUENCE: 67
gtaagcgaat tcacaagatt tgggctcaac tttcttg				37

<210> SEQ ID NO 68
<211> LENGTH: 309
<212> TYPE: DNA
<213> ORGANISM: Homo sapiens

<400> SEQUENCE: 68
gcctccacca agggcccatc ggtcttcccc ctggcaccct cctccaagag cacctctggg			60 ggcacagcag ccctgggctg cctggtcaag gactacttcc ccgaaccggt gacggtgtcg		120 tggaactcag gcgccctgac cagcggcgtg cacaccttcc cggctgtcct acagtcctca		180 ggactctact ccctcagcag cgtggtgacc gtgccctcca gcagcttggg cacccagacc		240 tacatctgca acgtgaatca caagcccagc aacaccaagg tggacaagaa agttgagccc		300 aaatcttgt										309

<210> SEQ ID NO 69
<211> LENGTH: 103
<212> TYPE: PRT
<213> ORGANISM: Homo sapiens

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 70
<211> LENGTH: 5379

<212> TYPE: DNA
<213> ORGANISM: Artificial Sequence
<220> FEATURE:
<223> OTHER INFORMATION: pYD15 plasmid

<400> SEQUENCE: 70

| | | | | | |
|---|---|---|---|---|---|
| cttgagccgg | cggatggtcg | aggtgaggtg | tggcaggctt | gagatccagc | tgttggggtg | 60 |
| agtactccct | ctcaaaagcg | ggcattactt | ctgcgctaag | attgtcagtt | tccaaaaacg | 120 |
| aggaggattt | gatattcacc | tggcccgatc | tggccataca | cttgagtgac | aatgacatcc | 180 |
| actttgcctt | tctctccaca | ggtgtccact | cccaggtcca | agtttgccgc | caccatggag | 240 |
| acagacacac | tcctgctatg | ggtactgctg | ctctgggttc | caggttccac | tggcggagac | 300 |
| ggagcttacg | ggcccatctg | tctttcccct | ggccccctcc | tccaagagca | cctctggggg | 360 |
| cacagcggcc | ctgggctgcc | tggtcaagga | ctacttcccc | gaaccggtga | cggtgtcgtg | 420 |
| gaactcaggc | gccctgacca | gcggcgtgca | caccttcccg | gctgtcctac | agtcctcagg | 480 |
| actctactcc | ctcagcagcg | tggtgaccgt | gccctcagc | agcttgggca | cccagaccta | 540 |
| catctgcaac | gtgaatcaca | agcccagcaa | caccaaggtg | gacaagaaag | ttgagcccaa | 600 |
| atcttgtgaa | ttcactcaca | catgcccacc | gtgcccagca | cctgaactcc | tggggggacc | 660 |
| gtcagtcttc | ctcttccccc | caaaacccaa | ggacaccctc | atgatctccc | ggacccctga | 720 |
| ggtcacatgc | gtggtggtgg | acgtgagcca | cgaagaccct | gaggtcaagt | tcaactggta | 780 |
| cgtggacggc | gtggaggtgc | ataatgccaa | gacaaagccg | cgggaggagc | agtacaacag | 840 |
| cacgtaccgt | gtggtcagcg | tcctcaccgt | cctgcaccag | gactggctga | atggcaagga | 900 |
| gtacaagtgc | aaggtctcca | acaaagccct | cccagccccc | atcgagaaaa | ccatctccaa | 960 |
| agccaaaggg | cagccccgag | aaccacaggt | gtacaccctg | cccccatccc | gggatgagct | 1020 |
| gaccaagaac | caggtcagcc | tgacctgcct | ggtcaaaggc | ttctatccca | gcgacatcgc | 1080 |
| cgtggagtgg | gagagcaatg | ggcagccgga | gaacaactac | aagaccacgc | ctcccgtgct | 1140 |
| ggactccgac | ggctccttct | tcctctacag | caagctcacc | gtggacaaga | gcaggtggca | 1200 |
| gcaggggaac | gtcttctcat | gctccgtgat | gcatgaggct | ctgcacaacc | actacacgca | 1260 |
| gaagagcctc | tccctgtctc | cgggaaatg | atccccgac | ctcgacctct | ggctaataaa | 1320 |
| ggaaatttat | tttcattgca | atagtgtgtt | ggaattttt | gtgtctctca | ctcggaagga | 1380 |
| catatgggag | ggcaaatcat | ttggtcgaga | tccctcggag | atctctagct | agagccccgc | 1440 |
| cgccggacga | actaaacctg | actacggcat | ctctgcccct | tcttcgcggg | gcagtgcatg | 1500 |
| taatcccttc | agttggttgg | tacaacttgc | caactgaacc | ctaaacgggt | agcatatgct | 1560 |
| tcccgggtag | tagtatatac | tatccagact | aaccctaatt | caatagcata | tgttacccaa | 1620 |
| cgggaagcat | atgctatcga | attagggtta | gtaaagggt | cctaaggaac | agcgatgtag | 1680 |
| gtgggcgggc | caagataggg | gcgcgattgc | tgcgatctgg | aggacaaatt | acacacactt | 1740 |
| gcgcctgagc | gccaagcaca | gggttgttgg | tcctcatatt | cacgaggtcg | ctgagagcac | 1800 |
| ggtgggctaa | tgttgccatg | gtagcatat | actacccaaa | tatctggata | gcatatgcta | 1860 |
| tcctaatcta | tatctgggta | gcataggcta | tcctaatcta | tatctgggta | gcatatgcta | 1920 |
| tcctaatcta | tatctgggta | gtatatgcta | tcctaattta | tatctgggta | gcataggcta | 1980 |
| tcctaatcta | tatctgggta | gcatatgcta | tcctaatcta | tatctgggta | gtatatgcta | 2040 |
| tcctaatctg | tatccgggta | gcatatgcta | tcctaataga | gattaggta | gtatatgcta | 2100 |
| tcctaattta | tatctgggta | gcatatacta | cccaaatatc | tggatagcat | atgctatcct | 2160 |
| aatctatatc | tgggtagcat | atgctatcct | aatctatatc | tgggtagcat | aggctatcct | 2220 |

```
aatctatatc tgggtagcat atgctatcct aatctatatc tgggtagtat atgctatcct    2280
aatttatatc tgggtagcat aggctatcct aatctatatc tgggtagcat atgctatcct    2340
aatctatatc tgggtagtat atgctatcct aatctgtatc cgggtagcat atgctatcct    2400
cacgatgata agctgtcaaa catgagaatt aattcttgaa gacgaaaggg cctcgtgata    2460
cgcctatttt tataggttaa tgtcatgata taatggtttt cttagacgtc aggtggcact    2520
tttcggggaa atgtgcgcgg aaccccctatt tgtttatttt tctaaataca ttcaaatatg    2580
tatccgctca tgagacaata accctgataa atgcttcaat aatattgaaa aaggaagagt    2640
atgagtattc aacatttccg tgtcgccctt attcccttttt ttgcggcatt ttgccttcct    2700 gttttttgctc acccagaaac gctggtgaaa gtaaaagatg ctgaagatca gttgggtgca    2760
cgagtgggtt acatcgaact ggatctcaac agcggtaaga tccttgagag ttttcgcccc    2820
gaagaacgtt ttccaatgat gagcactttt aaagttctgc tatgtggcgc ggtattatcc    2880
cgtgttgacg ccgggcaaga gcaactcggt cgccgcatac actattctca gaatgacttg    2940
gttgagtact caccagtcac agaaaagcat cttacggatg gcatgacagt aagagaatta    3000
tgcagtgctg ccataaccat gagtgataac actgcggcca acttacttct gacaacgatc    3060
ggaggaccga aggagctaac cgcttttttg cacaacatgg gggatcatgt aactcgcctt    3120
gatcgttggg aaccggagct gaatgaagcc ataccaaacg acgagcgtga caccacgatg    3180
cctgcagcaa tggcaacaac gttgcgcaaa ctattaactg gcgaactact tactctagct    3240
tcccggcaac aattaataga ctggatggag gcggataaag ttgcaggacc acttctgcgc    3300
tcggcccttc cggctggctg gtttattgct gataaatctg gagccggtga gcgtgggtct    3360
cgcggtatca ttgcagcact ggggccagat ggtaagccct cccgtatcgt agttatctac    3420
acgacgggga gtcaggcaac tatggatgaa cgaaatagac agatcgctga gataggtgcc    3480
tcactgatta agcattggta actgtcagac caagtttact catatatact ttagattgat    3540
ttaaaacttc attttttaatt taaaaggatc taggtgaaga tcctttttga taatctcatg    3600
accaaaatcc cttaacgtga gttttcgttc cactgagcgt cagacccgt agaaaagatc    3660 aaaggatctt cttgagatcc ttttttttctg cgcgtaatct gctgcttgca acaaaaaaaa    3720
ccaccgctac cagcggtggt ttgtttgccg gatcaagagc taccaactct ttttccgaag    3780
gtaactggct tcagcagagc gcagatacca atactgtcc ttctagtgta gccgtagtta    3840
ggccaccact tcaagaactc tgtagcaccg cctacatacc tcgctctgct aatcctgtta    3900
ccagtggctg ctgccagtgg cgataagtcg tgtcttaccg ggttggactc aagacgatag    3960
ttaccggata aggcgcagcg gtcgggctga cgggggggtt cgtgcacaca gcccagcttg    4020
gagcgaacga cctacaccga actgagatac ctacagcgtg agcattgaga aagcgccacg    4080
cttcccgaag ggagaaaggc ggacaggtat ccggtaagcg gcagggtcgg aacaggagag    4140
cgcacgaggg agcttccagg gggaaacgcc tggtatcttt atagtcctgt cgggtttcgc    4200
cacctctgac ttgagcgtcg attttttgtga tgctcgtcag ggggggcggag cctatgaaa    4260 aacgccagca acgcggcctt tttacggttc ctggccttttt gctggccttt tgctcacatg    4320
ttctttcctg cgttatcccc tgattctgtg ataaccgta ttaccgcctt tgagtgagct    4380
gataccgctc gccgcagccg aacgaccgag cgcagcgagt cagtgagcga ggaagcgtac    4440
atttatattg gctcatgtcc aatatgaccg ccatgttgac attgattatt gactagttat    4500
taatagtaat caattacggg gtcattagtt catagcccat atatggagtt ccgcgttaca    4560
taacttacgg taaatggccc gcctggctga ccgcccaacg acccccgccc attgacgtca    4620
```

```
ataatgacgt atgttcccat agtaacgcca atagggactt tccattgacg tcaatgggtg    4680
gagtatttac ggtaaactgc ccacttggca gtacatcaag tgtatcatat gccaagtccg    4740 cccctattg acgtcaatga cggtaaatgg cccgcctggc attatgccca gtacatgacc     4800
ttacgggact ttcctacttg gcagtacatc tacgtattag tcatcgctat taccatggtg    4860
atgcggtttt ggcagtacac caatgggcgt ggatagcggt ttgactcacg ggatttccaa    4920 gtctccacc ccattgacgt caatgggagt ttgttttggc accaaaatca acgggacttt     4980
ccaaaatgtc gtaataaccc cgccccgttg acgcaaatgg gcggtaggcg tgtacggtgg    5040
gaggtctata taagcagagc tcgtttagtg aaccgtcaga tcctcactct cttccgcatc    5100
gctgtctgcg agggccagct gttgggctcg cggttgagga caaactcttc gcggtctttc    5160
cagtactctt ggatcggaaa cccgtcggcc tccgaacgg actccgccac cgagggacct     5220
gagcgagtcc gcatcgaccg gatcggaaaa cctctcgaga aaggcgtcta accagtcaca    5280
gtcgcaaggt aggctgagca ccgtggcggg cggcagcggg tggcggtcgg ggttgtttct    5340
ggcggaggtg ctgctgatga tgtaattaaa gtaggcggt                            5379
```

```
<210> SEQ ID NO 71
<211> LENGTH: 43
<212> TYPE: DNA
<213> ORGANISM: Artificial Sequence
<220> FEATURE:
<223> OTHER INFORMATION: Primer specific for the heavy chain variable
      region of the 3D3 and 3G10 antibodies

<400> SEQUENCE: 71
gggttccagg ttccactggc gaggttcagc tgcagcagtc tgt                       43

<210> SEQ ID NO 72
<211> LENGTH: 43
<212> TYPE: DNA
<213> ORGANISM: Artificial Sequence
<220> FEATURE:
<223> OTHER INFORMATION: Primer specific for the heavy chain variable
      region of the 3C4 antibody

<400> SEQUENCE: 72
gggttccagg ttccactggc gaggtgcagc ttcaggagtc agg                       43

<210> SEQ ID NO 73
<211> LENGTH: 38
<212> TYPE: DNA
<213> ORGANISM: Artificial Sequence
<220> FEATURE:
<223> OTHER INFORMATION: reverse primer to amplify the 3D3, 3G10 and 3C4
      antibody heavy chains

<400> SEQUENCE: 73
ggggccaggg gaaagacaga tgggcccttc gttgaggc                             38

<210> SEQ ID NO 74
<211> LENGTH: 17
<212> TYPE: PRT
<213> ORGANISM: Artificial Sequence
<220> FEATURE:
<223> OTHER INFORMATION: light chain CDR1 consensus version 1
<220> FEATURE:
<221> NAME/KEY: MISC_FEATURE
<222> LOCATION: (1)..(1)
<223> OTHER INFORMATION: Xaa is a basic amino acid
<220> FEATURE:
<221> NAME/KEY: MISC_FEATURE
<222> LOCATION: (4)..(4)
```

```
<223> OTHER INFORMATION: Xaa is a basic amino acid
<220> FEATURE:
<221> NAME/KEY: MISC_FEATURE
<222> LOCATION: (8)..(8)
<223> OTHER INFORMATION: Xaa is His, Tyr or Asn
<220> FEATURE:
<221> NAME/KEY: MISC_FEATURE
<222> LOCATION: (9)..(9)
<223> OTHER INFORMATION: Xaa is Ser, Thr, Asn or Arg
<220> FEATURE:
<221> NAME/KEY: MISC_FEATURE
<222> LOCATION: (10)..(10)
<223> OTHER INFORMATION: Xaa is absent, Ser or Asn
<220> FEATURE:
<221> NAME/KEY: MISC_FEATURE
<222> LOCATION: (11)..(11)
<223> OTHER INFORMATION: Xaa is Asp, Phe or Asn
<220> FEATURE:
<221> NAME/KEY: MISC_FEATURE
<222> LOCATION: (12)..(12)
<223> OTHER INFORMATION: Xaa is Gly or Gln
<220> FEATURE:
<221> NAME/KEY: MISC_FEATURE
<222> LOCATION: (13)..(13)
<223> OTHER INFORMATION: Xaa is Lys, Leu or Asn
<220> FEATURE:
<221> NAME/KEY: MISC_FEATURE
<222> LOCATION: (14)..(14)
<223> OTHER INFORMATION: Xaa is Thr or Asn
<220> FEATURE:
<221> NAME/KEY: MISC_FEATURE
<222> LOCATION: (15)..(15)
<223> OTHER INFORMATION: Xaa is an aromatic amino acid
<220> FEATURE:
<221> NAME/KEY: MISC_FEATURE
<222> LOCATION: (17)..(17)
<223> OTHER INFORMATION: Xaa is Ala, Asn, Glu or Tyr

<400> SEQUENCE: 74

Xaa Ser Ser Xaa Ser Leu Leu Xaa Xaa Xaa Xaa Xaa Xaa Xaa Xaa Leu
1               5                   10                  15

Xaa

<210> SEQ ID NO 75
<211> LENGTH: 11
<212> TYPE: PRT
<213> ORGANISM: Artificial Sequence
<220> FEATURE:
<223> OTHER INFORMATION: light chain CDR1 consensus version 2
<220> FEATURE:
<221> NAME/KEY: MISC_FEATURE
<222> LOCATION: (6)..(6)
<223> OTHER INFORMATION: Xaa is an hydrophobic amino acid
<220> FEATURE:
<221> NAME/KEY: MISC_FEATURE
<222> LOCATION: (7)..(7)
<223> OTHER INFORMATION: Xaa is Gly or His
<220> FEATURE:
<221> NAME/KEY: MISC_FEATURE
<222> LOCATION: (8)..(8)
<223> OTHER INFORMATION: Xaa is Thr, Asn or Arg
<220> FEATURE:
<221> NAME/KEY: MISC_FEATURE
<222> LOCATION: (9)..(9)
<223> OTHER INFORMATION: Xaa is Phe, Tyr or Ala
<220> FEATURE:
<221> NAME/KEY: MISC_FEATURE
<222> LOCATION: (10)..(10)
<223> OTHER INFORMATION: Xaa is an hydrophobic amino acid
<220> FEATURE:
<221> NAME/KEY: MISC_FEATURE
<222> LOCATION: (11)..(11)
<223> OTHER INFORMATION: Xaa is Asn or Ala

<400> SEQUENCE: 75

Lys Ala Ser Gln Asp Xaa Xaa Xaa Xaa Xaa Xaa
```

```
1               5                   10
```

<210> SEQ ID NO 76
<211> LENGTH: 7
<212> TYPE: PRT
<213> ORGANISM: Artificial Sequence
<220> FEATURE:
<223> OTHER INFORMATION: light chain CDR2 consensus version 1
<220> FEATURE:
<221> NAME/KEY: MISC_FEATURE
<222> LOCATION: (2)..(2)
<223> OTHER INFORMATION: Xaa is Ala or Gly
<220> FEATURE:
<221> NAME/KEY: MISC_FEATURE
<222> LOCATION: (5)..(5)
<223> OTHER INFORMATION: Xaa is Arg or Thr
<220> FEATURE:
<221> NAME/KEY: MISC_FEATURE
<222> LOCATION: (6)..(6)
<223> OTHER INFORMATION: Xaa is Glu, Lys or Ala

<400> SEQUENCE: 76

Phe Xaa Ser Thr Xaa Xaa Ser
1               5

<210> SEQ ID NO 77
<211> LENGTH: 7
<212> TYPE: PRT
<213> ORGANISM: Artificial Sequence
<220> FEATURE:
<223> OTHER INFORMATION: light chain CDR2 consensus version 2
<220> FEATURE:
<221> NAME/KEY: MISC_FEATURE
<222> LOCATION: (1)..(1)
<223> OTHER INFORMATION: Xaa is Leu or Lys
<220> FEATURE:
<221> NAME/KEY: MISC_FEATURE
<222> LOCATION: (4)..(4)
<223> OTHER INFORMATION: Xaa is a basic amino acid
<220> FEATURE:
<221> NAME/KEY: MISC_FEATURE
<222> LOCATION: (5)..(5)
<223> OTHER INFORMATION: Xaa is Leu or Arg
<220> FEATURE:
<221> NAME/KEY: MISC_FEATURE
<222> LOCATION: (6)..(6)
<223> OTHER INFORMATION: Xaa is Asp or Phe

<400> SEQUENCE: 77

Xaa Val Ser Xaa Xaa Xaa Ser
1               5

<210> SEQ ID NO 78
<211> LENGTH: 7
<212> TYPE: PRT
<213> ORGANISM: Artificial Sequence
<220> FEATURE:
<223> OTHER INFORMATION: light chain CDR2 consensus version 3
<220> FEATURE:
<221> NAME/KEY: MISC_FEATURE
<222> LOCATION: (1)..(1)
<223> OTHER INFORMATION: Xaa is a basic amino acid
<220> FEATURE:
<221> NAME/KEY: MISC_FEATURE
<222> LOCATION: (7)..(7)
<223> OTHER INFORMATION: Xaa is Asp or Ala

<400> SEQUENCE: 78

Xaa Ala Asn Arg Leu Val Xaa
1               5

<210> SEQ ID NO 79
<211> LENGTH: 9

```
<212> TYPE: PRT
<213> ORGANISM: Artificial Sequence
<220> FEATURE:
<223> OTHER INFORMATION: light chain CDR3 consensus version 1
<220> FEATURE:
<221> NAME/KEY: MISC_FEATURE
<222> LOCATION: (1)..(1)
<223> OTHER INFORMATION: Xaa is Gln or Leu
<220> FEATURE:
<221> NAME/KEY: MISC_FEATURE
<222> LOCATION: (3)..(3)
<223> OTHER INFORMATION: Xaa is an aromatic amino acid
<220> FEATURE:
<221> NAME/KEY: MISC_FEATURE
<222> LOCATION: (4)..(4)
<223> OTHER INFORMATION: Xaa is Asp, Phe or Tyr
<220> FEATURE:
<221> NAME/KEY: MISC_FEATURE
<222> LOCATION: (5)..(5)
<223> OTHER INFORMATION: Xaa is Glu, Ala, Asn or Ser
<220> FEATURE:
<221> NAME/KEY: MISC_FEATURE
<222> LOCATION: (6)..(6)
<223> OTHER INFORMATION: Xaa is Ile, Phe or Thr

<400> SEQUENCE: 79

Xaa Gln Xaa Xaa Xaa Xaa Pro Leu Thr
1               5

<210> SEQ ID NO 80
<211> LENGTH: 9
<212> TYPE: PRT
<213> ORGANISM: Artificial Sequence
<220> FEATURE:
<223> OTHER INFORMATION: light chain CDR3 consensus version 2
<220> FEATURE:
<221> NAME/KEY: MISC_FEATURE
<222> LOCATION: (4)..(4)
<223> OTHER INFORMATION: Xaa is an aromatic amino acid
<220> FEATURE:
<221> NAME/KEY: MISC_FEATURE
<222> LOCATION: (5)..(5)
<223> OTHER INFORMATION: Xaa is Asn or Ser
<220> FEATURE:
<221> NAME/KEY: MISC_FEATURE
<222> LOCATION: (6)..(6)
<223> OTHER INFORMATION: Xaa is Ile or Thr

<400> SEQUENCE: 80

Gln Gln His Xaa Xaa Xaa Pro Leu Thr
1               5

<210> SEQ ID NO 81
<211> LENGTH: 9
<212> TYPE: PRT
<213> ORGANISM: Artificial Sequence
<220> FEATURE:
<223> OTHER INFORMATION: light chain CDR3 consensus version 3
<220> FEATURE:
<221> NAME/KEY: MISC_FEATURE
<222> LOCATION: (1)..(1)
<223> OTHER INFORMATION: Xaa is an aromatic amino acid
<220> FEATURE:
<221> NAME/KEY: MISC_FEATURE
<222> LOCATION: (4)..(4)
<223> OTHER INFORMATION: Xaa is a neutral hydrophilic amino acid
<220> FEATURE:
<221> NAME/KEY: MISC_FEATURE
<222> LOCATION: (6)..(6)
<223> OTHER INFORMATION: Xaa is Phe or Val
<220> FEATURE:
<221> NAME/KEY: MISC_FEATURE
<222> LOCATION: (8)..(8)
<223> OTHER INFORMATION: Xaa is Arg or Leu

<400> SEQUENCE: 81
```

Xaa Gln Gly Xaa His Xaa Pro Xaa Thr
1               5

<210> SEQ ID NO 82
<211> LENGTH: 10
<212> TYPE: PRT
<213> ORGANISM: Artificial Sequence
<220> FEATURE:
<223> OTHER INFORMATION: heavy chain CDR1 consensus
<220> FEATURE:
<221> NAME/KEY: MISC_FEATURE
<222> LOCATION: (3)..(3)
<223> OTHER INFORMATION: Xaa is Thr, Ile or Lys
<220> FEATURE:
<221> NAME/KEY: MISC_FEATURE
<222> LOCATION: (5)..(5)
<223> OTHER INFORMATION: Xaa is a neutral hydrophilic amino acid
<220> FEATURE:
<221> NAME/KEY: MISC_FEATURE
<222> LOCATION: (6)..(6)
<223> OTHER INFORMATION: Xaa is an acidic amino acid
<220> FEATURE:
<221> NAME/KEY: MISC_FEATURE
<222> LOCATION: (8)..(8)
<223> OTHER INFORMATION: Xaa is Glu, Asn or Asp
<220> FEATURE:
<221> NAME/KEY: MISC_FEATURE
<222> LOCATION: (9)..(9)
<223> OTHER INFORMATION: Xaa is an hydrophobic amino acid

<400> SEQUENCE: 82

Gly Tyr Xaa Phe Xaa Xaa Tyr Xaa Xaa His
1               5                   10

<210> SEQ ID NO 83
<211> LENGTH: 10
<212> TYPE: PRT
<213> ORGANISM: Artificial Sequence
<220> FEATURE:
<223> OTHER INFORMATION: heavy chain CDR2 consensus version 1
<220> FEATURE:
<221> NAME/KEY: MISC_FEATURE
<222> LOCATION: (1)..(1)
<223> OTHER INFORMATION: Xaa is Val or Gly
<220> FEATURE:
<221> NAME/KEY: MISC_FEATURE
<222> LOCATION: (2)..(2)
<223> OTHER INFORMATION: Xaa is an hydrophobic amino acid
<220> FEATURE:
<221> NAME/KEY: MISC_FEATURE
<222> LOCATION: (5)..(5)
<223> OTHER INFORMATION: Xaa is Ala, Gly or Glu
<220> FEATURE:
<221> NAME/KEY: MISC_FEATURE
<222> LOCATION: (8)..(8)
<223> OTHER INFORMATION: Xaa is Arg, Gly, Asp, Ala, Ser, Asn or Val
<220> FEATURE:
<221> NAME/KEY: MISC_FEATURE
<222> LOCATION: (10)..(10)
<223> OTHER INFORMATION: Xaa is an hydrophobic amino acid

<400> SEQUENCE: 83

Xaa Xaa Asp Pro Xaa Thr Gly Xaa Thr Xaa
1               5                   10

<210> SEQ ID NO 84
<211> LENGTH: 10
<212> TYPE: PRT
<213> ORGANISM: Artificial Sequence
<220> FEATURE:
<223> OTHER INFORMATION: heavy chain CDR2 consensus version 2
<220> FEATURE:
<221> NAME/KEY: MISC_FEATURE
<222> LOCATION: (2)..(2)

```
<223> OTHER INFORMATION: Xaa is an hydrophobic amino acid
<220> FEATURE:
<221> NAME/KEY: MISC_FEATURE
<222> LOCATION: (5)..(5)
<223> OTHER INFORMATION: Xaa is Ala, Glu or Gly
<220> FEATURE:
<221> NAME/KEY: MISC_FEATURE
<222> LOCATION: (8)..(8)
<223> OTHER INFORMATION: Xaa is Arg, Gly, Ala, Ser, Asn, Val or Asp

<400> SEQUENCE: 84

Val Xaa Asp Pro Xaa Thr Gly Xaa Thr Ala
1               5                   10

<210> SEQ ID NO 85
<211> LENGTH: 9
<212> TYPE: PRT
<213> ORGANISM: Artificial Sequence
<220> FEATURE:
<223> OTHER INFORMATION: heavy chain CDR2 consensus version 3
<220> FEATURE:
<221> NAME/KEY: MISC_FEATURE
<222> LOCATION: (3)..(3)
<223> OTHER INFORMATION: Xaa is Ser or Asn
<220> FEATURE:
<221> NAME/KEY: MISC_FEATURE
<222> LOCATION: (4)..(4)
<223> OTHER INFORMATION: Xaa is an aromatic amino acid
<220> FEATURE:
<221> NAME/KEY: MISC_FEATURE
<222> LOCATION: (5)..(5)
<223> OTHER INFORMATION: Xaa is Asp, Glu or Asn
<220> FEATURE:
<221> NAME/KEY: MISC_FEATURE
<222> LOCATION: (7)..(7)
<223> OTHER INFORMATION: Xaa is Asp or His
<220> FEATURE:
<221> NAME/KEY: MISC_FEATURE
<222> LOCATION: (8)..(8)
<223> OTHER INFORMATION: Xaa is Tyr, Ser or Asn
<220> FEATURE:
<221> NAME/KEY: MISC_FEATURE
<222> LOCATION: (9)..(9)
<223> OTHER INFORMATION: Xaa is Asp, Glu or Asn

<400> SEQUENCE: 85

Tyr Ile Xaa Xaa Xaa Gly Xaa Xaa Xaa
1               5

<210> SEQ ID NO 86
<211> LENGTH: 10
<212> TYPE: PRT
<213> ORGANISM: Artificial Sequence
<220> FEATURE:
<223> OTHER INFORMATION: heavy chain CDR2 consensus version 4
<220> FEATURE:
<221> NAME/KEY: MISC_FEATURE
<222> LOCATION: (1)..(1)
<223> OTHER INFORMATION: Xaa is Asn or Tyr
<220> FEATURE:
<221> NAME/KEY: MISC_FEATURE
<222> LOCATION: (7)..(7)
<223> OTHER INFORMATION: Xaa is Glu, Asp or Asn

<400> SEQUENCE: 86

Xaa Ile Asn Pro Tyr Asn Xaa Val Thr Glu
1               5                   10

<210> SEQ ID NO 87
<211> LENGTH: 10
<212> TYPE: PRT
<213> ORGANISM: Artificial Sequence
<220> FEATURE:
<223> OTHER INFORMATION: heavy chain CDR2 consensus version 5
```

```
<220> FEATURE:
<221> NAME/KEY: MISC_FEATURE
<222> LOCATION: (5)..(5)
<223> OTHER INFORMATION: Xaa is Asn or Tyr
<220> FEATURE:
<221> NAME/KEY: MISC_FEATURE
<222> LOCATION: (8)..(8)
<223> OTHER INFORMATION: Xaa is Gly or Thr
<220> FEATURE:
<221> NAME/KEY: MISC_FEATURE
<222> LOCATION: (9)..(9)
<223> OTHER INFORMATION: Xaa is Ile or Thr

<400> SEQUENCE: 87

Asp Ile Asn Pro Xaa Tyr Gly Xaa Xaa Thr
1               5                   10

<210> SEQ ID NO 88
<211> LENGTH: 6
<212> TYPE: PRT
<213> ORGANISM: Artificial Sequence
<220> FEATURE:
<223> OTHER INFORMATION: heavy chain CDR3 consensus version 1
<220> FEATURE:
<221> NAME/KEY: MISC_FEATURE
<222> LOCATION: (2)..(2)
<223> OTHER INFORMATION: Xaa is Gly or Ser
<220> FEATURE:
<221> NAME/KEY: MISC_FEATURE
<222> LOCATION: (3)..(3)
<223> OTHER INFORMATION: Xaa is Tyr or His
<220> FEATURE:
<221> NAME/KEY: MISC_FEATURE
<222> LOCATION: (4)..(4)
<223> OTHER INFORMATION: Xaa is Ala or Ser

<400> SEQUENCE: 88

Met Xaa Xaa Xaa Asp Tyr
1               5

<210> SEQ ID NO 89
<211> LENGTH: 7
<212> TYPE: PRT
<213> ORGANISM: Artificial Sequence
<220> FEATURE:
<223> OTHER INFORMATION: heavy chain CDR3 consensus version 2
<220> FEATURE:
<221> NAME/KEY: MISC_FEATURE
<222> LOCATION: (2)..(2)
<223> OTHER INFORMATION: Xaa is Gly or Ser
<220> FEATURE:
<221> NAME/KEY: MISC_FEATURE
<222> LOCATION: (5)..(5)
<223> OTHER INFORMATION: Xaa is absent or Met

<400> SEQUENCE: 89

Ile Xaa Tyr Ala Xaa Asp Tyr
1               5

<210> SEQ ID NO 90
<211> LENGTH: 7
<212> TYPE: PRT
<213> ORGANISM: Artificial Sequence
<220> FEATURE:
<223> OTHER INFORMATION: heavy chain CDR3 consensus version 3
<220> FEATURE:
<221> NAME/KEY: MISC_FEATURE
<222> LOCATION: (2)..(2)
<223> OTHER INFORMATION: Xaa is Arg or Trp
<220> FEATURE:
<221> NAME/KEY: MISC_FEATURE
<222> LOCATION: (3)..(3)
<223> OTHER INFORMATION: Xaa is an aromatic amino acid
<220> FEATURE:
```

```
<221> NAME/KEY: MISC_FEATURE
<222> LOCATION: (7)..(7)
<223> OTHER INFORMATION: Xaa is a basic amino acid

<400> SEQUENCE: 90

Ala Xaa Xaa Gly Leu Arg Xaa
1               5

<210> SEQ ID NO 91
<211> LENGTH: 17
<212> TYPE: PRT
<213> ORGANISM: Artificial Sequence
<220> FEATURE:
<223> OTHER INFORMATION: Exemplary embodiment of a light chain CDR1
<220> FEATURE:
<221> NAME/KEY: MISC_FEATURE
<222> LOCATION: (8)..(8)
<223> OTHER INFORMATION: Xaa is Asn or His
<220> FEATURE:
<221> NAME/KEY: MISC_FEATURE
<222> LOCATION: (9)..(9)
<223> OTHER INFORMATION: Xaa is Ser or Thr
<220> FEATURE:
<221> NAME/KEY: MISC_FEATURE
<222> LOCATION: (10)..(10)
<223> OTHER INFORMATION: Xaa is Ser, Asn or Asp
<220> FEATURE:
<221> NAME/KEY: MISC_FEATURE
<222> LOCATION: (11)..(11)
<223> OTHER INFORMATION: Xaa is Asn or Gly
<220> FEATURE:
<221> NAME/KEY: MISC_FEATURE
<222> LOCATION: (12)..(12)
<223> OTHER INFORMATION: Xaa is Gln, Asn or Lys
<220> FEATURE:
<221> NAME/KEY: MISC_FEATURE
<222> LOCATION: (13)..(13)
<223> OTHER INFORMATION: Xaa is Lys or Leu

<400> SEQUENCE: 91

Lys Ser Ser Gln Ser Leu Leu Xaa Xaa Xaa Xaa Xaa Xaa Asn Tyr Leu
1               5                   10                  15

Ala

<210> SEQ ID NO 92
<211> LENGTH: 11
<212> TYPE: PRT
<213> ORGANISM: Artificial Sequence
<220> FEATURE:
<223> OTHER INFORMATION: Exemplary embodiment of a light chain CDR1
<220> FEATURE:
<221> NAME/KEY: MISC_FEATURE
<222> LOCATION: (8)..(8)
<223> OTHER INFORMATION: Xaa is Asn or Thr
<220> FEATURE:
<221> NAME/KEY: MISC_FEATURE
<222> LOCATION: (9)..(9)
<223> OTHER INFORMATION: Xaa is Tyr or Phe

<400> SEQUENCE: 92

Lys Ala Ser Gln Asp Ile His Xaa Xaa Leu Asn
1               5                   10

<210> SEQ ID NO 93
<211> LENGTH: 7
<212> TYPE: PRT
<213> ORGANISM: Artificial Sequence
<220> FEATURE:
<223> OTHER INFORMATION: Exemplary embodiment of a light chain CDR2

<400> SEQUENCE: 93

Phe Ala Ser Thr Arg Glu Ser
1               5
```

```
<210> SEQ ID NO 94
<211> LENGTH: 7
<212> TYPE: PRT
<213> ORGANISM: Artificial Sequence
<220> FEATURE:
<223> OTHER INFORMATION: Exemplary embodiment of a light chain CDR2

<400> SEQUENCE: 94

Leu Val Ser Lys Leu Asp Ser
1               5

<210> SEQ ID NO 95
<211> LENGTH: 7
<212> TYPE: PRT
<213> ORGANISM: Artificial Sequence
<220> FEATURE:
<223> OTHER INFORMATION: Exemplary embodiment of a light chain CDR2

<400> SEQUENCE: 95

Arg Ala Asn Arg Leu Val Asp
1               5

<210> SEQ ID NO 96
<211> LENGTH: 9
<212> TYPE: PRT
<213> ORGANISM: Artificial Sequence
<220> FEATURE:
<223> OTHER INFORMATION: Exemplary embodiment of a light chain CDR3

<400> SEQUENCE: 96

Gln Gln His Tyr Ser Thr Pro Leu Thr
1               5

<210> SEQ ID NO 97
<211> LENGTH: 9
<212> TYPE: PRT
<213> ORGANISM: Artificial Sequence
<220> FEATURE:
<223> OTHER INFORMATION: Exemplary embodiment of a light chain CDR3
<220> FEATURE:
<221> NAME/KEY: MISC_FEATURE
<222> LOCATION: (1)..(1)
<223> OTHER INFORMATION: Xaa is Trp or Leu
<220> FEATURE:
<221> NAME/KEY: MISC_FEATURE
<222> LOCATION: (3)..(3)
<223> OTHER INFORMATION: Xaa is Tyr or Gly
<220> FEATURE:
<221> NAME/KEY: MISC_FEATURE
<222> LOCATION: (4)..(4)
<223> OTHER INFORMATION: Xaa is Asp or Thr
<220> FEATURE:
<221> NAME/KEY: MISC_FEATURE
<222> LOCATION: (5)..(5)
<223> OTHER INFORMATION: Xaa is Ala, Glu or His

<400> SEQUENCE: 97

Xaa Gln Xaa Xaa Xaa Phe Pro Arg Thr
1               5

<210> SEQ ID NO 98
<211> LENGTH: 10
<212> TYPE: PRT
<213> ORGANISM: Artificial Sequence
<220> FEATURE:
<223> OTHER INFORMATION: Exemplary embodiment of a heavy chain CDR1
<220> FEATURE:
<221> NAME/KEY: MISC_FEATURE
<222> LOCATION: (3)..(3)
```

```
<223> OTHER INFORMATION: Xaa is Thr or Ile
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (8)..(8)
<223> OTHER INFORMATION: Xaa is Glu or Asn
<220> FEATURE:
<221> NAME/KEY: MISC_FEATURE
<222> LOCATION: (9)..(9)
<223> OTHER INFORMATION: Xaa is Met, Ile or Val

<400> SEQUENCE: 98

Gly Tyr Xaa Phe Thr Xaa Tyr Xaa Xaa His
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Exemplary embodiment of a heavy chain CDR1
<220> FEATURE:
<221> NAME/KEY: MISC_FEATURE
<222> LOCATION: (3)..(3)
<223> OTHER INFORMATION: Xaa is Thr or Ser

<400> SEQUENCE: 99

Gly Phe Xaa Ile Thr Ser Gly Tyr Gly Trp His
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Exemplary embodiment of a heavy chain CDR2
<220> FEATURE:
<221> NAME/KEY: MISC_FEATURE
<222> LOCATION: (1)..(1)
<223> OTHER INFORMATION: Xaa is Val, Asn or Gly
<220> FEATURE:
<221> NAME/KEY: MISC_FEATURE
<222> LOCATION: (2)..(2)
<223> OTHER INFORMATION: Xaa is Ile or Leu
<220> FEATURE:
<221> NAME/KEY: MISC_FEATURE
<222> LOCATION: (5)..(5)
<223> OTHER INFORMATION: Xaa is Glu, Ala or Gly
<220> FEATURE:
<221> NAME/KEY: MISC_FEATURE
<222> LOCATION: (6)..(6)
<223> OTHER INFORMATION: Xaa is Thr or Tyr
<220> FEATURE:
<221> NAME/KEY: misc_feature
<222> LOCATION: (8)..(8)
<223> OTHER INFORMATION: Xaa can be any naturally occurring amino acid

<400> SEQUENCE: 100

Xaa Xaa Asp Pro Xaa Xaa Gly Xaa Thr Ala
1               5                   10

<210> SEQ ID NO 101
<211> LENGTH: 6
<212> TYPE: PRT
<213> ORGANISM: Artificial Sequence
<220> FEATURE:
<223> OTHER INFORMATION: Exemplary embodiment of a heavy chain CDR2
<220> FEATURE:
<221> NAME/KEY: MISC_FEATURE
<222> LOCATION: (3)..(3)
<223> OTHER INFORMATION: Xaa is Asn or Ser
```

```
<220> FEATURE:
<221> NAME/KEY: MISC_FEATURE
<222> LOCATION: (4)..(4)
<223> OTHER INFORMATION: Xaa is Phe or Tyr
<220> FEATURE:
<221> NAME/KEY: MISC_FEATURE
<222> LOCATION: (5)..(5)
<223> OTHER INFORMATION: Xaa is Asn or Asp

<400> SEQUENCE: 101

Tyr Ile Xaa Xaa Xaa Gly
1               5

<210> SEQ ID NO 102
<211> LENGTH: 6
<212> TYPE: PRT
<213> ORGANISM: Artificial Sequence
<220> FEATURE:
<223> OTHER INFORMATION: Exemplary embodiment of a heavy chain CDR3
<220> FEATURE:
<221> NAME/KEY: MISC_FEATURE
<222> LOCATION: (4)..(4)
<223> OTHER INFORMATION: Xaa is Ser or Ala

<400> SEQUENCE: 102

Met Gly Tyr Xaa Asp Tyr
1               5

<210> SEQ ID NO 103
<211> LENGTH: 10
<212> TYPE: PRT
<213> ORGANISM: Artificial Sequence
<220> FEATURE:
<223> OTHER INFORMATION: Exemplary embodiment of a heavy chain CDR3

<400> SEQUENCE: 103

Ala Ser Ser Tyr Asp Gly Phe Leu Ala Tyr
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Exemplary embodiment of a heavy chain CDR3
<220> FEATURE:
<221> NAME/KEY: MISC_FEATURE
<222> LOCATION: (2)..(2)
<223> OTHER INFORMATION: Xaa is Arg or Trp
<220> FEATURE:
<221> NAME/KEY: MISC_FEATURE
<222> LOCATION: (3)..(3)
<223> OTHER INFORMATION: Xaa is Trp or Phe
<220> FEATURE:
<221> NAME/KEY: MISC_FEATURE
<222> LOCATION: (7)..(7)
<223> OTHER INFORMATION: Xaa is Gln or Asn

<400> SEQUENCE: 104

Ala Xaa Xaa Gly Leu Arg Xaa
1               5

<210> SEQ ID NO 105
<211> LENGTH: 112
<212> TYPE: PRT
<213> ORGANISM: Artificial Sequence
<220> FEATURE:
<223> OTHER INFORMATION: Amino acid sequence of the 3z1A02 light chain

<400> SEQUENCE: 105

Asp Ala Val Met Thr Gln Ile Pro Leu Thr Leu Ser Val Thr Ile Gly
```

```
                 1               5                  10                 15
Gln Pro Ala Ser Leu Ser Cys Lys Ser Ser Gln Ser Leu Leu His Ser
                20                  25                 30

Asp Gly Lys Thr Tyr Leu Asn Trp Leu Leu Gln Arg Pro Gly Gln Ser
            35                  40                 45

Pro Lys Arg Leu Ile Ser Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Leu Tyr Tyr Cys Trp Gln Gly
                85                  90                  95

Thr His Phe Pro Arg Thr Phe Ala Gly Gly Thr Asn Leu Glu Ile Lys
            100                 105                110

<210> SEQ ID NO 106
<211> LENGTH: 112
<212> TYPE: PRT
<213> ORGANISM: Artificial Sequence
<220> FEATURE:
<223> OTHER INFORMATION: Amino acid sequence of the 3z1F06 light chain

<400> SEQUENCE: 106

Ser Ile Val Met Thr Gln Thr Pro Leu Thr Leu Ser Val Thr Ile Gly
1               5                  10                 15

Gln Pro Ala Ser Ile Thr Cys Lys Ser Ser Gln Ser Leu Leu Tyr Ser
                20                  25                 30

Asp Gly Lys Thr Tyr Leu Asn Trp Leu Leu Gln Arg Pro Gly Gln Ser
            35                  40                 45

Pro Lys Arg Leu Ile Ser Leu Val Ser Lys Leu Asp Ser Gly Val Pro
    50                  55                  60

Asp Gly Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                110

<210> SEQ ID NO 107
<211> LENGTH: 112
<212> TYPE: PRT
<213> ORGANISM: Artificial Sequence
<220> FEATURE:
<223> OTHER INFORMATION: Amino acid sequence of the 3z1E08 light chain

<400> SEQUENCE: 107

Asp Ala Val Met Thr Gln Ile Pro Leu Thr Leu Ser Val Thr Ile Gly
1               5                  10                 15

Gln Pro Ala Ser Ile Ser Cys Lys Ser Ser Gln Ser Leu Leu His Ser
                20                  25                 30

Asp Gly Lys Thr Tyr Leu Asn Trp Leu Leu Gln Arg Pro Gly Gln Ser
            35                  40                 45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
```

<210> SEQ ID NO 108
<211> LENGTH: 112
<212> TYPE: PRT
<213> ORGANISM: Artificial Sequence
<220> FEATURE:
<223> OTHER INFORMATION: Amino acid sequence of the 3z1G10 light chain

<400> SEQUENCE: 108

```
Asp Val Leu Met Thr Gln Thr Pro Arg Ser Leu Ser Val Ser Leu Gly
1               5                   10                  15
Asp Gln Ala Ser Ile Ser Cys Arg Ser Ser Gln Ser Leu Leu His Ser
            20                  25                  30
Asn Gly Asn Thr Tyr Leu Glu Trp Tyr Leu Gln Lys Pro Gly Gln Pro
        35                  40                  45
Pro Lys Val Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Gly Val Glu Ala Glu Asp Leu Gly Val Tyr Tyr Cys Phe Gln Gly
                85                  90                  95
Ser His Val Pro Leu Thr Phe Gly Ala Gly Thr Lys Leu Glu Leu Lys
            100                 105                 110
```

<210> SEQ ID NO 109
<211> LENGTH: 112
<212> TYPE: PRT
<213> ORGANISM: Artificial Sequence
<220> FEATURE:
<223> OTHER INFORMATION: Amino acid sequence of the 3z1E10 light chain

<400> SEQUENCE: 109

```
Asp Ile Val Met Thr Gln Ala Ala Pro Ser Val Pro Val Thr Pro Gly
1               5                   10                  15
Glu Ser Val Ser Ile Ser Cys Arg Ser Ser Lys Ser Leu Leu His Ser
            20                  25                  30
Asn Gly Asn Thr Tyr Leu Tyr Trp Phe Leu Gln Arg Pro Gly Gln Ser
        35                  40                  45
Pro Gln Leu Leu Ile Tyr Arg Met Ser Asn Leu Ala Ser Gly Val Pro
    50                  55                  60
Asp Arg Phe Ser Gly Ser Gly Ser Gly Thr Ala Phe Thr Leu Arg Ile
65                  70                  75                  80
Ser Arg Val Glu Ala Glu Asp Val Gly Val Tyr Tyr Cys Met Gln His
                85                  90                  95
Leu Glu Tyr Pro Tyr Thr Phe Gly Gly Gly Thr Lys Leu Glu Ile Lys
            100                 105                 110
```

<210> SEQ ID NO 110
<211> LENGTH: 113
<212> TYPE: PRT
<213> ORGANISM: Artificial Sequence
<220> FEATURE:
<223> OTHER INFORMATION: Amino acid sequence of the 3z1A09 light chain

<400> SEQUENCE: 110

```
Asp Ile Val Met Thr Gln Ser Pro Ser Ser Leu Ala Met Ser Leu Gly
1               5                   10                  15
Gln Lys Val Thr Met Ser Cys Lys Ser Ser Gln Ser Leu Leu Asn Ser
            20                  25                  30
```

```
Asn Asn Gln Leu Asn Tyr Leu Ala Trp Tyr Gln Gln Lys Pro Gly Gln
        35                  40                  45

Ser Pro Lys Leu Leu Val Tyr Phe Ala Ser Thr Arg Lys Ser Gly Val
 50                  55                  60

Pro Asp Arg Phe Ile Gly Ser Gly Ser Gly Thr Asp Phe Thr Leu Thr
 65                  70                  75                  80

Ile Thr Ser Val Gln Ala Glu Asp Leu Ala Asp Tyr Phe Cys Gln Gln
                 85                  90                  95

His Phe Asn Thr Pro Leu Thr Phe Gly Ala Gly Thr Lys Leu Glu Leu
                100                 105                 110

Lys

<210> SEQ ID NO 111
<211> LENGTH: 113
<212> TYPE: PRT
<213> ORGANISM: Artificial Sequence
<220> FEATURE:
<223> OTHER INFORMATION: Amino acid sequence of the 3z1B01 light chain

<400> SEQUENCE: 111

Asp Ile Val Met Thr Gln Ser Pro Ser Ser Leu Ala Ile Ser Val Gly
 1               5                  10                  15

Gln Lys Val Thr Met Ser Cys Lys Ser Gln Ser Leu Leu Asn Ser
                 20                  25                  30

Ser Asn Gln Lys Asn Tyr Leu Ala Trp Tyr Gln Gln Lys Pro Gly Gln
        35                  40                  45

Ser Pro Lys Leu Leu Val Phe Phe Ala Ser Thr Arg Glu Ser Gly Val
 50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                 85                  90                  95

His Tyr Ser Ile Pro Leu Thr Phe Gly Ala Gly Thr Lys Leu Glu Leu
                100                 105                 110

Lys

<210> SEQ ID NO 112
<211> LENGTH: 113
<212> TYPE: PRT
<213> ORGANISM: Artificial Sequence
<220> FEATURE:
<223> OTHER INFORMATION: Amino acid sequence of the 3z1G05 light chain

<400> SEQUENCE: 112

Asp Ile Val Met Thr Gln Ser Pro Ser Ser Leu Ala Met Ser Val Gly
 1               5                  10                  15

Gln Lys Val Thr Met Ser Cys Lys Ser Gln Ser Leu Leu Asn Ser
                 20                  25                  30

Ser Asn Gln Lys Asn Tyr Leu Ala Trp Tyr Gln Gln Lys Pro Gly Gln
        35                  40                  45

Ser Pro Lys Leu Leu Val Phe Phe Ala Ser Thr Arg Glu Ser Gly Val
 50                  55                  60

Pro Asp Arg Phe Ile Gly Ser Gly Ser Gly Thr Asp Phe Thr Leu Thr
 65                  70                  75                  80

Ile Thr Ser Val Gln Ala Glu Asp Leu Ala Asp Tyr Phe Cys Gln Gln
                 85                  90                  95

His Tyr Ser Ile Pro Leu Thr Phe Gly Ser Gly Thr Lys Leu Glu Leu
                100                 105                 110
```

<210> SEQ ID NO 113
<211> LENGTH: 113
<212> TYPE: PRT
<213> ORGANISM: Artificial Sequence
<220> FEATURE:
<223> OTHER INFORMATION: Amino acid sequence of the 3z1B02 light chain

<400> SEQUENCE: 113

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
            100                 105                 110

Lys
```

<210> SEQ ID NO 114
<211> LENGTH: 113
<212> TYPE: PRT
<213> ORGANISM: Artificial Sequence
<220> FEATURE:
<223> OTHER INFORMATION: Amino acid sequence of the 3z1B08 light chain

<400> SEQUENCE: 114

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys
```

<210> SEQ ID NO 115
<211> LENGTH: 113
<212> TYPE: PRT
<213> ORGANISM: Artificial Sequence
<220> FEATURE:
<223> OTHER INFORMATION: Amino acid sequence of the 3z1G08 light chain

<400> SEQUENCE: 115

```
Asp Ile Val Met Thr Gln Ser Pro Ser Ser Leu Ala Met Ser Val Gly
```

```
                1               5                  10                 15
Gln Lys Val Thr Met Ser Cys Lys Ser Ser Gln Ser Leu Leu Asn Ser
                                20                 25                 30

Ser Asn Gln Lys Asn Tyr Leu Ala Trp Tyr Gln Gln Lys Pro Gly Gln
            35                  40                 45

Ser Pro Lys Leu Leu Val Tyr Phe Ala Ser Thr Arg Glu Ser Gly Val
        50                  55                 60

Pro Asp Arg Phe Ile Gly Ser Gly Ser Gly Thr Asp Phe Thr Leu Thr
65                  70                  75                      80

Ile Ser Ser Val Gln Ala Glu Asp Leu Ala Asp Tyr Phe Cys Gln Gln
                    85                  90                  95

His Tyr Ser Thr Pro Leu Thr Phe Gly Ala Gly Thr Lys Leu Glu Leu
                100                 105                 110

Lys
```

<210> SEQ ID NO 116
<211> LENGTH: 113
<212> TYPE: PRT
<213> ORGANISM: Artificial Sequence
<220> FEATURE:
<223> OTHER INFORMATION: Amino acid sequence of the 3z1F07 light chain

<400> SEQUENCE: 116

```
Asp Ile Val Met Thr Gln Ser Pro Ser Ser Leu Ala Met Ser Val Gly
1               5                  10                 15

Gln Lys Val Thr Met Ser Cys Lys Ser Ser Gln Ser Leu Leu Asn Ser
                20                 25                 30

Ser Asn Gln Lys Asn Tyr Leu Ala Trp Tyr Gln Gln Lys Pro Gly Gln
            35                  40                 45

Ser Pro Lys Leu Leu Ile Tyr Phe Ala Ser Thr Arg Glu Ser Gly Val
        50                  55                 60

Pro Asp Arg Phe Ile Gly Ser Gly Ser Gly Thr Asp Phe Thr Leu Thr
65                  70                  75                      80

Ile Ser Ser Val Gln Ala Glu Asp Leu Ala Asp Tyr Phe Cys Gln Gln
                    85                  90                  95

His Tyr Ser Thr Pro Leu Thr Phe Gly Ala Gly Thr Lys Leu Glu Leu
                100                 105                 110

Lys
```

<210> SEQ ID NO 117
<211> LENGTH: 113
<212> TYPE: PRT
<213> ORGANISM: Artificial Sequence
<220> FEATURE:
<223> OTHER INFORMATION: Amino acid sequence of the 3z1E09 light chain

<400> SEQUENCE: 117

```
Asp Ile Val Met Thr Gln Ser Pro Ser Ser Leu Ala Met Ser Val Gly
1               5                  10                 15

Gln Lys Val Thr Met Ser Cys Lys Ser Ser Gln Ser Leu Leu Asn Ser
                20                 25                 30

Ser Asn Gln Lys Asn Tyr Leu Ala Trp Tyr Gln Gln Lys Pro Gly Gln
            35                  40                 45

Ser Pro Lys Leu Leu Val Tyr Phe Ala Ser Thr Arg Glu Ser Gly Val
        50                  55                 60

Pro Asp Arg Phe Ile Gly Ser Gly Ser Gly Thr Glu Phe Thr Leu Thr
65                  70                  75                      80
```

```
Ile Thr Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys

<210> SEQ ID NO 118
<211> LENGTH: 113
<212> TYPE: PRT
<213> ORGANISM: Artificial Sequence
<220> FEATURE:
<223> OTHER INFORMATION: Amino acid sequence of the 3z1C03 light chain

<400> SEQUENCE: 118

Asp Ile Val Met Thr Gln Ser Pro Ser Ser Leu Ala Met Ser Val Gly
1               5                   10                  15

Gln Lys Val Thr Met Ser Cys Lys Ser Gln Ser Leu Leu Asn Ser
            20                  25                  30

Ser Asn Gln Lys Asn Tyr Leu Ala Trp Tyr Gln Gln Lys Pro Gly Gln
            35                  40                  45

Ser Pro Lys Leu Leu Val Tyr Phe Gly Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Gly Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys

<210> SEQ ID NO 119
<211> LENGTH: 113
<212> TYPE: PRT
<213> ORGANISM: Artificial Sequence
<220> FEATURE:
<223> OTHER INFORMATION: Amino acid sequence of the 3z1E12 light chain

<400> SEQUENCE: 119

Asp Ile Val Met Thr Gln Ser Pro Ser Ser Leu Ala Met Ser Val Gly
1               5                   10                  15

Gln Lys Val Thr Met Asn Cys Lys Ser Gln Ser Leu Leu Asn Arg
            20                  25                  30

Ser Asn Gln Lys Asn Tyr Leu Ala Trp Tyr Gln Gln Lys Pro Gly Gln
            35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
            100                 105                 110

Lys

<210> SEQ ID NO 120
<211> LENGTH: 113
<212> TYPE: PRT
<213> ORGANISM: Artificial Sequence
<220> FEATURE:
```

<223> OTHER INFORMATION: Amino acid sequence of the 4z1A02 light chain

<400> SEQUENCE: 120

```
Asp Ile Val Met Thr Gln Ser Pro Ser Ser Leu Ala Met Ser Val Gly
1               5                   10                  15
Gln Lys Val Thr Met Asn Cys Lys Ser Ser Gln Ser Leu Leu Asn Asn
            20                  25                  30
Ser Asn Gln Lys Asn Tyr Leu Ala Trp Tyr Gln Gln Lys Pro Gly Gln
        35                  40                  45
Ser Pro Lys Leu Leu Leu Tyr Phe Ala Ser Thr Arg Glu Ser Gly Val
    50                  55                  60
Pro Asp Arg Phe Ile Gly Ser Gly Ser Gly Thr Tyr Phe Thr Leu Thr
65                  70                  75                  80
Ile Ser Ser Val Gln Ala Glu Asp Leu Ala Asp Tyr Phe Cys Gln Gln
                85                  90                  95
His Tyr Ser Thr Pro Leu Thr Phe Gly Ala Gly Thr Lys Leu Asp Leu
            100                 105                 110
Lys
```

<210> SEQ ID NO 121
<211> LENGTH: 113
<212> TYPE: PRT
<213> ORGANISM: Artificial Sequence
<220> FEATURE:
<223> OTHER INFORMATION: Amino acid sequence of the 3z1F10 light chain

<400> SEQUENCE: 121

```
Asp Ile Val Met Thr Gln Ser Pro Ser Ser Leu Thr Met Ser Val Gly
1               5                   10                  15
Gln Lys Val Thr Met Ser Cys Lys Ser Ser Gln Ser Leu Leu Asn Thr
            20                  25                  30
Ser Asn Gln Leu Asn Tyr Leu Ala Trp Tyr Gln Gln Lys Pro Gly Gln
        35                  40                  45
Ser Pro Lys Leu Leu Val Tyr Phe Ala Ser Thr Thr Glu Ser Gly Val
    50                  55                  60
Pro Asp Arg Phe Ile Gly Ser Gly Ser Gly Thr Asp Phe Thr Leu Thr
65                  70                  75                  80
Ile Ser Ser Val Gln Ala Glu Asp Leu Ala Asp Tyr Phe Cys Gln Gln
                85                  90                  95
His Tyr Ser Thr Pro Leu Thr Phe Gly Ala Gly Thr Lys Leu Glu Leu
            100                 105                 110
Lys
```

<210> SEQ ID NO 122
<211> LENGTH: 113
<212> TYPE: PRT
<213> ORGANISM: Artificial Sequence
<220> FEATURE:
<223> OTHER INFORMATION: Amino acid sequence of the 3z1F04 light chain

<400> SEQUENCE: 122

```
Asp Ile Val Met Thr Gln Ser Pro Ser Ser Leu Thr Val Thr Ala Gly
1               5                   10                  15
Glu Lys Val Thr Met Ser Cys Lys Ser Ser Gln Ser Leu Leu Asn Thr
            20                  25                  30
Ser Asn Gln Lys Asn Tyr Leu Ala Trp Tyr Gln Gln Lys Pro Gly Gln
        35                  40                  45
Ser Pro Lys Leu Leu Val Tyr Phe Ala Ser Thr Arg Ala Ser Gly Val
```

```
            50                  55                  60
Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                 85                  90                  95

His Tyr Ser Thr Pro Leu Thr Phe Gly Ala Gly Thr Lys Leu Glu Leu
                100                 105                 110

Lys

<210> SEQ ID NO 123
<211> LENGTH: 113
<212> TYPE: PRT
<213> ORGANISM: Artificial Sequence
<220> FEATURE:
<223> OTHER INFORMATION: Amino acid sequence of the 3z1B11 light chain

<400> SEQUENCE: 123

Asp Ile Val Met Thr Gln Ser Pro Ser Ser Leu Ala Met Ser Val Gly
 1                5                  10                  15

Gln Lys Val Thr Met Ser Cys Lys Ser Ser Gln Ser Leu Leu Asn Ser
                 20                  25                  30

Ser Asn Gln Lys Asn Tyr Leu Ala Trp Tyr Gln Gln Lys Pro Gly Gln
             35                  40                  45

Ser Pro Lys Leu Leu Val Tyr Phe Ala Ser Thr Arg Glu Ser Gly Val
         50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                 85                  90                  95

His Tyr Ser Thr Pro Leu Thr Phe Gly Ala Gly Thr Lys Leu Glu Leu
                100                 105                 110

Lys

<210> SEQ ID NO 124
<211> LENGTH: 113
<212> TYPE: PRT
<213> ORGANISM: Artificial Sequence
<220> FEATURE:
<223> OTHER INFORMATION: Amino acid sequence of the 3z1D03 ight chain

<400> SEQUENCE: 124

Asp Ile Val Met Thr Gln Ser Pro Ser Ser Leu Ala Val Ser Ile Gly
 1                5                  10                  15

Gln Lys Val Thr Met Asn Cys Lys Ser Ser Gln Ser Leu Leu Asn Ser
                 20                  25                  30

Asn Phe Gln Lys Asn Phe Leu Ala Trp Tyr Gln Gln Lys Pro Gly Gln
             35                  40                  45

Ser Pro Lys Leu Leu Ile Tyr Phe Ala Ser Thr Arg Glu Ser Ser Ile
         50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                 85                  90                  95

His Tyr Ser Thr Pro Leu Thr Phe Gly Ala Gly Thr Lys Leu Glu Leu
                100                 105                 110

Lys
```

```
<210> SEQ ID NO 125
<211> LENGTH: 113
<212> TYPE: PRT
<213> ORGANISM: Artificial Sequence
<220> FEATURE:
<223> OTHER INFORMATION: Amino acid sequence of the 3z1C03 light chain

<400> SEQUENCE: 125
```

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Lys Pro Gly Gln
        35                  40                  45

Ser Pro Lys Leu Leu Val Tyr Phe Gly Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Gly Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys

```
<210> SEQ ID NO 126
<211> LENGTH: 107
<212> TYPE: PRT
<213> ORGANISM: Artificial Sequence
<220> FEATURE:
<223> OTHER INFORMATION: Amino acid sequence of the 3z1G12 light chain

<400> SEQUENCE: 126
```

Asp Ile Val Met Thr Gln Ser Pro Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Glu Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Asp Phe Thr Leu Thr Ile Ser Ser Val Gln Ala
65                  70                  75                  80

Glu Asp Leu Ala Asp Tyr Phe Cys Gln Gln His Tyr Ser Ile Pro Leu
                85                  90                  95

Thr Phe Gly Ala Gly Thr Lys Leu Glu Leu Arg
            100                 105

```
<210> SEQ ID NO 127
<211> LENGTH: 107
<212> TYPE: PRT
<213> ORGANISM: Artificial Sequence
<220> FEATURE:
<223> OTHER INFORMATION: Amino acid sequence of the 3z1C04 light chain

<400> SEQUENCE: 127
```

Asp Ile Val Met Ser Gln Ser Pro Ser Ser Met Tyr Ala Ser Leu Gly
1               5                   10                  15

Glu Arg Val Thr Ile Thr Cys Lys Ala Ser Gln Asp Ile His Asn Phe
            20                  25                  30

Leu Asn Trp Phe Gln Gln Lys Pro Gly Lys Ser Pro Lys Thr Leu Ile

```
                35                  40                  45
Phe Arg Ala Asn Arg Leu Val Asp Gly Val Pro Ser Arg Phe Ser Gly
 50                  55                  60
Ser Gly Ser Gly Gln Asp Tyr Ser Leu Thr Ile Ser Ser Leu Glu Phe
 65                  70                  75                  80
Glu Asp Leu Gly Ile Tyr Ser Cys Leu Gln Tyr Asp Glu Ile Pro Leu
             85                  90                  95
Thr Phe Gly Ala Gly Thr Lys Leu Glu Leu Arg
            100                 105

<210> SEQ ID NO 128
<211> LENGTH: 107
<212> TYPE: PRT
<213> ORGANISM: Artificial Sequence
<220> FEATURE:
<223> OTHER INFORMATION: Amino acid sequence of the 3z1D01 light chain

<400> SEQUENCE: 128

Asp Ile Lys Met Thr Gln Ser Pro Ser Ser Met Tyr Ala Ser Leu Gly
 1               5                  10                  15
Glu Arg Val Thr Ile Thr Cys Lys Ala Ser Gln Asp Ile His Thr Tyr
             20                  25                  30
Leu Asn Trp Phe Gln Gln Lys Pro Gly Lys Ser Pro Glu Thr Leu Ile
         35                  40                  45
Tyr Arg Ala Asn Arg Leu Val Asp Gly Val Pro Ser Arg Phe Ser Gly
 50                  55                  60
Ser Gly Ser Gly Gln Asp Tyr Ser Leu Thr Ile Ser Ser Leu Glu Tyr
 65                  70                  75                  80
Glu Asp Met Gly Ile Tyr Tyr Cys Leu Gln Tyr Asp Glu Phe Pro Leu
             85                  90                  95
Thr Phe Gly Ala Gly Thr Lys Leu Glu Leu Lys
            100                 105

<210> SEQ ID NO 129
<211> LENGTH: 107
<212> TYPE: PRT
<213> ORGANISM: Artificial Sequence
<220> FEATURE:
<223> OTHER INFORMATION: Amino acid sequence of the 3z1C02 light chain

<400> SEQUENCE: 129

Asp Ile Gln Met Thr Gln Ser Pro Ser Ser Met Tyr Ala Ser Leu Gly
 1               5                  10                  15
Glu Arg Val Thr Leu Thr Cys Lys Ala Ser Gln Asp Ile His Asn Tyr
             20                  25                  30
Leu Asn Trp Phe Gln Gln Lys Pro Gly Lys Ser Pro Lys Thr Leu Ile
         35                  40                  45
His Arg Ala Asn Arg Leu Val Ala Gly Val Pro Ser Arg Phe Ser Gly
 50                  55                  60
Ser Gly Ser Gly Gln Asp Tyr Ser Leu Thr Ile Ser Ser Leu Glu Tyr
 65                  70                  75                  80
Glu Asp Leu Gly Ile Tyr Tyr Cys Leu Gln Tyr Asp Ala Phe Pro Leu
             85                  90                  95
Thr Phe Gly Ala Gly Thr Lys Leu Glu Leu Lys
            100                 105

<210> SEQ ID NO 130
<211> LENGTH: 107
<212> TYPE: PRT
```

```
<213> ORGANISM: Artificial Sequence
<220> FEATURE:
<223> OTHER INFORMATION: Amino acid sequence of the 3z1E06 light chain

<400> SEQUENCE: 130

Asp Ile Gln Met Thr Gln Ser Pro Ser Ser Met Tyr Ala Ser Leu Gly
1               5                   10                  15

Glu Arg Val Thr Leu Thr Cys Lys Ala Ser Gln Asp Ile His Asn Tyr
            20                  25                  30

Leu Asn Trp Phe Gln Gln Lys Pro Gly Lys Ser Pro Lys Thr Leu Ile
        35                  40                  45

His Arg Ala Asn Arg Leu Val Ala Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Leu Gly Ile Tyr Tyr Cys Leu Gln Tyr Asp Ala Phe Pro Leu
                85                  90                  95

Thr Phe Gly Ala Gly Thr Lys Leu Glu Leu Lys
            100                 105

<210> SEQ ID NO 131
<211> LENGTH: 107
<212> TYPE: PRT
<213> ORGANISM: Artificial Sequence
<220> FEATURE:
<223> OTHER INFORMATION: Amino acid sequence of the 3z1H03 light chain

<400> SEQUENCE: 131

Asp Ile Val Met Ser Gln Ser Pro Ser Ser Met Tyr Ala Ser Leu Gly
1               5                   10                  15

Glu Arg Val Thr Ile Thr Cys Lys Ala Ser Gln Asp Ile His Arg Phe
            20                  25                  30

Leu Asn Trp Phe Gln Gln Lys Pro Gly Lys Ser Pro Lys Thr Leu Ile
        35                  40                  45

Phe His Ala Asn Arg Leu Val Asp Gly Val Pro Ser Arg Phe Ser Gly
    50                  55                  60

Ser Gly Ser Gly Leu Asp Tyr Ser Leu Thr Ile Ser Ser Leu Glu Tyr
65                  70                  75                  80

Glu Asp Met Gly Ile Tyr Phe Cys Leu Gln Tyr Asp Ala Phe Pro Leu
                85                  90                  95

Thr Phe Gly Ala Gly Thr Lys Leu Glu Leu Lys
            100                 105

<210> SEQ ID NO 132
<211> LENGTH: 115
<212> TYPE: PRT
<213> ORGANISM: Artificial Sequence
<220> FEATURE:
<223> OTHER INFORMATION: Amino acid sequence of the 3z1A02 heavy chain

<400> SEQUENCE: 132

His Glu Ile Gln Leu Gln Gln Ser Gly Pro Glu Leu Val Lys Pro Gly
1               5                   10                  15

Ala Ser Val Lys Met Ser Cys Lys Thr Ser Gly Tyr Thr Phe Thr Asp
            20                  25                  30

Tyr Asn Met His Trp Val Lys Gln Lys Pro Gly Gln Gly Leu Glu Trp
        35                  40                  45

Ile Gly Tyr Ile Asn Pro Tyr Asn Asp Val Thr Glu Tyr Asn Glu Lys
    50                  55                  60
```

```
Phe Lys Gly Arg Ala Thr Leu Thr Ser Asp Lys Ser Ser Thr Ala
 65                  70                  75                  80

Tyr Met Asp Leu Ser Ser Leu Thr Ser Asp Asp Ser Ala Val Tyr Phe
                 85                  90                  95

Cys Ala Trp Phe Gly Leu Arg Gln Trp Gly Gln Gly Thr Leu Val Thr
                100                 105                 110

Val Ser Thr
115
```

<210> SEQ ID NO 133
<211> LENGTH: 115
<212> TYPE: PRT
<213> ORGANISM: Artificial Sequence
<220> FEATURE:
<223> OTHER INFORMATION: Amino acid sequence of the 3z1F06 heavy chain

<400> SEQUENCE: 133

```
His Glu Val Gln Leu Gln Gln Ser Gly Pro Glu Leu Val Lys Pro Gly
  1               5                  10                  15

Ala Ser Val Lys Met Ser Cys Lys Ala Ser Gly Tyr Ile Phe Thr Glu
                 20                  25                  30

Tyr Asn Ile His Trp Val Lys Gln Lys Pro Gly Gln Gly Pro Glu Trp
             35                  40                  45

Ile Gly Asn Ile Asn Pro Tyr Asn Asp Val Thr Glu Tyr Asn Glu Lys
         50                  55                  60

Phe Lys Gly Lys Ala Thr Leu Thr Ser Asp Lys Ala Ser Ser Thr Ala
 65                  70                  75                  80

Tyr Met Asp Leu Ser Ser Leu Thr Ser Glu Asp Ser Ala Val Tyr Tyr
                 85                  90                  95

Cys Ala Arg Trp Gly Leu Arg Asn Trp Gly Gln Gly Thr Leu Val Thr
                100                 105                 110

Val Ser Ala
115
```

<210> SEQ ID NO 134
<211> LENGTH: 115
<212> TYPE: PRT
<213> ORGANISM: Artificial Sequence
<220> FEATURE:
<223> OTHER INFORMATION: Amino acid sequence of the 3z1E08 heavy chain

<400> SEQUENCE: 134

```
His Glu Val Gln Leu Gln Gln Ser Val Pro Glu Leu Val Lys Pro Gly
  1               5                  10                  15

Ala Ser Val Lys Met Ser Cys Lys Thr Ser Gly Tyr Thr Phe Thr Glu
                 20                  25                  30

Tyr Asn Met His Trp Val Lys Gln Lys Pro Gly Gln Gly Pro Glu Trp
             35                  40                  45

Ile Gly Asn Ile Asn Pro Tyr Asn Asn Val Thr Glu Tyr Asn Glu Lys
         50                  55                  60

Phe Lys Gly Lys Ala Thr Leu Thr Ser Asp Lys Ser Ser Ser Thr Ala
 65                  70                  75                  80

Tyr Leu Asp Leu Ser Ser Leu Thr Ser Glu Asp Ser Ala Val Tyr Tyr
                 85                  90                  95

Cys Ala Arg Trp Gly Leu Arg Asn Trp Gly Gln Gly Thr Leu Val Thr
                100                 105                 110

Val Ser Ala
115
```

```
<210> SEQ ID NO 135
<211> LENGTH: 114
<212> TYPE: PRT
<213> ORGANISM: Artificial Sequence
<220> FEATURE:
<223> OTHER INFORMATION: Amino acid sequence of the 3z1A09 heavy chain

<400> SEQUENCE: 135

His Gln Val Gln Val Gln Gln Pro Gly Ala Glu Leu Val Arg Pro Gly
1               5                   10                  15

Ala Ser Val Thr Leu Ser Cys Lys Ala Ser Gly Tyr Ile Phe Thr Asp
            20                  25                  30

Tyr Glu Val His Trp Val Arg Gln Arg Pro Val His Gly Leu Glu Trp
        35                  40                  45

Ile Gly Val Ile Asp Pro Glu Thr Gly Asp Thr Ala Tyr Asn Gln Lys
    50                  55                  60

Phe Lys Gly Lys Ala Thr Leu Thr Ala Asp Lys Ser Ser Thr Ala
65                  70                  75                  80

Tyr Met Glu Leu Ser Ser Leu Thr Ala Glu Asp Ser Ala Val Tyr Tyr
                85                  90                  95

Cys Ile Gly Tyr Ala Asp Tyr Trp Gly Gln Gly Thr Thr Leu Thr Val
            100                 105                 110

Ser Ser

<210> SEQ ID NO 136
<211> LENGTH: 114
<212> TYPE: PRT
<213> ORGANISM: Artificial Sequence
<220> FEATURE:
<223> OTHER INFORMATION: Amino acid sequence of the 3z1B01 heavy chain

<400> SEQUENCE: 136

His Gln Val Gln Leu Gln Gln Pro Gly Ala Glu Leu Val Arg Pro Gly
1               5                   10                  15

Ala Ser Val Thr Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45

Ile Gly Val Ile Asp Pro Glu Thr Gly Thr Ala Tyr Asn Gln Lys
    50                  55                  60

Phe Lys Gly Lys Ala Thr Leu Thr Thr Asp Lys Ser Ser Thr Ala
65                  70                  75                  80

Tyr Met Glu Leu Arg Ser Leu Thr Ser Glu Asp Ser Ala Val Tyr Tyr
                85                  90                  95

Cys Met Gly Tyr Ser Asp Tyr Trp Gly Gln Gly Thr Thr Leu Thr Val
            100                 105                 110

Ser Ser

<210> SEQ ID NO 137
<211> LENGTH: 114
<212> TYPE: PRT
<213> ORGANISM: Artificial Sequence
<220> FEATURE:
<223> OTHER INFORMATION: Amino acid sequence of the 3z1B02 heavy chain

<400> SEQUENCE: 137

His Glu Val Gln Leu Gln Gln Ser Gly Ala Glu Leu Val Arg Pro Gly
1               5                   10                  15

Ala Ser Val Thr Leu Ser Cys Lys Ala Ser Gly Tyr Thr Phe Thr Asp
```

```
                    20                  25                  30
Tyr Glu Ile His Trp Val Lys Gln Thr Pro Val His Gly Leu Glu Trp
                35                  40                  45
Ile Gly Val Ile Asp Pro Glu Thr Gly Ala Thr Ala Tyr Asn Gln Lys
 50                  55                  60
Phe Lys Gly Lys Ala Thr Leu Thr Ala Asp Lys Ser Ser Ser Thr Ala
 65                  70                  75                  80
Tyr Met Glu Leu Ser Ser Leu Thr Ser Glu Asp Ser Ala Val Tyr Tyr
                85                  90                  95
Cys Met Gly Tyr Ser Asp Tyr Trp Gly Gln Gly Thr Thr Leu Thr Val
                100                 105                 110
Ser Ser

<210> SEQ ID NO 138
<211> LENGTH: 114
<212> TYPE: PRT
<213> ORGANISM: Artificial Sequence
<220> FEATURE:
<223> OTHER INFORMATION: Amino acid sequence of the 3z1F04 heavy chain

<400> SEQUENCE: 138

His Glu Val Gln Leu Gln Gln Ser Gly Ala Glu Leu Val Arg Pro Gly
 1               5                  10                  15
Ala Ser Val Thr Leu Ser Cys Lys Ala Ser Gly Tyr Thr Phe Thr Asp
                20                  25                  30
Tyr Glu Ile His Trp Val Lys Gln Thr Pro Val His Gly Leu Glu Trp
                35                  40                  45
Ile Gly Val Ile Asp Pro Glu Thr Gly Ser Thr Ala Tyr Asn Gln Lys
 50                  55                  60
Phe Lys Gly Lys Ala Thr Leu Thr Ala Asp Lys Ala Ser Ser Thr Ala
 65                  70                  75                  80
Tyr Met Glu Leu Ser Ser Leu Thr Ser Glu Asp Ser Ala Val Tyr Tyr
                85                  90                  95
Cys Met Gly Tyr Ser Asp Tyr Trp Gly Gln Gly Thr Thr Leu Thr Val
                100                 105                 110
Ser Ser

<210> SEQ ID NO 139
<211> LENGTH: 114
<212> TYPE: PRT
<213> ORGANISM: Artificial Sequence
<220> FEATURE:
<223> OTHER INFORMATION: Amino acid sequence of the 3z1E09 heavy chain

<400> SEQUENCE: 139

His Glu Val Gln Leu Gln Gln Ser Gly Ala Glu Leu Val Arg Pro Gly
 1               5                  10                  15
Ala Ser Ala Thr Leu Ser Cys Lys Ala Ser Gly Tyr Thr Phe Thr Asp
                20                  25                  30
Tyr Glu Met His Trp Val Lys Gln Thr Pro Val His Gly Leu Glu Trp
                35                  40                  45
Ile Gly Val Ile Asp Pro Glu Thr Gly Ser Thr Ala Tyr Asn Gln Lys
 50                  55                  60
Phe Lys Gly Lys Ala Thr Leu Thr Ala Asp Lys Ser Ser Ser Thr Ala
 65                  70                  75                  80
Tyr Met Glu Leu Ser Ser Leu Thr Ser Glu Asp Ser Ala Val Tyr Tyr
                85                  90                  95
```

```
Cys Met Gly Tyr Ala Asp Tyr Trp Gly Gln Gly Thr Leu Thr Val
            100                 105                 110
Ser Ser

<210> SEQ ID NO 140
<211> LENGTH: 114
<212> TYPE: PRT
<213> ORGANISM: Artificial Sequence
<220> FEATURE:
<223> OTHER INFORMATION: Amino acid sequence of the 3z1B08 heavy chain

<400> SEQUENCE: 140

His Glu Val Gln Leu Gln Gln Ser Gly Ala Glu Leu Val Arg Pro Gly
1               5                   10                  15

Ala Ser Val Thr Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45

Ile Gly Val Ile Asp Pro Glu Thr Gly Asp Thr Ala Tyr Asn Gln Asn
    50                  55                  60

Phe Thr Gly Lys Ala Thr Leu Thr Ala Asp Lys Ser Ser Ser Thr Ala
65                  70                  75                  80

Tyr Met Glu Leu Ser Ser Leu Thr Ser Glu Asp Ser Ala Val Tyr Tyr
                85                  90                  95

Cys Met Gly Tyr Ala Asp Tyr Trp Gly Gln Gly Thr Leu Thr Val
            100                 105                 110
Ser Ser

<210> SEQ ID NO 141
<211> LENGTH: 114
<212> TYPE: PRT
<213> ORGANISM: Artificial Sequence
<220> FEATURE:
<223> OTHER INFORMATION: Amino acid sequence of the 3z1G08 heavy chain

<400> SEQUENCE: 141

His Gln Val Gln Leu Lys Gln Ser Gly Ala Glu Leu Val Arg Pro Gly
1               5                   10                  15

Ala Ser Val Thr Leu Ser Cys Lys Ala Ser Gly Tyr Thr Phe Thr Asp
            20                  25                  30

Tyr Glu Val His Trp Val Lys Gln Thr Pro Val His Gly Leu Glu Trp
        35                  40                  45

Ile Gly Val Ile Asp Pro Ala Thr Gly Asp Thr Ala Tyr Asn Gln Lys
    50                  55                  60

Phe Lys Gly Lys Ala Thr Leu Thr Ala Asp Lys Ser Ser Ser Thr Ala
65                  70                  75                  80

Tyr Met Glu Val Ser Ser Leu Thr Ser Glu Asp Ser Ala Val Tyr Tyr
                85                  90                  95

Cys Met Gly Tyr Ser Asp Tyr Trp Gly Gln Gly Thr Leu Thr Val
            100                 105                 110
Ser Ser

<210> SEQ ID NO 142
<211> LENGTH: 114
<212> TYPE: PRT
<213> ORGANISM: Artificial Sequence
<220> FEATURE:
<223> OTHER INFORMATION: Amino acid sequence of the 3z1F07 heavy chain

<400> SEQUENCE: 142
```

-continued

```
His Gln Ala Tyr Leu Gln Gln Ser Gly Ala Glu Leu Val Arg Pro Gly
1               5                   10                  15

Ala Ser Val Thr Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45

Ile Gly Val Ile Asp Pro Glu Thr Gly Asp Thr Ala Tyr Asn Gln Lys
    50                  55                  60

Phe Lys Asp Lys Ala Thr Leu Thr Ala Asp Lys Ala Ser Ser Thr Ala
65              70                  75                  80

Tyr Met Glu Leu Ser Ser Leu Thr Ser Glu Asp Ser Ala Val Tyr Tyr
                85                  90                  95

Cys Met Gly Tyr Ser Asp Tyr Trp Gly Gln Gly Thr Thr Leu Thr Val
            100                 105                 110

Ser Ser

<210> SEQ ID NO 143
<211> LENGTH: 114
<212> TYPE: PRT
<213> ORGANISM: Artificial Sequence
<220> FEATURE:
<223> OTHER INFORMATION: Amino acid sequence of the 3z1E12 heavy chain

<400> SEQUENCE: 143

His Gln Val Gln Leu Gln Gln Ser Glu Ala Glu Leu Val Lys Pro Gly
1               5                   10                  15

Ala Ser Val Lys Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45

Ile Gly Val Ile Asp Pro Glu Thr Gly Asp Thr Ala Tyr Asn Gln Lys
    50                  55                  60

Phe Lys Gly Lys Ala Thr Leu Thr Ala Asp Lys Ser Ser Ser Thr Ala
65              70                  75                  80

Tyr Met Glu Leu Ser Arg Leu Thr Ser Glu Asp Ser Ala Val Tyr Tyr
                85                  90                  95

Cys Met Gly His Ser Asp Tyr Trp Gly Gln Gly Thr Thr Leu Thr Val
            100                 105                 110

Ser Ser

<210> SEQ ID NO 144
<211> LENGTH: 114
<212> TYPE: PRT
<213> ORGANISM: Artificial Sequence
<220> FEATURE:
<223> OTHER INFORMATION: Amino acid sequence of the 3z1D03 heavy chain

<400> SEQUENCE: 144

His Glu Val Gln Leu Gln Gln Ser Val Ala Glu Leu Val Arg Pro Gly
1               5                   10                  15

Ala Ser Val Thr Leu Ser Cys Lys Ala Ser Gly Tyr Ile Phe Thr Asp
            20                  25                  30

Tyr Glu Ile His Trp Val Lys Gln Thr Pro Val His Gly Leu Glu Trp
        35                  40                  45

Ile Gly Val Ile Asp Pro Glu Thr Gly Asn Thr Ala Phe Asn Gln Lys
    50                  55                  60

Phe Lys Gly Lys Ala Thr Leu Thr Ala Asp Ile Ser Ser Ser Thr Ala
```

```
                65                  70                  75                  80
Tyr Met Glu Leu Ser Ser Leu Thr Ser Glu Asp Ser Ala Val Tyr Tyr
                        85                  90                  95
Cys Met Gly Tyr Ser Asp Tyr Trp Gly Gln Gly Thr Thr Leu Thr Val
                    100                 105                 110
Ser Ser

<210> SEQ ID NO 145
<211> LENGTH: 114
<212> TYPE: PRT
<213> ORGANISM: Artificial Sequence
<220> FEATURE:
<223> OTHER INFORMATION: Amino acid sequence of the 3z1G12 heavy chain

<400> SEQUENCE: 145

His Glu Val Gln Leu Gln Gln Ser Val Ala Glu Leu Val Arg Pro Gly
1               5                   10                  15
Ala Ser Val Thr Val Ser Cys Lys Ala Ser Gly Tyr Ile Phe Thr Asp
                20                  25                  30
Tyr Glu Ile His Trp Val Lys Gln Thr Pro Ala His Gly Leu Glu Trp
            35                  40                  45
Ile Gly Val Ile Asp Pro Glu Thr Gly Asn Thr Ala Phe Asn Gln Lys
50                  55                  60
Phe Lys Gly Lys Ala Thr Leu Thr Ala Asp Ile Ser Ser Ser Thr Ala
65                  70                  75                  80
Tyr Met Glu Leu Ser Ser Leu Thr Ser Glu Asp Ser Ala Val Tyr Tyr
                        85                  90                  95
Cys Met Gly Tyr Ser Asp Tyr Trp Gly Gln Gly Thr Thr Leu Thr Val
                    100                 105                 110
Ser Ser

<210> SEQ ID NO 146
<211> LENGTH: 114
<212> TYPE: PRT
<213> ORGANISM: Artificial Sequence
<220> FEATURE:
<223> OTHER INFORMATION: Amino acid sequence of the 3z1F10 heavy chain

<400> SEQUENCE: 146

His Glu Val Gln Leu Gln Gln Ser Val Ala Glu Leu Val Arg Pro Gly
1               5                   10                  15
Ala Pro Val Thr Leu Ser Cys Lys Ala Ser Gly Tyr Thr Phe Thr Asp
                20                  25                  30
Tyr Glu Val His Trp Val Lys Gln Thr Pro Val His Gly Leu Glu Trp
            35                  40                  45
Ile Gly Val Ile Asp Pro Glu Thr Gly Ala Thr Ala Tyr Asn Gln Lys
50                  55                  60
Phe Lys Gly Lys Ala Thr Leu Thr Ala Asp Lys Ser Ser Ser Ala Ala
65                  70                  75                  80
Tyr Met Glu Leu Ser Arg Leu Thr Ser Glu Asp Ser Ala Val Tyr Tyr
                        85                  90                  95
Cys Met Ser Tyr Ser Asp Tyr Trp Gly Gln Gly Thr Thr Leu Thr Val
                    100                 105                 110
Ser Ser

<210> SEQ ID NO 147
<211> LENGTH: 114
<212> TYPE: PRT
```

```
<213> ORGANISM: Artificial Sequence
<220> FEATURE:
<223> OTHER INFORMATION: Amino acid sequence of the 3z1C03 heavy chain

<400> SEQUENCE: 147

His Glu Val Gln Leu Gln Gln Ser Val Ala Glu Val Val Arg Pro Gly
1               5                   10                  15

Ala Ser Val Thr Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45

Ile Gly Val Ile Asp Pro Glu Thr Gly Val Thr Ala Tyr Asn Gln Arg
    50                  55                  60

Phe Arg Asp Lys Ala Thr Leu Thr Thr Asp Lys Ser Ser Ser Thr Ala
65                  70                  75                  80

Tyr Met Glu Leu Ser Ser Leu Thr Ser Glu Asp Ser Ala Val Tyr Phe
                85                  90                  95

Cys Met Gly Tyr Ser Asp Tyr Trp Gly Gln Gly Thr Thr Leu Thr Val
            100                 105                 110

Ser Ser

<210> SEQ ID NO 148
<211> LENGTH: 114
<212> TYPE: PRT
<213> ORGANISM: Artificial Sequence
<220> FEATURE:
<223> OTHER INFORMATION: Amino acid sequence of the 3z1C03 heavy chain

<400> SEQUENCE: 148

His Glu Val Gln Leu Gln Gln Ser Val Ala Glu Val Val Arg Pro Gly
1               5                   10                  15

Ala Ser Val Thr Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45

Ile Gly Val Ile Asp Pro Glu Thr Gly Val Thr Ala Tyr Asn Gln Arg
    50                  55                  60

Phe Arg Asp Lys Ala Thr Leu Thr Thr Asp Lys Ser Ser Ser Thr Ala
65                  70                  75                  80

Tyr Met Glu Leu Ser Ser Leu Thr Ser Glu Asp Ser Ala Val Tyr Phe
                85                  90                  95

Cys Met Gly Tyr Ser Asp Tyr Trp Gly Gln Gly Thr Thr Leu Thr Val
            100                 105                 110

Ser Ser

<210> SEQ ID NO 149
<211> LENGTH: 114
<212> TYPE: PRT
<213> ORGANISM: Artificial Sequence
<220> FEATURE:
<223> OTHER INFORMATION: Amino acid sequence of the 3z1G05 heavy chain

<400> SEQUENCE: 149

His Gln Val Gln Leu Gln Gln Pro Gly Ala Glu Leu Val Arg Pro Gly
1               5                   10                  15

Ala Ser Val Thr Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45
```

```
Ile Gly Val Leu Asp Pro Gly Thr Gly Arg Thr Ala Tyr Asn Gln Lys
        50                  55                  60

Phe Lys Asp Lys Ala Thr Leu Ser Ala Asp Lys Ser Ser Ser Thr Ala
 65                  70                  75                  80

Tyr Met Glu Leu Ser Ser Leu Thr Ser Glu Asp Ser Ala Val Tyr Tyr
                85                  90                  95

Cys Met Ser Tyr Ser Asp Tyr Trp Gly Pro Gly Thr Thr Leu Thr Val
                100                 105                 110

Ser Ser
```

<210> SEQ ID NO 150
<211> LENGTH: 114
<212> TYPE: PRT
<213> ORGANISM: Artificial Sequence
<220> FEATURE:
<223> OTHER INFORMATION: Amino acid sequence of the 3z1B11 heavy chain

<400> SEQUENCE: 150

```
His Glu Val Gln Leu Gln Gln Ser Val Ala Glu Leu Val Arg Pro Gly
 1                5                  10                  15

Ala Ser Val Thr Leu Ser Cys Lys Ala Ser Gly Tyr Thr Phe Thr Asp
                20                  25                  30

Tyr Glu Met His Trp Val Lys Gln Thr Pro Val Arg Gly Leu Glu Trp
            35                  40                  45

Ile Gly Val Ile Asp Pro Ala Thr Gly Asp Thr Ala Tyr Asn Gln Lys
        50                  55                  60

Phe Lys Gly Lys Ala Thr Leu Thr Ala Asp Lys Ser Ser Ser Ala Ala
 65                  70                  75                  80

Phe Met Glu Leu Ser Ser Leu Thr Ser Glu Asp Ser Ala Val Tyr Tyr
                85                  90                  95

Cys Met Gly Tyr Ser Asp Tyr Trp Gly Gln Gly Thr Thr Leu Thr Val
                100                 105                 110

Ser Ser
```

<210> SEQ ID NO 151
<211> LENGTH: 115
<212> TYPE: PRT
<213> ORGANISM: Artificial Sequence
<220> FEATURE:
<223> OTHER INFORMATION: Amino acid sequence of the 3z1E06 heavy chain

<400> SEQUENCE: 151

```
His Gln Val Gln Leu Gln Gln Ser Gly Ala Glu Leu Val Arg Pro Gly
 1                5                  10                  15

Ala Ser Val Thr Leu Ser Cys Lys Ala Ser Gly Tyr Thr Phe Ser Asp
                20                  25                  30

Tyr Glu Met His Trp Val Lys Gln Thr Pro Val His Gly Leu Glu Trp
            35                  40                  45

Ile Gly Gly Ile Asp Pro Glu Thr Gly Asp Thr Val Tyr Asn Gln Lys
        50                  55                  60

Phe Lys Gly Lys Ala Thr Leu Thr Ala Asp Lys Ser Ser Ser Thr Ala
 65                  70                  75                  80

Tyr Met Glu Leu Ser Ser Leu Thr Ser Glu Asp Ser Ala Val Tyr Tyr
                85                  90                  95

Cys Ile Ser Tyr Ala Met Asp Tyr Trp Gly Gln Gly Thr Ser Val Thr
                100                 105                 110

Val Ser Ser
```

<210> SEQ ID NO 152
<211> LENGTH: 115
<212> TYPE: PRT
<213> ORGANISM: Artificial Sequence
<220> FEATURE:
<223> OTHER INFORMATION: Amino acid sequence of the 4z1A02 heavy chain

<400> SEQUENCE: 152

```
His Gln Val Lys Leu Gln Gln Ser Gly Thr Glu Leu Val Arg Pro Gly
1               5                   10                  15

Ala Ser Val Thr Leu Ser Cys Lys Ala Ser Gly Tyr Lys Phe Thr Asp
            20                  25                  30

Tyr Glu Met His Trp Val Lys Gln Thr Pro Val His Gly Leu Glu Trp
        35                  40                  45

Ile Gly Gly Ile Asp Pro Glu Thr Gly Gly Thr Ala Tyr Asn Gln Lys
    50                  55                  60

Phe Lys Gly Lys Ala Ile Leu Thr Ala Asp Lys Ser Thr Thr Ala
65                  70                  75                  80

Tyr Met Glu Leu Arg Ser Leu Thr Ser Glu Asp Ser Ala Val Tyr Tyr
                85                  90                  95

Cys Ile Ser Tyr Ala Met Asp Tyr Trp Gly Gln Gly Thr Ser Val Thr
            100                 105                 110

Val Ser Ser
    115
```

<210> SEQ ID NO 153
<211> LENGTH: 117
<212> TYPE: PRT
<213> ORGANISM: Artificial Sequence
<220> FEATURE:
<223> OTHER INFORMATION: Amino acid sequence of the 3z1E10 heavy chain

<400> SEQUENCE: 153

```
His Glu Val Gln Leu Gln Gln Ser Gly Pro Glu Leu Val Lys Pro Gly
1               5                   10                  15

Ala Ser Val Lys Ile Ser Cys Lys Ala Ser Gly Asp Thr Phe Thr Asp
            20                  25                  30

Tyr Tyr Met Asn Trp Val Lys Gln Ser His Gly Lys Ser Leu Glu Trp
        35                  40                  45

Ile Gly Asp Ile Asn Pro Asn Tyr Gly Gly Ile Thr Tyr Asn Gln Lys
    50                  55                  60

Phe Lys Gly Lys Ala Thr Leu Thr Val Asp Thr Ser Ser Ser Thr Ala
65                  70                  75                  80

Tyr Met Glu Leu Arg Gly Leu Thr Ser Glu Asp Ser Ala Val Tyr Tyr
                85                  90                  95

Cys Gln Ala Tyr Tyr Arg Asn Ser Asp Tyr Trp Gly Gln Gly Thr Thr
            100                 105                 110

Leu Thr Val Ser Ser
        115
```

<210> SEQ ID NO 154
<211> LENGTH: 116
<212> TYPE: PRT
<213> ORGANISM: Artificial Sequence
<220> FEATURE:
<223> OTHER INFORMATION: Amino acid sequence of the 3z1G10 heavy chain

<400> SEQUENCE: 154

His Glu Ile Gln Leu Gln Gln Ser Gly Pro Glu Leu Val Lys Pro Gly
1               5                   10                  15

Ala Ser Val Lys Ile Ser Cys Lys Ala Ser Gly Tyr Thr Phe Thr Asp
            20                  25                  30

Asn Tyr Met Asn Trp Val Lys Gln Ser His Gly Lys Ser Leu Glu Trp
        35                  40                  45

Ile Gly Asp Ile Asn Pro Tyr Tyr Gly Thr Thr Tyr Asn Gln Lys
50                  55                  60

Phe Lys Gly Lys Ala Thr Leu Thr Val Asp Lys Ser Ser Arg Thr Ala
65                  70                  75                  80

Tyr Met Glu Leu Arg Gly Leu Thr Ser Glu Ser Ala Val Tyr Tyr
                85                  90                  95

Cys Ala Arg Asp Asp Trp Phe Asp Tyr Trp Gly Gln Gly Thr Leu Val
            100                 105                 110

Thr Val Ser Ala
        115

<210> SEQ ID NO 155
<211> LENGTH: 118
<212> TYPE: PRT
<213> ORGANISM: Artificial Sequence
<220> FEATURE:
<223> OTHER INFORMATION: Amino acid sequence of the 3z1D01 heavy chain

<400> SEQUENCE: 155

His Glu Val Gln Leu Gln Glu Ser Gly Pro Asp Leu Val Lys Pro Ser
1               5                   10                  15

Gln Ser Leu Ser Leu Thr Cys Thr Val Thr Gly Phe Ser Ile Thr Ser
            20                  25                  30

Gly Tyr Gly Trp His Trp Ile Arg Gln Phe Pro Gly Asp Lys Leu Glu
        35                  40                  45

Trp Met Gly Tyr Ile Ser Phe Asn Gly Asp Tyr Asn Tyr Asn Pro Ser
    50                  55                  60

Leu Lys Ser Arg Ile Ser Ile Thr Arg Asp Thr Ser Lys Asn Gln Phe
65                  70                  75                  80

Phe Leu Gln Leu Ser Ser Val Thr Thr Glu Asp Thr Ala Thr Tyr Tyr
                85                  90                  95

Cys Ala Ser Ser Tyr Asp Gly Leu Phe Ala Tyr Trp Gly Gln Gly Thr
            100                 105                 110

Leu Val Thr Val Ser Ala
        115

<210> SEQ ID NO 156
<211> LENGTH: 118
<212> TYPE: PRT
<213> ORGANISM: Artificial Sequence
<220> FEATURE:
<223> OTHER INFORMATION: Amino acid sequence of the 3z1C02 heavy chain

<400> SEQUENCE: 156

His Asp Val Gln Leu Gln Glu Ser Gly Pro Asp Leu Val Lys Pro Ser
1               5                   10                  15

Gln Ser Leu Ser Leu Thr Cys Thr Val Thr Gly Phe Ser Ile Thr Ser
            20                  25                  30

Gly Tyr Gly Trp His Trp Ile Arg Gln Phe Pro Gly Asn Lys Leu Glu
        35                  40                  45

Trp Met Gly Tyr Ile Ser Phe Asn Gly Asp Ser Asn Tyr Asn Pro Ser
    50                  55                  60

```
Leu Lys Ser Arg Ile Ser Ile Thr Arg Asp Thr Ser Lys Asn Gln Phe
 65                 70                  75                  80

Phe Leu Gln Leu Asn Ser Val Thr Ser Glu Asp Thr Ala Thr Tyr Tyr
                 85                  90                  95

Cys Ala Ser Ser Tyr Asp Gly Leu Phe Ala Tyr Trp Gly Gln Gly Pro
            100                 105                 110

Leu Val Thr Val Ser Ala
        115

<210> SEQ ID NO 157
<211> LENGTH: 118
<212> TYPE: PRT
<213> ORGANISM: Artificial Sequence
<220> FEATURE:
<223> OTHER INFORMATION: Amino acid sequence of the 3z1C04 heavy chain

<400> SEQUENCE: 157

His Glu Val Gln Leu Gln Glu Ser Gly Pro Asp Leu Val Lys Pro Ser
 1               5                  10                  15

Gln Ser Leu Ser Leu Thr Cys Thr Val Thr Gly Phe Ser Ile Thr Ser
                 20                  25                  30

Gly Tyr Gly Trp His Trp Ile Arg Gln Phe Pro Gly Asn Lys Leu Glu
             35                  40                  45

Trp Met Gly Tyr Ile Asn Tyr Asp Gly His Asn Asp Tyr Asn Pro Ser
 50                  55                  60

Leu Lys Ser Arg Ile Ser Ile Thr Gln Asp Thr Ser Lys Asn Gln Phe
 65                  70                  75                  80

Phe Leu Gln Leu Asn Ser Val Thr Thr Glu Asp Thr Ala Thr Tyr Tyr
                 85                  90                  95

Cys Ala Ser Ser Tyr Asp Gly Leu Phe Ala Tyr Trp Gly Gln Gly Thr
            100                 105                 110

Leu Val Thr Val Ser Ala
        115

<210> SEQ ID NO 158
<211> LENGTH: 16
<212> TYPE: PRT
<213> ORGANISM: Artificial Sequence
<220> FEATURE:
<223> OTHER INFORMATION: Amino acid sequence of the 3z1A02 light chain
      CDR1

<400> SEQUENCE: 158

Lys Ser Ser Gln Ser Leu Leu His Ser Asp Gly Lys Thr Tyr Leu Asn
 1               5                  10                  15

<210> SEQ ID NO 159
<211> LENGTH: 7
<212> TYPE: PRT
<213> ORGANISM: Artificial Sequence
<220> FEATURE:
<223> OTHER INFORMATION: Amino acid sequence of the 3z1A02 light chain
      CDR2

<400> SEQUENCE: 159

Leu Val Ser Lys Leu Asp Ser
 1               5

<210> SEQ ID NO 160
<211> LENGTH: 9
<212> TYPE: PRT
<213> ORGANISM: Artificial Sequence
<220> FEATURE:
```

```
<223> OTHER INFORMATION: Amino acid sequence of the 3z1A02 light chain
      CDR3

<400> SEQUENCE: 160

Trp Gln Gly Thr His Phe Pro Arg Thr
1               5

<210> SEQ ID NO 161
<211> LENGTH: 10
<212> TYPE: PRT
<213> ORGANISM: Artificial Sequence
<220> FEATURE:
<223> OTHER INFORMATION: Amino acid sequence of the 3z1A02 heavy chain
      CDR1

<400> SEQUENCE: 161

Gly Tyr Thr Phe Thr Asp Tyr Asn Met His
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Amino acid sequence of the 3z1A02 heavy chain
      CDR2

<400> SEQUENCE: 162

Tyr Ile Asn Pro Tyr Asn Asp Val Thr Glu
1               5                   10

<210> SEQ ID NO 163
<211> LENGTH: 7
<212> TYPE: PRT
<213> ORGANISM: Artificial Sequence
<220> FEATURE:
<223> OTHER INFORMATION: Amino acid sequence of the 3z1A02 heavy chain
      CDR3

<400> SEQUENCE: 163

Ala Trp Phe Gly Leu Arg Gln
1               5

<210> SEQ ID NO 164
<211> LENGTH: 16
<212> TYPE: PRT
<213> ORGANISM: Artificial Sequence
<220> FEATURE:
<223> OTHER INFORMATION: Amino acid sequence of the 3z1E10 light chain
      CDR1

<400> SEQUENCE: 164

Arg Ser Ser Lys Ser Leu Leu His Ser Asn Gly Asn Thr Tyr Leu Tyr
1               5                   10                  15

<210> SEQ ID NO 165
<211> LENGTH: 7
<212> TYPE: PRT
<213> ORGANISM: Artificial Sequence
<220> FEATURE:
<223> OTHER INFORMATION: Amino acid sequence of the 3z1E10 light chain
      CDR2

<400> SEQUENCE: 165

Arg Met Ser Asn Leu Ala Ser
1               5

<210> SEQ ID NO 166
```

```
<211> LENGTH: 9
<212> TYPE: PRT
<213> ORGANISM: Artificial Sequence
<220> FEATURE:
<223> OTHER INFORMATION: Amino acid sequence of the 3z1E10 light chain
      CDR3

<400> SEQUENCE: 166

Met Gln His Leu Glu Tyr Pro Tyr Thr
1               5

<210> SEQ ID NO 167
<211> LENGTH: 10
<212> TYPE: PRT
<213> ORGANISM: Artificial Sequence
<220> FEATURE:
<223> OTHER INFORMATION: Amino acid sequence of the 3z1E10 heavy chain
      CDR1

<400> SEQUENCE: 167

Gly Asp Thr Phe Thr Asp Tyr Tyr Met Asn
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Amino acid sequence of the 3z1E10 heavy chain
      CDR2

<400> SEQUENCE: 168

Asp Ile Asn Pro Asn Tyr Gly Gly Ile Thr
1               5                   10

<210> SEQ ID NO 169
<211> LENGTH: 9
<212> TYPE: PRT
<213> ORGANISM: Artificial Sequence
<220> FEATURE:
<223> OTHER INFORMATION: Amino acid sequence of the 3z1E10 heavy chain
      CDR3

<400> SEQUENCE: 169

Gln Ala Tyr Tyr Arg Asn Ser Asp Tyr
1               5

<210> SEQ ID NO 170
<211> LENGTH: 11
<212> TYPE: PRT
<213> ORGANISM: Artificial Sequence
<220> FEATURE:
<223> OTHER INFORMATION: Amino acid sequence of the 3z1G12 light chain
      CDR1

<400> SEQUENCE: 170

Lys Ala Ser Gln Asp Val Gly Thr Ala Val Ala
1               5                   10

<210> SEQ ID NO 171
<211> LENGTH: 7
<212> TYPE: PRT
<213> ORGANISM: Artificial Sequence
<220> FEATURE:
<223> OTHER INFORMATION: Amino acid sequence of the 3z1G12 light chain
      CDR2

<400> SEQUENCE: 171

Trp Thr Ser Thr Arg His Thr
```

```
<210> SEQ ID NO 172
<211> LENGTH: 9
<212> TYPE: PRT
<213> ORGANISM: Artificial Sequence
<220> FEATURE:
<223> OTHER INFORMATION: Amino acid sequence of the 3z1G12 light chain
      CDR3

<400> SEQUENCE: 172

Gln Gln His Tyr Ser Ile Pro Leu Thr
1               5

<210> SEQ ID NO 173
<211> LENGTH: 10
<212> TYPE: PRT
<213> ORGANISM: Artificial Sequence
<220> FEATURE:
<223> OTHER INFORMATION: Amino acid sequence of the 3z1G12 heavy chain
      CDR1

<400> SEQUENCE: 173

Gly Tyr Ile Phe Thr Asp Tyr Glu Ile His
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Amino acid sequence of the 3z1G12 heavy chain
      CDR2

<400> SEQUENCE: 174

Val Ile Asp Pro Glu Thr Gly Asn Thr Ala
1               5                   10

<210> SEQ ID NO 175
<211> LENGTH: 6
<212> TYPE: PRT
<213> ORGANISM: Artificial Sequence
<220> FEATURE:
<223> OTHER INFORMATION: Amino acid sequence of the 3z1G12 heavy chain
      CDR3

<400> SEQUENCE: 175

Met Gly Tyr Ser Asp Tyr
1               5

<210> SEQ ID NO 176
<211> LENGTH: 240
<212> TYPE: PRT
<213> ORGANISM: Artificial Sequence
<220> FEATURE:
<223> OTHER INFORMATION: Humanized 3D3 antibody light chain

<400> SEQUENCE: 176

Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Leu Leu Asn Ser Asn Phe Gln Lys Asn Phe Leu Ala Trp Tyr Gln Gln
        50                  55                  60
```

```
Lys Pro Gly Gln Pro Pro Lys Leu Leu Ile Tyr Phe Ala Ser Thr Arg
 65                  70                  75                  80

Glu Ser Ser Val Pro Asp Arg Phe Ser Gly Ser Gly Ser Gly Thr Asp
                 85                  90                  95

Phe Thr Leu Thr Ile Ser Ser Leu Gln Ala Glu Asp Val Ala Val Tyr
            100                 105                 110

Tyr Cys Gln Gln His Tyr Ser Thr Pro Leu Thr Phe Gly Gln Gly Thr
        115                 120                 125

Lys Leu Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 177
<211> LENGTH: 462
<212> TYPE: PRT
<213> ORGANISM: Artificial Sequence
<220> FEATURE:
<223> OTHER INFORMATION: Humanized 3D3 antibody heavy chain

<400> SEQUENCE: 177

Met Asp Trp Thr Trp Arg Ile Leu Phe Leu Val Ala Ala Ala Thr Gly
  1               5                  10                  15

Thr His Ala Glu Val Gln Leu Val Gln Ser Gly Ala Glu Val Lys Lys
             20                  25                  30

Pro Gly Ala Ser Val Lys Val Ser Cys Lys Ala Ser Gly Tyr Ile Phe
         35                  40                  45

Thr Asp Tyr Glu Ile His Trp Val Arg Gln Ala Pro Gly Gln Gly Leu
     50                  55                  60

Glu Trp Met Gly Val Ile Asp Pro Glu Thr Gly Asn Thr Ala Phe Asn
 65                  70                  75                  80

Gln Lys Phe Lys Gly Arg Val Thr Ile Thr Ala Asp Thr Ser Thr Ser
                 85                  90                  95

Thr Ala Tyr Met Glu Leu Ser Ser Leu Thr Ser Glu Asp Thr Ala Val
            100                 105                 110

Tyr Tyr Cys Met Gly Tyr Ser Asp Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
```

```
                195             200                 205
Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
    450                 455                 460

<210> SEQ ID NO 178
<211> LENGTH: 113
<212> TYPE: PRT
<213> ORGANISM: Artificial Sequence
<220> FEATURE:
<223> OTHER INFORMATION: Humanized 3D3 antibody light chain variable
      region

<400> SEQUENCE: 178

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Asn Phe Gln Lys Asn Phe Leu Ala Trp Tyr Gln Gln Lys Pro Gly Gln
        35                  40                  45

Pro Pro Lys Leu Leu Ile Tyr Phe Ala Ser Thr Arg Glu Ser Ser Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Thr Pro Leu Thr Phe Gly Gln Gly Thr Lys Leu Glu Ile
```

Lys

<210> SEQ ID NO 179
<211> LENGTH: 113
<212> TYPE: PRT
<213> ORGANISM: Artificial Sequence
<220> FEATURE:
<223> OTHER INFORMATION: Humanized 3D3 antibody heavy chain variable region

<400> SEQUENCE: 179

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
            20                  25                  30

Glu Ile His Trp Val Arg Gln Ala Pro Gly Gln Gly Leu Glu Trp Met
        35                  40                  45

Gly Val Ile Asp Pro Glu Thr Gly Asn Thr Ala Phe Asn Gln Lys Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Met Gly Tyr Ser Asp Tyr Trp Gly Gln Gly Thr Leu Val Thr Val Ser
            100                 105                 110

Ser

<210> SEQ ID NO 180
<211> LENGTH: 234
<212> TYPE: PRT
<213> ORGANISM: Artificial Sequence
<220> FEATURE:
<223> OTHER INFORMATION: Humanized 3C4 antibody light chain

<400> SEQUENCE: 180

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Ile His Asn Phe Leu Asn Trp Phe Gln Gln Lys Pro Gly Lys Ala Pro
    50                  55                  60

Lys Thr Leu Ile Phe Arg Ala Asn Arg Leu Val Asp Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Ser Cys Leu Gln Tyr Asp
            100                 105                 110

Glu Ile Pro Leu Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

```
Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 181
<211> LENGTH: 466
<212> TYPE: PRT
<213> ORGANISM: Artificial Sequence
<220> FEATURE:
<223> OTHER INFORMATION: Humanized 3C4 antibody heavy chain

<400> SEQUENCE: 181

Met Asp Trp Thr Trp Arg Ile Leu Phe Leu Val Ala Ala Thr Gly
1               5                   10                  15

Thr His Ala Glu Val Gln Leu Gln Glu Ser Gly Pro Gly Leu Val Lys
            20                  25                  30

Pro Ser Gln Thr Leu Ser Leu Thr Cys Thr Val Ser Gly Phe Ser Ile
        35                  40                  45

Thr Ser Gly Tyr Gly Trp His Trp Ile Arg Gln His Pro Gly Lys Gly
    50                  55                  60

Leu Glu Trp Ile Gly Tyr Ile Asn Tyr Asp Gly His Asn Asp Tyr Asn
65                  70                  75                  80

Pro Ser Leu Lys Ser Arg Val Thr Ile Ser Gln Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Ser Ser Tyr Asp Gly Leu Phe Ala Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300
```

-continued

```
Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
        340                 345                 350

Lys Thr Ile Ser Lys Ala Lys Gly Gln Pro Arg Glu Pro Gln Val Tyr
            355                 360                 365

Thr Leu Pro Pro Ser Arg Asp Glu Leu Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
        420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 182
<211> LENGTH: 107
<212> TYPE: PRT
<213> ORGANISM: Artificial Sequence
<220> FEATURE:
<223> OTHER INFORMATION: Humanized 3C4 antibody light chain variable
      region

<400> SEQUENCE: 182

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Ile His Asn Phe
            20                  25                  30

Leu Asn Trp Phe Gln Gln Lys Pro Gly Lys Ala Pro Lys Thr Leu Ile
        35                  40                  45

Phe Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Ser Cys Leu Gln Tyr Asp Glu Ile Pro Leu
                85                  90                  95

Thr Phe Gly Gln Gly Thr Lys Leu Glu Ile Lys
            100                 105

<210> SEQ ID NO 183
<211> LENGTH: 116
<212> TYPE: PRT
<213> ORGANISM: Artificial Sequence
<220> FEATURE:
<223> OTHER INFORMATION: Humanized 3C4 antibody heavy chain variable
      region

<400> SEQUENCE: 183

Glu Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Ser Gly
```

```
                     20                  25                  30
Tyr Gly Trp His Trp Ile Arg Gln His Pro Gly Lys Gly Leu Glu Trp
             35                  40                  45

Ile Gly Tyr Ile Asn Tyr Asp Gly His Asn Asp Tyr Asn Pro Ser Leu
     50                  55                  60

Lys Ser Arg Val Thr Ile Ser Gln Asp Thr Ser Lys Asn Gln Phe Ser
 65                  70                  75                  80

Leu Lys Leu Ser Ser Val Thr Ala Ala Asp Thr Ala Val Tyr Tyr Cys
             85                  90                  95

Ala Ser Ser Tyr Asp Gly Leu Phe Ala Tyr Trp Gly Gln Gly Thr Leu
            100                 105                 110

Val Thr Val Ser
        115

<210> SEQ ID NO 184
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.111

<400> SEQUENCE: 184

Lys Ser Ser Gln Ser Leu Leu Asn Ser Ser Asn Gln Lys Asn Tyr Leu
 1               5                  10                  15

Ala

<210> SEQ ID NO 185
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.112

<400> SEQUENCE: 185

Lys Ser Ser Gln Ser Leu Leu Asn Ser Ser Asn Gln Lys Asn Tyr Leu
 1               5                  10                  15

Ala

<210> SEQ ID NO 186
<211> LENGTH: 17
<212> TYPE: PRT
<213> ORGANISM: Artificial Sequence
<220> FEATURE:
<223> OTHER INFORMATION: CDRL1 corresponding to resid3es 24-40 of
      SEQ ID NO.113

<400> SEQUENCE: 186

Lys Ser Ser Gln Ser Leu Leu Asn Ser Ser Asn Gln Lys Asn Tyr Leu
 1               5                  10                  15

Ala

<210> SEQ ID NO 187
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.114

<400> SEQUENCE: 187

Lys Ser Ser Gln Ser Leu Leu Asn Ser Ser Asn Gln Lys Asn Tyr Leu
```

```
1               5                   10                  15
Ala

<210> SEQ ID NO 188
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.115

<400> SEQUENCE: 188

Lys Ser Ser Gln Ser Leu Leu Asn Ser Ser Asn Gln Lys Asn Tyr Leu
1               5                   10                  15

Ala

<210> SEQ ID NO 189
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.116

<400> SEQUENCE: 189

Lys Ser Ser Gln Ser Leu Leu Asn Ser Ser Asn Gln Lys Asn Tyr Leu
1               5                   10                  15

Ala

<210> SEQ ID NO 190
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.117

<400> SEQUENCE: 190

Lys Ser Ser Gln Ser Leu Leu Asn Ser Ser Asn Gln Lys Asn Tyr Leu
1               5                   10                  15

Ala

<210> SEQ ID NO 191
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.118

<400> SEQUENCE: 191

Lys Ser Ser Gln Ser Leu Leu Asn Ser Ser Asn Gln Lys Asn Tyr Leu
1               5                   10                  15

Ala

<210> SEQ ID NO 192
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.123

<400> SEQUENCE: 192

Lys Ser Ser Gln Ser Leu Leu Asn Ser Ser Asn Gln Lys Asn Tyr Leu
```

```
                 1               5                  10                  15
Ala

<210> SEQ ID NO 193
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.125

<400> SEQUENCE: 193

Lys Ser Ser Gln Ser Leu Leu Asn Ser Ser Asn Gln Lys Asn Tyr Leu
 1               5                  10                  15
Ala

<210> SEQ ID NO 194
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.119

<400> SEQUENCE: 194

Lys Ser Ser Gln Ser Leu Leu Asn Arg Ser Asn Gln Lys Asn Tyr Leu
 1               5                  10                  15
Ala

<210> SEQ ID NO 195
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.120

<400> SEQUENCE: 195

Lys Ser Ser Gln Ser Leu Leu Asn Asn Ser Asn Gln Lys Asn Tyr Leu
 1               5                  10                  15
Ala

<210> SEQ ID NO 196
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.121

<400> SEQUENCE: 196

Lys Ser Ser Gln Ser Leu Leu Asn Thr Ser Asn Gln Leu Asn Tyr Leu
 1               5                  10                  15
Ala

<210> SEQ ID NO 197
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.122

<400> SEQUENCE: 197

Lys Ser Ser Gln Ser Leu Leu Asn Thr Ser Asn Gln Lys Asn Tyr Leu
```

```
                1               5                  10                  15
Ala

<210> SEQ ID NO 198
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.110

<400> SEQUENCE: 198

Lys Ser Ser Gln Ser Leu Leu Asn Ser Asn Asn Gln Leu Asn Tyr Leu
1               5                  10                  15
Ala

<210> SEQ ID NO 199
<211> LENGTH: 17
<212> TYPE: PRT
<213> ORGANISM: Artificial Sequence
<220> FEATURE:
<223> OTHER INFORMATION: CDRL1 corresponding to residues 24-40 of
      SEQ ID NO.124

<400> SEQUENCE: 199

Lys Ser Ser Gln Ser Leu Leu Asn Ser Asn Phe Gln Lys Asn Phe Leu
1               5                  10                  15
Ala

<210> SEQ ID NO 200
<211> LENGTH: 16
<212> TYPE: PRT
<213> ORGANISM: Artificial Sequence
<220> FEATURE:
<223> OTHER INFORMATION: CDRL1 corresponding to residues 24-39 of
      SEQ ID NO.105

<400> SEQUENCE: 200

Lys Ser Ser Gln Ser Leu Leu His Ser Asp Gly Lys Thr Tyr Leu Asn
1               5                  10                  15

<210> SEQ ID NO 201
<211> LENGTH: 16
<212> TYPE: PRT
<213> ORGANISM: Artificial Sequence
<220> FEATURE:
<223> OTHER INFORMATION: CDRL1 corresponding to residues 24-39 of
      SEQ ID NO.107

<400> SEQUENCE: 201

Lys Ser Ser Gln Ser Leu Leu His Ser Asp Gly Lys Thr Tyr Leu Asn
1               5                  10                  15

<210> SEQ ID NO 202
<211> LENGTH: 16
<212> TYPE: PRT
<213> ORGANISM: Artificial Sequence
<220> FEATURE:
<223> OTHER INFORMATION: CDRL1 corresponding to residues 24-39 of
      SEQ ID NO.106

<400> SEQUENCE: 202

Lys Ser Ser Gln Ser Leu Leu Tyr Ser Asp Gly Lys Thr Tyr Leu Asn
1               5                  10                  15

<210> SEQ ID NO 203
```

```
<211> LENGTH: 16
<212> TYPE: PRT
<213> ORGANISM: Artificial Sequence
<220> FEATURE:
<223> OTHER INFORMATION: CDRL1 corresponding to residues 24-39 of
      SEQ ID NO.108

<400> SEQUENCE: 203

Arg Ser Ser Gln Ser Leu Leu His Ser Asn Gly Asn Thr Tyr Leu Glu
1               5                   10                  15

<210> SEQ ID NO 204
<211> LENGTH: 16
<212> TYPE: PRT
<213> ORGANISM: Artificial Sequence
<220> FEATURE:
<223> OTHER INFORMATION: CDRL1 corresponding to residues 24-39 of
      SEQ ID NO.109

<400> SEQUENCE: 204

Arg Ser Ser Lys Ser Leu Leu His Ser Asn Gly Asn Thr Tyr Leu Tyr
1               5                   10                  15

<210> SEQ ID NO 205
<211> LENGTH: 11
<212> TYPE: PRT
<213> ORGANISM: Artificial Sequence
<220> FEATURE:
<223> OTHER INFORMATION: CDRL1 corresponding to residues 24-34 of
      SEQ ID NO.:127

<400> SEQUENCE: 205

Lys Ala Ser Gln Asp Ile His Asn Phe Leu Asn
1               5                   10

<210> SEQ ID NO 206
<211> LENGTH: 11
<212> TYPE: PRT
<213> ORGANISM: Artificial Sequence
<220> FEATURE:
<223> OTHER INFORMATION: CDRL1 corresponding to residues 24-34 of
      SEQ ID NO.:131

<400> SEQUENCE: 206

Lys Ala Ser Gln Asp Ile His Arg Phe Leu Asn
1               5                   10

<210> SEQ ID NO 207
<211> LENGTH: 11
<212> TYPE: PRT
<213> ORGANISM: Artificial Sequence
<220> FEATURE:
<223> OTHER INFORMATION: CDRL1 corresponding to residues 24-34 of
      SEQ ID NO.:129

<400> SEQUENCE: 207

Lys Ala Ser Gln Asp Ile His Asn Tyr Leu Asn
1               5                   10

<210> SEQ ID NO 208
<211> LENGTH: 11
<212> TYPE: PRT
<213> ORGANISM: Artificial Sequence
<220> FEATURE:
<223> OTHER INFORMATION: CDRL1 corresponding to residues 24-34 of
      SEQ ID NO.:130

<400> SEQUENCE: 208

Lys Ala Ser Gln Asp Ile His Asn Tyr Leu Asn
```

```
<210> SEQ ID NO 209
<211> LENGTH: 11
<212> TYPE: PRT
<213> ORGANISM: Artificial Sequence
<220> FEATURE:
<223> OTHER INFORMATION: CDRL1 corresponding to residues 24-34 of
      SEQ ID NO.:128

<400> SEQUENCE: 209

Lys Ala Ser Gln Asp Ile His Thr Tyr Leu Asn
1               5                   10

<210> SEQ ID NO 210
<211> LENGTH: 11
<212> TYPE: PRT
<213> ORGANISM: Artificial Sequence
<220> FEATURE:
<223> OTHER INFORMATION: CDRL1 corresponding to residues 24-34 of
      SEQ ID NO.:126

<400> SEQUENCE: 210

Lys Ala Ser Gln Asp Val Gly Thr Ala Val Ala
1               5                   10

<210> SEQ ID NO 211
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:111

<400> SEQUENCE: 211

Phe Ala Ser Thr Arg Glu Ser
1               5

<210> SEQ ID NO 212
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:112

<400> SEQUENCE: 212

Phe Ala Ser Thr Arg Glu Ser
1               5

<210> SEQ ID NO 213
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:121

<400> SEQUENCE: 213

Phe Ala Ser Thr Thr Glu Ser
1               5

<210> SEQ ID NO 214
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:113
```

-continued

```
<400> SEQUENCE: 214

Phe Ala Ser Thr Arg Glu Ser
1               5

<210> SEQ ID NO 215
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:114

<400> SEQUENCE: 215

Phe Ala Ser Thr Arg Glu Ser
1               5

<210> SEQ ID NO 216
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:125

<400> SEQUENCE: 216

Phe Gly Ser Thr Arg Glu Ser
1               5

<210> SEQ ID NO 217
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:118

<400> SEQUENCE: 217

Phe Gly Ser Thr Arg Glu Ser
1               5

<210> SEQ ID NO 218
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:115

<400> SEQUENCE: 218

Phe Ala Ser Thr Arg Glu Ser
1               5

<210> SEQ ID NO 219
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:116

<400> SEQUENCE: 219

Phe Ala Ser Thr Arg Glu Ser
1               5

<210> SEQ ID NO 220
<211> LENGTH: 7
<212> TYPE: PRT
```

```
<213> ORGANISM: Artificial Sequence
<220> FEATURE:
<223> OTHER INFORMATION: CDRL2 corresponding to residues 56-62 of
      SEQ ID NO.:117

<400> SEQUENCE: 220

Phe Ala Ser Thr Arg Glu Ser
1               5

<210> SEQ ID NO 221
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:119

<400> SEQUENCE: 221

Phe Ala Ser Thr Arg Glu Ser
1               5

<210> SEQ ID NO 222
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:120

<400> SEQUENCE: 222

Phe Ala Ser Thr Arg Glu Ser
1               5

<210> SEQ ID NO 223
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:123

<400> SEQUENCE: 223

Phe Ala Ser Thr Arg Glu Ser
1               5

<210> SEQ ID NO 224
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:124

<400> SEQUENCE: 224

Phe Ala Ser Thr Arg Glu Ser
1               5

<210> SEQ ID NO 225
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:110

<400> SEQUENCE: 225

Phe Ala Ser Thr Arg Lys Ser
1               5
```

```
<210> SEQ ID NO 226
<211> LENGTH: 7
<212> TYPE: PRT
<213> ORGANISM: Artificial Sequence
<220> FEATURE:
<223> OTHER INFORMATION: CDRL2 corresponding to residues 56-62 of
      SEQ ID NO.:122

<400> SEQUENCE: 226

Phe Ala Ser Thr Arg Ala Ser
1               5

<210> SEQ ID NO 227
<211> LENGTH: 7
<212> TYPE: PRT
<213> ORGANISM: Artificial Sequence
<220> FEATURE:
<223> OTHER INFORMATION: CDRL2 corresponding to residues 55-61 of
      SEQ ID NO.:105

<400> SEQUENCE: 227

Leu Val Ser Lys Leu Asp Ser
1               5

<210> SEQ ID NO 228
<211> LENGTH: 7
<212> TYPE: PRT
<213> ORGANISM: Artificial Sequence
<220> FEATURE:
<223> OTHER INFORMATION: CDRL2 corresponding to residues 55-61 of
      SEQ ID NO.:106

<400> SEQUENCE: 228

Leu Val Ser Lys Leu Asp Ser
1               5

<210> SEQ ID NO 229
<211> LENGTH: 7
<212> TYPE: PRT
<213> ORGANISM: Artificial Sequence
<220> FEATURE:
<223> OTHER INFORMATION: CDRL2 corresponding to residues 55-61 of
      SEQ ID NO.:107

<400> SEQUENCE: 229

Leu Val Ser Lys Leu Asp Ser
1               5

<210> SEQ ID NO 230
<211> LENGTH: 7
<212> TYPE: PRT
<213> ORGANISM: Artificial Sequence
<220> FEATURE:
<223> OTHER INFORMATION: CDRL2 corresponding to residues 55-61 of
      SEQ ID NO.:108

<400> SEQUENCE: 230

Lys Val Ser Asn Arg Phe Ser
1               5

<210> SEQ ID NO 231
<211> LENGTH: 7
<212> TYPE: PRT
<213> ORGANISM: Artificial Sequence
<220> FEATURE:
<223> OTHER INFORMATION: CDRL2 corresponding to residues 50-56 of
      SEQ ID NO.:127

<400> SEQUENCE: 231
```

Arg Ala Asn Arg Leu Val Asp
1               5

<210> SEQ ID NO 232
<211> LENGTH: 7
<212> TYPE: PRT
<213> ORGANISM: Artificial Sequence
<220> FEATURE:
<223> OTHER INFORMATION: CDRL2 corresponding to residues 50-56 of
      SEQ ID NO.:128

<400> SEQUENCE: 232

Arg Ala Asn Arg Leu Val Asp
1               5

<210> SEQ ID NO 233
<211> LENGTH: 7
<212> TYPE: PRT
<213> ORGANISM: Artificial Sequence
<220> FEATURE:
<223> OTHER INFORMATION: CDRL2 corresponding to residues 50-56 of
      SEQ ID NO.:131

<400> SEQUENCE: 233

His Ala Asn Arg Leu Val Asp
1               5

<210> SEQ ID NO 234
<211> LENGTH: 7
<212> TYPE: PRT
<213> ORGANISM: Artificial Sequence
<220> FEATURE:
<223> OTHER INFORMATION: CDRL2 corresponding to residues 50-56 of
      SEQ ID NO.:129

<400> SEQUENCE: 234

Arg Ala Asn Arg Leu Val Ala
1               5

<210> SEQ ID NO 235
<211> LENGTH: 7
<212> TYPE: PRT
<213> ORGANISM: Artificial Sequence
<220> FEATURE:
<223> OTHER INFORMATION: CDRL2 corresponding to residues 50-56 of
      SEQ ID NO.:130

<400> SEQUENCE: 235

Arg Ala Asn Arg Leu Val Ala
1               5

<210> SEQ ID NO 236
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:114

<400> SEQUENCE: 236

Gln Gln His Tyr Ser Thr Pro Leu Thr
1               5

<210> SEQ ID NO 237
<211> LENGTH: 9
<212> TYPE: PRT
<213> ORGANISM: Artificial Sequence
<220> FEATURE:

<223> OTHER INFORMATION: CDRL3 corresponding to residues 95-103 of
      SEQ ID NO.:115

<400> SEQUENCE: 237

Gln Gln His Tyr Ser Thr Pro Leu Thr
1               5

<210> SEQ ID NO 238
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:116

<400> SEQUENCE: 238

Gln Gln His Tyr Ser Thr Pro Leu Thr
1               5

<210> SEQ ID NO 239
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:117

<400> SEQUENCE: 239

Gln Gln His Tyr Ser Thr Pro Leu Thr
1               5

<210> SEQ ID NO 240
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:118

<400> SEQUENCE: 240

Gln Gln His Tyr Ser Thr Pro Leu Thr
1               5

<210> SEQ ID NO 241
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:120

<400> SEQUENCE: 241

Gln Gln His Tyr Ser Thr Pro Leu Thr
1               5

<210> SEQ ID NO 242
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:121

<400> SEQUENCE: 242

Gln Gln His Tyr Ser Thr Pro Leu Thr
1               5

<210> SEQ ID NO 243

```
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:122

<400> SEQUENCE: 243

Gln Gln His Tyr Ser Thr Pro Leu Thr
1               5

<210> SEQ ID NO 244
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:123

<400> SEQUENCE: 244

Gln Gln His Tyr Ser Thr Pro Leu Thr
1               5

<210> SEQ ID NO 245
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:124

<400> SEQUENCE: 245

Gln Gln His Tyr Ser Thr Pro Leu Thr
1               5

<210> SEQ ID NO 246
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:125

<400> SEQUENCE: 246

Gln Gln His Tyr Ser Thr Pro Leu Thr
1               5

<210> SEQ ID NO 247
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:111

<400> SEQUENCE: 247

Gln Gln His Tyr Ser Ile Pro Leu Thr
1               5

<210> SEQ ID NO 248
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:112

<400> SEQUENCE: 248

Gln Gln His Tyr Ser Ile Pro Leu Thr
```

```
<210> SEQ ID NO 249
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:113

<400> SEQUENCE: 249

Gln Gln His Tyr Ser Ile Pro Leu Thr
1               5

<210> SEQ ID NO 250
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:119

<400> SEQUENCE: 250

Gln Gln His Tyr Ser Ile Pro Leu Thr
1               5

<210> SEQ ID NO 251
<211> LENGTH: 9
<212> TYPE: PRT
<213> ORGANISM: Artificial Sequence
<220> FEATURE:
<223> OTHER INFORMATION: CDRL3 corresponding to residues 89-97 of
      SEQ ID NO.:126

<400> SEQUENCE: 251

Gln Gln His Tyr Ser Ile Pro Leu Thr
1               5

<210> SEQ ID NO 252
<211> LENGTH: 9
<212> TYPE: PRT
<213> ORGANISM: Artificial Sequence
<220> FEATURE:
<223> OTHER INFORMATION: CDRL3 corresponding to residues 95-103 of
      SEQ ID NO.:110

<400> SEQUENCE: 252

Gln Gln His Phe Asn Thr Pro Leu Thr
1               5

<210> SEQ ID NO 253
<211> LENGTH: 9
<212> TYPE: PRT
<213> ORGANISM: Artificial Sequence
<220> FEATURE:
<223> OTHER INFORMATION: CDRL3 corresponding to residues 89-97 of
      SEQ ID NO.:129

<400> SEQUENCE: 253

Leu Gln Tyr Asp Ala Phe Pro Leu Thr
1               5

<210> SEQ ID NO 254
<211> LENGTH: 9
<212> TYPE: PRT
<213> ORGANISM: Artificial Sequence
<220> FEATURE:
<223> OTHER INFORMATION: CDRL3 corresponding to residues 89-97 of
      SEQ ID NO.:130
```

```
<400> SEQUENCE: 254

Leu Gln Tyr Asp Ala Phe Pro Leu Thr
1               5

<210> SEQ ID NO 255
<211> LENGTH: 9
<212> TYPE: PRT
<213> ORGANISM: Artificial Sequence
<220> FEATURE:
<223> OTHER INFORMATION: CDRL3 corresponding to residues 89-97 of
      SEQ ID NO.:131

<400> SEQUENCE: 255

Leu Gln Tyr Asp Ala Phe Pro Leu Thr
1               5

<210> SEQ ID NO 256
<211> LENGTH: 9
<212> TYPE: PRT
<213> ORGANISM: Artificial Sequence
<220> FEATURE:
<223> OTHER INFORMATION: CDRL3 corresponding to residues 89-97 of
      SEQ ID NO.:128

<400> SEQUENCE: 256

Leu Gln Tyr Asp Glu Phe Pro Leu Thr
1               5

<210> SEQ ID NO 257
<211> LENGTH: 9
<212> TYPE: PRT
<213> ORGANISM: Artificial Sequence
<220> FEATURE:
<223> OTHER INFORMATION: CDRL3 corresponding to residues 89-97 of
      SEQ ID NO.:127

<400> SEQUENCE: 257

Leu Gln Tyr Asp Glu Ile Pro Leu Thr
1               5

<210> SEQ ID NO 258
<211> LENGTH: 9
<212> TYPE: PRT
<213> ORGANISM: Artificial Sequence
<220> FEATURE:
<223> OTHER INFORMATION: CDRL3 corresponding to residues 94-102 of
      SEQ ID NO.:105

<400> SEQUENCE: 258

Trp Gln Gly Thr His Phe Pro Arg Thr
1               5

<210> SEQ ID NO 259
<211> LENGTH: 9
<212> TYPE: PRT
<213> ORGANISM: Artificial Sequence
<220> FEATURE:
<223> OTHER INFORMATION: CDRL3 corresponding to residues 94-102 of
      SEQ ID NO.:106

<400> SEQUENCE: 259

Trp Gln Gly Thr His Phe Pro Arg Thr
1               5

<210> SEQ ID NO 260
<211> LENGTH: 9
<212> TYPE: PRT
```

```
<213> ORGANISM: Artificial Sequence
<220> FEATURE:
<223> OTHER INFORMATION: CDRL3 corresponding to residues 94-102 of
      SEQ ID NO.:107

<400> SEQUENCE: 260

Trp Gln Gly Thr His Phe Pro Arg Thr
1               5

<210> SEQ ID NO 261
<211> LENGTH: 9
<212> TYPE: PRT
<213> ORGANISM: Artificial Sequence
<220> FEATURE:
<223> OTHER INFORMATION: CDRL3 corresponding to residues 94-102 of
      SEQ ID NO.:108

<400> SEQUENCE: 261

Phe Gln Gly Ser His Val Pro Leu Thr
1               5

<210> SEQ ID NO 262
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:136

<400> SEQUENCE: 262

Gly Tyr Thr Phe Thr Asp Tyr Glu Ile His
1               5                   10

<210> SEQ ID NO 263
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:137

<400> SEQUENCE: 263

Gly Tyr Thr Phe Thr Asp Tyr Glu Ile His
1               5                   10

<210> SEQ ID NO 264
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:138

<400> SEQUENCE: 264

Gly Tyr Thr Phe Thr Asp Tyr Glu Ile His
1               5                   10

<210> SEQ ID NO 265
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:140

<400> SEQUENCE: 265

Gly Tyr Thr Phe Thr Asp Tyr Glu Ile His
1               5                   10
```

<210> SEQ ID NO 266
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:142

<400> SEQUENCE: 266

Gly Tyr Thr Phe Thr Asp Tyr Glu Ile His
1               5                   10

<210> SEQ ID NO 267
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:143

<400> SEQUENCE: 267

Gly Tyr Thr Phe Thr Asp Tyr Glu Ile His
1               5                   10

<210> SEQ ID NO 268
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:147

<400> SEQUENCE: 268

Gly Tyr Thr Phe Thr Asp Tyr Glu Ile His
1               5                   10

<210> SEQ ID NO 269
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:148

<400> SEQUENCE: 269

Gly Tyr Thr Phe Thr Asp Tyr Glu Ile His
1               5                   10

<210> SEQ ID NO 270
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:149

<400> SEQUENCE: 270

Gly Tyr Thr Phe Thr Asp Tyr Glu Ile His
1               5                   10

<210> SEQ ID NO 271
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:144

<400> SEQUENCE: 271

```
<210> SEQ ID NO 272
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:145

<400> SEQUENCE: 272

Gly Tyr Ile Phe Thr Asp Tyr Glu Ile His
1               5                   10

<210> SEQ ID NO 273
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:135

<400> SEQUENCE: 273

Gly Tyr Ile Phe Thr Asp Tyr Glu Val His
1               5                   10

<210> SEQ ID NO 274
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:141

<400> SEQUENCE: 274

Gly Tyr Thr Phe Thr Asp Tyr Glu Val His
1               5                   10

<210> SEQ ID NO 275
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:146

<400> SEQUENCE: 275

Gly Tyr Thr Phe Thr Asp Tyr Glu Val His
1               5                   10

<210> SEQ ID NO 276
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:139

<400> SEQUENCE: 276

Gly Tyr Thr Phe Thr Asp Tyr Glu Met His
1               5                   10

<210> SEQ ID NO 277
<211> LENGTH: 10
<212> TYPE: PRT
<213> ORGANISM: Artificial Sequence
<220> FEATURE:
```

```
<223> OTHER INFORMATION: CDRH1 corresponding to residues 27-36 of
      SEQ ID NO.:151

<400> SEQUENCE: 277

Gly Tyr Thr Phe Ser Asp Tyr Glu Met His
1               5                   10

<210> SEQ ID NO 278
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:150

<400> SEQUENCE: 278

Gly Tyr Thr Phe Thr Asp Tyr Glu Met His
1               5                   10

<210> SEQ ID NO 279
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:152

<400> SEQUENCE: 279

Gly Tyr Lys Phe Thr Asp Tyr Glu Met His
1               5                   10

<210> SEQ ID NO 280
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:132

<400> SEQUENCE: 280

Gly Tyr Thr Phe Thr Asp Tyr Asn Met His
1               5                   10

<210> SEQ ID NO 281
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:133

<400> SEQUENCE: 281

Gly Tyr Ile Phe Thr Glu Tyr Asn Ile His
1               5                   10

<210> SEQ ID NO 282
<211> LENGTH: 10
<212> TYPE: PRT
<213> ORGANISM: Artificial Sequence
<220> FEATURE:
<223> OTHER INFORMATION: CDRH1 corresponding to residues 27-36 of
      SEQ ID NO.:134

<400> SEQUENCE: 282

Gly Tyr Thr Phe Thr Glu Tyr Asn Met His
1               5                   10

<210> SEQ ID NO 283
```

```
<211> LENGTH: 11
<212> TYPE: PRT
<213> ORGANISM: Artificial Sequence
<220> FEATURE:
<223> OTHER INFORMATION: CDRH1 corresponding to residues 27-37 of
      SEQ ID NO.:155

<400> SEQUENCE: 283

Gly Phe Ser Ile Thr Ser Gly Tyr Gly Trp His
1               5                   10

<210> SEQ ID NO 284
<211> LENGTH: 11
<212> TYPE: PRT
<213> ORGANISM: Artificial Sequence
<220> FEATURE:
<223> OTHER INFORMATION: CDRH1 corresponding to residues 27-37 of
      SEQ ID NO.:156

<400> SEQUENCE: 284

Gly Phe Ser Ile Thr Ser Gly Tyr Gly Trp His
1               5                   10

<210> SEQ ID NO 285
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:141

<400> SEQUENCE: 285

Val Ile Asp Pro Ala Thr Gly Asp Thr Ala
1               5                   10

<210> SEQ ID NO 286
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:150

<400> SEQUENCE: 286

Val Ile Asp Pro Ala Thr Gly Asp Thr Ala
1               5                   10

<210> SEQ ID NO 287
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:135

<400> SEQUENCE: 287

Val Ile Asp Pro Glu Thr Gly Asp Thr Ala
1               5                   10

<210> SEQ ID NO 288
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:142

<400> SEQUENCE: 288

Val Ile Asp Pro Glu Thr Gly Asp Thr Ala
```

<210> SEQ ID NO 289
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:143

<400> SEQUENCE: 289

Val Ile Asp Pro Glu Thr Gly Asp Thr Ala
1               5                   10

<210> SEQ ID NO 290
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:140

<400> SEQUENCE: 290

Val Ile Asp Pro Glu Thr Gly Asp Thr Ala
1               5                   10

<210> SEQ ID NO 291
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:147

<400> SEQUENCE: 291

Val Ile Asp Pro Glu Thr Gly Val Thr Ala
1               5                   10

<210> SEQ ID NO 292
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:148

<400> SEQUENCE: 292

Val Ile Asp Pro Glu Thr Gly Val Thr Ala
1               5                   10

<210> SEQ ID NO 293
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:144

<400> SEQUENCE: 293

Val Ile Asp Pro Glu Thr Gly Asn Thr Ala
1               5                   10

<210> SEQ ID NO 294
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:145

```
<400> SEQUENCE: 294

Val Ile Asp Pro Glu Thr Gly Asn Thr Ala
1               5                   10

<210> SEQ ID NO 295
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:138

<400> SEQUENCE: 295

Val Ile Asp Pro Glu Thr Gly Ser Thr Ala
1               5                   10

<210> SEQ ID NO 296
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:139

<400> SEQUENCE: 296

Val Ile Asp Pro Glu Thr Gly Ser Thr Ala
1               5                   10

<210> SEQ ID NO 297
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:137

<400> SEQUENCE: 297

Val Ile Asp Pro Glu Thr Gly Ala Thr Ala
1               5                   10

<210> SEQ ID NO 298
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:146

<400> SEQUENCE: 298

Val Ile Asp Pro Glu Thr Gly Ala Thr Ala
1               5                   10

<210> SEQ ID NO 299
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:151

<400> SEQUENCE: 299

Gly Ile Asp Pro Glu Thr Gly Asp Thr Val
1               5                   10

<210> SEQ ID NO 300
<211> LENGTH: 10
<212> TYPE: PRT
```

```
<213> ORGANISM: Artificial Sequence
<220> FEATURE:
<223> OTHER INFORMATION: CDRH2 corresponding to residues 51-60 of
      SEQ ID NO.:152

<400> SEQUENCE: 300

Gly Ile Asp Pro Glu Thr Gly Gly Thr Ala
1               5                   10

<210> SEQ ID NO 301
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:136

<400> SEQUENCE: 301

Val Ile Asp Pro Glu Thr Gly Gly Thr Ala
1               5                   10

<210> SEQ ID NO 302
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:149

<400> SEQUENCE: 302

Val Leu Asp Pro Gly Thr Gly Arg Thr Ala
1               5                   10

<210> SEQ ID NO 303
<211> LENGTH: 9
<212> TYPE: PRT
<213> ORGANISM: Artificial Sequence
<220> FEATURE:
<223> OTHER INFORMATION: CDRH2 corresponding to residues 52-60 of
      SEQ ID NO.:155

<400> SEQUENCE: 303

Tyr Ile Ser Phe Asn Gly Asp Tyr Asn
1               5

<210> SEQ ID NO 304
<211> LENGTH: 9
<212> TYPE: PRT
<213> ORGANISM: Artificial Sequence
<220> FEATURE:
<223> OTHER INFORMATION: CDRH2 corresponding to residues 52-60 of
      SEQ ID NO.:156

<400> SEQUENCE: 304

Tyr Ile Ser Phe Asn Gly Asp Ser Asn
1               5

<210> SEQ ID NO 305
<211> LENGTH: 9
<212> TYPE: PRT
<213> ORGANISM: Artificial Sequence
<220> FEATURE:
<223> OTHER INFORMATION: CDRH2 corresponding to residues 52-60 of
      SEQ ID NO.:157

<400> SEQUENCE: 305

Tyr Ile Asn Tyr Asp Gly His Asn Asp
1               5
```

<210> SEQ ID NO 306
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:133

<400> SEQUENCE: 306

Asn Ile Asn Pro Tyr Asn Asp Val Thr Glu
1               5                   10

<210> SEQ ID NO 307
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:134

<400> SEQUENCE: 307

Asn Ile Asn Pro Tyr Asn Asn Val Thr Glu
1               5                   10

<210> SEQ ID NO 308
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:132

<400> SEQUENCE: 308

Tyr Ile Asn Pro Tyr Asn Asp Val Thr Glu
1               5                   10

<210> SEQ ID NO 309
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:153

<400> SEQUENCE: 309

Asp Ile Asn Pro Asn Tyr Gly Gly Ile Thr
1               5                   10

<210> SEQ ID NO 310
<211> LENGTH: 10
<212> TYPE: PRT
<213> ORGANISM: Artificial Sequence
<220> FEATURE:
<223> OTHER INFORMATION: CDRH2 corresponding to residues 51-60 of
      SEQ ID NO.:154

<400> SEQUENCE: 310

Asp Ile Asn Pro Tyr Tyr Gly Thr Thr Thr
1               5                   10

<210> SEQ ID NO 311
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:146

<400> SEQUENCE: 311

Met Ser Tyr Ser Asp Tyr
1               5

<210> SEQ ID NO 312
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:149

<400> SEQUENCE: 312

Met Ser Tyr Ser Asp Tyr
1               5

<210> SEQ ID NO 313
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:136

<400> SEQUENCE: 313

Met Gly Tyr Ser Asp Tyr
1               5

<210> SEQ ID NO 314
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:137

<400> SEQUENCE: 314

Met Gly Tyr Ser Asp Tyr
1               5

<210> SEQ ID NO 315
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:138

<400> SEQUENCE: 315

Met Gly Tyr Ser Asp Tyr
1               5

<210> SEQ ID NO 316
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:141

<400> SEQUENCE: 316

Met Gly Tyr Ser Asp Tyr
1               5

<210> SEQ ID NO 317
<211> LENGTH: 6
<212> TYPE: PRT
<213> ORGANISM: Artificial Sequence
<220> FEATURE:

```
<223> OTHER INFORMATION: CDRH3 corresponding to residues 98-103 of
      SEQ ID NO.:142

<400> SEQUENCE: 317

Met Gly Tyr Ser Asp Tyr
1               5

<210> SEQ ID NO 318
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:143

<400> SEQUENCE: 318

Met Gly His Ser Asp Tyr
1               5

<210> SEQ ID NO 319
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:144

<400> SEQUENCE: 319

Met Gly Tyr Ser Asp Tyr
1               5

<210> SEQ ID NO 320
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:145

<400> SEQUENCE: 320

Met Gly Tyr Ser Asp Tyr
1               5

<210> SEQ ID NO 321
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:147

<400> SEQUENCE: 321

Met Gly Tyr Ser Asp Tyr
1               5

<210> SEQ ID NO 322
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:148

<400> SEQUENCE: 322

Met Gly Tyr Ser Asp Tyr
1               5

<210> SEQ ID NO 323
```

```
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:150

<400> SEQUENCE: 323

Met Gly Tyr Ser Asp Tyr
1               5

<210> SEQ ID NO 324
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:139

<400> SEQUENCE: 324

Met Gly Tyr Ala Asp Tyr
1               5

<210> SEQ ID NO 325
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:140

<400> SEQUENCE: 325

Met Gly Tyr Ala Asp Tyr
1               5

<210> SEQ ID NO 326
<211> LENGTH: 7
<212> TYPE: PRT
<213> ORGANISM: Artificial Sequence
<220> FEATURE:
<223> OTHER INFORMATION: CDRH3 corresponding to residues 98-104 of
      SEQ ID NO.:151

<400> SEQUENCE: 326

Ile Ser Tyr Ala Met Asp Tyr
1               5

<210> SEQ ID NO 327
<211> LENGTH: 7
<212> TYPE: PRT
<213> ORGANISM: Artificial Sequence
<220> FEATURE:
<223> OTHER INFORMATION: CDRH3 corresponding to residues 98-104 of
      SEQ ID NO.:152

<400> SEQUENCE: 327

Ile Ser Tyr Ala Met Asp Tyr
1               5

<210> SEQ ID NO 328
<211> LENGTH: 6
<212> TYPE: PRT
<213> ORGANISM: Artificial Sequence
<220> FEATURE:
<223> OTHER INFORMATION: CDRH3 corresponding to residues 98-103 of
      SEQ ID NO.:135

<400> SEQUENCE: 328

Ile Gly Tyr Ala Asp Tyr
```

-continued

```
<210> SEQ ID NO 329
<211> LENGTH: 7
<212> TYPE: PRT
<213> ORGANISM: Artificial Sequence
<220> FEATURE:
<223> OTHER INFORMATION: CDRH3 corresponding to residues 98-104 of
      SEQ ID NO.:133

<400> SEQUENCE: 329

Ala Arg Trp Gly Leu Arg Asn
1               5

<210> SEQ ID NO 330
<211> LENGTH: 7
<212> TYPE: PRT
<213> ORGANISM: Artificial Sequence
<220> FEATURE:
<223> OTHER INFORMATION: CDRH3 corresponding to residues 98-104 of
      SEQ ID NO.:134

<400> SEQUENCE: 330

Ala Arg Trp Gly Leu Arg Asn
1               5

<210> SEQ ID NO 331
<211> LENGTH: 7
<212> TYPE: PRT
<213> ORGANISM: Artificial Sequence
<220> FEATURE:
<223> OTHER INFORMATION: CDRH3 corresponding to residues 98-104 of
      SEQ ID NO.:132

<400> SEQUENCE: 331

Ala Trp Phe Gly Leu Arg Gln
1               5

<210> SEQ ID NO 332
<211> LENGTH: 10
<212> TYPE: PRT
<213> ORGANISM: Artificial Sequence
<220> FEATURE:
<223> OTHER INFORMATION: CDRH3 corresponding to residues 98-107 of
      SEQ ID NO.:155

<400> SEQUENCE: 332

Ala Ser Ser Tyr Asp Gly Leu Phe Ala Tyr
1               5                   10

<210> SEQ ID NO 333
<211> LENGTH: 10
<212> TYPE: PRT
<213> ORGANISM: Artificial Sequence
<220> FEATURE:
<223> OTHER INFORMATION: CDRH3 corresponding to residues 98-107 of
      SEQ ID NO.:156

<400> SEQUENCE: 333

Ala Ser Ser Tyr Asp Gly Leu Phe Ala Tyr
1               5                   10

<210> SEQ ID NO 334
<211> LENGTH: 10
<212> TYPE: PRT
<213> ORGANISM: Artificial Sequence
<220> FEATURE:
<223> OTHER INFORMATION: CDRH3 corresponding to residues 98-107 of
      SEQ ID NO.:157
```

<400> SEQUENCE: 334

Ala Ser Ser Tyr Asp Gly Leu Phe Ala Tyr
1               5                   10

ANTIBODIES THAT SPECIFICALLY BLOCK THE BIOLOGICAL ACTIVITY OF KIDNEY ASSOCIATED ANTIGEN 1 (KAAG1)

This patent application is a divisional application of U.S. Ser. No. 13/127,439 filed on May 3, 2011, which is a national stage filing under 35 U.S.C. §371 of international application PCT/CA2009/001586 filed on Nov. 3, 2009 which claimed priority to U.S. provisional application No. 61/193,184 filed on Nov. 3, 2008 and U.S. provisional application No. 61/213,666 filed on Jun. 30, 2009. The entire contents of each of these priority applications are incorporated herein by reference.

SEQUENCE LISTING

In accordance with 37 C.F.R. §1.52(e)(5), a Sequence Listing in the form of a text file (entitled "Sequence Listing", created on Jun. 12, 2013 of 211 kilobytes) is incorporated herein by reference in its entirety.

FIELD OF THE INVENTION

The present invention relates to monoclonal antibodies and antigen binding fragments thereof that specifically binds to KAAG1 and their use for treating certain diseases including diagnosing, preventing and treating malignant tumors related to ovarian cancer. The present invention also relates to the use of these antibodies for diagnosis, prevention and treatment of various other cancer types.

BACKGROUND OF THE INVENTION

Among gynecologic malignancies, ovarian cancer accounts for the highest tumor-related mortality in women in the United States (Jemal et al., 2005). It is the fourth leading cause of cancer-related death in women in the U.S (Menon et al., 2005). The American Cancer Society estimated a total of 22,220 new cases in 2005 and attributed 16,210 deaths to the disease (Bonome et al., 2005). For the past 30 years, the statistics have remained largely the same—the majority of women who develop ovarian cancer will die of this disease (Chambers and Vanderhyden, 2006). The disease carries a 1:70 lifetime risk and a mortality rate of >60% (Chambers and Vanderhyden, 2006). The high mortality rate is due to the difficulties with the early detection of ovarian cancer when the malignancy has already spread beyond the ovary. Indeed, >80% of patients are diagnosed with advanced staged disease (stage III or IV) (Bonome et al., 2005). These patients have a poor prognosis that is reflected in <45% 5-year survival rate, although 80% to 90% will initially respond to chemotherapy (Berek et al., 2000). This increased success compared to 20% 5-year survival rate years earlier is, at least in part, due to the ability to optimally debulk tumor tissue when it is confined to the ovaries, which is a significant prognostic factor for ovarian cancer (Bristow R. E., 2000; Brown et al., 2004). In patients who are diagnosed with early disease (stage I), the 5-yr survival ranges from >90 (Chambers and Vanderhyden, 2006).

Ovarian cancer comprises a heterogeneous group of tumors that are derived from the surface epithelium of the ovary or from surface inclusions. They are classified into serous, mucinous, endometrioid, clear cell, and Brenner (transitional) types corresponding to the different types of epithelia in the organs of the female reproductive tract (Shih and Kurman, 2005). Of these, serous tumors account for ~60% of the ovarian cancer cases diagnosed. Each histologic subcategory is further divided into three groups: benign, intermediate (borderline tumor or low malignancy potential (LMP)), and malignant, reflecting their clinical behavior (Seidman et al., 2002). LMP represents 10% to 15% of tumors diagnosed as serous and is a conundrum as they display atypical nuclear structure and metastatic behavior, yet they are considerably less aggressive than high-grade serous tumors. The 5-year survival for patients with LMP tumors is 95% in contrast to a <45% survival for advanced high-grade disease over the same period (Berek et al., 2000).

Presently, the diagnosis of ovarian cancer is accomplished, in part, through routine analysis of the medical history of patients and by performing physical, ultrasound and x-ray examinations, and hematological screening. Two alternative strategies have been reported for early hematological detection of serum biomarkers. One approach is the analysis of serum samples by mass spectrometry to find proteins or protein fragments of unknown identity that detect the presence or absence of cancer (Mor et al., 2005; Kozak et al., 2003). However, this strategy is expensive and not broadly available. Alternatively, the presence or absence of known proteins/peptides in the serum is being detected using antibody microarrays, ELISA, or other similar approaches. Serum testing for a protein biomarker called CA-125 (cancer antigen-125) has long been widely performed as a marker for ovarian cancer. However, although ovarian cancer cells may produce an excess of these protein molecules, there are some other cancers, including cancer of the fallopian tube or endometrial cancer (cancer of the lining of the uterus), 60% of people with pancreatic cancer, and 20%-25% of people with other malignancies with elevated levels of CA-125. The CA-125 test only returns a true positive result for about 50% of Stage I ovarian cancer patients and has a 80% chance of returning true positive results from stage II, III, and IV ovarian cancer patients. The other 20% of ovarian cancer patients do not show any increase in CA-125 concentrations. In addition, an elevated CA-125 test may indicate other benign activity not associated with cancer, such as menstruation, pregnancy, or endometriosis. Consequently, this test has very limited clinical application for the detection of early stage disease when it is still treatable, exhibiting a positive predictive value (PPV) of <10%. Even with the addition of ultrasound screening to CA-125, the PPV only improves to around 20% (Kozak et al., 2003). Thus, this test is not an effective screening test.

Despite improved knowledge of the etiology of the disease, aggressive cytoreductive surgery, and modern combination chemotherapy, there has been only little change in mortality. Poor outcomes have been attributed to (1) lack of adequate screening tests for early disease detection in combination with only subtle presentation of symptoms at this stage—diagnosis is frequently being made only after progression to later stages, at which point the peritoneal dissemination of the cancer limits effective treatment and (2) the frequent development of resistance to standard chemotherapeutic strategies limiting improvement in the 5-year survival rate of patients. The initial chemotherapy regimen for ovarian cancer includes the combination of carboplatin (Paraplatin) and paclitaxel (taxol). Years of clinical trials have proved this combination to be most effective after effective surgery—reduces tumor volume in about 80% of the women with newly diagnosed ovarian cancer and 40% to 50% will have complete regression—but studies continue to look for ways to improve it. Recent abdominal infusion of chemotherapeutics to target hard-to-reach cells in combination with intravenous delivery has increased the effectiveness. However, severe side effects often lead to an incomplete course of treatment. Some other chemotherapeutic agents include doxorubicin, cisplatin, cyclophosphamide, bleomycin, etoposide, vinblastine, topotecan hydrochloride, ifosfamide, 5-fluorouracil and melphalan. More recently, clinical trials have demonstrated that intraperitoneal administration of cisplatin confers a survival advantage compared to systemic intravenous chemotherapy (Cannistra and McGuire, 2007). The excellent survival rates for women with early stage disease receiving chemotherapy provide a strong rationale for research efforts to develop strategies to improve the detection of ovarian cancer. Furthermore, the discovery of new ovarian cancer-related biomarkers will lead to the development of more effective therapeutic strategies with minimal side effects for the future treatment of ovarian cancer.

Notwithstanding these recent advances in the understanding and the treatment for ovarian cancer, the use of chemotherapy is invariably associated with severe adverse reactions, which limit their use. Consequently, the need for more specific strategies such as combining antigen tissue specificity with the selectivity of monoclonal antibodies should permit a significant reduction in off-target-associated side effects. The use of monoclonal antibodies for the therapy of ovarian cancer is beginning to emerge with an increasing number of ongoing clinical trials (Oei et al., 2008; Nicodemus and berek, 2005). Most of these trials have examined the use of monoclonal antibodies conjugated to radioisotopes, such as yttrium-90, or antibodies that target tumor antigens already identified in other cancer types. An example of this is the use of bevacizumab, which targets vascular endothelial growth factor (Burger, 2007). There are very few ovarian cancer specific antigens that are currently under investigation as therapeutic targets for monoclonal antibodies. Some examples include the use of a protein termed B7-H4 (Simon et al., 2006) and more recently folate receptor-alpha (Ebel et al., 2007), the latter of which has recently entered Phase II clinical trials.

Kidney associated antigen 1 (KAAG1) was originally cloned from a cDNA library derived from a histocompatibility leukocyte antigen-B7 renal carcinoma cell line as an antigenic peptide presented to cytotoxic T lymphocytes (Van den Eynde et al., 1999; Genebank accession no. Q9UBP8). The locus containing KAAG1 was found to encode two genes transcribed in both directions on opposite strands. The sense strand was found to encode a transcript that encodes a protein termed DCDC2. Expression studies by these authors found that the KAAG1 antisense transcript was tumor specific and exhibited very little expression in normal tissues whereas the DCDC2 sense transcript was ubiquitously expressed (Van den Eynde et al., 1999). The expression of the KAAG1 transcript in cancer, and in particular ovarian cancer, renal cancer, lung cancer, colon cancer, breast cancer and melanoma was disclosed in the published patent application No. PCT/CA2007/001134. Van den Eynde et al., also observed RNA expression in renal carcinomas, colorectal carcinomas, melanomas, sarcomas, leukemias, brain tumors, thyroid tumors, mammary carcinomas, prostatic carcinomas, oesophageal carcinomas, bladder tumor, lung carcinomas and head and neck tumors. Recently, strong genetic evidence obtained through linkage disequilibrium studies found that the VMP/DCDC2/KAAG1 locus was associated with dyslexia (Schumacher et al., 2006; Cope et al., 2005). One of these reports pointed to the DCDC2 marker as the culprit in dyslexic patients since the function of this protein in cortical neuron migration was in accordance with symptoms of these patients who often display abnormal neuronal migration and maturation (Schumacher et al., 2006).

SUMMARY OF THE INVENTION

This invention relates to the expression of KAAG1 in tumor cells. The invention also relates to specific anti-KAAG1 antibodies and antigen binding fragments as well as kits useful for the treatment, detection and diagnosis of cancer. The antibodies and antigen binding fragments may more particularly be useful for the treatment, detection and diagnosis of cancer where tumor cells expresses KAAG1, such as ovarian cancer, skin cancer, renal cancer, colorectal cancer, sarcoma, leukemia, brain cancer, cancer of the thyroid, breast cancer, prostate cancer, cancer of the oesophagus, bladder cancer, lung cancer and head and neck cancer.

The present invention provides in one aspect thereof, an isolated or substantially purified antibody or antigen binding fragment which may be capable of specific binding to Kidney associated antigen 1 (KAAG1 defined in SEQ ID NO.:2) or to a KAAG1 variant.

More specifically and in accordance with an embodiment of the invention, the antibody or antigen binding fragment may bind to a domain located between amino acid 30 and amino acid 84 of KAAG1.

In accordance with another embodiment of the invention, the antibody or antigen binding fragment may be capable of binding to an epitope comprised within amino acid 1 to 35 of KAAG1.

In accordance with a further embodiment of the invention, the antibody or antigen binding fragment may be capable of binding to an epitope comprised within amino acid 36 to 60 of KAAG1.

In accordance with yet a further embodiment of the invention, the antibody or antigen binding fragment may be capable of binding to an epitope comprised within amino acid 61 to 84 of KAAG1.

The antibody or antigen binding fragment of the present invention is especially capable of specific binding to a secreted form of KAAG1, i.e., a form of KAAG1 where the signal peptide has been cleaved.

The antibody or antigen binding fragment of the present invention is especially capable of binding to the extracellular region of KAAG1.

As such, the present invention encompasses diagnostic and/or therapeutic antibodies or antigen binding fragments having specificity for a secreted form of KAAG1 or for an extracellular region of KAAG1. Also encompassed by the present invention are antibodies or antigen binding fragments having the same epitope specificity as the antibody of the present invention. A candidate antibody may be identified by determining whether it will bind to the epitope to which the antibodies described herein binds and/or by performing competition assays with antibodies or antigen binding fragments known to bind to the epitope.

Therefore another aspect the present invention provides an isolated antibody or antigen binding fragment capable of competing with the antibody or antigen binding fragment described herein.

Isolated antibodies or antigen binding fragments of the present invention include those which may be capable of inducing killing (elimination, destruction, lysis) of KAAG1-expressing tumor cells or KAAG1 variant-expressing tumor cells (e.g., in an ADCC-dependent manner).

Isolated antibodies or antigen binding fragments of the present invention also include those which are characterized by their ability to reduce spreading of KAAG1-expressing tumor cells and also those which are characterized by their ability to decrease or impair formation of KAAG1-expressing tumors.

The antibodies or antigen binding fragments may be particularly effective when KAAG1 is expressed at the surface of the KAAG1-expressing tumor cells and may be particularly useful in targeting KAAG1-expressing tumor cells characterized by anchorage-independent growth.

The invention relates to monoclonal antibodies, polyclonal antibodies, chimeric antibodies, humanized antibodies and human antibodies (isolated) as well as antigen binding fragments having the characteristics described herein. Antibodies or antigen binding fragments encompassing permutations of the light and/or heavy chains between a monoclonal, chimeric, humanized or human antibody are also encompassed herewith.

The antibodies or antigen binding fragments of the present invention may thus comprise amino acids of a human constant region and/or framework amino acids of a human antibody.

The term "antibody" refers to intact antibody, monoclonal or polyclonal antibodies. The term "antibody" also encompasses multispecific antibodies such as bispecific antibodies. Human antibodies are usually made of two light chains and two heavy chains each comprising variable regions and constant regions. The light chain variable region comprises 3 CDRs, identified herein as CDRL1, CDRL2 and CDRL3 flanked by framework regions. The heavy chain variable region comprises 3 CDRs, identified herein as CDRH1, CDRH2 and CDRH3 flanked by framework regions.

The term "antigen-binding fragment", as used herein, refers to one or more fragments of an antibody that retain the ability to bind to an antigen (e.g., KAAG1, secreted form of KAAG1 or variants thereof). It has been shown that the antigen-binding function of an antibody can be performed by fragments of an intact antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR), e.g., $V_H$ CDR3. Furthermore, although the two domains of the Fv fragment, $V_L$ and $V_H$, are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region may be modified by replacing one or more cysteine residues with serine residues so as to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A typical antigen binding site is comprised of the variable regions formed by the pairing of a light chain immunoglobulin and a heavy chain immunoglobulin. The structure of the antibody variable regions is very consistent and exhibits very similar structures. These variable regions are typically comprised of relatively homologous framework regions (FR) interspaced with three hypervariable regions termed Complementarity Determining Regions (CDRs). The overall binding activity of the antigen binding fragment is often dictated by the sequence of the CDRs. The FRs often play a role in the proper positioning and alignment in three dimensions of the CDRs for optimal antigen binding.

Antibodies and/or antigen binding fragments of the present invention may originate, for example, from a mouse, a rat or any other mammal or from other sources such as through recombinant DNA technologies.

Further scope, applicability and advantages of the present invention will become apparent from the non-restrictive detailed description given hereinafter. It should be understood, however, that this detailed description, while indicating exemplary embodiments of the invention, is given by way of example only, with reference to the accompanying drawings.

BRIEF DESCRIPTION OF THE DRAWINGS

FIG. 3B shows the results of an ELISA of one of the 96-well plates containing individual monoclonal antibodies selected from Omniclonal library #3 containing anti-KAAG1 Fabs. The results showed that 48 (highlighted in grey) of the Fabs interacted very efficiently with KAAG1. The wells indicated by bold numbers contained the exemplary monoclonals 3D3, 3G10, and 3C4.

FIG. 4C shows a drawing that describes the results from ELISA analyses to map the epitopes that are bound by the anti-KAAG1 antibodies contained in Omniclonal library #3. The results showed that the majority of monoclonals interact with central region of KAAG1 and that certain antibodies bound to the amino- or carboxyl-termini of KAAG1.

FIGS. 9A, 9B and 9C is a summary of alignment results obtained for selected CDRL1, CDRL2 or CDRL3 sequences using the ClustalW2 program; where "*" means that the residues in that column are identical in all sequences in the alignment, ":" means that conserved substitutions have been observed and "." means that semi-conserved substitutions are observed. Consensus CDRs were generated using the ClustalW program (Larkin M. A., et al., (2007) ClustalW and ClustalX version 2. *Bioinformatics* 2007 23(21): 2947-2948).

FIGS. 10A, 10B and 10C is a summary of alignment results obtained for selected CDRH1, CDRH2 or CDRH3 sequences using the ClustalW2 program; where "*" means that the residues in that column are identical in all sequences in the alignment, ":" means that conserved substitutions have been observed and "." means that semi-conserved substitutions are observed. Consensus CDRs were generated using the ClustalW program (Larkin M. A., et al., (2007) ClustalW and ClustalX version 2. *Bioinformatics* 2007 23(21): 2947-2948).

FIG. 11 represents sequence comparison between each of the light chain variable regions generated and representative light chain variable regions identified in SEQ ID NOs:16, 20, 24 or 105. Percent sequence identity and percent sequence similarity has been determined using Blast2 sequence program as indicated herein.

FIG. 12 represents sequence comparison between each of the heavy chain variable regions generated and representative heavy chain variable regions identified in SEQ ID NOs:18, 22, 26 or 132. Percent sequence identity and percent sequence similarity has been determined using Blast2 sequence program as indicated herein.

FIG. 19B is a table summarizing the kinetics parameters of the humanized 3D3 antibody, the chimeric 3D3 antibody as well as hybrid antibodies encompassing permutations of the light and heavy chains of the chimeric or humanized antibody.

FIG. 20A represents sequence alignment of the monoclonal 3D3 light chain variable region (SEQ ID NO.:16) and the humanized 3D3 light chain variable region (SEQ ID NO.: 178). The humanized 3D3 light chain variable region is 86% identical (94% sequence similarity) to the monoclonal 3D3 light chain variable region and their three CDRs are 100% (indicated in bold).

FIG. 20B represents sequence alignment of the monoclonal 3D3 heavy chain variable region (SEQ ID NO.:18) and the humanized 3D3 heavy chain variable region (SEQ ID NO.:179). The humanized 3D3 heavy chain variable region is 82% identical (91% sequence similarity) to the monoclonal 3D3 heavy chain variable region and their three CDRs are 100% (indicated in bold).

FIG. 21A represents sequence alignment of the monoclonal 3C4 light chain variable region (SEQ ID NO.:24) and the humanized 3C4 light chain variable region (SEQ ID NO.: 182). The humanized 3C4 light chain variable region is 85% identical (93% sequence similarity) to the monoclonal 3C4 light chain variable region and their three CDRs are 100% (indicated in bold).

FIG. 21B represents sequence alignment of the monoclonal 3C4 heavy chain variable region (SEQ ID NO.:26) and the humanized 3C4 heavy chain variable region (SEQ ID NO.:183). The humanized 3C4 heavy chain variable region is 86% identical (93% sequence similarity) to the monoclonal 3C4 heavy chain variable region and their three CDRs are 100% (indicated in bold).

DETAILED DESCRIPTION OF THE INVENTION

Figure 1A:
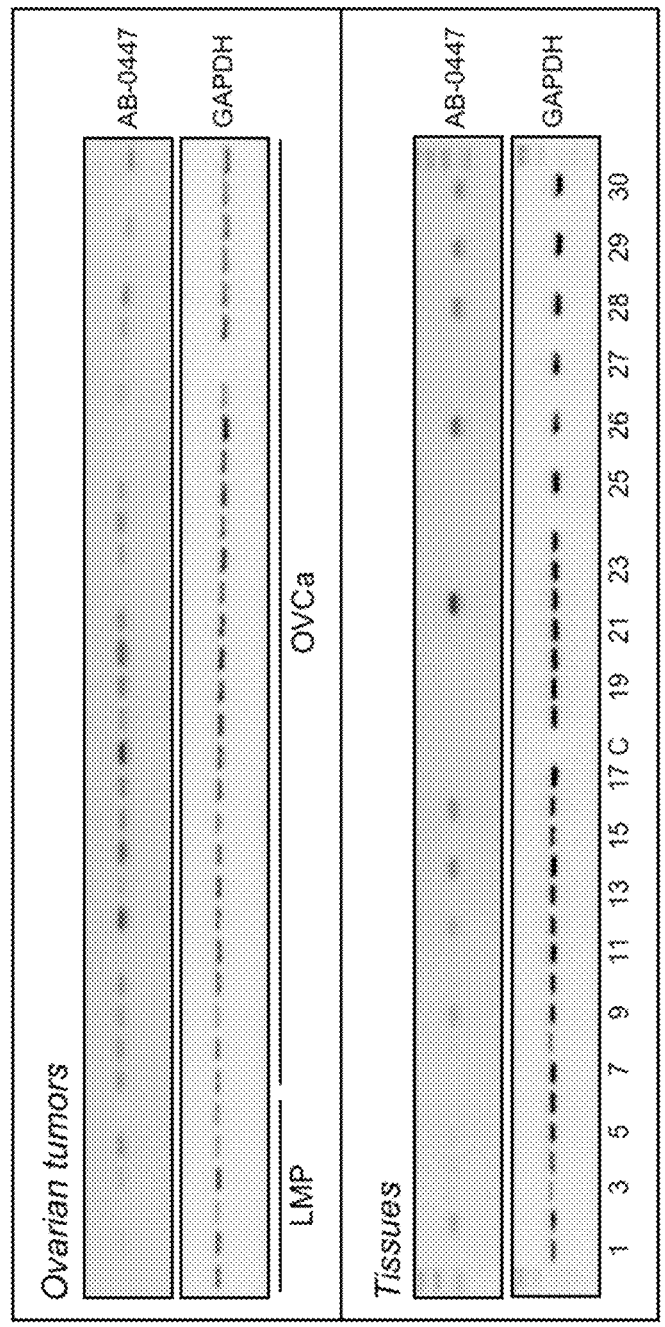
FIG. 1A shows the expression profiling analyses using semi-quantitative RT-PCR reactions carried out to measure the level of KAAG1 mRNA expression in RNA samples derived from greater than 20 ovarian tumors, benign (low malignancy potential) tumors, ovarian cancer cell lines, and 30 normal tissues. The control panels show GAPDH expression, a house-keeping gene used to compare the amount of starting material in each RT-PCR reaction.

The Expression and Biological Activity of KAAG1 in Cancer Cells

The present invention relates to the use of antibodies to target tumors found in various cancer types, in particular ovarian cancer. In order to direct the antibodies to the tumors, the identification of tumor-specific antigens that are expressed at the cell surface of the cancer cells must be carried out. There are several technologies that are available to identify tumor-specific antigens and the method that was used to identify KAAG1 in ovarian tumors, an innovative discovery platform called Subtractive Transcription-based Amplification of mRNA (STAR), is described in the published patent application No. PCT/CA2007/001134.

Analysis of the ovarian cancer STAR libraries yielded many genes that encode secreted and cell surface proteins. One of these, termed AB-0447, contained an open reading frame that encoded a polypeptide of 84 amino acids, corresponding to SEQ ID NO.:2 that was encoded by a cDNA of 885 base pairs with the nucleotide sequence shown in SEQ ID NO.:1. A search of publicly available databases revealed that the AB-0447 nucleotide sequence was identical to that of a gene called KAAG1. Bioinformatic analysis predicted a membrane-anchored protein that presents its functional domain to the extracellular compartment. KAAG1 was originally cloned from a kidney cancer library as a cell surface antigen, a result that confirms its membrane localization. Additionally, our studies showed that the protein was processed at its amino-terminus, a result that was consistent with cleavage of a functional signal peptide at or between amino acids 30 and 34. Furthermore, transient expression of the full-length cDNA resulted in detection of cleaved KAAG1 in the culture medium. This last finding indicated that this membrane-anchored protein could be shed from the cells when expressed at high levels. In contrast, expression of an amino-truncated mutant of KAAG1 resulted in intra-cellular retention of the protein. There are currently no published reports that shed any light on its function and the over-expression of KAAG1 in ovarian cancer, as disclosed by this invention, has never been previously documented.

We have thus investigated whether KAAG1 could be used for antibody-based diagnostics and therapeutics.

Several ovarian cancer cell-based models have been established, such as TOV-21G, TOV-112D, OV-90, and others, and are familiar to those skilled in the art. These cells are part of a collection of human ovarian cancer cell lines derived from patients with ovarian tumors or ascites fluid. These cell lines have undergone an in-depth analysis, including global gene expression patterns on microarrays that make them excellent cell-based models for human ovarian cancer. The growth properties, gene expression patterns, and response to chemotherapeutic drugs indicated that these cell lines are very representative of ovarian tumor behavior in vivo (Benoit et al., 2007). RT-PCR analysis of total RNA isolated from these ovarian cancer cell lines showed that the KAAG1 transcript was weakly expressed in the cell lines derived from primary tumors. In contrast, cell lines derived from ascitic fluid contained high levels of KAAG1 expression. The increased expression of KAAG1 in cells from the ascitic fluid suggested that the environment of the cells influences the regulation of the KAAG1 gene. Ascitic cells are associated with advanced disease and this pattern of expression implies that increased KAAG1 levels are associated with anchorage-independent growth. In concordance with this latter suggestion, KAAG1 expression was found to significantly increase in cell lines derived from primary tumors when these cells were cultured as spheroids in 3D cultures. These spheroids have been extensively characterized and were found to display many properties associated with tumors in vivo (Cody et al., 2008). Thus, expression of KAAG1 was found to be significantly increased in models that mimic tumor progression, in particular during the evolution of ovarian cancer.

With the demonstration that KAAG1 expression is regulated in ovarian cancer cells, the function of this gene in ovarian cancer cell behavior was examined in cell-based assays. To that effect, RNA interference (RNAi) was used to knock down the expression of the endogenous KAAG1 gene in the ovarian cancer cell lines and it was found that decreased expression of KAAG1 resulted in a significant reduction in the migration of the cells as determined in a standard cell motility assay, as exemplified by a wound healing (or scratch) assay. This type of assay measures the speed at which cells fill a denuded area in a confluent monolayer. Decreased expression of KAAG1 resulted in a reduction in the survival of ovarian cancer cell lines as measured by a clonogenic assay, such as a colony survival assay. Those skilled in the art may use other methods to evaluate the requirement of KAAG1 in the behavior of cancer cells, in particular ovarian cancer cells.

Based on the expression of KAAG1 in a large proportion of ovarian tumors, its limited expression in normal tissues, and a concordance between expression levels and increased malignancy, and a putative biological role for KAAG1 in the behavior of ovarian cancer cell lines, KAAG1 was chosen as a therapeutic target for the development of antibodies for the detection, prevention, and treatment of ovarian cancer. Expression of KAAG1 in cancer, other than ovarian cancer also lead the Applicant to the evaluation of therapeutic or diagnostic antibodies for other cancer indications.

Therefore, a variety of anti-KAAG1 antibodies and antigen binding fragments thereof, such as monoclonal antibodies, polyclonal antibodies, chimeric and humanized antibodies (including humanized monoclonal antibodies), antibody fragments, single chain antibodies, domain antibodies, and polypeptides with an antigen binding region, useful for targeting KAAG1 are provided.

KAAG1 as Antigen and Epitopes Derived from KAAG1

The Applicant has come to the unexpected discovery that KAAG1 is expressed in several tumor types and is also found in blood and in ascitic fluid of patients. This antigen may thus be useful for targeting tumor cells expressing the antigen in vivo and in the development of detection assays for measuring the tumor associated antigen in vitro or in vivo. The KAAG1 antigen circulating in blood lacks the signal peptide.

The present invention therefore provides a KAAG1 antigen useful for generating antibodies specific for the circulating form of KAAG1 and/or specific for tumor-expressed KAAG1. The KAAG1 antigen (i.e., epitope) may comprise a fragment of at least 10 amino acids (and up to 84 amino acids) of KAAG1 and may especially bind to the extracellular region of KAAG1.

An exemplary antigen is the whole KAAG1 protein or a variant form having at least 80% sequence identity with SEQ ID NO.:2 or a fragment thereof.

Another exemplary antigen derived from KAAG1 is the secreted or circulating form of KAAG1 which lacks the signal peptide or the extracellular region of KAAG1. This antigen may more particularly lack amino acids 1 to 25, 1 to 26, 1 to 27, 1 to 28, 1 to 29, 1 to 30, 1 to 31, 1 to 32, 1 to 33, 1 to 34, 1 to 35 or 1 to 36 of KAAG1.

The antigen or the epitope described herein may be fused with a carrier such as keyhole limpet (KHL), bovine serum albumin (BSA), ovalbumin (OVA) or else in order to generate antibodies and antigen binding fragments.

The present invention also provides an epitope comprised within amino acid 1 to 35 of SEQ ID NO.:2, within amino acid 36 to 60 of SEQ ID NO.:2 or within amino acid 61 to 84 of SEQ ID NO.:2 to generate antibodies and antigen binding fragments described herein. The present invention further provides a composition for generating antibodies to a secreted or circulating form of KAAG1 or to an extracellular region of KAAG1, the composition may comprise an epitope of KAAG1 comprised within amino acids 30 to 84 of SEQ ID NO.:2 and a carrier. The epitope may especially comprise at least 10 amino acids of KAAG1.

Exemplary embodiments of compositions are pharmaceutical composition for generating antibodies to a secreted or circulating form of KAAG1 or to the extracellular region of KAAG1. The pharmaceutical composition may comprise an epitope of KAAG1 comprised within amino acids 30 to 84 of SEQ ID NO.:2 and a pharmaceutically acceptable carrier.

In yet a further aspect the invention provides a method for generating antibodies to a secreted or circulating form of KAAG1. The method may comprise administering a polypeptide comprising an epitope of KAAG1 comprised within amino acids 30 to 84 of SEQ ID NO.:2 wherein the epitope lacks a KAAG1 signal peptide.

Alternatively, the method may comprise administering an epitope which comprises the signal peptide and selecting antibodies which only binds to the secreted form or the extracellular region of the protein.

In an additional aspect, the present invention provides the use of an epitope of KAAG1 comprised within amino acids 30 to 84 of SEQ ID NO.:2 for generating antibodies to a secreted or circulating form of KAAG1.

Antibodies and Antigen Binding Fragments that Binds to KAAG1

Antibodies were initially isolated from Fab libraries for their specificity towards the antigen of interest. Comparison of the amino acid sequences of the light chain variable domains or the heavy chain variable domains of antibodies showing the greatest characteristics allowed us to derive consensus sequences within the CDRs and within the variable regions. The consensus for CDRs are provided in SEQ ID Nos: 74 to 90.

The variable regions described herein may be fused with constant regions of a desired species thereby allowing recognition of the antibody by effector cells of the desired species. The constant region may originate, for example, from an IgG1, IgG2, IgG3, or IgG4 subtype. Cloning or synthesizing a constant region in frame with a variable region is well within the scope of a person of skill in the art and may be performed, for example, by recombinant DNA technology.

In certain embodiments of the present invention, antibodies that bind to KAAG1 may be of the IgG1, IgG2, IgG3, or IgG4 subtype. More specific embodiments of the invention relates to an antibody of the IgG1 subtype. The antibody may be a humanized antibody of the IgG1 subtype that is biologically active in mediating antibody-dependent cellular cytotoxicity (ADCC), complement-mediated cytotoxicity (CMC), or associated with immune complexes. The typical ADCC involves activation of natural killer (NK) cells and is reliant on the recognition of antibody-coated cells by Fc receptors on the surface of the NK cells. The Fc receptors recognize the Fc domain of antibodies such as is present on IgG1, which bind to the surface of a target cell, in particular a cancerous cell that expresses an antigen, such as KAAG1. Once bound to the Fc receptor of IgG the NK cell releases cytokines and cytotoxic granules that enter the target cell and promote cell death by triggering apoptosis.

In some instances, anti-KAAG1 antibodies with substantially identical light and heavy chain variable regions to antibody 3D3, will interact with an epitope spanned by amino acids 36-60, inclusively, of KAAG1. In other instances, anti-KAAG1 antibodies with substantially identical light and heavy chain variable regions to antibody 3G10, will interact with an epitope spanned by amino acids 61-84, inclusively, of KAAG1. In yet another instance, anti-KAAG1 antibodies with substantially identical light and heavy chain variable regions to antibody 3C4 will interact with an epitope spanned by amino acids 1-35, inclusively, of KAAG1.

The present invention described a collection of antibodies that bind to KAAG1. In certain embodiments, the antibodies may be selected from the group consisting of polyclonal antibodies, monoclonal antibodies such as chimeric or humanized antibodies, antibody fragments such as antigen binding fragments, single chain antibodies, domain antibodies, and polypeptides with an antigen binding region.

In an aspect of the invention, the isolated antibody or antigen binding fragment of the present invention may be capable of inducing killing (elimination, destruction, lysis) of KAAG1-expressing tumor cells or KAAG1 variant-expressing tumor cells (e.g., in an ADCC-dependent manner).

In a further aspect of the invention, the isolated antibody or antigen binding fragment of the present invention may especially be characterized by its capacity of reducing spreading of KAAG1-expressing tumor cells.

In an additional aspect of the invention, the isolated antibody or antigen binding fragment of the present invention may be characterized by its capacity of decreasing or impairing formation of KAAG1-expressing tumors.

In accordance with an embodiment of the invention, the antibody or antigen binding fragment may be more particularly effective when KAAG1 is expressed at the surface of the KAAG1-expressing tumor cells.

Also in accordance with the present invention, the antibody or antigen binding fragment may be especially useful in targeting KAAG1-expressing tumor cells which are characterized by anchorage-independent growth.

In a further aspect, the present invention relates to an isolated antibody or antigen binding fragment for use in the treatment of cancer comprising tumor cells expressing KAAG1.

In yet a further aspect, the present invention relates to an isolated antibody or antigen binding fragment for use in the detection of cancer comprising tumor cells expressing KAAG1.

In an exemplary embodiment of the invention, the isolated antibody or antigen binding fragment may comprise amino acids of a constant region, which may originate, for example, from a human antibody.

In another exemplary embodiment of the invention, the isolated antibody or antigen binding fragment may comprise framework amino acids of a human antibody.

Without being limited to the exemplary embodiments presented herein, the Applicant as generated specific antibodies and antigen binding fragments which may be useful for the purposes described herein.

The present invention therefore provides in an exemplary embodiment, an isolated antibody or antigen binding fragment comprising a light chain variable domain having;
  a. a CDRL1 sequence selected from the group consisting of SEQ ID NO.:74 and SEQ ID NO.:75;
  b. a CDRL2 sequence selected from the group consisting of SEQ ID NO.:76, SEQ ID NO.: 77 and SEQ ID NO.:78, or;
  c. a CDRL3 sequence selected from the group consisting of SEQ ID NO.:79, SEQ ID NO.:80 and SEQ ID NO.:81.

The isolated antibody or antigen binding fragment may also comprise a heavy chain variable domain having;
  a. a CDRH1 sequence comprising SEQ ID NO.:82;
  b. a CDRH2 sequence selected from the group consisting of SEQ ID NO.:83, SEQ ID NO.:84, SEQ ID NO.:85, SEQ ID NO.:86 and SEQ ID NO.:87, or;
  c. a CDRH3 sequence selected from the group consisting of SEQ ID NO.:88, SEQ ID NO.:89 and SEQ ID NO.:90.

In an exemplary embodiment, the antibody or antigen binding fragment may comprise any individual CDR or a combination of CDR1, CDR2 and/or CDR3 of the light chain variable region. The CDR3 may more particularly be selected. Combination may include for example, CDRL1 and CDRL3; CDRL1 and CDRL2; CDRL2 and CDRL3 and; CDRL1, CDRL2 and CDRL3.

In another exemplary embodiment, the antibody or antigen binding fragment may comprise any individual CDR or a combination of CDR1, CDR2 and/or CDR3 of the heavy chain variable region. The CDR3 may more particularly be selected. Combination may include for example, CDRH1 and CDRH3; CDRH1 and CDRH2; CDRH2 and CDRH3 and; CDRH1, CDRH2 and CDRH3.

In accordance with the present invention, the antibody or antigen binding fragment may comprise at least two CDRs of a CDRL1, a CDRL2 or a CDRL3.

Also in accordance with the present invention, the antibody or antigen binding fragment may comprise one CDRL1, one CDRL2 and one CDRL3.

Further in accordance with the present invention, the antibody or antigen binding fragment may comprise:
  a. At least two CDRs of a CDRL1, CDRL2 or CDRL3 and;
  b. At least two CDRs of a CDRH1, one CDRH2 or one CDRH3.

The antibody or antigen binding fragment may more preferably comprise one CDRL1, one CDRL2 and one CDRL3.

The antibody or antigen binding fragment may also more preferably comprise one CDRH1, one CDRH2 and one CDRH3.

Other exemplary embodiments of the invention relates to an isolated antibody or antigen binding fragment comprising a heavy chain variable domain having;
  a. a CDRH1 sequence comprising SEQ ID NO.:82;
  b. a CDRH2 sequence selected from the group consisting of SEQ ID NO.:83, SEQ ID NO.:84, SEQ ID NO.:85, SEQ ID NO.:86 and SEQ ID NO.:87, or;
  c. a CDRH3 sequence selected from the group consisting of SEQ ID NO.:88, SEQ ID NO.:89 and SEQ ID NO.:90.

In accordance with the present invention, the antibody or antigen binding fragment may comprise one CDRH1, one CDRH2 or one CDRH3.

In accordance with the present invention, the antibody or antigen binding fragment may also comprise one CDRH1, one CDRH2 and one CDRH3.

When only one of the light chain variable domain or the heavy chain variable domain is available, an antibody or antigen-binding fragment may be reconstituted by screening a library of complementary variable domains using methods known in the art (Portolano et al. The Journal of Immunology (1993) 150:880-887, Clarkson et al., Nature (1991) 352:624-628).

Also encompassed by the present invention are polypeptides or antibodies comprising variable chains having at least one conservative amino acid substitution in at least one of the CDRs described herein (in comparison with the original CDR).

The present invention also encompasses polypeptides or antibodies comprising variable chains having at least one conservative amino acid substitution in at least two of the CDRs (in comparison with the original CDRs).

The present invention also encompasses polypeptides or antibodies comprising variable chains having at least one conservative amino acid substitution in the 3 CDRs (in comparison with the original CDRs).

The present invention also encompasses polypeptides or antibodies comprising variable chains having at least two conservative amino acid substitutions in at least one of the CDRs (in comparison with the original CDRs).

The present invention also encompasses polypeptides or antibodies comprising variable chains having at least two conservative amino acid substitutions in at least two of the CDRs (in comparison with the original CDRs).

The present invention also encompasses polypeptides or antibodies comprising variable chains having at least two conservative amino acid substitutions in the 3 CDRs (in comparison with the original CDRs).

In another aspect, the present invention relates to a polypeptide, antibody or antigen binding fragment comprising (on a single polypeptide chain or on separate polypeptide chains) at least one complementarity-determining region of a light chain variable domain and at least one complementarity-determining region of a heavy chain variable domain of one of the antibodies or antigen binding fragment described herein.

The present invention relates in another aspect thereof to anti-KAAG1 antibodies that may comprise (on a single polypeptide chain or on separate polypeptide chains) all six complementarity-determining regions (CDRs) of the antibody or antigen binding fragment described herein.

The antibodies or antigen binding fragment of the present invention may further comprise additional amino acids flanking the amino and/or carboxy region of the CDR(s). Those additional amino acids may be as illustrated in Table A or Table B or may include, for example, conservative amino acid substitution.

In accordance with the present invention, the antibody may comprise a CDRL1 sequence comprising or consisting of formula:

(SEQ ID NO.: 74)
$X_{1a}SSX_{2a}SLLX_{3a}X_{4a}X_{5a}X_{6a}X_{7a}X_{8a}X_{9a}X_{10a}LX_{11a}$ wherein $X_{1a}$ may be a basic amino acid;
wherein $X_{2a}$ may be a basic amino acid;
wherein $X_{3a}$ may be H, Y or N;
wherein $X_{4a}$ may be S, T, N or R;
wherein $X_{5a}$ may be absent, S or N;
wherein $X_{6a}$ may be D, F or N;
wherein $X_{7a}$ may be G or Q;
wherein $X_{8a}$ may be K, L or N;
wherein $X_{9a}$ may be T or N;
wherein $X_{10a}$ may be an aromatic amino acid, and;
wherein $X_{11a}$ may be A, N, E or Y.

In an exemplary embodiment of the invention $X_{1a}$ may be K or R.

In a further embodiment of the invention $X_{2a}$ may be Q or K.

In yet a further embodiment of the invention $X_{3a}$ may be N or H.

In an additional embodiment of the invention $X_{10a}$ may be Y or F.

More specific embodiments of the invention include CDRL1 of SEQ ID NO.:74 where: $X_{1a}$ is K; $X_{2a}$ is Q; $X_{3a}$ is N; $X_{3a}$ is H; $X_{4a}$ is S; $X_{4a}$ is T; $X_{5a}$ is S; $X_{5a}$ is absent; $X_{6a}$ is N; $X_{7a}$ is Q; $X_{7a}$ is G; $X_{8a}$ is K; $X_{9a}$ is N; $X_{9a}$ is T; $X_{10a}$ is Y; or $X_{11a}$ is A.

In accordance with the present invention, the antibody may comprise a CDRL1 sequence comprising or consisting of formula:

$$KASQDX_{1b}X_{2b}X_{3b}X_{4b}X_{5b}X_{6b}$$
(SEQ ID NO.: 75)

wherein $X_{1b}$ may be an hydrophobic amino acid;
wherein $X_{2b}$ may be G or H;
wherein $X_{3b}$ may be T, N or R;
wherein $X_{4b}$ may be F, Y or A;
wherein $X_{5b}$ may be an hydrophobic amino acid, and;
wherein $X_{6b}$ may be N or A.

In an exemplary embodiment of the invention $X_{1b}$ may be V or I.

In another exemplary embodiment of the invention $X_{5b}$ may be V or L.

More specific embodiments of the invention include CDRL1 of SEQ ID NO.:75 where $X_{1b}$ is I; $X_{2b}$ is H; $X_{3b}$ is T; $X_{3b}$ is N; $X_{4b}$ is Y; $X_{4b}$ is F; $X_{5b}$ is L or $X_{6b}$ is N.

In accordance with the present invention, the antibody may comprise a CDRL2 sequence comprising or consisting of formula:

$$FX_{1c}STX_{2c}X_{3c}S$$
(SEQ ID NO.: 76)

Wherein $X_{1c}$ is A or G;
Wherein $X_{2c}$ is R or T, and;
Wherein $X_{3c}$ is E, K or A.

In an exemplary embodiment of the invention $X_{1c}$ may be A and $X_{2c}$ may be T.

In another exemplary embodiment of the invention $X_{1c}$ may be A and $X_{2c}$ may be R.

Other specific embodiments of the invention include CDRL2 of SEQ ID NO.:76 where $X_{1c}$ is A; $X_{2c}$ is R or $X_{3c}$ is E.

In accordance with the present invention, the antibody may comprise a CDRL2 sequence comprising or consisting of formula:

$$X_{1d}VSX_{2d}X_{3d}X_{4d}S$$
(SEQ ID NO.: 77)

Wherein $X_{1d}$ may be L or K;
Wherein $X_{2d}$ may be a basic amino acid;
Wherein $X_{3d}$ may be L or R and;
Wherein $X_{4d}$ may be D or F.

In an exemplary embodiment of the invention $X_{2d}$ may be K or N.

Other specific embodiments of the invention include CDRL2 of SEQ ID NO.:77 where $X_{1d}$ is L; $X_{2d}$ is K; $X_{3d}$ is L or $X_{4d}$ is D.

In accordance with the present invention, the antibody may comprise a CDRL2 sequence comprising or consisting of formula:

$$X_{1e}ANRLVX_{2e}$$
(SEQ ID NO.: 78)

Wherein $X_{1e}$ may be a basic amino acid, and;
Wherein $X_{2e}$ may be D or A.

In an exemplary embodiment of the invention $X_{1e}$ may be R or H.

Other specific embodiments of the invention include CDRL2 of SEQ ID NO.:78 where $X_{1e}$ is R or $X_{2e}$ is D.

In accordance with the present invention, the antibody may comprise a CDRL3 sequence comprising or consisting of formula:

$$X_{1f}QX_{2f}X_{3f}X_{4f}X_{5f}PLT$$
(SEQ ID NO.: 79)

Wherein $X_{1f}$ may be Q or L;
Wherein $X_{2f}$ may be an aromatic amino acid;
Wherein $X_{3f}$ may be D, F or Y;
Wherein $X_{4f}$ may be E, A, N or S, and;
Wherein $X_{5f}$ may be I, F or T.

In an exemplary embodiment of the invention $X_{2f}$ may be Y or H.

In another exemplary embodiment of the invention $X_{3f}$ may be Y or D.

In yet another exemplary embodiment of the invention $X_{5f}$ may be I or T.

Other specific embodiments of the invention include CDRL3 of SEQ ID NO.:79 where $X_{1f}$ is Q; $X_{2f}$ is H; $X_{3f}$ is D; $X_{3f}$ is Y; $X_{4f}$ is S; $X_{4f}$ is E; $X_{4f}$ is A; $X_{5f}$ is T, or $X_{5f}$ is I.

In accordance with the present invention, the antibody may comprise a CDRL3 sequence comprising or consisting of formula:

$$QQHX_{1g}X_{2g}X_{3g}PLT$$
(SEQ ID NO.: 80)

Wherein $X_{1g}$ may be an aromatic amino acid;
Wherein $X_{2g}$ may be N or S, and;
Wherein $X_{3g}$ may be I or T.

In an exemplary embodiment of the invention $X_{1g}$ may be F or Y

Other specific embodiments of the invention include CDRL3 of SEQ ID NO.:80 where $X_{2g}$ is S or $X_{3g}$ is T.

In accordance with the present invention, the antibody may comprise a CDRL3 sequence comprising or consisting of formula:

$$X_{1h}QGX_{2h}HX_{3h}PX_{4h}T \quad \text{(SEQ ID NO.: 81)}$$

Wherein $X_{1h}$ may be an aromatic amino acid;
Wherein $X_{2h}$ may be a neutral hydrophilic amino acid;
Wherein $X_{3h}$ may be F or V, and;
Wherein $X_{4h}$ may be R or L.

In an exemplary embodiment of the invention $X_{1h}$ may be W or F.

In another exemplary embodiment of the invention $X_{2h}$ may be S or T.

Other specific embodiments of the invention include CDRL3 of SEQ ID NO.:81 where $X_{1h}$ is W; $X_{2h}$ is T; $X_{3h}$ is F, or $X_{4h}$ is R.

In accordance with the present invention, the antibody may comprise a CDRH1 sequence comprising or consisting of formula:

$$GYX_{1i}FX_{2i}X_{3i}YX_{4i}X_{5i}H \quad \text{(SEQ ID NO.: 82)}$$

Wherein $X_{1i}$ may be T, I or K;
Wherein $X_{2i}$ may be a neutral hydrophilic amino acid;
Wherein $X_{3i}$ may be an acidic amino acid;
Wherein $X_{4i}$ may be E, N or D, and;
Wherein $X_{5i}$ may be hydrophobic amino acid.

In an exemplary embodiment of the invention $X_{2i}$ may be T or S.

In another exemplary embodiment of the invention $X_{3i}$ may be D or E.

In yet another exemplary embodiment of the invention $X_{4i}$ may be N or E.

In a further exemplary embodiment of the invention $X_{5i}$ may be M, I or v.

Other specific embodiments of the invention include CDRH1 of SEQ ID NO.:82 where $X_{2i}$ is T; $X_{3i}$ is D; $X_{4i}$ is E; $X_{5i}$ is I or $X_{5i}$ is M.

In accordance with the present invention, the antibody may comprise a CDRH2 sequence comprising or consisting of formula:

$$X_{1j}X_{2j}DPX_{3j}TGX_{4j}TX_{5j} \quad \text{(SEQ ID NO.: 83)}$$

Wherein $X_{1j}$ may be V or G
Wherein $X_{2j}$ may be a hydrophobic amino acid;
Wherein $X_{3j}$ may be A, G or E;
Wherein $X_{4j}$ may be R, G, D, A, S, N or V, and;
Wherein $X_{5j}$ may be a hydrophobic amino acid.

In an exemplary embodiment of the invention $X_{2j}$ may be I or L.

In another exemplary embodiment of the invention $X_{5j}$ may be A or V.

Other specific embodiments of the invention include CDRH2 of SEQ ID NO.:83 where $X_{1j}$ is V; $X_{2j}$ is I; $X_{3j}$ is E; $X_{4j}$ is D or $X_{5j}$ is A.

In accordance with the present invention, the antibody may comprise a CDRH2 sequence comprising or consisting of formula:

$$VX_{1k}DPX_{2k}TGX_{3k}TA \quad \text{(SEQ ID NO.: 84)}$$

Wherein $X_{1k}$ may be an hydrophobic amino acid;
Wherein $X_{2k}$ may be A, E or G;
Wherein $X_{3k}$ may be R, G, A, S, N V or D.

In an exemplary embodiment of the invention $X_{1k}$ may be L or I.

Other specific embodiments of the invention include CDRH2 of SEQ ID NO.:84 where $X_{1k}$ is I; $X_{2k}$ is E, or $X_{3k}$ is D.

In accordance with the present invention, the antibody may comprise a CDRH2 sequence comprising or consisting of formula:

$$YIX_{1l}X_{2l}X_{3l}GX_{4l}X_{5l}X_{6l} \quad \text{(SEQ ID NO.: 85)}$$

Wherein $X1_l$ may be S or N;
Wherein $X_{2l}$ may be an aromatic amino acid
Wherein $X_{3l}$ may be D, E or N;
Wherein $X4_l$ may be a D or H;
Wherein $X_{5l}$ may be Y, S or N;
Wherein $X_{6l}$ may be D, E or N.

In an exemplary embodiment of the invention $X_{3l}$ may be D or N.

In another exemplary embodiment of the invention $X_{6l}$ may be D or N.

Other specific embodiments of the invention include CDRH2 of SEQ ID NO.:85 where $X_{2l}$ is F or Y, $X_{3l}$ is N, $X_{4l}$ is D or $X_{6l}$ is N.

In accordance with the present invention, the antibody may comprise a CDRH2 sequence comprising or consisting of formula:

$$X_{1m}INPYNX_{2m}VTE \quad \text{(SEQ ID NO.: 86)}$$

wherein $X_{1m}$ may be N or Y, and;
wherein $X_{2m}$ may be E, D or N.

In an exemplary embodiment of the invention $X_{2m}$ may be D or N.

Other specific embodiments of the invention include CDRH2 of SEQ ID NO.:86 where $X_{1m}$ is N or $X_{2m}$ is D.

In accordance with the present invention, the antibody may comprise a CDRH2 sequence comprising or consisting of formula:

$$DINPX_{1n}YGX_{2n}X_{3n}T \quad \text{(SEQ ID NO.: 87)}$$

Wherein $X_{1n}$ may be N or Y,
Wherein $X_{2n}$ may be G or T and;
wherein $X_{3n}$ may be I or T.

In accordance with the present invention, the antibody may comprise a CDRH3 sequence comprising or consisting of formula:

$$MX_{1o}X_{2o}X_{3o}DY \quad \text{(SEQ ID NO.: 88)}$$

Wherein $X_{1o}$ may be G or S;
Wherein $X_{2o}$ may be Y or H, and;
wherein $X_{3o}$ may be A or S.

Other specific embodiments of the invention include CDRH3 of SEQ ID NO.:88 where $X_{1o}$ is G; $X_{2o}$ is Y or $X_{3o}$ is S.

In accordance with the present invention, the antibody may comprise a CDRH3 sequence comprising or consisting of formula:

$IX_{1p}YAX_{2p}DY$ (SEQ ID NO.: 89)

Wherein $X_{1p}$ may be G or S and;
Wherein $X_{2p}$ may be absent or M.

Other specific embodiments of the invention include CDRH3 of SEQ ID NO.:89 where $X_{1p}$ is S or $X_{2p}$ is M.

In accordance with the present invention, the antibody may comprise a CDRH3 sequence comprising or consisting of formula:

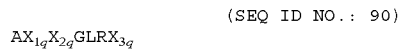
$AX_{1q}X_{2q}GLRX_{3q}$ (SEQ ID NO.: 90)

Wherein $X_{1q}$ may be R or W;
Wherein $X_{2q}$ may be an aromatic amino acid and;
wherein $X_{3q}$ may be a basic amino acid.

In an exemplary embodiment of the invention $X_{2q}$ may be W or F.

In another exemplary embodiment of the invention $X_{3q}$ may be Q or N.

Other specific embodiments of the invention include CDRH3 of SEQ ID NO.:90 where $X_{1q}$ is R; $X_{2q}$ is W or $X_{3q}$ is N.

The framework region of the heavy and/or light chains described herein may be derived from one or more of the framework regions illustrated in Tables A and B. The antibody or antigen binding fragments may thus comprise one or more of the CDRs described herein (e.g., selected from the specific CDRs or consensus CDRs of SEQ ID NO.:74 to 90) and framework regions originating from those illustrated in Tables A and B. In Tables A and B, the expected CDRs are shown in bold, while the framework regions are not.

Table 2 describes the sequences of the nucleotides and the amino acids corresponding to the complete light and heavy chain immunoglobulins of specific examples of anti-KAAG1 antibodies.

TABLE 2 complete sequences of light and heavy chain immunoglobulins that bind to KAAG1

| Antibody designation | Chain type | Nucleotide sequence (SEQ ID NO.:) | Amino acid sequence (SEQ ID NO.:) |
|---|---|---|---|
| 3D3 | Light (L) | 3 | 4 |
| 3D3 | Heavy (H) | 5 | 6 |
| 3G10 | Light | 7 | 8 |
| 3G10 | Heavy | 9 | 10 |
| 3C4 | Light | 11 | 12 |
| 3C4 | Heavy | 13 | 14 |

An antibody or antigen binding fragment that can bind KAAG1 may comprise any one L chain with any one H chain immunoglobulin that is listed in Table 2. In certain embodiments, the light chain of antibody 3D3 may be combined with the heavy chain of antibody 3D3 or the heavy chain of 3G10 to form a complete antibody with KAAG1-binding activity. In an exemplary embodiment of the present invention, the 3D3 L chain may be combined with the 3D3 H chain, the 3G10 L chain may be combined with the 3G10 H chain, or the 3C4 L chain may be combined with the 3C4 H chain. Additionally, some examples of antibodies or antigen binding fragment may consist of any combination of two L chains and any two H chains from the list of antibodies listed in Table 2.

The complete nucleotide sequences of the light and heavy immunoglobulin chains of antibody 3D3 are shown in SEQ ID NOS:3 and 5, respectively, and the corresponding amino acid sequences of the light and heavy immunoglobulin chains of antibody 3D3 are shown in SEQ ID NOS:4 and 6, respectively. Thus, in an exemplary embodiment, an antibody that binds to KAAG1 may comprise the light chain amino acid shown in SEQ ID NO.:4 combined with the heavy chain amino acid sequence shown in SEQ ID NO.:6. In another embodiment, the antibody may comprise two identical 3D3 light chains comprising of SEQ ID NO.:4 and two identical 3D3 heavy chains comprising SEQ ID NO.:6.

The complete nucleotide sequences of the light and heavy immunoglobulin chains of antibody 3G10 are shown in SEQ ID NOS:7 and 9, respectively, and the corresponding amino acid sequences of the light and heavy immunoglobulin chains of antibody 3G10 are shown in SEQ ID NOS:8 and 10, respectively. Thus, in an exemplary embodiment, an antibody that binds to KAAG1 may comprise the light chain amino acid shown in SEQ ID NO.:8 combined with the heavy chain amino acid sequence shown in SEQ ID NO.:10. In another embodiment, the antibody may comprise two identical 3G10 light chains comprising SEQ ID NO.:8 and two identical 3G10 heavy chains comprising SEQ ID NO.:10.

The complete nucleotide sequences of the light and heavy immunoglobulin chains of antibody 3C4 are shown in SEQ ID NOS:11 and 13, respectively and the corresponding amino acid sequences of the light and heavy immunoglobulin chains of antibody 3C4 are shown in SEQ ID NOS:12 and 14, respectively. Thus, in an exemplary embodiment, an antibody that binds to KAAG1 may comprise the light chain amino acid shown in SEQ ID NO.:12 combined with the heavy chain amino acid sequence shown in SEQ ID NO.:14. In another embodiment, the antibody may comprise two identical 3C4 light chains comprising SEQ ID NO.:12 and two identical 3C4 heavy chains comprising SEQ ID NO.:14.

Variants of other anti-KAAG1 antibodies or antigen binding fragments formed by the combination of light and/or heavy immunoglobulin chains may each independently have at least 70%, 75%, 80%, 85%, 90%, 95%, 97%, or 99% identity to the amino acid sequences listed in Table 2 are also provided. In certain embodiments, the antibody variants may comprise at least one light chain and one heavy chain. In other instances, the antibody variants may comprise two identical light chains and two identical heavy chains. In accordance with the present invention, the region of variation may be located in the constant region or in the variable region. Also in accordance with the present invention, the region of variation may be located in the framework region.

Also encompassed by the present invention are antibodies comprising a light chain comprising one of the variable region illustrated in Table A and a heavy chain comprising one of the variable region illustrated in Table B. The light chain and heavy chain may comprise a constant domain. Combinations of light chains and heavy chains of Table 2, Table A and Table B are also encompassed by the present invention.

Antibodies or antigen binding fragments that contain the light chain and heavy chain variable regions are also provided in the present invention. Additionally, certain embodiments include antigen binding fragments, variants, and derivatives of these light and heavy chain variable regions.

Yet other exemplary embodiments of the invention includes an isolated antibody or antigen binding fragment capable of specific binding to SEQ ID NO.:2, to an extracellular portion of SEQ ID NO.:2, or to a secreted form of SEQ ID NO.:2 or to a variant thereof, the antibody comprising:

a. the light chain variable domain defined in SEQ ID NO.:16 and the heavy chain variable domain defined in SEQ ID NO.:18,
b. the light chain variable domain defined in SEQ ID NO.:20 and the heavy chain variable domain defined in SEQ ID NO.:22;
c. the light chain variable domain defined in SEQ ID NO.:24 and the heavy chain variable domain defined in SEQ ID NO.:26;
d. the light chain variable domain defined in SEQ ID NO.:105 and the heavy chain variable domain defined in SEQ ID NO.:132,
e. the light chain variable domain defined in SEQ ID NO.:106 and the heavy chain variable domain defined in SEQ ID NO.:133,
f. the light chain variable domain defined in SEQ ID NO.:107 and the heavy chain variable domain defined in SEQ ID NO.:134,
g. the light chain variable domain defined in SEQ ID NO.:108 and the heavy chain variable domain defined in SEQ ID NO.:154,
h. the light chain variable domain defined in SEQ ID NO.:109 and the heavy chain variable domain defined in SEQ ID NO.:153,
i. the light chain variable domain defined in SEQ ID NO.:110 and the heavy chain variable domain defined in SEQ ID NO.:135,
j. the light chain variable domain defined in SEQ ID NO.:111 and the heavy chain variable domain defined in SEQ ID NO.:136,
k. the light chain variable domain defined in SEQ ID NO.:112 and the heavy chain variable domain defined in SEQ ID NO.:149,
l. the light chain variable domain defined in SEQ ID NO.:113 and the heavy chain variable domain defined in SEQ ID NO.:137,
m. the light chain variable domain defined in SEQ ID NO.:114 and the heavy chain variable domain defined in SEQ ID NO.:140,
n. the light chain variable domain defined in SEQ ID NO.:115 and the heavy chain variable domain defined in SEQ ID NO.:141,
o. the light chain variable domain defined in SEQ ID NO.:116 and the heavy chain variable domain defined in SEQ ID NO.:142,
p. the light chain variable domain defined in SEQ ID NO.:117 and the heavy chain variable domain defined in SEQ ID NO.:139,
q. the light chain variable domain defined in SEQ ID NO.:119 and the heavy chain variable domain defined in SEQ ID NO.:143,
r. the light chain variable domain defined in SEQ ID NO.:120 and the heavy chain variable domain defined in SEQ ID NO.:152,
s. the light chain variable domain defined in SEQ ID NO.:121 and the heavy chain variable domain defined in SEQ ID NO.:146,
t. the light chain variable domain defined in SEQ ID NO.:122 and the heavy chain variable domain defined in SEQ ID NO.:138,
u. the light chain variable domain defined in SEQ ID NO.:123 and the heavy chain variable domain defined in SEQ ID NO.:150,
v. the light chain variable domain defined in SEQ ID NO.:124 and the heavy chain variable domain defined in SEQ ID NO.:144,
w. the light chain variable domain defined in SEQ ID NO.:126 and the heavy chain variable domain defined in SEQ ID NO.:145,
x. the light chain variable domain defined in SEQ ID NO.:127 and the heavy chain variable domain defined in SEQ ID NO.:157,
y. the light chain variable domain defined in SEQ ID NO.:128 and the heavy chain variable domain defined in SEQ ID NO.:155,
z. the light chain variable domain defined in SEQ ID NO.:129 and the heavy chain variable domain defined in SEQ ID NO.:156, or;
aa. the light chain variable domain defined in SEQ ID NO.:130 and the heavy chain variable domain defined in SEQ ID NO.:151.

It is to be understood herein, that the light chain variable region of the specific combination provided above may be changed for any other light chain variable region. Similarly, the heavy chain variable region of the specific combination provided above may be changed for any other heavy chain variable region.

Specific examples of sequences present in these light and heavy chain variable regions are disclosed in Table 3.

TABLE 3

Sequences of light and heavy chain variable regions that bind to KAAG1

| Antibody designation | Variable region type | Nucleotide sequence (SEQ ID NO.:) | Amino acid sequence (SEQ ID NO.:) |
|---|---|---|---|
| 3D3 | Light (VL) | 15 | 16 |
| 3D3 | Heavy (VH) | 17 | 18 |
| 3G10 | Light | 19 | 20 |
| 3G10 | Heavy | 21 | 22 |
| 3C4 | Light | 23 | 24 |
| 3C4 | Heavy | 25 | 26 |
| 3z1A02 | Light | | 105 |
| 3z1A02 | Heavy | | 132 |
| 3z1E10 | Light | | 109 |
| 3z1E10 | Heavy | | 153 |
| 3z1G12L | Light | | 126 |
| 3z1G12H | Heavy | | 145 |

Therefore, antibodies and antigen binding fragments that bind to KAAG1 may comprise one light variable region and one heavy variable region of the same designated antibody or in any combinations. For example, in an exemplary embodiment, an anti-KAAG1 antibody or fragment may comprise the 3D3 light chain variable region (SEQ ID NO.:16) and the 3D3 heavy chain variable region (SEQ ID NO.:18). In an alternate embodiment, an anti-KAAG1 antibody or fragment may comprise the 3D3 light chain variable region (SEQ ID NO.:16) and the 3G10 heavy chain variable region (SEQ ID NO.:22). In another embodiment, the anti-KAAG1 antibodies may comprise two identical light chain variable regions and two identical heavy chain regions. In yet another embodiment, the anti-KAAG1 antibodies may comprise two different light chain variable regions and two different heavy chain regions.

Variants of other anti-KAAG1 antibodies formed by the combination of light and/or heavy chain variable regions that each have at least 70%, 75%, 80%, 85%, 90%, 95%, 97%, or 99% identity to the amino acid sequences listed in Table 3 are also provided. Those skilled in the art will also recognize that the anti-KAAG1 antibody variants may include conservative amino acid changes, amino acid substitutions, deletions, or additions in the amino acid sequences of the light and/or heavy chain variable regions listed in Table 3.

In accordance with the present invention, the region of variation may be located in the framework region of the variable region.

TABLE 4

Sequences of the light and heavy chain CDRs

| Antibody designation | Chain type | CDR | SEQ ID NO.: | Amino acid sequence |
|---|---|---|---|---|
| 3D3 | Light (L) | CDR L1 | 27 | KSSQSLLNSNFQKNFLA |
| 3D3 | Light | CDR L2 | 28 | FASTRES |
| 3D3 | Light | CDR L3 | 29 | QQHYSTPLT |
| 3D3 | Heavy (H) | CDR H1 | 30 | GYIFTDYEIH |
| 3D3 | Heavy | CDR H2 | 31 | VIDPETGNTA |
| 3D3 | Heavy | CDR H3 | 32 | MGYSDY |
| 3G10 | Light | CDR L1 | 33 | RSSQSLLHSNGNTYLE |
| 3G10 | Light | CDR L2 | 34 | KVSNRFS |
| 3G10 | Light | CDR L3 | 35 | FQGSHVPLT |
| 3G10 | Heavy | CDR H1 | 36 | GYTFTDNYMN |
| 3G10 | Heavy | CDR H2 | 37 | DINPYYGTTT |
| 3G10 | Heavy | CDR H3 | 38 | ARDDWFDY |
| 3C4 | Light | CDR L1 | 39 | KASQDIHNFLN |
| 3C4 | Light | CDR L2 | 40 | RANRLVD |
| 3C4 | Light | CDR L3 | 41 | LQYDEIPLT |
| 3C4 | Heavy | CDR H1 | 42 | GFSITSGYGWH |
| 3C4 | Heavy | CDR H2 | 43 | YINYDGHND |
| 3C4 | Heavy | CDR H3 | 44 | ASSYDGLFAY |
| 3z1A02 | Light | CDR L1 | 158 | KSSQSLLHSDGKTYLN |
| 3z1A02 | Light | CDR L2 | 159 | LVSKLDS |
| 3z1A02 | Light | CDR L3 | 160 | WQGTHFPRT |
| 3z1A02 | Heavy | CDR H1 | 161 | GYTFTD YNMH |
| 3z1A02 | Heavy | CDR H2 | 162 | YINPYNDVTE |
| 3z1A02 | Heavy | CDR H3 | 163 | AWFGL RQ |
| 3z1E10 | Light | CDR L1 | 164 | RSSKSLLHSNGN TYLY |
| 3z1E10 | Light | CDR L2 | 165 | RMSNLAS |
| 3z1E10 | Light | CDR L3 | 166 | MQHLEYPYT |
| 3z1E10 | Heavy | CDR H1 | 167 | GDTFTD YYMN |
| 3z1E10 | Heavy | CDR H2 | 168 | DINPNYGGIT |
| 3z1E10 | Heavy | CDR H3 | 169 | QAYYRNS DY |
| 3z1G12L | Light | CDR L1 | 170 | KASQDVGTAVA |
| 3z1G12L | Light | CDR L2 | 171 | WTSTRHT |
| 3z1G12L | Light | CDR L3 | 172 | QQHYSIPLT |
| 3z1G12H | Heavy | CDR H1 | 173 | GYIFTDYEIH |
| 3z1G12H | Heavy | CDR H2 | 174 | VIDPETGNTA |
| 3z1G12H | Heavy | CDR H3 | 175 | MGYSDY |

In certain embodiments of the present invention, the anti-KAAG1 antibodies or antigen binding fragments may comprise the CDR sequences shown in Table 4 or have substantial sequence identity to the CDR sequences of Table 4. In an exemplary embodiment, the 3D3 anti-KAAG1 antibody may comprise a light chain variable region containing CDR1, 2, and 3 that are encoded by SEQ ID NOS:27, 28, and 29, respectively, and/or a heavy chain variable region containing CDR1, 2, and 3 that are encoded by SEQ ID NOS:30, 31, and 32, respectively. In other embodiments the CDR3 region may be sufficient to provide antigen binding. As such polypeptides comprising the CDR3L or the CDR3H or both the CDR3L and the CDR3H are encompassed by the present invention.

Additionally, the anti-KAAG1 antibodies or antigen binding fragments may include any combination of the CDRs listed in Table 4. For example, the antibodies or antigen binding fragments may include the light chain CDR3 and the heavy chain CDR3. It is understood that the CDRs that are contained in the anti-KAAG1 antibodies or antigen binding fragments may be variant CDRs with 80%, 85%, 90%, or 95% sequence identity to the CDR sequences presented in Table 4. Those skilled in the art will also recognize that the variants may include conservative amino acid changes, amino acid substitutions, deletions, or additions in the CDR sequences listed in Table 4.

Other exemplary embodiments of the invention includes an isolated antibody or antigen binding fragment capable of specific binding to SEQ ID NO.:2, to an extracellular portion of SEQ ID NO.:2 or to a secreted form of SEQ ID NO.:2 or to a variant thereof, the antibody comprising:
  a. the 3CDRs of a light chain variable domain defined in SEQ ID NO.:16 and/or the 3CDRs of a heavy chain variable domain defined in SEQ ID NO.:18,
  b. the 3CDRs of a light chain variable domain defined in SEQ ID NO.:20 and/or the 3CDRs of a heavy chain variable domain defined in SEQ ID NO.:22;
  c. the 3CDRs of a light chain variable domain defined in SEQ ID NO.:24 and/or the 3CDRs of a heavy chain variable domain defined in SEQ ID NO.:26;
  d. the 3CDRs of a light chain variable domain defined in SEQ ID NO.:105 and/or the 3CDRs of a heavy chain variable domain defined in SEQ ID NO.:132,
  e. the 3CDRs of a light chain variable domain defined in SEQ ID NO.:106 and/or the 3CDRs of a heavy chain variable domain defined in SEQ ID NO.:133,
  f. the 3CDRs of a light chain variable domain defined in SEQ ID NO.:107 and/or the 3CDRs of a heavy chain variable domain defined in SEQ ID NO.:134, g. the 3CDRs of a light chain variable domain defined in SEQ ID NO.:108 and/or the 3CDRs of a heavy chain variable domain defined in SEQ ID NO.:154,
h. the 3CDRs of a light chain variable domain defined in SEQ ID NO.:109 and/or the 3CDRs of a heavy chain variable domain defined in SEQ ID NO.:153,
i. the 3CDRs of a light chain variable domain defined in SEQ ID NO.:110 and/or the 3CDRs of a heavy chain variable domain defined in SEQ ID NO.:135,
j. the 3CDRs of a light chain variable domain defined in SEQ ID NO.:111 and/or the 3CDRs of a heavy chain variable domain defined in SEQ ID NO.:136,
k. the 3CDRs of a light chain variable domain defined in SEQ ID NO.:112 and/or the 3CDRs of a heavy chain variable domain defined in SEQ ID NO.:149,
l. the 3CDRs of a light chain variable domain defined in SEQ ID NO.:113 and/or the 3CDRs of a heavy chain variable domain defined in SEQ ID NO.:137,
m. the 3CDRs of a light chain variable domain defined in SEQ ID NO.:114 and/or the 3CDRs of a heavy chain variable domain defined in SEQ ID NO.:140,
n. the 3CDRs of a light chain variable domain defined in SEQ ID NO.:115 and/or the 3CDRs of a heavy chain variable domain defined in SEQ ID NO.:141,
o. the 3CDRs of a light chain variable domain defined in SEQ ID NO.:116 and/or the 3CDRs of a heavy chain variable domain defined in SEQ ID NO.:142,
p. the 3CDRs of a light chain variable domain defined in SEQ ID NO.:117 and/or the 3CDRs of a heavy chain variable domain defined in SEQ ID NO.:139,
q. the 3CDRs of a light chain variable domain defined in SEQ ID NO.:119 and/or the 3CDRs of a heavy chain variable domain defined in SEQ ID NO.:143,
r. the 3CDRs of a light chain variable domain defined in SEQ ID NO.:120 and/or the 3CDRs of a heavy chain variable domain defined in SEQ ID NO.:152,
s. the 3CDRs of a light chain variable domain defined in SEQ ID NO.:121 and/or the 3CDRs of a heavy chain variable domain defined in SEQ ID NO.:146,
t. the 3CDRs of a light chain variable domain defined in SEQ ID NO.:122 and/or the 3CDRs of a heavy chain variable domain defined in SEQ ID NO.:138,
u. the 3CDRs of a light chain variable domain defined in SEQ ID NO.:123 and/or the 3CDRs of a heavy chain variable domain defined in SEQ ID NO.:150,
v. the 3CDRs of a light chain variable domain defined in SEQ ID NO.:124 and/or the 3CDRs of a heavy chain variable domain defined in SEQ ID NO.:144,
w. the 3CDRs of a light chain variable domain defined in SEQ ID NO.:126 and/or the 3CDRs of a heavy chain variable domain defined in SEQ ID NO.:145,
x. the 3CDRs of a light chain variable domain defined in SEQ ID NO.:127 and/or the 3CDRs of a heavy chain variable domain defined in SEQ ID NO.:157,
y. the 3CDRs of a light chain variable domain defined in SEQ ID NO.:128 and/or the 3CDRs of a heavy chain variable domain defined in SEQ ID NO.:155,
z. the 3CDRs of a light chain variable domain defined in SEQ ID NO.:129 and/or the 3CDRs of a heavy chain variable domain defined in SEQ ID NO.:156, or;
aa. the 3CDRs of a light chain variable domain defined in SEQ ID NO.:130 and/or the 3CDRs of a heavy chain variable domain defined in SEQ ID NO.:151.

Again, the light chain variable region of the specific combination provided above may be changed for any other light chain variable region described herein. Similarly, the heavy chain variable region of the specific combination provided above may be changed for any other heavy chain variable region described herein.

Variant Antibody and Antigen Binding Fragments

The present invention also encompasses variants of the antibodies or antigen binding fragments described herein. Variant antibodies or antigen binding fragments included are those having a variation in the amino acid sequence. For example, variant antibodies or antigen binding fragments included are those having at least one variant CDR (two, three, four, five or six variant CDRs or even twelve variant CDRs), a variant light chain variable domain, a variant heavy chain variable domain, a variant light chain and/or a variant heavy chain. Variant antibodies or antigen binding fragments included in the present invention are those having, for example, similar or improved binding affinity in comparison with the original antibody or antigen binding fragment.

As used herein the term "variant" applies to any of the sequence described herein and includes for example, a variant CDR (either CDRL1, CDRL2, CDRL3, CDRH1, CDRH2 and/or CDRH3), a variant light chain variable domain, a variant heavy chain variable domain, a variant light chain, a variant heavy chain, a variant antibody, a variant antigen binding fragment and a KAAG1 variant.

Variant antibodies or antigen binding fragments encompassed by the present invention are those which may comprise an insertion, a deletion or an amino acid substitution (conservative or non-conservative). These variants may have at least one amino acid residue in its amino acid sequence removed and a different residue inserted in its place.

The sites of greatest interest for substitutional mutagenesis include the hypervariable regions (CDRs), but modifications in the framework region or even in the constant region are also contemplated. Conservative substitutions may be made by exchanging an amino acid (of a CDR, variable chain, antibody, etc.) from one of the groups listed below (group 1 to 6) for another amino acid of the same group.

Other exemplary embodiments of conservative substitutions are shown in Table 1A under the heading of "preferred substitutions". If such substitutions result in a undesired property, then more substantial changes, denominated "exemplary substitutions" in Table 1A, or as further described below in reference to amino acid classes, may be introduced and the products screened.

It is known in the art that variants may be generated by substitutional mutagenesis and retain the biological activity of the polypeptides of the present invention. These variants have at least one amino acid residue in the amino acid sequence removed and a different residue inserted in its place. For example, one site of interest for substitutional mutagenesis may include a site in which particular residues obtained from various species are identical. Examples of substitutions identified as "conservative substitutions" are shown in Table 1A. If such substitutions result in a change not desired, then other type of substitutions, denominated "exemplary substitutions" in Table 1A, or as further described herein in reference to amino acid classes, are introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(group 1) hydrophobic: norleucine, methionine (Met), Alanine (Ala), Valine (Val), Leucine (Leu), Isoleucine (Ile)
(group 2) neutral hydrophilic: Cysteine (Cys), Serine (Ser), Threonine (Thr)
(group 3) acidic: Aspartic acid (Asp), Glutamic acid (Glu)
(group 4) basic: Asparagine (Asn), Glutamine (Gln), Histidine (His), Lysine (Lys), Arginine (Arg)
(group 5) residues that influence chain orientation: Glycine (Gly), Proline (Pro); and
(group 6) aromatic: Tryptophan (Trp), Tyrosine (Tyr), Phenylalanine (Phe)

Non-conservative substitutions will entail exchanging a member of one of these classes for another.

TABLE 1A

Amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg, Asp | Gln |
| Asp (D) | Glu, Asn | Glu |
| Cys (C) | Ser, Ala | Ser |
| Gln (Q) | Asn; Glu | Asn |
| Glu (E) | Asp, Gln | Asp |
| Gly (G) | Ala | Ala |
| His (H) | Asn, Gln, Lys, Arg, | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Tyr |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, norleucine | Leu |

Variation in the amino acid sequence of the variant antibody or antigen binding fragment may include an amino acid addition, deletion, insertion, substitution etc., one or more modification in the backbone or side-chain of one or more amino acid, or an addition of a group or another molecule to one or more amino acids (side-chains or backbone).

Variant antibody or antigen binding fragment may have substantial sequence similarity and/or sequence identity in its amino acid sequence in comparison with that the original antibody or antigen binding fragment amino acid sequence. The degree of similarity between two sequences is based upon the percentage of identities (identical amino acids) and of conservative substitution.

Generally, the degree of similarity and identity between variable chains has been determined herein using the Blast2 sequence program (Tatiana A. Tatusova, Thomas L. Madden (1999), "Blast 2 sequences—a new tool for comparing protein and nucleotide sequences", FEMS Microbiol Lett. 174: 247-250) using default settings, i.e., blastp program, BLOSUM62 matrix (open gap 11 and extension gap penalty 1; gapx dropoff 50, expect 10.0, word size 3) and activated filters.

Percent identity will therefore be indicative of amino acids which are identical in comparison with the original peptide and which may occupy the same or similar position.

Percent similarity will be indicative of amino acids which are identical and those which are replaced with conservative amino acid substitution in comparison with the original peptide at the same or similar position.

Variants of the present invention therefore comprise those which may have at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with an original sequence or a portion of an original sequence.

Exemplary embodiments of variants are those having at least 81% sequence identity to a sequence described herein and 81%, 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 82% sequence identity to a sequence described herein and 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Further exemplary embodiments of variants are those having at least 85% sequence identity to a sequence described herein and 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 90% sequence identity to a sequence described herein and 90%, 91%, 92%, 93%, 94%, 95%, 96%, 97%, 98%, 99% or 100% sequence similarity with an original sequence or a portion of an original sequence.

Additional exemplary embodiments of variants are those having at least 95% sequence identity to a sequence described herein and 95%, 96%, 97%, 98%, 99% or 100% sequence similarity with an original sequence or a portion of an original sequence.

Yet additional exemplary embodiments of variants are those having at least 97% sequence identity to a sequence described herein and 97%, 98%, 99% or 100% sequence similarity with an original sequence or a portion of an original sequence.

For a purpose of concision the applicant provides herein a Table 1B illustrating exemplary embodiments of individual variants encompassed by the present invention and comprising the specified % sequence identity and % sequence similarity. Each "X" is to be construed as defining a given variant.

TABLE 1B

| | | Percent (%) sequence identity | | | | | | | | | | | | | | | | | | | |
|---|---|---|---|---|---|---|---|---|---|---|---|---|---|---|---|---|---|---|---|---|---|
| | | 80 | 81 | 82 | 83 | 84 | 85 | 86 | 87 | 88 | 89 | 90 | 91 | 92 | 93 | 94 | 95 | 96 | 97 | 98 | 99 | 100 |
| Percent | 80 | X | | | | | | | | | | | | | | | | | | | | |
| (%) | 81 | X | X | | | | | | | | | | | | | | | | | | | |
| sequence | 82 | X | X | X | | | | | | | | | | | | | | | | | | |
| similarity | 83 | X | X | X | X | | | | | | | | | | | | | | | | | |

TABLE 1B-continued

| | | Percent (%) sequence identity | | | | | | | | | | | | | | | | | | | |
|---|---|---|---|---|---|---|---|---|---|---|---|---|---|---|---|---|---|---|---|---|---|
| | | 80 | 81 | 82 | 83 | 84 | 85 | 86 | 87 | 88 | 89 | 90 | 91 | 92 | 93 | 94 | 95 | 96 | 97 | 98 | 99 | 100 |
| 84 | X | X | X | X | X | | | | | | | | | | | | | | | | |
| 85 | X | X | X | X | X | X | | | | | | | | | | | | | | | |
| 86 | X | X | X | X | X | X | X | | | | | | | | | | | | | | |
| 87 | X | X | X | X | X | X | X | X | | | | | | | | | | | | | |
| 88 | X | X | X | X | X | X | X | X | X | | | | | | | | | | | | |
| 89 | X | X | X | X | X | X | X | X | X | X | | | | | | | | | | | |
| 90 | X | X | X | X | X | X | X | X | X | X | X | | | | | | | | | | |
| 91 | X | X | X | X | X | X | X | X | X | X | X | X | | | | | | | | | |
| 92 | X | X | X | X | X | X | X | X | X | X | X | X | X | | | | | | | | |
| 93 | X | X | X | X | X | X | X | X | X | X | X | X | X | X | | | | | | | |
| 94 | X | X | X | X | X | X | X | X | X | X | X | X | X | X | X | | | | | | |
| 95 | X | X | X | X | X | X | X | X | X | X | X | X | X | X | X | X | | | | | |
| 96 | X | X | X | X | X | X | X | X | X | X | X | X | X | X | X | X | X | | | | |
| 97 | X | X | X | X | X | X | X | X | X | X | X | X | X | X | X | X | X | X | | | |
| 98 | X | X | X | X | X | X | X | X | X | X | X | X | X | X | X | X | X | X | X | | |
| 99 | X | X | X | X | X | X | X | X | X | X | X | X | X | X | X | X | X | X | X | X | |
| 100 | X | X | X | X | X | X | X | X | X | X | X | X | X | X | X | X | X | X | X | X | X |

The present invention encompasses CDRs, light chain variable domains, heavy chain variable domains, light chains, heavy chains, antibodies and/or antigen binding fragments which comprise at least 80% identity with the sequence described herein.

Exemplary embodiments of the antibody or antigen binding fragment of the present invention are those comprising a light chain variable domain comprising a sequence selected from the group consisting of a sequence at least 70%, 75%, 80% identical to SEQ ID NO.:16, a sequence at least 70%. 75%, 80% identical to SEQ ID NO.:20, a sequence at least 70%. 75%, 80% identical to SEQ ID NO.:24, a sequence at least 70%. 75%, 80% identical to SEQ ID NO.:105, a sequence at least 70%. 75%, 80% identical to SEQ ID NO.: 109 and a sequence at least 70%. 75%, 80% identical to SEQ ID NO.:126.

These light chain variable domain may comprise a CDRL1 sequence at least 80% identical to SEQ ID NO.:27, a CDRL2 sequence at least 80% identical to SEQ ID NO.:28 and a CDRL3 sequence at least 80% identical to SEQ ID NO.:29.

In an exemplary embodiment of the present invention, any of the antibodies provided herein may comprise a CDRL1 sequence which may be at least 90% identical to SEQ ID NO.:27.

In another exemplary embodiment of the present invention, any of the antibodies provided herein may comprise a CDRL1 sequence which may be 100% identical to SEQ ID NO.:27.

In another exemplary embodiment of the present invention, any of the antibodies provided herein may comprise a CDRL2 sequence at least 90% identical to SEQ ID NO.:28.

In yet another exemplary embodiment of the present invention, any of the antibodies provided herein may comprise a CDRL2 sequence which may be 100% identical to SEQ ID NO.:28.

In another exemplary embodiment of the present invention, any of the antibodies provided herein may comprise a CDRL3 sequence which may be at least 90% identical to SEQ ID NO.:29.

In an additional exemplary embodiment of the present invention, any of the antibodies provided herein may comprise a CDRL3 sequence which may be 100% identical to SEQ ID NO.:29.

The light chain variable domain listed above may comprise a CDRL1 sequence at least 80% identical to SEQ ID NO.:33, a CDRL2 sequence at least 80% identical to SEQ ID NO.:34 and a CDRL3 sequence at least 80% identical to SEQ ID NO.:35.

In an exemplary embodiment of the present invention, any of the antibodies provided herein may comprise a CDRL1 sequence which may be at least 90% identical to SEQ ID NO.:33.

In a further exemplary embodiment of the present invention, any of the antibodies provided herein may comprise a CDRL1 sequence which may be 100% identical to SEQ ID NO.:33.

In yet a further exemplary embodiment of the present invention, any of the antibodies provided herein may comprise a CDRL2 sequence which may be at least 90% identical to SEQ ID NO.:34.

In another exemplary embodiment of the present invention, any of the antibodies provided herein may comprise a CDRL2 sequence which may be 100% identical to SEQ ID NO.:34.

In another exemplary embodiment of the present invention, any of the antibodies provided herein may comprise a CDRL3 sequence which may be at least 90% identical to SEQ ID NO.:35.

In yet another exemplary embodiment of the present invention, any of the antibodies provided herein may comprise a CDRL3 sequence which may be 100% identical to SEQ ID NO.:35.

The light chain variable domain listed above may comprise a CDRL1 sequence at least 80% identical to SEQ ID NO.:39, a CDRL2 sequence at least 80% identical to SEQ ID NO.:40 and a CDRL3 sequence at least 80% identical to SEQ ID NO.:41.

In an exemplary embodiment of the present invention, any of the antibodies provided herein may comprise a CDRL1 sequence which may be at least 90% identical to SEQ ID NO.:39.

In an additional exemplary embodiment of the present invention, any of the antibodies provided herein may comprise a CDRL1 sequence which may be 100% identical to SEQ ID NO.:39.

In another exemplary embodiment of the present invention, any of the antibodies provided herein may comprise a CDRL2 sequence which may be at least 90% identical to SEQ ID NO.:40.

In a further exemplary embodiment of the present invention, any of the antibodies provided herein may comprise a CDRL2 sequence which may be 100% identical to SEQ ID NO.:40.

In an additional exemplary embodiment of the present invention, any of the antibodies provided herein may comprise a CDRL3 sequence which may be at least 90% identical to SEQ ID NO.:41.

In another exemplary embodiment of the present invention, any of the antibodies provided herein may comprise a CDRL3 sequence which may be 100% identical to SEQ ID NO.:41.

The light chain variable domain listed above may comprise a CDRL1 sequence at least 80% identical to SEQ ID NO.:158, a CDRL2 sequence at least 80% identical to SEQ ID NO.:159 and a CDRL3 sequence at least 80% identical to SEQ ID NO.:160.

In an exemplary embodiment of the present invention, any of the antibodies provided herein may comprise a CDRL1 sequence which may be at least 90% identical to SEQ ID NO.:158.

In another exemplary embodiment of the present invention, any of the antibodies provided herein may comprise a CDRL1 sequence which may be 100% identical to SEQ ID NO.:158.

In a further exemplary embodiment of the present invention, any of the antibodies provided herein may comprise a CDRL2 sequence which may be at least 90% identical to SEQ ID NO.:159.

In yet a further exemplary embodiment of the present invention, any of the antibodies provided herein may comprise a CDRL2 sequence which may be 100% identical to SEQ ID NO.:159.

In another exemplary embodiment of the present invention, any of the antibodies provided herein may comprise a CDRL3 sequence which may be at least 90% identical to SEQ ID NO.:160.

In yet another exemplary embodiment of the present invention, any of the antibodies provided herein may comprise a CDRL3 sequence which may be 100% identical to SEQ ID NO.:160.

The light chain variable domain listed above may comprise a CDRL1 sequence at least 80% identical to SEQ ID NO.:164, a CDRL2 sequence at least 80% identical to SEQ ID NO.:165 and a CDRL3 sequence at least 80% identical to SEQ ID NO.:166.

In an exemplary embodiment of the present invention, any of the antibodies provided herein may comprise a CDRL1 sequence which may be at least 90% identical to SEQ ID NO.:164.

In a further exemplary embodiment of the present invention, any of the antibodies provided herein may comprise a CDRL1 sequence which may be 100% identical to SEQ ID NO.:164.

In an additional exemplary embodiment of the present invention, any of the antibodies provided herein may comprise a CDRL2 sequence which may be at least 90% identical to SEQ ID NO.:165.

In another exemplary embodiment of the present invention, any of the antibodies provided herein may comprise a CDRL2 sequence which may be 100% identical to SEQ ID NO.:165.

In yet another exemplary embodiment of the present invention, any of the antibodies provided herein may comprise a CDRL3 sequence which may be at least 90% identical to SEQ ID NO.:166.

In a further exemplary embodiment of the present invention, any of the antibodies provided herein may comprise a CDRL3 sequence which may be 100% identical to SEQ ID NO.:166.

The light chain variable domain listed above may comprise a CDRL1 sequence at least 80% identical to SEQ ID NO.:170, a CDRL2 sequence at least 80% identical to SEQ ID NO.:171 and a CDRL3 sequence at least 80% identical to SEQ ID NO.:172.

In an exemplary embodiment of the present invention, any of the antibodies provided herein may comprise a CDRL1 sequence which may be at least 90% identical to SEQ ID NO.:170.

In an additional exemplary embodiment of the present invention, any of the antibodies provided herein may comprise a CDRL1 sequence which may be 100% identical to SEQ ID NO.: 170.

In another exemplary embodiment of the present invention, any of the antibodies provided herein may comprise a CDRL2 sequence which may be at least 90% identical to SEQ ID NO.: 171.

In yet another exemplary embodiment of the present invention, any of the antibodies provided herein may comprise a CDRL2 sequence which may be 100% identical to SEQ ID NO.: 171.

In a further exemplary embodiment of the present invention, any of the antibodies provided herein may comprise a CDRL3 sequence which may be at least 90% identical to SEQ ID NO.: 172.

In another exemplary embodiment of the present invention, any of the antibodies provided herein may comprise a CDRL3 sequence which may be 100% identical to SEQ ID NO.: 172.

An exemplary embodiment of a variant antibody light chain variable region encompasses a light chain variable region having CDR amino acid sequences that are 100% identical to the CDR amino acid sequence of SEQ ID NO.:16 and having up to 22 amino acid modifications (e.g., conservative or non-conservative amino acid substitutions) in its framework region in comparison with the framework region of SEQ ID NO.:16. A SEQ ID NO.:16 variant is provided in SEQ ID NO.:178.

An exemplary embodiment of a variant antibody light chain variable region encompasses a light chain variable region having CDR amino acid sequences that are 100% identical to the CDR amino acid sequence of SEQ ID NO.:20 and having up to 22 amino acid modifications (e.g., conservative or non-conservative amino acid substitutions) in its framework region in comparison with the framework region of SEQ ID NO.:20.

An exemplary embodiment of a variant antibody light chain variable region encompasses a light chain variable region having CDR amino acid sequences that are 100% identical to the CDR amino acid sequence of SEQ ID NO.:24 and having up to 21 amino acid modifications (e.g., conservative or non-conservative amino acid substitutions) in its framework region in comparison with the framework region of SEQ ID NO.:24. A SEQ ID NO.:24 variant is provided in SEQ ID NO.:182.

An exemplary embodiment of a variant antibody light chain variable region encompasses a light chain variable region having CDR amino acid sequences that are 100% identical to the CDR amino acid sequence of SEQ ID NO.: 105 and having up to 22 amino acid modifications (e.g., conservative or non-conservative amino acid substitutions) in its framework region in comparison with the framework region of SEQ ID NO.:105.

An exemplary embodiment of a variant antibody light chain variable region encompasses a light chain variable region having CDR amino acid sequences that are 100% identical to the CDR amino acid sequence of SEQ ID NO.: 109 and having up to 22 amino acid modifications (e.g., conservative or non-conservative amino acid substitutions) in its framework region in comparison with the framework region of SEQ ID NO.:109.

An exemplary embodiment of a variant antibody light chain variable region encompasses a light chain variable region having CDR amino acid sequences that are 100% identical to the CDR amino acid sequence of SEQ ID NO.: 126 and having up to 21 amino acid modifications (e.g., conservative or non-conservative amino acid substitutions) in its framework region in comparison with the framework region of SEQ ID NO.:126.

In some instances, the variant antibody light chain variable region may comprise amino acid deletions or additions (in combination or not with amino acid substitutions). Often 1, 2, 3, 4 or 5 amino acid deletions or additions may be tolerated.

In an exemplary embodiment, the antibody or antigen binding fragment may comprise a heavy chain variable domain comprising a sequence selected from the group consisting of a sequence at least 80% identical to SEQ ID NO.:18, a sequence at least 70%. 75%, 80% identical to SEQ ID NO.:22, a sequence at least 70%. 75%, 80% identical to SEQ ID NO.:26, a sequence at least 70%. 75%, 80% identical to SEQ ID NO.:132, a sequence at least 70%. 75%, 80% identical to SEQ ID NO.: 145 and a sequence at least 70%. 75%, 80% identical to SEQ ID NO.:153.

These heavy chain variable domains may comprise a CDRH1 sequence at least 80% identical to SEQ ID NO.:30, a CDRH2 sequence at least 80% identical to SEQ ID NO.:31 and a CDRH3 sequence at least 80% identical to SEQ ID NO.:32.

In an exemplary embodiment of the present invention, any of the antibodies provided herein may comprise a CDRH1 sequence which may be at least 90% identical to SEQ ID NO.:30.

In another exemplary embodiment of the present invention, any of the antibodies provided herein may comprise a CDRH1 sequence which may be 100% identical to SEQ ID NO.:30.

In yet another exemplary embodiment of the present invention, any of the antibodies provided herein may comprise a CDRH2 sequence which may be at least 90% identical to SEQ ID NO.:31.

In a further exemplary embodiment of the present invention, any of the antibodies provided herein may comprise a CDRH2 sequence which may be 100% identical to SEQ ID NO.:31.

In yet a further exemplary embodiment of the present invention, any of the antibodies provided herein may comprise a CDRH3 sequence which may be at least 90% identical to SEQ ID NO.:32.

In an additional exemplary embodiment of the present invention, any of the antibodies provided herein may comprise a CDRH3 sequence which may be 100% identical to SEQ ID NO.:32.

The heavy chain variable domain listed above may comprise a CDRH1 sequence at least 80% identical to SEQ ID NO.:36, a CDRH2 sequence at least 80% identical to SEQ ID NO.:37 and a CDRH3 sequence at least 80% identical to SEQ ID NO.:38.

In an exemplary embodiment of the present invention, any of the antibodies provided herein may comprise a CDRH1 sequence which may be at least 90% identical to SEQ ID NO.:36.

In another exemplary embodiment of the present invention, any of the antibodies provided herein may comprise a CDRH1 sequence which may be 100% identical to SEQ ID NO.:36.

In an additional exemplary embodiment of the present invention, any of the antibodies provided herein may comprise a CDRH2 sequence which may be at least 90% identical to SEQ ID NO.:37.

In a further exemplary embodiment of the present invention, any of the antibodies provided herein may comprise a CDRH2 sequence which may be 100% identical to SEQ ID NO.:37.

In another exemplary embodiment of the present invention, any of the antibodies provided herein may comprise a CDRH3 sequence which may be at least 90% identical to SEQ ID NO.:38.

In another exemplary embodiment of the present invention, any of the antibodies provided herein may comprise a CDRH3 sequence which may be 100% identical to SEQ ID NO.:38.

The heavy chain variable domain listed above may comprise a CDRH1 sequence at least 80% identical to SEQ ID NO.:42, a CDRH2 sequence at least 80% identical to SEQ ID NO.:43 and a CDRH3 sequence at least 80% identical to SEQ ID NO.:44.

In another exemplary embodiment of the present invention, any of the antibodies provided herein may comprise a CDRH1 sequence which may be at least 90% identical to SEQ ID NO.:42.

In an additional exemplary embodiment of the present invention, any of the antibodies provided herein may comprise a CDRH1 sequence which may be 100% identical to SEQ ID NO.:42.

In another exemplary embodiment of the present invention, any of the antibodies provided herein may comprise a CDRH2 sequence which may be at least 90% identical to SEQ ID NO.:43.

In a further exemplary embodiment of the present invention, any of the antibodies provided herein may comprise a CDRH2 sequence which may be 100% identical to SEQ ID NO.:43.

In yet a further exemplary embodiment of the present invention, any of the antibodies provided herein may comprise a CDRH3 sequence which may be at least 90% identical to SEQ ID NO.:44.

In an additional exemplary embodiment of the present invention, any of the antibodies provided herein may comprise a CDRH3 sequence which may be 100% identical to SEQ ID NO.:44.

The heavy chain variable domain listed above may comprise a CDRH1 sequence at least 80% identical to SEQ ID NO.:161, a CDRH2 sequence at least 80% identical to SEQ ID NO.:162 and a CDRH3 sequence at least 80% identical to SEQ ID NO.:163.

In an exemplary embodiment of the present invention, any of the antibodies provided herein may comprise a CDRH1 sequence which may be at least 90% identical to SEQ ID NO.:161.

In another exemplary embodiment of the present invention, any of the antibodies provided herein may comprise a CDRH1 sequence which may be 100% identical to SEQ ID NO.:161.

In a further exemplary embodiment of the present invention, any of the antibodies provided herein may comprise a CDRH2 sequence which may be at least 90% identical to SEQ ID NO.:162.

In an additional exemplary embodiment of the present invention, any of the antibodies provided herein may comprise a CDRH2 sequence which may be 100% identical to SEQ ID NO.:162.

In another exemplary embodiment of the present invention, any of the antibodies provided herein may comprise a CDRH3 sequence which may be at least 90% identical to SEQ ID NO.:163.

In yet another exemplary embodiment of the present invention, any of the antibodies provided herein may comprise a CDRH3 sequence which may be 100% identical to SEQ ID NO.:163.

The heavy chain variable domain listed above may comprise a CDRH1 sequence at least 80% identical to SEQ ID NO.:167, a CDRH2 sequence at least 80% identical to SEQ ID NO.:168 and a CDRH3 sequence at least 80% identical to SEQ ID NO.:169.

In an exemplary embodiment of the present invention, any of the antibodies provided herein may comprise a CDRH1 sequence which may be at least 90% identical to SEQ ID NO.:166.

In a further exemplary embodiment of the present invention, any of the antibodies provided herein may comprise a CDRH1 sequence which may be 100% identical to SEQ ID NO.:166.

In an additional exemplary embodiment of the present invention, any of the antibodies provided herein may comprise a CDRH2 sequence which may be at least 90% identical to SEQ ID NO.:168.

In another exemplary embodiment of the present invention, any of the antibodies provided herein may comprise a CDRH2 sequence which may be 100% identical to SEQ ID NO.:168.

In an additional exemplary embodiment of the present invention, any of the antibodies provided herein may comprise a CDRH3 sequence which may be at least 90% identical to SEQ ID NO.:169.

In an exemplary embodiment of the present invention, any of the antibodies provided herein may comprise a CDRH3 sequence which may be 100% identical to SEQ ID NO.:169.

The heavy chain variable domain listed above may comprise a CDRH1 sequence at least 80% identical to SEQ ID NO.:173, a CDRH2 sequence at least 80% identical to SEQ ID NO.:174 and a CDRH3 sequence at least 80% identical to SEQ ID NO.:175.

In an exemplary embodiment of the present invention, any of the antibodies provided herein may comprise a CDRH1 sequence which may be at least 90% identical to SEQ ID NO.:173.

In an exemplary embodiment of the present invention, any of the antibodies provided herein may comprise a CDRH1 sequence which may be 100% identical to SEQ ID NO.: 173.

In an additional exemplary embodiment of the present invention, any of the antibodies provided herein may comprise a CDRH2 sequence which may be at least 90% identical to SEQ ID NO.: 174.

In a further exemplary embodiment of the present invention, any of the antibodies provided herein may comprise a CDRH2 sequence which may be 100% identical to SEQ ID NO.: 174.

In another exemplary embodiment of the present invention, any of the antibodies provided herein may comprise a CDRH3 sequence which may be at least 90% identical to SEQ ID NO.: 175.

In yet another exemplary embodiment of the present invention, any of the antibodies provided herein may comprise a CDRH3 sequence which may be 100% identical to SEQ ID NO.: 175.

An exemplary embodiment of a variant antibody heavy chain variable region encompasses a heavy chain variable region having CDR amino acid sequences that are 100% identical to the CDR amino acid sequence of SEQ ID NO.:18 and having up to 22 amino acid modifications (e.g., conservative or non-conservative amino acid substitutions) in its framework region in comparison with the framework region of SEQ ID NO.:18. A SEQ ID NO.:18 variant is provided in SEQ ID NO.:179.

An exemplary embodiment of a variant antibody heavy chain variable region encompasses a heavy chain variable region having CDR amino acid sequences that are 100% identical to the CDR amino acid sequence of SEQ ID NO.:22 and having up to 23 amino acid modifications (e.g., conservative or non-conservative amino acid substitutions) in its framework region in comparison with the framework region of SEQ ID NO.:22.

An exemplary embodiment of a variant antibody heavy chain variable region encompasses a heavy chain variable region having CDR amino acid sequences that are 100% identical to the CDR amino acid sequence of SEQ ID NO.:26 and having up to 23 amino acid modifications (e.g., conservative or non-conservative amino acid substitutions) in its framework region in comparison with the framework region of SEQ ID NO.:26. A SEQ ID NO.:26 variant is provided in SEQ ID NO.:183.

An exemplary embodiment of a variant antibody heavy chain variable region encompasses a heavy chain variable region having CDR amino acid sequences that are 100% identical to the CDR amino acid sequence of SEQ ID NO.: 132 and having up to 23 amino acid modifications (e.g., conservative or non-conservative amino acid substitutions) in its framework region in comparison with the framework region of SEQ ID NO.:132.

An exemplary embodiment of a variant antibody heavy chain variable region encompasses a heavy chain variable region having CDR amino acid sequences that are 100% identical to the CDR amino acid sequence of SEQ ID NO.: 153 and having up to 23 amino acid modifications (e.g., conservative or non-conservative amino acid substitutions) in its framework region in comparison with the framework region of SEQ ID NO.:153.

An exemplary embodiment of a variant antibody heavy chain variable region encompasses a heavy chain variable region having CDR amino acid sequences that are 100% identical to the CDR amino acid sequence of SEQ ID NO.: 145 and having up to 22 amino acid modifications (e.g., conservative or non-conservative amino acid substitutions) in its framework region in comparison with the framework region of SEQ ID NO.:145.

In some instances, the variant antibody heavy chain variable region may comprise amino acid deletions or additions (in combination or not with amino acid substitutions). Often 1, 2, 3, 4 or 5 amino acid deletions or additions may be tolerated.

Production of the Antibodies in Cells

The anti-KAAG1 antibodies that are disclosed herein can be made by a variety of methods familiar to those skilled in the art, such as hybridoma methodology or by recombinant DNA methods.

In an exemplary embodiment of the invention, the anti-KAAG1 antibodies may be produced by the conventional hybridoma technology, where a mouse is immunized with an antigen, spleen cells isolated and fused with myeloma cells lacking HGPRT expression and hybrid cells selected by hypoxanthine, aminopterin and thymine (HAT) containing media.

In an additional exemplary embodiment of the invention, the anti-KAAG1 antibodies may be produced by recombinant DNA methods.

In order to express the anti-KAAG1 antibodies, nucleotide sequences able to encode any one of a light and heavy immunoglobulin chains described herein or any other may be inserted into an expression vector, i.e., a vector that contains the elements for transcriptional and translational control of the inserted coding sequence in a particular host. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

A variety of expression vector/host cell systems known to those of skill in the art may be utilized to express a polypeptide or RNA derived from nucleotide sequences able to encode any one of a light and heavy immunoglobulin chains described herein. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long-term production of recombinant proteins in mammalian systems, stable expression in cell lines may be effected. For example, nucleotide sequences able to encode any one of a light and heavy immunoglobulin chains described herein may be transformed into cell lines using expression vectors that may contain viral origins of replication and/or endogenous expression elements and a selectable or visible marker gene on the same or on a separate vector. The invention is not to be limited by the vector or host cell employed. In certain embodiments of the present invention, the nucleotide sequences able to encode any one of a light and heavy immunoglobulin chains described herein may each be ligated into a separate expression vector and each chain expressed separately. In another embodiment, both the light and heavy chains able to encode any one of a light and heavy immunoglobulin chains described herein may be ligated into a single expression vector and expressed simultaneously.

Alternatively, RNA and/or polypeptide may be expressed from a vector comprising nucleotide sequences able to encode any one of a light and heavy immunoglobulin chains described herein using an in vitro transcription system or a coupled in vitro transcription/translation system respectively.

In general, host cells that contain nucleotide sequences able to encode any one of a light and heavy immunoglobulin chains described herein and/or that express a polypeptide encoded by the nucleotide sequences able to encode any one of a light and heavy immunoglobulin chains described herein, or a portion thereof, may be identified by a variety of procedures known to those of skill in the art. These procedures include, but are not limited to, DNA/DNA or DNA/RNA hybridizations, PCR amplification, and protein bioassay or immunoassay techniques that include membrane, solution, or chip based technologies for the detection and/or quantification of nucleic acid or amino acid sequences. Immunological methods for detecting and measuring the expression of polypeptides using either specific polyclonal or monoclonal antibodies are known in the art. Examples of such techniques include enzyme-linked immunosorbent assays (ELISAs), radioimmunoassays (RIAs), and fluorescence activated cell sorting (FACS). Those of skill in the art may readily adapt these methodologies to the present invention.

Host cells comprising nucleotide sequences able to encode any one of a light and heavy immunoglobulin chains described herein may thus be cultured under conditions for the transcription of the corresponding RNA (mRNA, siRNA, shRNA etc.) and/or the expression of the polypeptide from cell culture. The polypeptide produced by a cell may be secreted or may be retained intracellularly depending on the sequence and/or the vector used. In an exemplary embodiment, expression vectors containing nucleotide sequences able to encode any one of a light and heavy immunoglobulin chains described herein may be designed to contain signal sequences that direct secretion of the polypeptide through a prokaryotic or eukaryotic cell membrane.

Due to the inherent degeneracy of the genetic code, other DNA sequences that encode the same, substantially the same or a functionally equivalent amino acid sequence may be produced and used, for example, to express a polypeptide encoded by nucleotide sequences able to encode any one of a light and heavy immunoglobulin chains described herein. The nucleotide sequences of the present invention may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In addition, a host cell strain may be chosen for its ability to modulate expression of the inserted sequences or to process the expressed polypeptide in the desired fashion. Such modifications of the polypeptide include, but are not limited to, acetylation, carboxylation, glycosylation, phosphorylation, lipidation, and acylation. In an exemplary embodiment, anti-KAAG1 antibodies that contain particular glycosylation structures or patterns may be desired. Post-translational processing, which cleaves a "prepro" form of the polypeptide, may also be used to specify protein targeting, folding, and/or activity. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Those of skill in the art will readily appreciate that natural, modified, or recombinant nucleic acid sequences may be ligated to a heterologous sequence resulting in translation of a fusion polypeptide containing heterologous polypeptide moieties in any of the aforementioned host systems. Such heterologous polypeptide moieties may facilitate purification of fusion polypeptides using commercially available affinity matrices. Such moieties include, but are not limited to, glutathione S-transferase (GST), maltose binding protein, thioredoxin, calmodulin binding peptide, 6-His (His), FLAG, c-myc, hemaglutinin (HA), and antibody epitopes such as monoclonal antibody epitopes.

In yet a further aspect, the present invention relates to a polynucleotide which may comprise a nucleotide sequence encoding a fusion protein. The fusion protein may comprise a fusion partner (e.g., HA, Fc, etc.) fused to the polypeptide (e.g., complete light chain, complete heavy chain, variable regions, CDRs etc.) described herein.

Those of skill in the art will also readily recognize that the nucleic acid and polypeptide sequences may be synthesized, in whole or in part, using chemical or enzymatic methods well known in the art. For example, peptide synthesis may be performed using various solid-phase techniques and machines such as the ABI 431A Peptide synthesizer (PE Biosystems) may be used to automate synthesis. If desired, the amino acid sequence may be altered during synthesis and/or combined with sequences from other proteins to produce a variant protein.

Antibody Conjugates

The antibody or antigen binding fragment of the present invention may be conjugated with a detectable moiety (i.e., for detection or diagnostic purposes) or with a therapeutic moiety (for therapeutic purposes)

A "detectable moiety" is a moiety detectable by spectroscopic, photochemical, biochemical, immunochemical, chemical and/or other physical means. A detectable moiety may be coupled either directly and/or indirectly (for example via a linkage, such as, without limitation, a DOTA or NHS linkage) to antibodies and antigen binding fragments thereof of the present invention using methods well known in the art. A wide variety of detectable moieties may be used, with the choice depending on the sensitivity required, ease of conjugation, stability requirements and available instrumentation. A suitable detectable moiety include, but is not limited to, a fluorescent label, a radioactive label (for example, without limitation, $^{125}I$, $In^{111}$, $Tc^{99}$, $I^{131}$ and including positron emitting isotopes for PET scanner etc), a nuclear magnetic resonance active label, a luminescent label, a chemiluminescent label, a chromophore label, an enzyme label (for example and without limitation horseradish peroxidase, alkaline phosphatase, etc.), quantum dots and/or a nanoparticle. Detectable moiety may cause and/or produce a detectable signal thereby allowing for a signal from the detectable moiety to be detected.

In another exemplary embodiment of the invention, the antibody or antigen binding fragment thereof may be coupled (modified) with a therapeutic moiety (e.g., drug, cytotoxic moiety).

In an exemplary embodiment, the anti-KAAG1 antibodies and antigen binding fragments may comprise a chemotherapeutic or cytotoxic agent. For example, the antibody and antigen binding fragments may be conjugated to the chemotherapeutic or cytotoxic agent. Such chemotherapeutic or cytotoxic agents include, but are not limited to, Yttrium-90, Scandium-47, Rhenium-186, Iodine-131, Iodine-125, and many others recognized by those skilled in the art (e.g., lutetium (e.g., $Lu^{177}$), bismuth (e.g., $Bi^{213}$), copper (e.g., $Cu^{67}$)). In other instances, the chemotherapeutic or cytotoxic agent may be comprised of, among others known to those skilled in the art, 5-fluorouracil, adriamycin, irinotecan, taxanes, pseudomonas endotoxin, ricin and other toxins.

Alternatively, in order to carry out the methods of the present invention and as known in the art, the antibody or antigen binding fragment of the present invention (conjugated or not) may be used in combination with a second molecule (e.g., a secondary antibody, etc.) which is able to specifically bind to the antibody or antigen binding fragment of the present invention and which may carry a desirable detectable, diagnostic or therapeutic moiety.

Pharmaceutical Compositions of the Antibodies and their Use

Pharmaceutical compositions of the anti-KAAG1 antibodies (conjugated or not) are also encompassed by the present invention. The pharmaceutical composition may comprise an anti-KAAG1 antibody or an antigen binding fragment and may also contain a pharmaceutically acceptable carrier.

Other aspects of the invention relate to a composition which may comprise the antibody or antigen binding fragment described herein and a carrier.

The present invention also relates to a pharmaceutical composition which may comprise the antibody or antigen binding fragment described herein and a pharmaceutically acceptable carrier.

Yet other aspects of the invention relate to the use of the isolated antibody or antigen binding fragment described herein in the treatment or diagnosis of ovarian cancer.

In addition to the active ingredients, a pharmaceutical composition may contain pharmaceutically acceptable carriers comprising water, PBS, salt solutions, gelatins, oils, alcohols, and other excipients and auxiliaries that facilitate processing of the active compounds into preparations that may be used pharmaceutically. In other instances, such preparations may be sterilized.

As used herein, "pharmaceutical composition" means therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's orfixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and humans.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

The term "treatment" for purposes of this disclosure refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

The anti-KAAG1 antibodies and antigen binding fragments therein may have therapeutic uses in the treatment of various cancer types, such as ovarian cancer, renal cancer, colon cancer, lung cancer, melanoma, etc. In an exemplary embodiment, the antibodies and fragments have therapeutic uses in ovarian cancer. In certain instances, the anti-KAAG1 antibodies and fragments may interact with cancer cells that express KAAG1 and induce an immunological reaction by mediating ADCC. In other instances, the anti-KAAG1 antibodies and fragments may block the interaction of KAAG1 with its protein partners.

The anti-KAAG1 antibodies and antigen binding fragments therein may have therapeutic uses in the treatment of various types of ovarian cancer. Several different cell types may give rise to different ovarian cancer histotypes. The most common form of ovarian cancer is comprised of tumors that originate in the epithelial cell layer of the ovary or the fallopian tube. Such epithelial ovarian cancers include serous tumors, endometroid tumors, mucinous tumors, clear cell tumors, and borderline tumors. In other embodiments, the anti-KAAG1 antibodies and antigen binding fragments therein have uses in the treatment of other types of ovarian cancer such as germ line and sex cord ovarian cancer.

In certain instances, the anti-KAAG1 antibodies and antigen binding fragments therein may be administered concurrently in combination with other treatments given for the same condition. As such, the antibodies may be administered with anti-mitotics (e.g., taxanes), platinum-based agents (e.g., cisplatin), DNA damaging agents (e.g. Doxorubicin) and other anti-cancer therapies that are known to those skilled in the art. In other instances, the anti-KAAG1 antibodies and antigen binding fragments therein may be administered with other therapeutic antibodies. These include, but are not limited to, antibodies that target EGFR, CD-20, and Her2.

The present invention relates in a further aspect thereof to a method for inhibiting the growth of a KAAG1-expressing cell, the method which may comprise contacting the cell with an effective amount of the antibody or antigen binding fragment described herein.

The present invention also encompasses method of treating cancer or inhibiting the growth of a KAAG1 expressing cells in a mammal, the method may comprise administering the antibody or antigen binding fragment described herein to a mammal in need.

In further aspects, the present invention provides method of treatment, diagnostic methods and method of detection using the antibody or antigen binding fragment of the present invention and the use of these antibodies or antigen binding fragment in the manufacture of a pharmaceutical composition or drug for such purposes.

Method of treatment encompassed by the present invention includes administering an antibody or antigen binding fragment described herein to a mammal in need, and especially to a patient having or susceptible of having a cancer.

The invention also provides in further aspects, methods for reducing tumor spread, tumor invasion, tumor formation or for inducing tumor lysis, which may comprise administering an isolated antibody or antigen binding fragment to a mammal in need.

The invention therefore relates to the use of the isolated antibody described herein in the (manufacture of a pharmaceutical composition for) treatment of cancer, reduction of tumor spread, tumor invasion, tumor formation or for inducing tumor lysis of KAAG1-expressing tumor cells.

The antibody or antigen binding fragment may more particularly be applicable for malignant tumor including, for example, a malignant tumor having the ability to metastasize and/or tumor cells characterized by anchorage-independent growth. The antibody or antigen binding fragment of the present invention may also be used in the diagnosis of cancer. The diagnosis of cancer may be performed in vivo by administering the antibody or antigen binding fragment of the present invention to a mammal having or suspected of having a cancer. The diagnosis may also be performed ex vivo by contacting a sample obtained from the mammal with the antibody or antigen binding fragment and determining the presence or absence of cells (tumor cells) expressing KAAG1.

The present invention also encompasses method of detecting cancer or detecting a KAAG1 expressing cells in a mammal, the method may comprise administering the antibody or antigen binding fragment described herein to a mammal in need.

The present invention relates in another aspect thereof to a method for detecting a KAAG1-expressing cell, the method may comprise contacting the cell with an antibody or antigen binding fragment described herein and detecting a complex formed by the antibody and the KAAG1-expressing cell. Exemplary embodiments of antibodies or antigen binding fragments used in detection methods are those which are capable of binding to the extracellular region of KAAG1.

Other exemplary embodiments of antibodies or antigen binding fragments used in detection methods are those which bind to KAAG1 expressed at the surface of a tumor cells.

Patients which would benefit from treatment, detection or diagnostic methods described herein are those which have or are suspected of having ovarian cancer (e.g., serous, endometroid, clear cell or mucinous), skin cancer (e.g., melanomas, squamous cell carcinomas), renal cancer (e.g., papillary cell carcinomas, clear cell carcinomas), colorectal cancer (e.g., colorectal carcinomas), sarcoma, leukemia, brain tumor, thyroid tumor, breast cancer (e.g., mammary carcinomas), prostate cancer (e.g., prostatic carcinomas), oesophageal tumor, bladder tumor, lung tumor (e.g., lung carcinomas) or head and neck tumor and especially when the cancer is characterized as being malignant and/or when the KAAG1-expressing cells are characterized by anchorage-independent growth.

Especially encompassed by the present invention are patients having or susceptible of having ovarian cancer (e.g., serous, endometroid, clear cell or mucinous), skin cancer (e.g., melanomas, squamous cell carcinomas) or renal cancer (e.g., papillary cell carcinomas) and especially when the cancer is characterized as being malignant and/or when the KAAG1-expressing cells are characterized by anchorage-independent growth.

Another aspect of the invention relates a method for detecting KAAG1 (SEQ ID NO.:2), a KAAG1 variant having at least 80% sequence identity with SEQ ID NO.:2 or a secreted form of circulating form of KAAG1 or KAAG1 variant, the method may comprise contacting a cell expressing KAAG1 or the KAAG1 variant or a sample (biopsy, serum, plasma, urine etc.) comprising or suspected of comprising KAAG1 or the KAAG1 variant with the antibody or antigen binding fragments described herein and measuring binding. The sample may originate from a mammal (e.g., a human) which may have cancer (e.g., ovarian cancer) or may be suspected of having cancer (e.g., ovarian cancer). The sample may be a tissue sample obtained from the mammal or a cell culture supernatant.

In accordance with the invention the sample may be a serum sample, a plasma sample, a blood sample or ascitic fluid obtained from the mammal. The antibody or antigen binding fragment described herein may advantageously detect a secreted or circulating form (circulating in blood) of KAAG1.

The method may comprise quantifying the complex formed by the antibody or antigen binding fragment bound to KAAG1 or to the KAAG1 variant.

The binding of an antibody to an antigen will cause an increase in the expected molecular weight of the antigen. A physical change therefore occurs upon specific binding of the antibody or antigen binding fragment and the antigen.

Such changes may be detected using, for example, electrophoresis followed by Western blot and coloration of the gel or blot, mass spectrometry, HPLC coupled with a computer or else. Apparatus capable of computing a shift in molecular weight are known in the art and include for example, Phosphorimager™.

When the antibody comprises for example a detectable label, the antigen-antibody complex may be detected by the fluorescence emitted by the label, radiation emission of the label, enzymatic activity of a label provided with its substrate or else.

Detection and/or measurement of binding between an antibody or antigen binding fragment and an antigen may be performed by various methods known in the art. Binding between an antibody or antigen binding fragment and an antigen may be monitored with an apparatus capable of detecting the signal emitted by the detectable label (radiation emission, fluorescence, color change etc.). Such apparatus provides data which indicates that binding as occurred and may also provide indication as to the amount of antibody bound to the antigen. The apparatus (usually coupled with a computer) may also be capable of calculating the difference between a background signal (e.g., signal obtained in the absence of antigen-antibody binding) or background noise and the signal obtained upon specific antibody-antigen binding. Such apparatuses may thus provide the user with indications and conclusions as to whether the antigen has been detected or not.

Additional aspects of the invention relates to kits which may include one or more container containing one or more antibodies or antigen binding fragments described herein.

Nucleic Acids, Vectors and Cells

Antibodies are usually made in cells allowing expression of the light chain and heavy chain expressed from a vector(s) comprising a nucleic acid sequence encoding the light chain and heavy chain.

The present therefore encompasses nucleic acids capable of encoding any of the CDRs, light chain variable domains, heavy chain variable domains, light chains, heavy chains described herein.

The present invention therefore relates in a further aspect to a nucleic acid encoding a light chain variable domain and/or a heavy chain variable domain of an antibody which is capable of specific binding to KAAG1.

In accordance with an embodiment of the invention, the nucleic acid may especially encode a light chain variable domain and/or heavy chain variable domain of an antibody which may be capable of inducing killing (elimination, destruction, lysis) of KAAG1-expressing tumor cells.

In accordance with another embodiment of the invention, the nucleic acid may especially encode a light chain variable domain and/or heavy chain variable domain of an antibody which may be capable of reducing spreading of KAAG1-expressing tumor cells.

In accordance with yet another embodiment of the invention, the nucleic acid may particularly encode a light chain variable domain and/or heavy chain variable domain of an antibody which may be capable of decreasing or impairing formation of KAAG1-expressing tumors.

Exemplary embodiments of nucleic acids of the present invention include nucleic acids encoding a light chain variable domain comprising:
  a. a CDRL1 sequence selected from the group consisting of SEQ ID NO.:74 and SEQ ID NO.:75;
  b. a CDRL2 sequence selected from the group consisting of SEQ ID NO.:76, SEQ ID NO.: 77 and SEQ ID NO.:78, or;
  c. a CDRL3 sequence selected from the group consisting of SEQ ID NO.:79, SEQ ID NO.:80 and SEQ ID NO.:81.

In accordance with the present invention, the nucleic acid may encode a light chain variable domain which may comprise at least two CDRs of a CDRL1, a CDRL2 or a CDRL3.

Also in accordance with the present invention, the nucleic acid may encode a light chain variable domain which may comprise one CDRL1, one CDRL2 and one CDRL3.

The present invention also relates to a nucleic acid encoding a heavy chain variable domain comprising:
  a. a CDRH1 sequence comprising SEQ ID NO.:82;
  b. a CDRH2 sequence selected from the group consisting of SEQ ID NO.:83, SEQ ID NO.:84, SEQ ID NO.:85, SEQ ID NO.:86 and SEQ ID NO.:87, or;
  c. a CDRH3 sequence selected from the group consisting of SEQ ID NO.:88, SEQ ID NO.:89 and SEQ ID NO.: 90.

In accordance with the present invention, the nucleic acid may encode a heavy chain variable domain which may comprise at least two CDRs of a CDRH1, a CDRH2 or a CDRH3.

In accordance with the present invention, the nucleic acid may encode a heavy chain variable domain which may comprise one CDRH1, one CDRH2 and one CDRH3.

Also encompassed by the present invention are nucleic acids encoding antibody variants having at least one conservative amino acid substitution.

In accordance with the present invention, the nucleic acid may encode a CDR comprising at least one conservative amino acid substitution.

In accordance with the present invention, the nucleic acid may encode a CDR comprising at least one conservative amino acid substitution in at least two of the CDRs.

In accordance with the present invention, the nucleic acid may encode a CDR comprising at least one conservative amino acid substitution in the 3 CDRs.

In accordance with the present invention, the nucleic acid may encode a CDR comprising at least two conservative amino acid substitutions in at least one of the CDRs.

In accordance with the present invention, the nucleic acid may encode a CDR comprising at least two conservative amino acid substitutions in at least two of the CDRs.

In accordance with the present invention, the nucleic acid may encode a CDR comprising at least two conservative amino acid substitutions in the 3 CDRs.

Other aspects of the invention relate to a nucleic acid encoding a light chain variable domain having at least 70%. 75%, 80% sequence identity to a sequence selected from the group consisting of SEQ ID NO.:16, SEQ ID NO.:20, SEQ ID NO.:24, SEQ ID NO.:105, SEQ ID NO.:106, SEQ ID NO.: 107, SEQ ID NO.:108, SEQ ID NO.:109, SEQ ID NO.:110, SEQ ID NO.:111, SEQ ID NO.:112, SEQ ID NO.:113, SEQ ID NO.:114, SEQ ID NO.:115, SEQ ID NO.:116, SEQ ID NO.:117, SEQ ID NO.:118, SEQ ID NO.:119, SEQ ID NO.: 120, SEQ ID NO.:121, SEQ ID NO.:122, SEQ ID NO.:123, SEQ ID NO.:124, SEQ ID NO.:125, SEQ ID NO.:126, SEQ ID NO.:127. SEQ ID NO.:128, SEQ ID NO.:129, SEQ ID NO.:130 and SEQ ID NO.:131.

Yet other aspects of the invention relate to a nucleic acid encoding a heavy chain variable domain having at least 70%. 75%, 80% sequence identity to a sequence selected from the group consisting of SEQ ID NO.:18, SEQ ID NO.:22, SEQ ID NO.:26, SEQ ID NO.:132, SEQ ID NO.:133, SEQ ID NO.: 134, SEQ ID NO.:135, SEQ ID NO.:136, SEQ ID NO.:137, SEQ ID NO.:138, SEQ ID NO.:139, SEQ ID NO.:140, SEQ ID NO.:141, SEQ ID NO.:142, SEQ ID NO.:143, SEQ ID NO.:144, SEQ ID NO.:145, SEQ ID NO.:146, SEQ ID NO.: 147, SEQ ID NO.:148, SEQ ID NO.:149, SEQ ID NO.:150, SEQ ID NO.:151, SEQ ID NO.:152, SEQ ID NO.:153, SEQ ID NO.:154, SEQ ID NO.:155, SEQ ID NO.:156, SEQ ID NO.:157. Other aspects of the invention relates to the use of a nucleic acid selected from the group consisting of SEQ ID NO.:1, a fragment of 10 to 884 nucleotides of SEQ ID NO.:1 and a complement of any of the preceding for impairing migration or survival of tumor cells expressing KAAG1. Exemplary embodiments of such nucleic acid comprise siRNAs, antisense, ribozymes and the like.

In yet another aspect, the present invention relates to a vector comprising the nucleic acids described herein.

In accordance with the present invention, the vector may be an expression vector.

Vector that contains the elements for transcriptional and translational control of the inserted coding sequence in a particular host are known in the art. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

In another aspect the present invention relates to an isolated cell which may comprise the nucleic acid described herein.

The isolated cell may comprise a nucleic acid encoding a light chain variable domain and a nucleic acid encoding a heavy chain variable domain either on separate vectors or on the same vector. The isolated cell may also comprise a nucleic acid encoding a light chain and a nucleic acid encoding a heavy chain either on separate vectors or on the same vector.

In accordance with the present invention, the cell may be capable of expressing, assembling and/or secreting an antibody or antigen binding fragment thereof.

In another aspect, the present invention provides a cell which may comprise and/or may express the antibody described herein.

In accordance with the invention, the cell may comprise a nucleic acid encoding a light chain variable domain and a nucleic acid encoding a heavy chain variable domain.

The cell may be capable of expressing, assembling and/or secreting an antibody or antigen binding fragment thereof.

The examples below are presented to further outline details of the present invention.

EXAMPLES

Example 1

This example describes the pattern of expression of the KAAG1 gene in ovarian tumors and ovarian cancer cell line.

PCR analysis was performed to verify the percentage of ovarian tumors that express the mRNA encoding KAAG1 (indicated as AB-0447 in the Figure). The results showed that the KAAG1 gene is expressed in greater than 85% of ovarian tumors from all stages of the disease and 100% of late stage tumors. The expression of KAAG1 is lower or undetectable in LMP samples (see FIG. 1A). For each sample, 1 μg of amplified RNA was reverse transcribed with random hexamers using Thermoscript RT (Invitrogen). The cDNA was diluted and ½₀₀th of the reaction was used as template for each PCR reaction with gene-specific primers as indicated. The primers used to amplify the KAAG1 mRNA contained the sequences shown in SEQ ID NOS:45 and 46. PCR reactions were carried out in 96-well plates and half of the 25 μl reaction was electrophoresed on a 1% agarose gel. The gels were visualized and photographed with a gel documentation system (Bio-Rad). The upper panel of FIG. 1A shows the results from 6 LMP samples (LMP) and 22 ovarian tumor and 6 ovarian cell line (last 6 lanes on the right, OVCa) samples. The lower panel of FIG. 1 shows the RNA samples from 30 normal tissues that were tested as indicated.

KAAG1 expression was weakly detected in a few normal tissues whereas the mRNA was evident in the fallopian tube and the pancreas (see FIG. 1A). The amount of total RNA used in these reactions was controlled with parallel PCR amplifications of glyceraldehyde-3-phosphate dehydrogenase (GAPDH), a housekeeping gene, and the results showed that equivalent starting material was present in each sample (see FIG. 1A). The primers used to amplify the GAPDH gene contained the sequences shown in SEQ ID NOs: 47 and 48. Thus, the expression of the KAAG1 gene fulfills an important selection criteria: it is over-expressed in a large proportion of ovarian tumors and its expression is low or absent in most normal tissues. These data suggest that ovarian tumors may be specifically targeted with high affinity monoclonal antibodies against KAAG1.

Figure 1B:
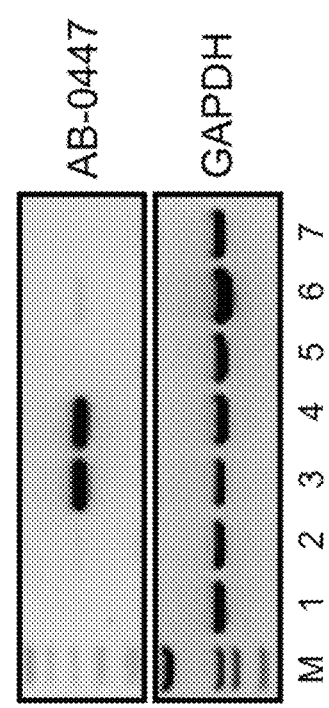
FIG. 1B shows semi-quantitative RT-PCR experiments demonstrating that KAAG1 mRNA is expressed in ovarian cancer cell lines, in particular those that are derived from ascites.
Figures 1C, 1D:
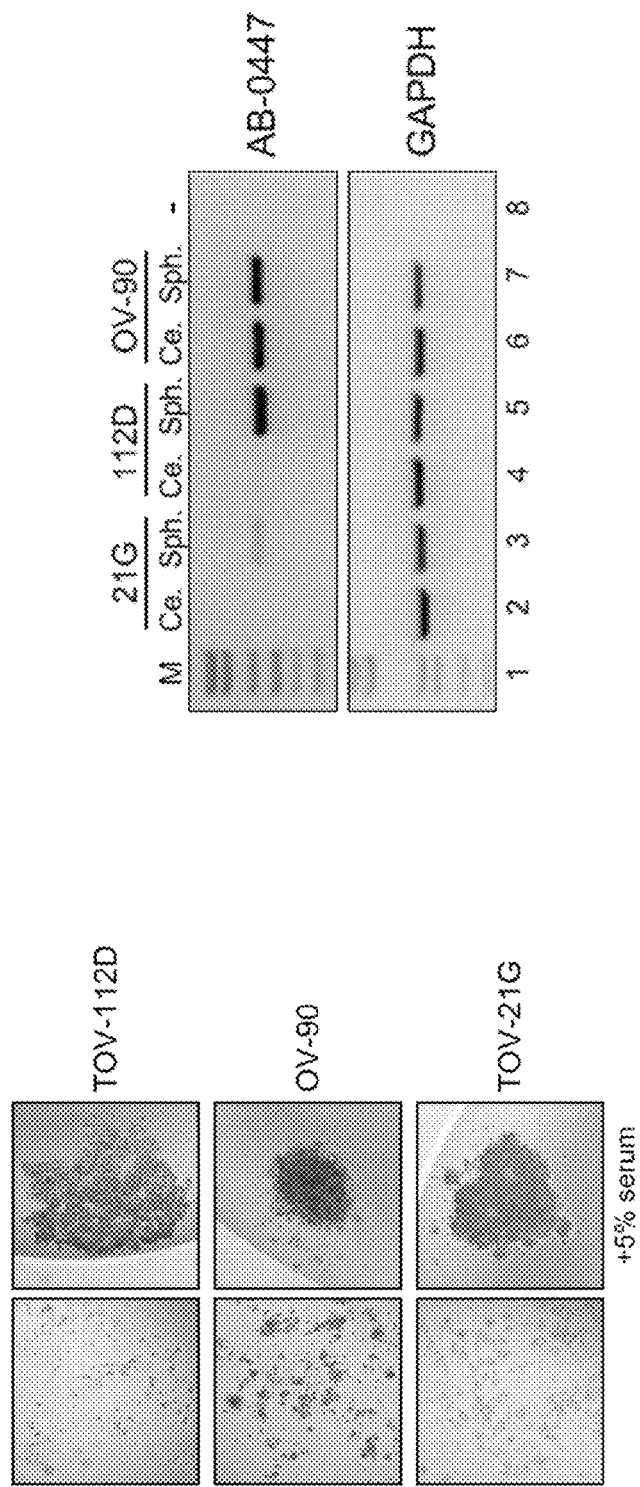
FIG. 1C shows a diagram illustrating the ability of ovarian cancer cell lines to form 3D structures called spheroids. The left panels show the cells grown in medium lacking serum whereas 5% serum stimulated the formation of the spheroid structures.
FIG. 1D shows semi-quantitative RT-PCR experiments demonstrating that the KAAG1 mRNA is highly induced during the formation of spheroids in ovarian cancer cell lines.

Early stage cancer or tumors tend to be made up of cells that are in a high state of differentiation but as the tumor progresses to a more aggressive and invasive state, the cancer cells become increasingly undifferentiated. There are needs to identify factors that contribute to this transition and exploit these proteins as targets for the development of therapeutics. Several ovarian cancer cell lines are available that were derived from primary tumors and serve as excellent models for the functional studies. The expression of KAAG1 was examined in these cell lines. Four lines termed TOV-21G, TOV-112D, TOV-1946, and TOV-2223G were established from primary tumors whereas OV-90 and OV-1946 are cell lines derived from cells contained in ascites fluid of patients with advanced ovarian cancer. Total RNA from cells established from primary tumors (see in FIG. 1B, lanes 1, TOV-21G; 2, TOV-112D; 5, TOV-1946; 6, TOV-2223G) and cells established from ascitic cells (lanes 3, OV-90; 4, OV-1946) was converted to cDNA with reverse transcriptase and used as template in PCR reactions with KAAG1-specific primers (SEQ ID NOS:45 and 46). As a negative control, the reaction was carried out with total RNA from normal ovary. Equal amounts of starting material were utilized as evidenced by parallel PCR reactions with GAPDH (SEQ ID NOS:47 and 48). A sample of the PCR reaction was electrophoresed on an agarose gel and visualized with ethidium bromide. As shown in FIG. 1B, KAAG1 was detectable but weakly expressed in the cell lines from the primary tumors and PCR reactions performed at a higher number of cycles revealed the KAAG1 transcript in all four of these cell lines. Conversely, both cell lines established from the ascitic fluid cells exhibited high level of the KAAG1 transcript. The increased expression in cells from the ascitic fluid suggests that the environment of the cells influences the regulation of the KAAG1 gene.

Ascitic cells are associated with advanced disease and the pattern of expression disclosed in FIG. 1B implies that increased KAAG1 levels are associated with anchorage-independent growth. This question was addressed by culturing the cells in hanging droplets, a condition that prevents the cells from adhering to the petri dish, as is the case when they are grown as monolayers. These so called three-dimensional cultures allow the cells to associate and the formation of spheroids is observed (see FIG. 1C). Spheroids were cultures as follows: TOV-112D, OV-90, or TOV-21G cells (4 000 in 15 µl) were incubated for 4 days in medium in the absence (left panels, FIG. 1C) or presence of 5% FBS (right panels, FIG. 1C, +5% serum). The magnification of the image was set to 100×. These spheroids have been extensively characterized and exhibit many of the properties found in primary tumors including morphological and functional properties as well as the molecular signature as measured by microarray-based expression profiling.

Total RNA was isolated from spheroid preparations and RT-PCR was performed as described for FIG. 1A. TOV-21G, TOV-112D, OV-90 cells were seeded as described in the legend for FIG. 1C under conditions to produce spheroids. After 4 days, total RNA was isolated and used to perform RT-PCR reactions with KAAG1-specific primers (SEQ ID NOS:45 and 46). PCR reactions were electrophoresed on agarose gels. Conducting parallel reactions to amplify GAPDH (SEQ ID NOS:47 and 48) demonstrated that equal amounts of starting material were present in each sample. The following acronyms are used in FIG. 1D: Ce., cells grown as monolayers; Sph., cells grown as spheroids. Strikingly, KAAG1 expression was up-regulated when TOV-21G and TOV-112D were grown as spheroids (see FIG. 1D). In the case of the OV-90 cells, the level of expression of the KAAG1 gene was unchanged and remained very high. Presumably, the level of expression attained in the cell lines derived from the ascitic fluid, as exemplified by the OV-90 cells and the OV-1946 cells (see FIG. 1A) has reached a maximum.

These results correlated with the previous data showing high expression in cell lines derived from ascitic fluid and confirm that expression of KAAG1 is influenced by the microenvironment of the cancer cells. Additionally, the up-regulation of KAAG1 transcription that was observed in spheroids implies that high levels of KAAG1 are present in malignant ovarian cancer.

Example 2

This example describes in vitro results that suggest a critical role for KAAG1 in the survival of ovarian cancer cells.

With the demonstration that KAAG1 expression is regulated in ovarian cancer cells, the function of this gene in these cells was examined. To address this question, in vitro assays were conducted to determine if this protein plays a role in cancer cell proliferation, migration, and/or survival. RNAi was used to knock down the expression of the endogenous KAAG1 gene in the TOV-21G ovarian cancer cell line. The design of two separate short-hairpin RNA (shRNA) sequences was performed using web-based software that is freely available to those skilled in the art (Qiagen for example). These chosen sequences, usually 19-mers, were included in two complementary oligonucleotides that form the template for the shRNAs, i.e. the 19-nt sense sequence, a 9-nt linker region (loop), the 19-nt antisense sequence followed by a 5-6 poly-T tract for termination of the RNA polymerase III. The sequences of the 19-mers that were used to knock down the expression of KAAG1 are shown in SEQ ID NOS:49 and 50. Appropriate restriction sites were inserted at the ends of these oligonucleotides to facilitate proper positioning of the inserts so that the transcriptional start point is at a precise location downstream of the hU6 promoter. The plasmid utilized in all RNA interference studies, pSilencer 2.0 (SEQ ID NO.:51), was purchase from a commercial supplier (Ambion, Austin, Tex.). Two different shRNA expression vectors were constructed to increase the chance of observing RNAi effects and the specificity of phenotypic observations. TOV-21G cells were seeded in 6-well plates and transfected 24 h later with 1 µg of pSil-shRNA vector. Sh.1 and sh.2 were used to designate 2 different shRNA sequences targeting the KAAG1 gene. Stable transfectants were selected for 5-7 days, expanded, and grown to confluence. All of the following in vitro cell-based assays were performed using these stably transfected cell lines that contain shRNAs specific for KAAG1.

Figure 2A:
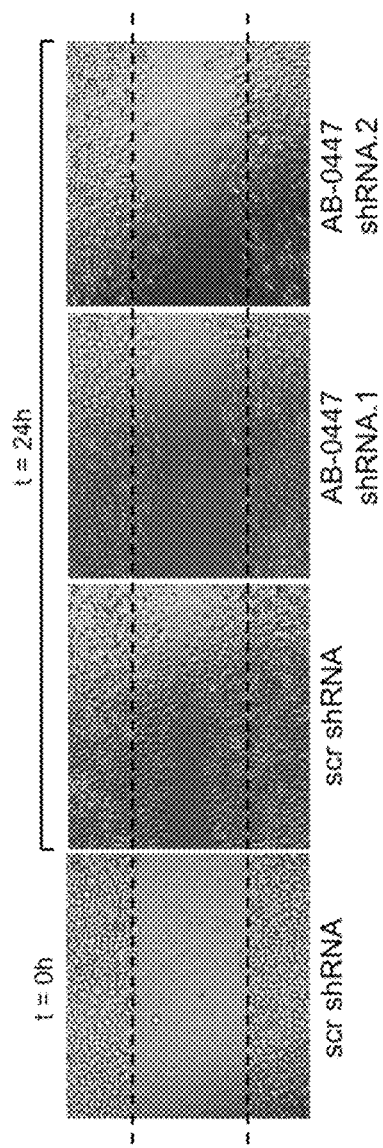
FIG. 2A shows a diagram illustrating the wound or scratch assay, a cell-based assay that is a measurement of a cell line's ability to migrate into a denuded area over a pre-determined period of time. TOV-21G cells harboring KAAG1 shRNAs display a reduced capacity to fill in the denuded area.

The migration or mobility of the cells was measured in a standard cell motility assay. This scratch assay, as it is called, measures the speed at which cells fill a denuded area in a confluent monolayer. As illustrated in FIG. 2A, TOV-21G cells containing the scrambled shRNA filled up the wound almost completely after 24 h compared to the control untreated cells (compare middle-left panel with left panel). By contrast, the ability of TOV-21G cells expressing KAAG1 shRNAs to fill the denuded area was greatly reduced. In fact, the number of cells that filled the denuded area in the presence of the KAAG1 shRNA cells more closely resembled the number of cells at time 0h (compare the left panel with the right panels).

Figure 2B:
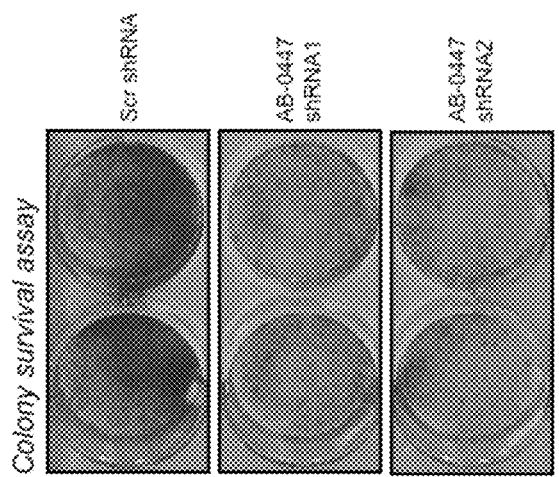
FIG. 2B shows an illustration of the clonogenic assay, also known as a colony survival assay. It measured the survival of diluted cells over a period of several days. TOV-21G cells harboring KAAG1 shRNAs display reduced survival.

To examine the longer-term effects of reduced expression of KAAG1 in ovarian cancer cells, the cells were extensively diluted and cultured for 10 days in a colony survival assay. TOV-21G cells were seeded in 12-well plates at a density of 50 000 cells/well and transfected 24 h later with 1 µg of pSil-shRNA vector. Sh-1 and sh-2 are used to designate 2 different shRNA sequences targeting the same gene. The next day, fresh medium was applied containing 2 µg/ml puromycin and the selection of the cells was carried out for 3 days. The cells were washed and fresh medium without puromycin was added and growth continued for another 5 days. To visualize the remaining colonies, the cells were washed in PBS and fixed and stained simultaneously in 1% crystal violet/10% ethanol in PBS for 15 minutes at room temperature. Following extensive washing in PBS, the dried plates were scanned for photographic analysis. A significant decrease in the survival of the cancer cell line was observed and a representative experiment is displayed in FIG. 2B. Identical results were obtained when the shRNAs were transfected into another ovarian cancer cell line, TOV-112D.

Thus, taken together, the regulated expression of KAAG1 in detached cells coupled with the requirement of this gene in the migration and the survival of ovarian cancer cells supports an important role for KAAG1 in ovarian cancer cells. Furthermore, these experiments suggest that an antagonist of KAAG1 protein, such as a monoclonal antibody, would result in reduced invasiveness and decreased tumor survival.

Example 3

This example provides details pertaining to the family of monoclonal antibodies that bind to KAAG1.

The antibodies that bind KAAG1 were generated using the Biosite phage display technology. A detailed description of the technology and the methods for generating these antibodies can be found in the U.S. Pat. No. 6,057,098. Briefly, the technology utilizes stringent panning of phage libraries that display the antigen binding fragments (Fabs). After a several rounds of panning, a library, termed the Omniclonal, was obtained that was enriched for recombinant Fabs containing light and heavy chain variable regions that bound to KAAG1 with very high affinity and specificity. From this library, more precisely designated Omniclonal AL0003Z1, 96 individual recombinant monoclonal Fabs were prepared from E. coli and tested for KAAG1 binding.

Figure 3A:
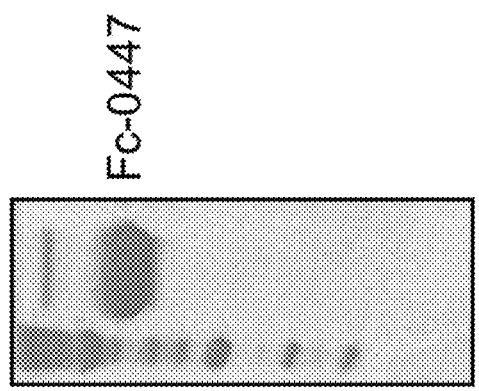
FIG. 3A shows a polyacrylamide gel that was stained with Coomassie Blue and contains a sample (10 μg) of purified Fc-KAAG1 fusion protein that was produced in transiently transfected 293E cells.

To measure the relative binding of each individual monoclonal antibody, recombinant human KAAG1 was produced in 293E cells using the large-scale transient transfection technology (Durocher et al., 2002; Durocher, 2004). The entire coding region of the KAAG1 cDNA was amplified by PCR using a forward primer that incorporated a BamHI restriction site (SEQ ID NO.:52) and a reverse primer that incorporated a HindIII restriction site (SEQ ID NO.:53). The resulting PCR product measured 276 base pairs and following digestion with BamHI and HindIII, the fragment was ligated into the expression vector pYD5 (SEQ ID NO.:54) that was similarly digested with the same restriction enzymes. The pYD5 expression plasmid contains the coding sequence for the human Fc domain that allows fusion proteins to be generated as well as the sequence encoding the IgG1 signal peptide to allow the secretion of the fusion protein into the culture medium. For each milliliter of cells, one microgram of the expression vector, called pYD5-0447, was transfected in 293E cells grown in suspension to a density of 1.5-2.0 million cells/ml. The transfection reagent used was polyethylenimine (PEI), (linear, MW 25,000, Cat#23966 Polysciences, Inc., Warrington, Pa.) which was included at a DNA:PEI ratio of 1:3. Growth of the cells was continued for 5 days after which the culture medium was harvested for purification of the recombinant Fc-KAAG1 fusion protein. The protein was purified using Protein-A agarose as instructed by the manufacturer (Sigma-Aldrich Canada Ltd., Oakville, ON). A representative polyacrylamide gel showing a sample of the purified Fc-KAAG1 (indicated as Fc-0447) is shown in FIG. 3A.

The 96-well master plate of monoclonal preparations contained different concentrations of purified anti-KAAG1 Fabs in each well. A second stock master plate was prepared by diluting the Fabs to a final concentration of 10 μg/ml from which all subsequent dilutions were performed for ELISA measurements. To carry out the binding of Fc-KAAG1 to the monoclonal preparations, the Fc-KAAG1 was biotinylated with NHS-biotin (Pierce, Rockford, Ill.) and 10 ng/well was coated in a streptavidin 96-well plate. One nanogram of each Fab monoclonal preparation was added to each well and incubated at room temperature for 30 minutes. Bound antibody was detected with HRP-conjugated mouse anti-kappa light chain antibody in the presence of TMB liquid substrate (Sigma-Aldrich Canada Ltd., Oakville, ON) and readings were conducted at 450 nm in microtiter plate reader. As shown in FIG. 3B, a total of 48 (highlighted in grey) monoclonal antibodies displayed significant binding in this assay (>0.1 arbitrary $OD_{450}$ units). The antibodies were purposely diluted to 1 ng/well to accentuate the binding of those antibodies with the most affinity for KAAG1. As a control, the antibodies did not bind to biotinylated Fc domain. These data also revealed that the binding of the antibodies varied from well to well indicating that they exhibited different affinities for KAAG1.

Example 4

This example describes the epitope mapping studies to determine which region of KAAG1 the antibodies bind to.

Figure 4A:
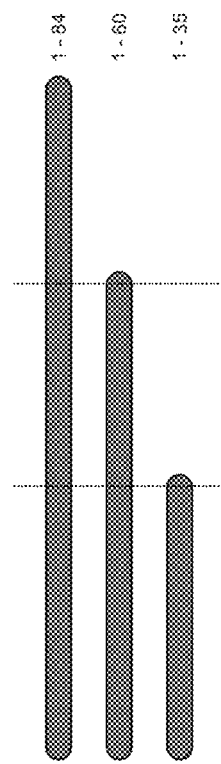
FIG. 4A shows a polyacrylamide gel that was stained with Coomassie Blue and contains a sample (10 μg) of purified Fc-KAAG1 fusion protein (lane 1), a truncated mutant of KAAG1 spanning amino acids 1-60 (lane 2), and another truncated mutant of KAAG1 spanning amino acids 1-35 (lane 3) that were produced in transiently transfected 293E cells. All proteins were Fc fusion proteins.
Figure 4B:
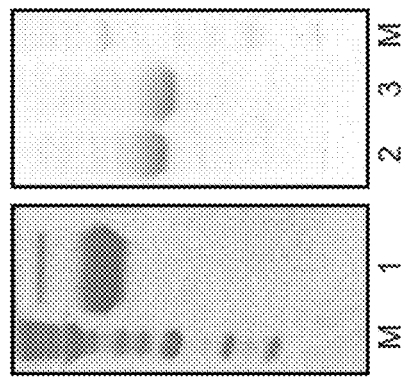
FIG. 4B is a scheme that illustrates the truncated mutants of KAAG1 that were generated for the epitope mapping studies.
Figure 4C:
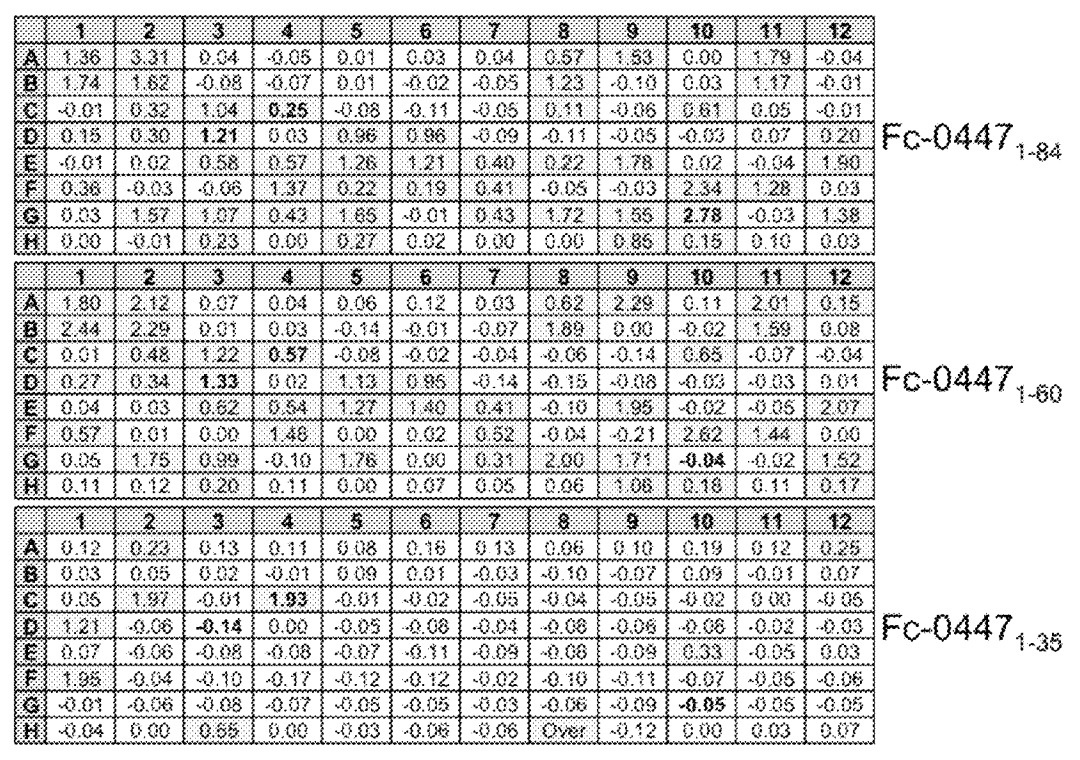

To further delineate the regions of KAAG1 that are bound by the monoclonal antibodies, truncated mutants of KAAG1 were expressed and used in the ELISA. As for the full length KAAG1, the truncated versions were amplified by PCR and ligated into BamHI/HindIII digested pYD5. The primers that were used combined the forward oligonucleotide with the sequence shown in SEQ ID NO.:52 with primers of SEQ ID NOS:55 and 56, to produce Fc-fused fragments that ended at amino acid number 60 and 35 of KAAG1, respectively. The expression of these mutants was conducted as was described above for the full length Fc-KAAG1 and purified with Protein-A agarose. A representative gel of the protein preparations that were used in the ELISA is shown in FIG. 4A and a schematic of the mutant proteins used for epitope mapping is depicted in FIG. 4B.

The results showed that the library was comprised of antibodies that could bind to each of the delineated KAAG1 regions. In particular, of the 48 mAbs that bound to KAAG1 in the first ELISA, nine (wells A2, A12, C2, C4, D1, E10, F1, H3, and H8) were found to interact with the first 35 amino acids of KAAG1 whereas five (D12, E8, F5, G10, and H5) were found to interact with the last 25 amino acids of KAAG1. Thus, the remaining 34 antibodies interacted with a region of KAAG1 spanned by amino acids 36-59. These results were in agreement with the sequence analysis of 24 representative light and heavy chain variable regions. Indeed, alignment of these sequences revealed that the antibodies clustered into three groups based on the percentage identity in their respective CDRs. Antibodies contained in each cluster all interacted with the same region of KAAG1.

Therefore, based on the relative binding affinity of the mAb, differential epitope interaction characteristics, and the differences in variable domain sequences, three antibodies from the plate described in Example 3 were selected for further analysis as exemplary anti-KAAG1 monoclonal antibodies.

Example 5

Figure 5:
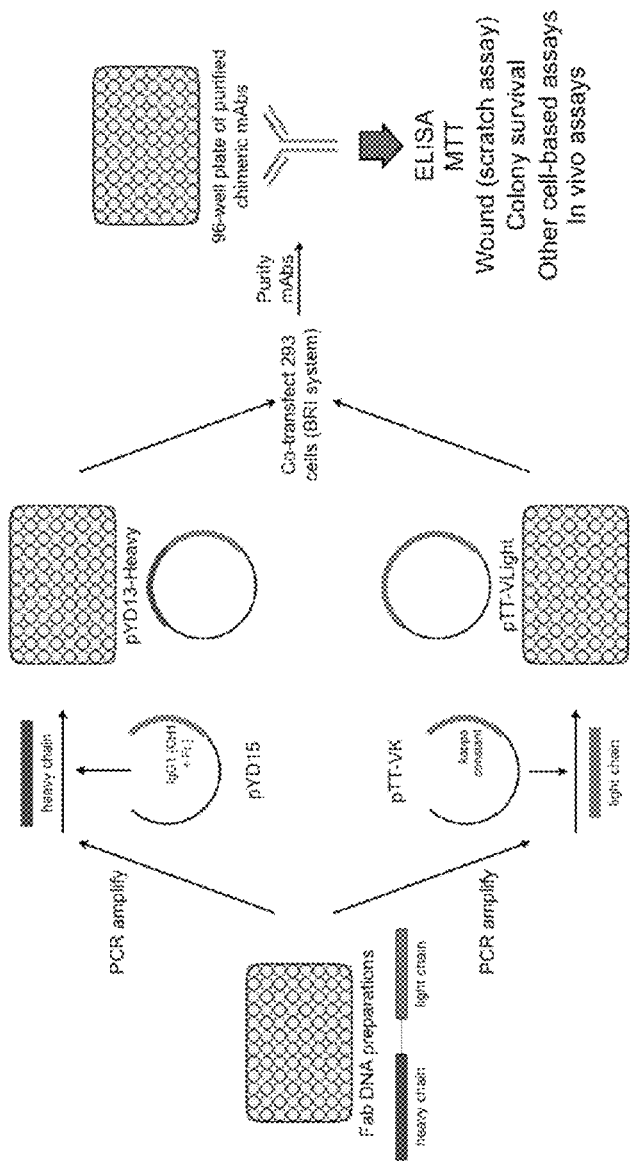
FIG. 5 presents a scheme that illustrates the steps involved to convert the mouse Fabs into IgG1 mouse-human chimeric mAbs.

This example discloses the methods used to convert the Fabs into full IgG1 chimeric monoclonal antibodies. A scheme of the methodology is presented in FIG. 5.

Aside from the possibility of conducting interaction studies between the Fab monoclonals and the KAAG1 protein, the use of Fabs is limited with respect to conducting meaningful in vitro and in vivo studies to validate the biological function of the antigen. Thus, it was necessary to transfer the light and heavy chain variable regions contained in the Fabs to full antibody scaffolds, to generate mouse-human chimeric IgG1s. The expression vectors for both the light and heavy immunoglobulin chains were constructed such that i) the original bacterial signal peptide sequences upstream of the Fab expression vectors were replaced by mammalian signal peptides and ii) the light and heavy chain constant regions in the mouse antibodies were replaced with human constant regions. The methods to accomplish this transfer utilized standard molecular biology techniques that are familiar to those skilled in the art. A brief overview of the methodology is described here (see FIG. 5).

Light chain expression vector—an existing mammalian expression plasmid, called pTTVH8G (Durocher et al., 2002), designed to be used in the 293E transient transfection system was modified to accommodate the mouse light chain variable region. The resulting mouse-human chimeric light chain contained a mouse variable region followed by the human kappa constant domain. The cDNA sequence encoding the human kappa constant domain was amplified by PCR with primers OGS1773 and OGS1774 (SEQ ID NOS:57 and 58, respectively). The nucleotide sequence and the corresponding amino acid sequence for the human kappa constant region are shown in SEQ ID NOS:59 and 60, respectively. The resulting 321 base pair PCR product was ligated into pTTVH8G immediately downstream of the signal peptide sequence of human VEGF A (NM_003376). This cloning step also positioned unique restriction endonuclease sites that permitted the precise positioning of the cDNAs encoding the mouse light chain variable regions. The sequence of the final expression plasmid, called pTTVK1, is shown in SEQ ID NO.:61. Based on the sequences disclosed in Table 3, PCR primers specific for the light chain variable regions of antibodies 3D3, 3G10, and 3C4 (SEQ ID NOS:15, 19, and 23, respectively) were designed that incorporated, at their 5'-end, a sequence identical to the last 20 base pairs of the VEGF A signal peptide. The sequences of these primers are shown in SEQ ID NOS:62, 63, and 64. The same reverse primer was used to amplify all three light chain variable regions since the extreme 3'-ends were identical. This primer (SEQ ID NO.:65) incorporated, at its 3'-end, a sequence identical to the first 20 base pairs of the human kappa constant domain. Both the PCR fragments and the digested pTTVK1 were treated with the 3'-5' exonuclease activity of T4 DNA polymerase resulting in complimentary ends that were joined by annealing. The annealing reactions were transformed into competent *E. coli* and the expression plasmids were verified by sequencing to ensure that the mouse light chain variable regions were properly inserted into the pTTVK1 expression vector. Those skilled in the art will readily recognize that the method used for construction of the light chain expression plasmids applies to all anti-KAAG1 antibodies contained in the original Fab library.

Heavy chain expression vector—the expression vector that produced the heavy chain immunoglobulins was designed in a similar manner to the pTTVK1 described above for production of the light chain immunoglobulins. Plasmid pYD11 (Durocher et al., 2002), which contains the human IgGK signal peptide sequence as well as the CH2 and CH3 regions of the human Fc domain of IgG1, was modified by ligating the cDNA sequence encoding the human constant CH1 region. PCR primers OGS1769 and OGS1770 (SEQ ID NOS:66 and 67), designed to contain unique restriction endonuclease sites, were used to amplify the human IgG1 CH1 region containing the nucleotide sequence and corresponding amino acid sequence shown in SEQ ID NOS:68 and 69. Following ligation of the 309 base pair fragment of human CH1 immediately downstream of the IgGK signal peptide sequence, the modified plasmid (SEQ ID NO.:70) was designated pYD15. When a selected heavy chain variable region is ligated into this vector, the resulting plasmid encodes a full IgG1 heavy chain immunoglobulin with human constant regions. Based on the sequences disclosed in Table 3, PCR primers specific for the heavy chain variable regions of antibodies 3D3, 3G10, and 3C4 (SEQ ID NOS:17, 21, and 25, respectively) were designed that incorporated, at their 5'-end, a sequence identical to the last 20 base pairs of the IgGK signal peptide. The sequences of these primers are shown in SEQ ID NOS:71 (3D3 and 3G10 have the same 5'-end sequence) and 72. The same reverse primer was used to amplify all three heavy chain variable regions since the extreme 3'-ends were identical. This primer (SEQ ID NO.:73) incorporated, at its 3'-end, a sequence identical to the first 20 base pairs of the human CH1 constant domain. Both the PCR fragments and the digested pYD15 were treated with the 3'-5' exonuclease activity of T4 DNA polymerase resulting in complimentary ends that were joined by annealing. The annealing reactions were transformed into competent *E. coli* and the expression plasmids were verified by sequencing to ensure that the mouse heavy chain variable regions were properly inserted into the pYD15 expression vector. Those skilled in the art will readily recognize that the method used for construction of the heavy chain expression plasmids applies to all anti-KAAG1 antibodies contained in the original Fab library.

Figure 6:
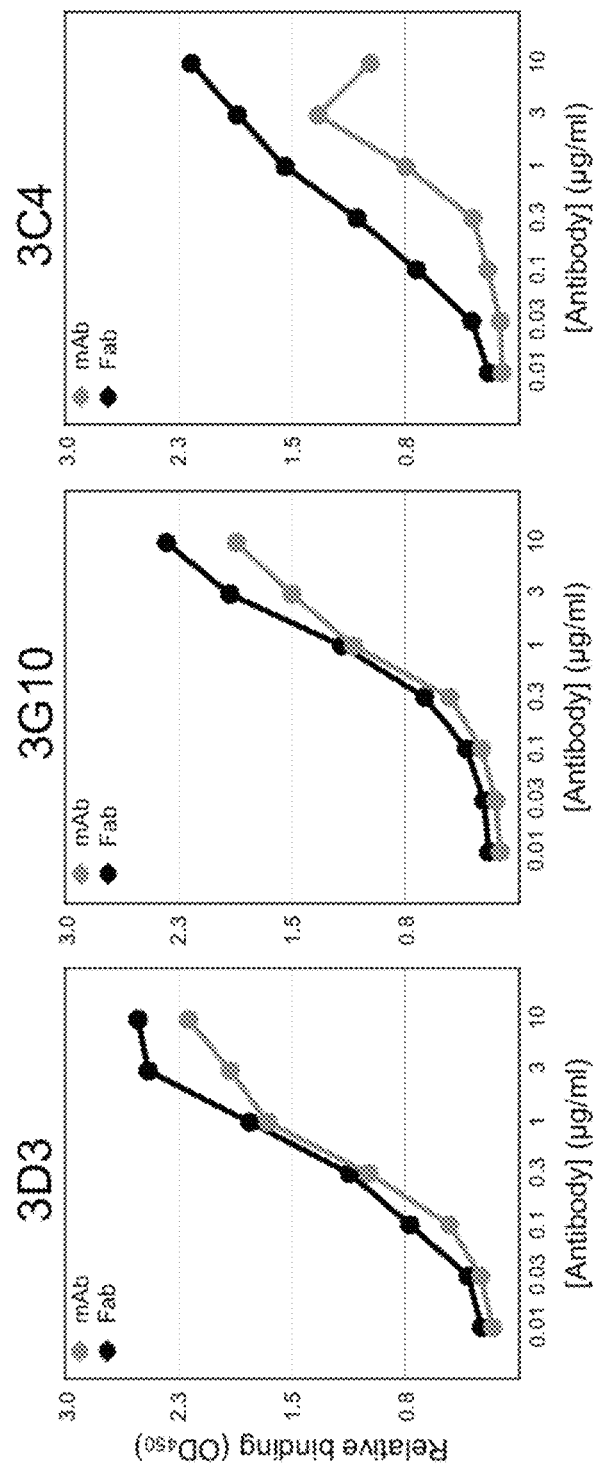
FIG. 6 shows drawings that compare the binding of the mouse anti-KAAG1 Fabs with the binding of the corresponding IgG1 chimeric monoclonal antibodies for exemplary antibodies 3D3, 3G10, and 3C4. The results indicate that the relative binding of the Fab variable regions was maintained when transferred to a full human IgG1 scaffold.

Expression of human IgG1s in 293E cells—The expression vectors prepared above that encoded the light and heavy chain immunoglobulins were expressed in 293E cells using the transient transfection system (Durocher et al., 2002). The methods used for co-transfecting the light and heavy chain expression vectors were described in Example 3. The ratio of light to heavy chain was optimized in order to achieve the most yield of antibody in the tissue culture medium and it was found to be 9:1 (L:H). The ability of the chimeric anti-KAAG1 monoclonal antibodies to bind to recombinant Fc-KAAG1 was measured in the ELISA and compared with the original mouse Fabs. The method was described in Example 3. As depicted in FIG. 6, the binding of the 3D3, and 3G10 chimeric IgG1 monoclonal antibodies was very similar to the Fabs. In the case of the 3C4, the binding activity of the chimeric was slightly less than the Fab. Despite this, this result shows that the transposition of the variable domains from the mouse Fabs into a human IgG1 backbone did not significantly affect the capacity of the light and heavy chain variable regions to confer KAAG1 binding.

Example 6

This example describes the use of anti-KAAG1 antibodies to block the activity of KAAG1 in ovarian cancer cell models.

Figure 7:
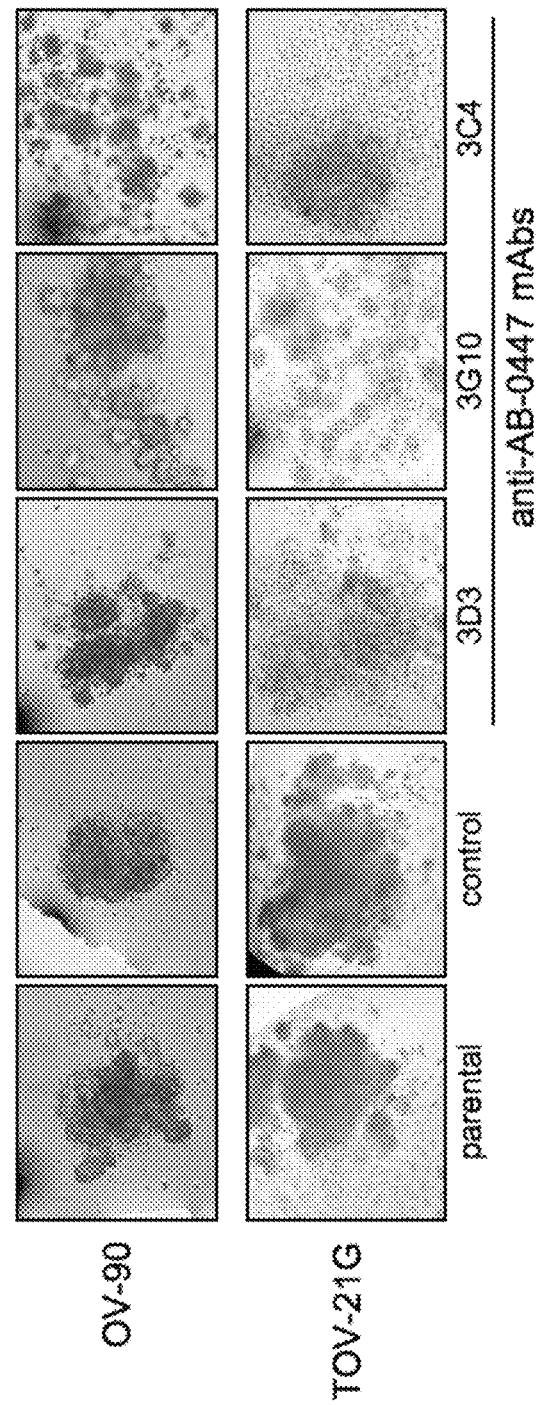
FIG. 7 shows depictions of spheroid formation experiments using TOV-21G and OV-90 ovarian cancer cell lines in the presence of chimeric IgG1 anti-KAAG1 monoclonal antibodies. Loosely packed structures are indicative of less invasive cancer cell lines. The results show spheroids treated with the exemplary anti-KAAG1 antibodies 3D3, 3G10, or 3C4.

Example 2 disclosed RNAi studies showing that KAAG1 played an important role in the behavior of ovarian cancer cells. The monoclonal antibodies described above were used to determine whether it was possible to reproduce these results by targeting KAAG1 at the cell surface. TOV-21G and OV-90 cells were cultured under conditions to produce spheroids and treated with 10 µg/ml of 3D3, 3G10, or 3C4 anti-KAAG1 chimeric monoclonal antibody. As illustrated in FIG. 7, both cell lines efficiently formed spheroids when left untreated (parental) or when treated with antibody dilution buffer (control). In contrast, the presence of anti-KAAG1 antibodies resulted in loosely packed structures and in certain cases, the cells were unable to assemble into spheroids. These results confirm the earlier observations and suggest that the anti-KAAG1 monoclonal antibodies can modulate the activity of KAAG1 during the formation of spheroids. Since spheroid formation by cancer cell lines is an in vitro model for tumor formation, the results also suggest that blocking KAAG1 could lead to decreased tumor formation in vivo.

Example 7

This example describes the use of anti-KAAG1 antibodies for detecting the expression of KAAG1 in ovarian tumors.

Figure 8A:
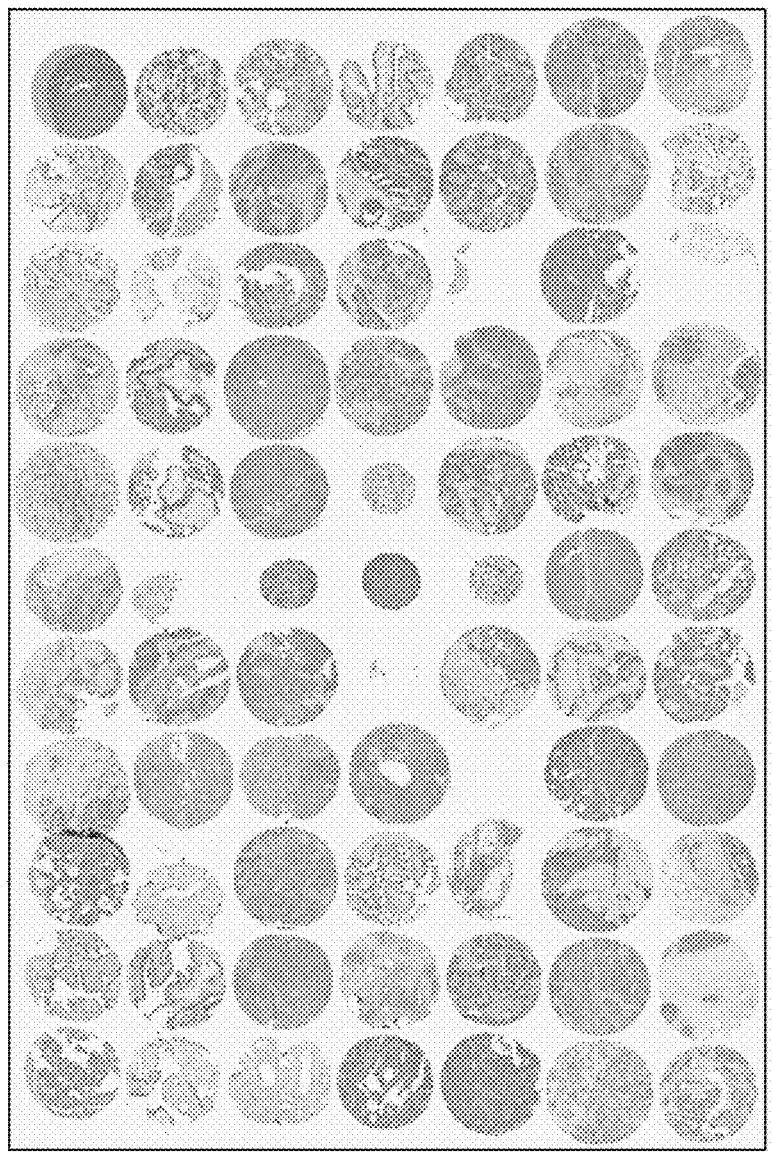
FIG. 8A shows a scan of a tissue microarray containing approximately 70 biopsy samples obtained from ovarian tumor patients. The samples were blotted with the 3D3 anti-KAAG1 antibody and showed that the vast majority of ovarian tumors expressed very high level of KAAG1 antigen.
Figure 8B:
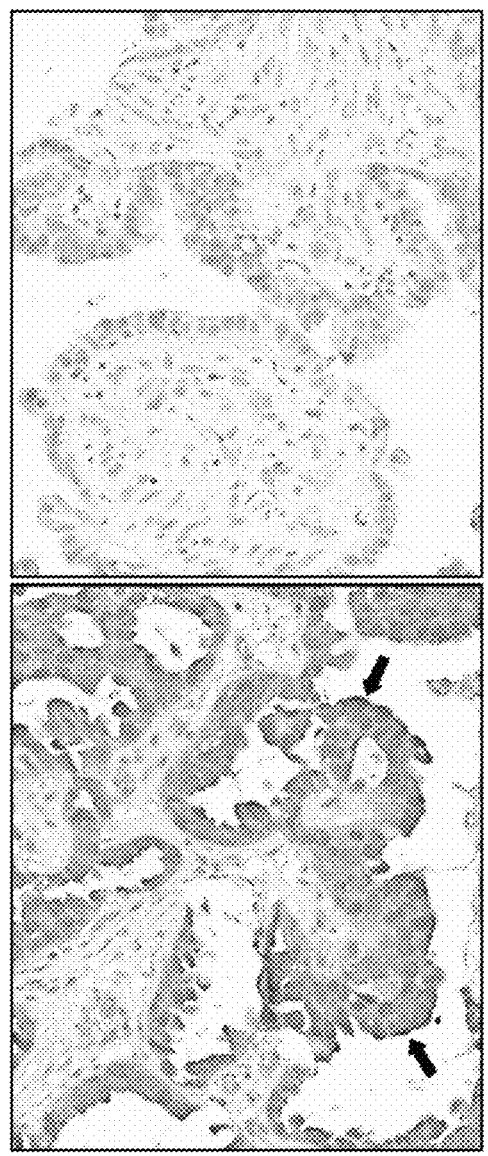
FIG. 8B a higher magnification picture from the tissue microarray experiment. The arrows show the membrane localization of KAAG1 at the apical surface of the epithelial layer of cells in serous ovarian tumors.
Figure 8C:
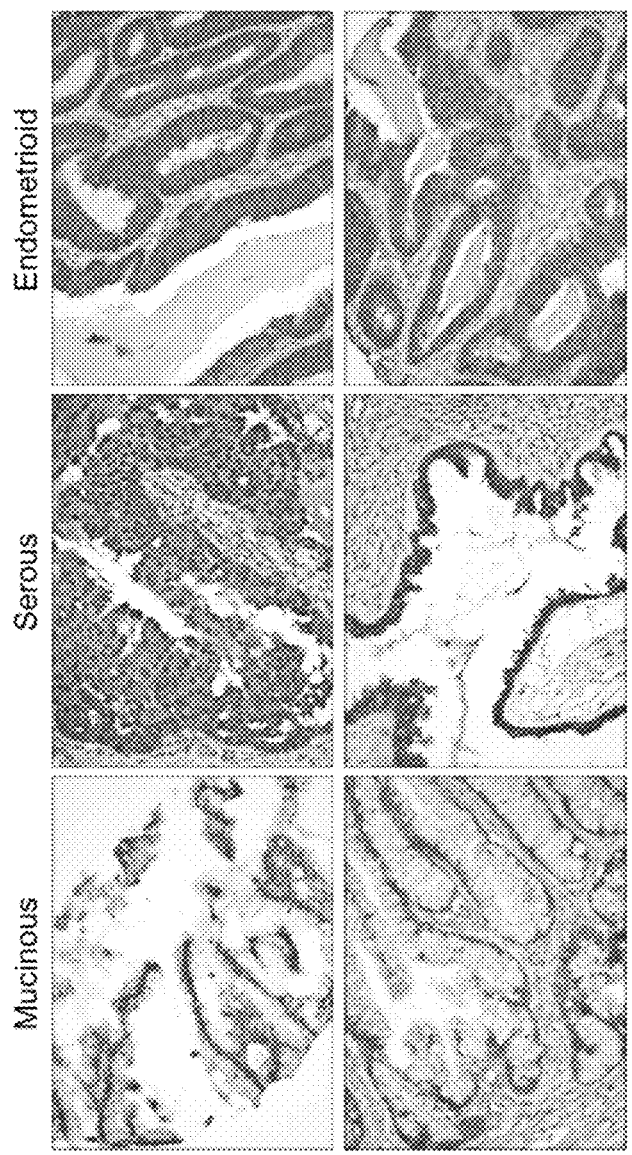
FIG. 8O illustrates other immunohistochemical studies that demonstrate that KAAG1 is highly expressed in all ovarian cancer types. The histotypes shown are serous, mucinous and endometroid.

As a means of confirming the expression of KAAG1 protein in ovarian cancer tumors and in order determine if expression of the gene correlated with the presence of the protein, immunohistochemistry was conducted. Tissue microarrays were obtained that contained dozens of ovarian tumor samples generated from patient biopsies. Paraffin-embedded epithelial ovarian tumor samples were placed on glass slides and fixed for 15 min at 50° C. Deparaffinization was conducted by treating 2x with xylene followed by dehydration in successive 5 min washes in 100%, 80%, and 70% ethanol. The slides were washed 2x in PBS for 5 min and treated with antigen retrieval solution (citrate-EDTA) to unmask the antigen. Endogenous peroxide reactive species were removed by incubating slides with $H_2O_2$ in methanol and blocking was performed by incubating the slides with serum-free blocking solution (Dakocytomation) for 20 min at room temperature. The primary mAb (anti-KAAG1 3D3) was added for 1 h at room temperature. KAAG1-reactive antigen was detected by incubating with biotin-conjugated mouse anti-kappa followed by streptavidin-HRP tertiary antibody. Positive staining was revealed by treating the slides with DAB-hydrogen peroxide substrate for less than 5 min and subsequently counterstained with hematoxylin. The KAAG1 protein was found to be expressed at very high levels in the vast majority of ovarian tumor samples. A representative array containing 70 tumors is depicted in FIG. 8A. As demonstrated by the expression profiling studies that were performed using RT-PCR, KAAG1 transcripts were present in greater than 85% of ovarian tumor samples analyzed. Clearly, there is an excellent correlation between the transcription of the KAAG1 gene and the presence of the protein in ovarian cancer. Some of the samples were inspected at a higher magnification to determine which cells were expressing the KAAG1 protein. As depicted in FIG. 8B, KAAG1 is predominantly expressed in the surface epithelium of ovarian tumors. In addition, strong intensity was observed on the apical side of these epithelial cells (see arrows in FIG. 8B, magnification: 20x). Finally, immunohistochemistry was repeated on ovarian tumor samples that originated from different histotypes. As explained earlier, epithelial ovarian cancer can be classified into 4 major histotypes: serous, endometroid, clear cell, and mucinous. The expression of KAAG1 was detected in all types of epithelial ovarian cancer, in particular serous and endometroid histotypes (see FIG. 8C).

Taken together, these immunohistochemical studies illustrate the utility of detecting KAAG1 in ovarian cancer with the monoclonal antibodies.

Example 8

$IgG_1$ Antibodies Against KAAG1 can Mediate ADCC

Antibody-Dependent Cell Cytotoxicity (ADCC) is a mechanism of cell-mediated immunity whereby effector cells, typically natural killer (NK) cells, of the immune system actively lyse target cells that have been bound by specific antibodies. The interaction between the NK cells and the antibody occurs via the constant Fc domain of the antibody and high-affinity Fcγ receptors on the surface of the NK cells. $IgG_1$s have the highest affinity for the Fc receptors while $IgG_2$ mAbs exhibit very poor affinity. For this reason the chimeric antibodies targeting KAAG1 were designed as $IgG_1$s. This type of effector function that is mediated in this manner can often lead to the selective killing of cancer cells that express high level of antigen on their cell surfaces.

Figure 13:
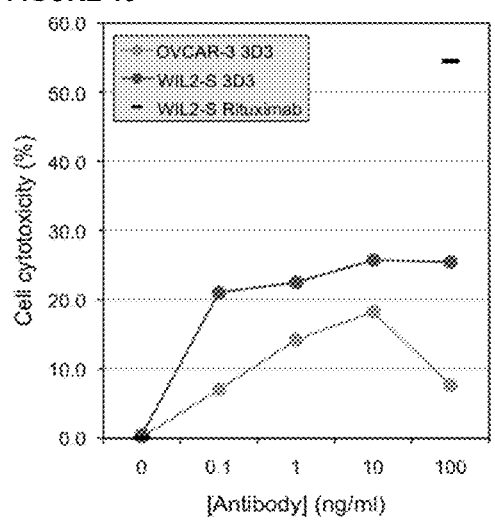
FIG. 13 An IgG$_1$ antibody that targets KAAG1 can efficiently mediate ADCC activity in vitro. PBMNCs (AllCells, LLC, Emoryville, Calif.) were incubated with 3D3 for 30 min and mixed with either OVCAR-3 or WIL2-S cells at a ratio of 1:25. The cells were incubated for 4 h at 37 C and cell lysis was determined by measuring LDH levels in the medium. Cell cytotoxicity was calculated as follows: % cytotoxicity= (experimental−effector spontaneous−target spontaneous)× 100/(target maximum−target spontaneous).

An in vitro assay to measure ADCC activity of the anti-KAAG1 $IgG_1$ chimeric antibodies was adapted from a previously published method, which measured the ADCC activity of the anti-CD20 rituxan in the presence of a lymphoma cell line called WIL2-S (Idusogie et al., (2000) J. Immunol. 164, 4178-4184). Human peripheral blood mononuclear cells (PBMNCs) were used as a source of NK cells which were activated in the presence of increasing concentration of the 3D3 chimeric $IgG_1$ antibody (see FIG. 13). The target cells were incubated with the activated PBMNCs at a ratio of 1 to 25. As shown, cell death increased in a dose-dependent manner both in the presence of OVCAR-3 and the lymphoma cell line, the latter of which was shown to express KAAG1 by RT-PCR (not shown). As a positive control, the results from the published method were reproduced where high level of ADCC was obtained for rituxan in the presence of WIL2-S cells.

ADCC was also observed with other ovarian cancer cell lines that express relatively high levels of KAAG1. These results demonstrate that $IgG_1$ antibodies that are specific for KAAG1, as exemplified by 3D3, can enhance the lysis of cancer cells which express the antigen on their cell surface.

Example 9

Antibodies Against KAAG1 can Reduce the Invasion of Ovarian Tumors

Patients that develop ovarian cancer have lesions that typically initiate by an uncontrolled growth of the cells in the epithelial layer of the ovary or, in some instances, the fallopian tube. If detected early, these primary tumors are surgically removed and first-line chemotherapy can result in very good response rates and improved overall survival. Unfortunately, 70% of the patients will suffer recurrent disease resulting in the spread of hundreds of micro-metastatic tumors throughout the abdominal cavity. Second-line therapies can be efficacious, but often patients either respond poorly or the tumors develop chemoresistance. Treatment options are limited and there are urgent needs for new therapies to circumvent resistance to cytotoxic drugs.

In order to test the efficacy of anti-KAAG1 antibodies in vivo, an animal model of ovarian cancer was used that is the closest representation of the clinical manifestation of the disease in humans. The TOV-112D cell line is of endometrioid origin and expresses the KAAG1 antigen as measured by RT-PCR. Previous IHC studies showed that ovarian tumors of the endometrioid histotype contain strong expression of KAAG1 thus rendering the 112D cell line an appropriate selection for testing anti-KAAG1 antibodies.

Figure 14A:
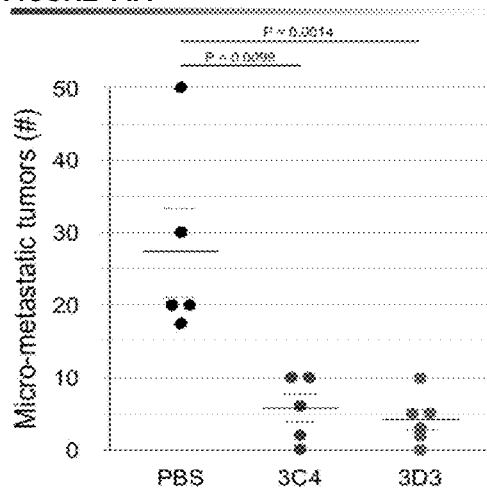
FIG. 14 Anti-KAAG1 mAbs prevent the spread of TOV-112D ovarian tumors in vivo. $1\times10^6$ cells were implanted in the peritoneal cavity of SCID mice in a volume of 200 μL. Treatment with either PBS or antibodies diluted in PBS was performed 2 days later at a dose of 25 mg/kg qwk. The mice were sacrificed as soon as the tumors were detected by palpation of the abdomen. The number of tumors were scored visually (B) and the data in panel A is expressed as the average number of tumors/mouse±SE.
Figure 14B:
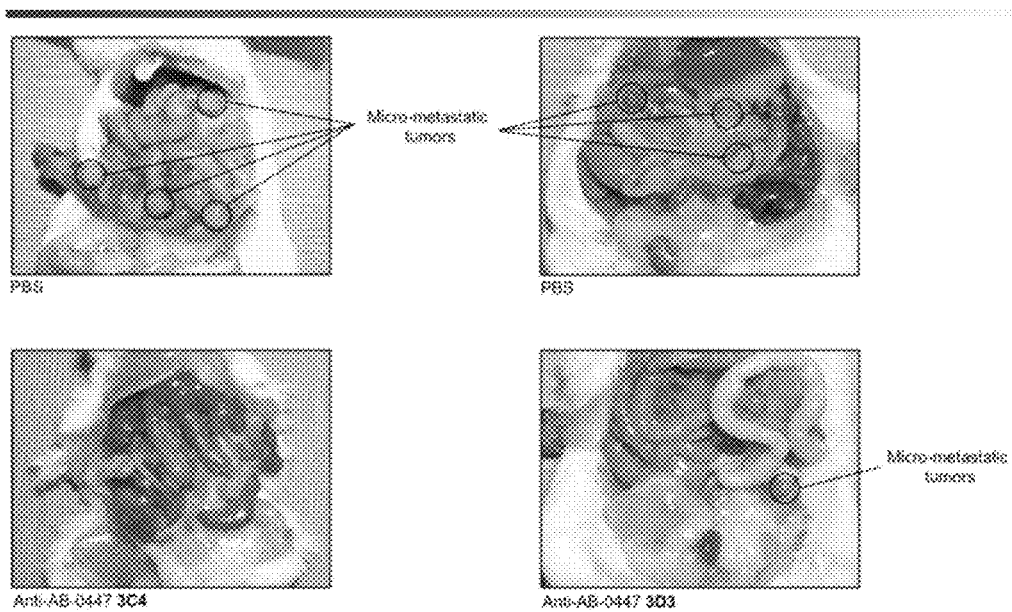

The intra-peritoneal inoculation of the TOV-112D cell line in SCID mice resulted in the implantation of dozens of micrometastatic tumors that closely resemble those that are observed in humans. Mice treated with PBS, the diluent for the antibodies, contained upon examination, an average of 25-30 tumors per animal (FIGS. 14A and 14B). In some cases, the number of tumors was so high in the abdominal cavity of these mice that the number of tumors could not be easily determine; these mice were excluded from the statistical analysis. When the mice were treated with the 3C4 and 3D3 antibodies, the number of micro-metastatic tumors was drastically reduced. In addition, there was at least one animal per group treated with anti-KAAG1 where no tumors were seen. A second experiment was conducted in mice containing a larger number of TOV-112D tumors (>50/animal) and very similar results were obtained. Moreover, there was very little difference between the groups treated with the 3C4 compared to the 3D3 antibody. However, the tendency in these in vivo experiments as well as the results obtained in the cell-based assays show that the 3D3 antibody displayed slightly more efficacy. Whether, this is due to a more accessible epitope or a higher affinity of 3D3 compared to 3C4 for the antigen still remains to be established. The results from these two experiments demonstrated that targeting KAAG1 on the surface of ovarian cancer cells could lead to a significant reduction in the spread of the tumors in vivo.

Furthermore, these findings are in complete agreement with the observations that were made in the cell-based assays. For example, the increased expression of the KAAG1 mRNA in the spheroids compared to cell lines grown as monolayers; the reduction in cell migration in the presence of KAAG1 shRNAs, the reduction in the ability of cell lines to form spheroids when treated with KAAG1 antibodies; and finally, enhancement of ADCC activity by anti-KAAG1 IgG$_1$s. Taken together, the results strongly suggest that targeting KAAG1 with an antibody has great therapeutic potential in recurrent ovarian cancer.

Example 10

Figure 15:
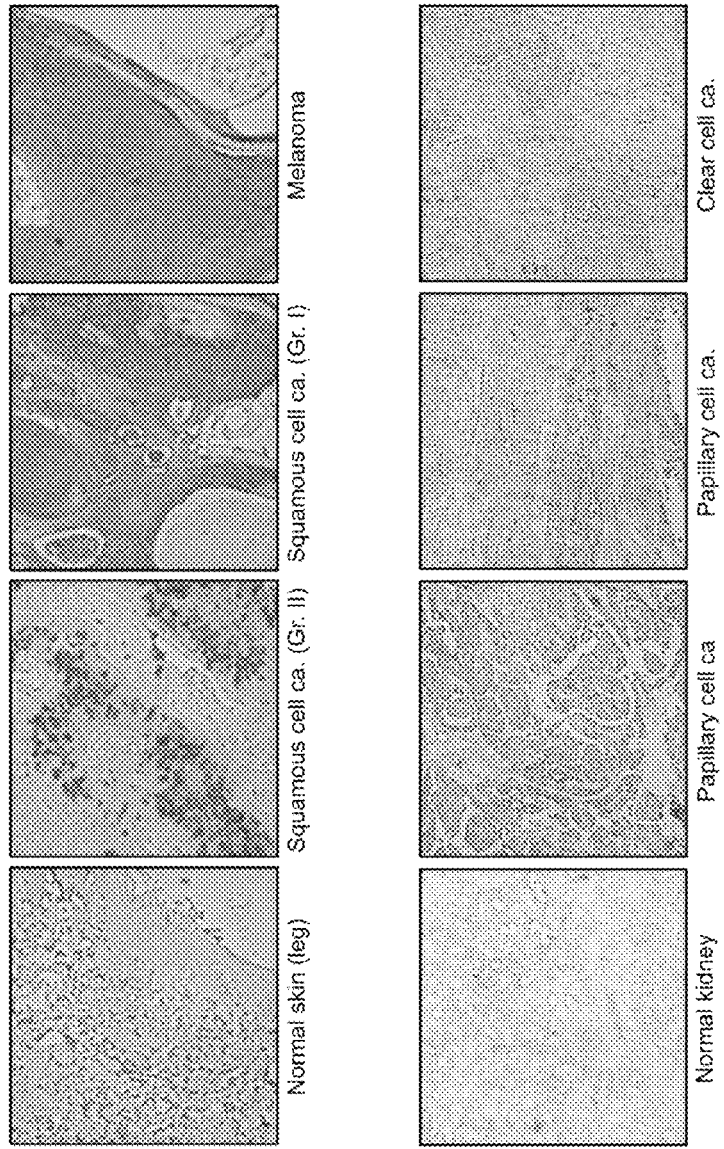
FIG. 15 shows immunohistochemistry performed with an anti-KAAG1 antibody on human skin tumor tissue microarrays (Pantomics Inc., Richmond, Calif.) of several sections isolated from squamous cell carcinomas and melanomas.

KAAG1 is Expressed in Skin Tumors and Renal Cell Carcinomas and is a Therapeutic Target in these Indications The mRNA profiling studies that were conducted showed that the transcript encoding the KAAG1 antigen was highly expressed in cell lines derived from melanoma samples and renal carcinomas. These results were disclosed in Sooknanan et al., 2007. To confirm the transcriptional regulation of the KAAG1 gene in these cancer types, immunohistochemistry was performed with an anti-KAAG1 antibody on human skin tumor tissue microarrays (Pantomics Inc., Richmond, Calif.) containing several sections isolated from squamous cell carcinomas and melanomas. The analysis of this array showed that there was very strong staining in biopsies isolated from squamous cell carcinomas and melanomas (FIG. 15, top panel). Both of these types are among the most common forms of skin cancers and interestingly, the squamous cell carcinomas are the most metastatic, a fact that again links the expression of KAAG1 to an invasive phenotype. As previously observed, the presence of KAAG1 was very weak or absent on the three normal skin samples that were contained on the array. Similarly, KAAG1 was detected in many of the samples contained in an array of renal cancer. Most of the positive samples were predominantly of the papillary cell carcinoma type and a few clear cell carcinomas expressed KAAG1 protein. Papillary carcinomas represent approximately 20% of renal cancer cases.

Figure 16:
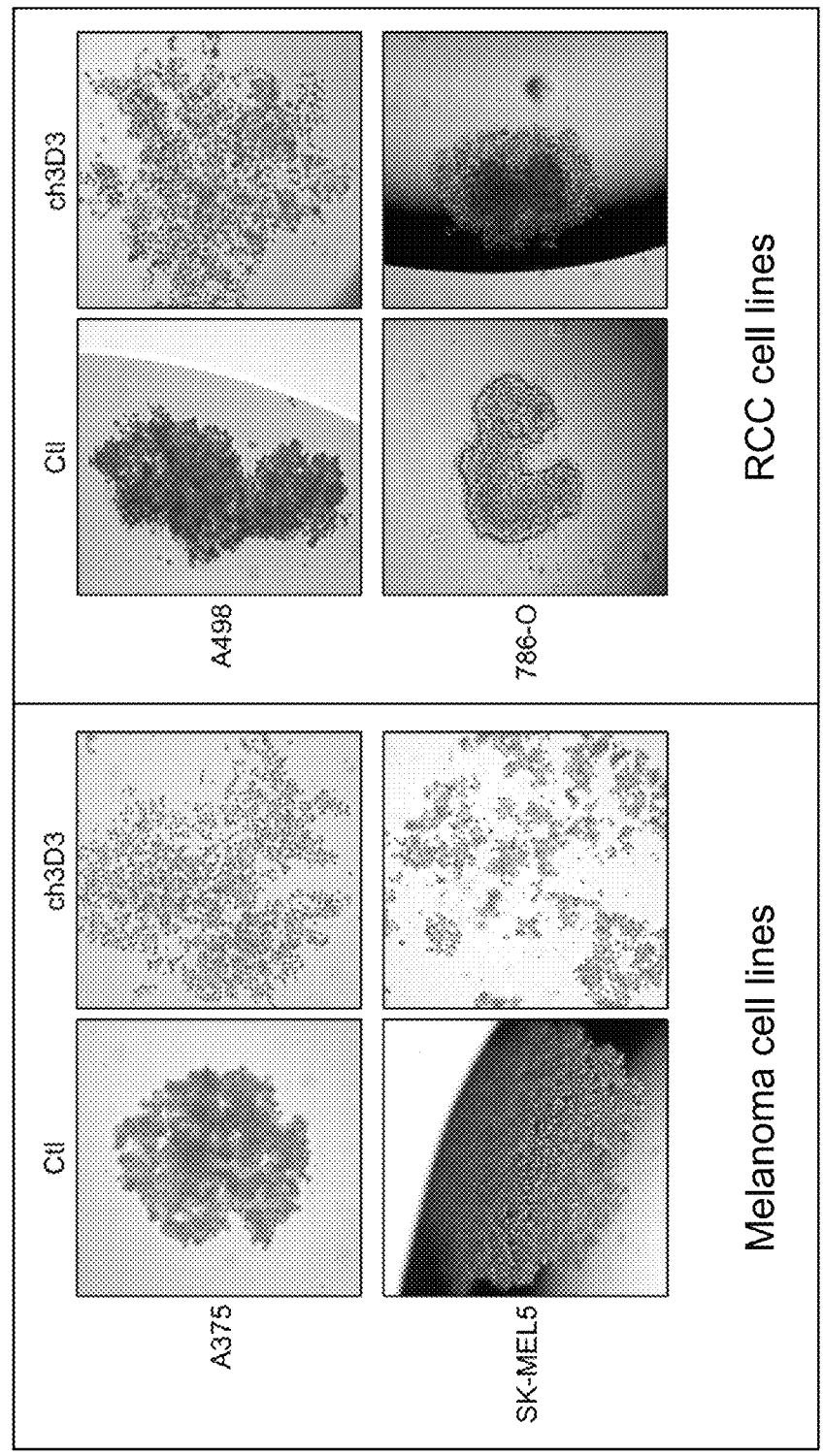
FIG. 16 illustrates spheroid formation of melanoma cell lines (A375 and SK-MEL5) and of renal cell carcinoma cell lines (A498 and 786-O) in the presence or absence of the chimeric 3D3 antibody.

In order to test if the function of KAAG1 is the same in these types of cancer compared to its role in ovarian cancer, cell lines derived from melanoma and renal cell carcinomas were obtained and tested in the spheroid culture assay (see Example 1 and 6). For the melanoma model, A375 and SK-MEL5 cells, two malignant melanoma cell lines, were cultured under conditions that allowed them to form spheroids in the presence of 5% FBS. The cultures were incubated with or without the anti-KAAG1 chimeric 3D3 antibody at a concentration of 5 mg/ml. As shown in FIG. 16, inclusion of 3D3 antibody in the cultures prevented the proper assembly of spheroid structures in melanoma cell lines. This result suggested that KAAG1 plays a similar role in melanoma as it does in ovarian cancer. Cell lines derived from renal cell carcinoma were also tested. The A-498 cell line is a renal papillary cell carcinoma cell line whereas the 786-O is a renal clear cell carcinoma. As depicted in FIG. 16, only the A-498 spheroids were affected by the presence of the 3D3 anti-KAAG1 antibody while the 786-O cell line was unaffected in this assay. These results parallel the immunohistochemistry results described above and indicate that the inhibition of spheroids formation is dependent on the presence of KAAG1 on the surface of renal cancer cells derived predominantly from papillary kidney cancers. It is possible however, that the anti-KAAG1 antibody may work in other types of assays for renal clear cell carcinoma.

Taken together, these data are strongly supportive of a critical function in role of KAAG1 in melanoma and kidney cancer and indicate that blocking KAAG1 with antibodies in these indications has therapeutic potential.

Example 11

KAAG1 is Expressed on the Surface of Ovarian Cancer Cells.

Figure 17A:
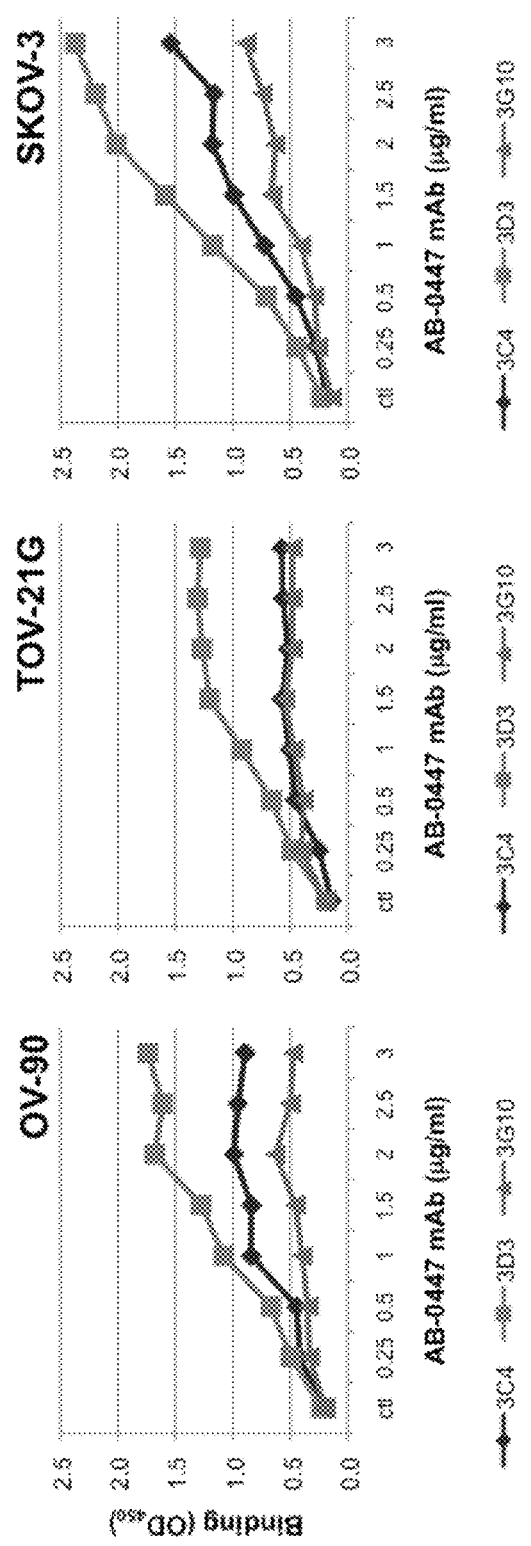
FIG. 17A represents graphs illustrating the binding of increasing concentrations of the 3C4, 3D3 and 3G10 antibodies to cell lines (OV-90, TOV-21G and SKOV-3) fixed under condition that do not permeate the cells.
Figure 17B:
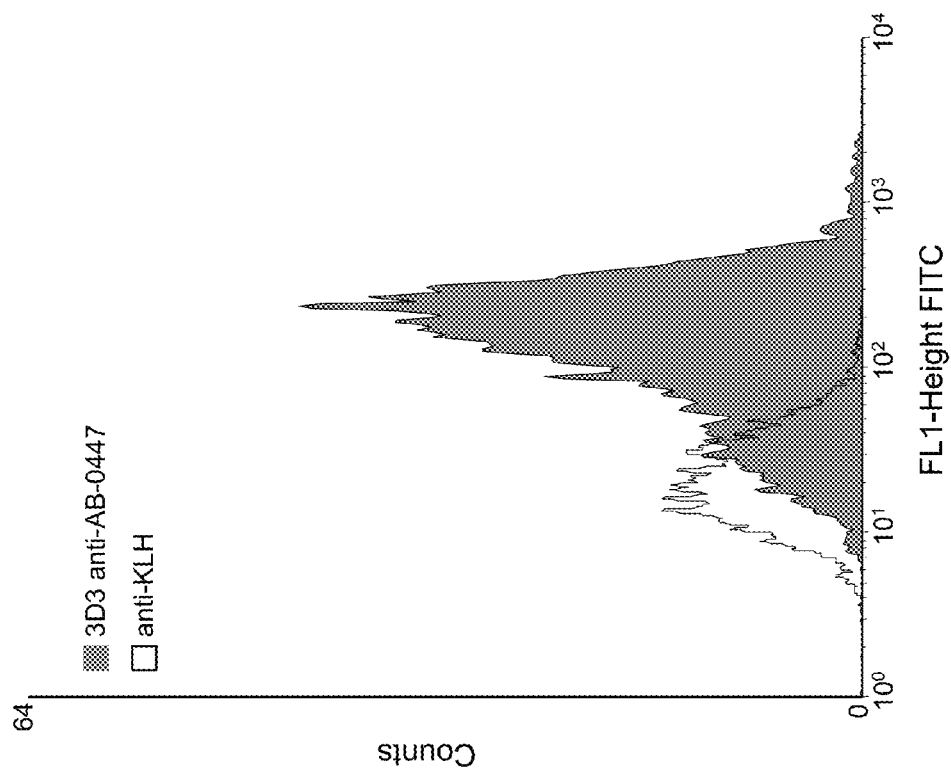
FIG. 17B is a graph illustrating the results of flow cytometry performed on SKOV-3 cell line with the 3D3 antibody.

The combined results from the bioinformatics analysis of the primary structure of the cDNA encoding KAAG1, biochemical studies, and immunohistochemical detection of the protein in epithelial cells suggested that the KAAG1 antigen was located on the cell surface. However, more direct evidence was required to demonstrate that KAAG1 is indeed a membrane-bound protein. In one approach, ovarian cancer cell lines known to express KAAG1 were plated in micro-titer plates, fixed under conditions that do not permeate the cells, and incubated with increasing concentration of anti-KAAG1 chimeric antibodies. Following extensive washing of the cells, bound antibody was detected with HRP-conjugated anti-human IgG as a secondary antibody in a modified cell-based ELISA (see FIG. 17A). The first observation that can be made from these experiments is that the antibodies could be specifically captured by the cells suggesting that the KAAG1 was present at the cell surface. Secondly, the amount of binding was strongest on SKOV-3 cells and the TOV-21G cells exhibited the weakest binding. This was in complete agreement with RT-PCR data which demonstrated that the KAAG1 mRNA was expressed in similar proportions in these cell lines (not shown). Additionally, the 3D3 antibody produced the strongest signal implying that the epitope targeted by this antibody was the most accessible in this assay. The 3G10 could only detect KAAG1 in the cell line that expressed the highest level of AB-0447 (SKOV-3 cells, see right panel of FIG. 17A). A second approach used was flow cytometry. In this case, a mouse 3D3 anti-KAAG1 antibody was incubated with SKOV-3 ovarian cancer cells at saturating conditions and following extensive washing, the bound 3D3 anti-KAAG1 antibody was detected with anti-mouse IgG conjugated to FITC in a flow cytometer. As shown in FIG. 17B, the signal at the surface of SKOV-3 cells was much higher compared to same cells labeled with the negative control, an anti-KLH (Keyhole limpet hemocyanin) antibody, specific for a non-mammalian unrelated protein, which was at a fluorescence level the same as the background readings. Taken together, these results demonstrate that KAAG1 is located on the surface of cells.

Example 12

Methods for the Use of Humanized Anti-KAAG1 Antibodies

Figure 18A:
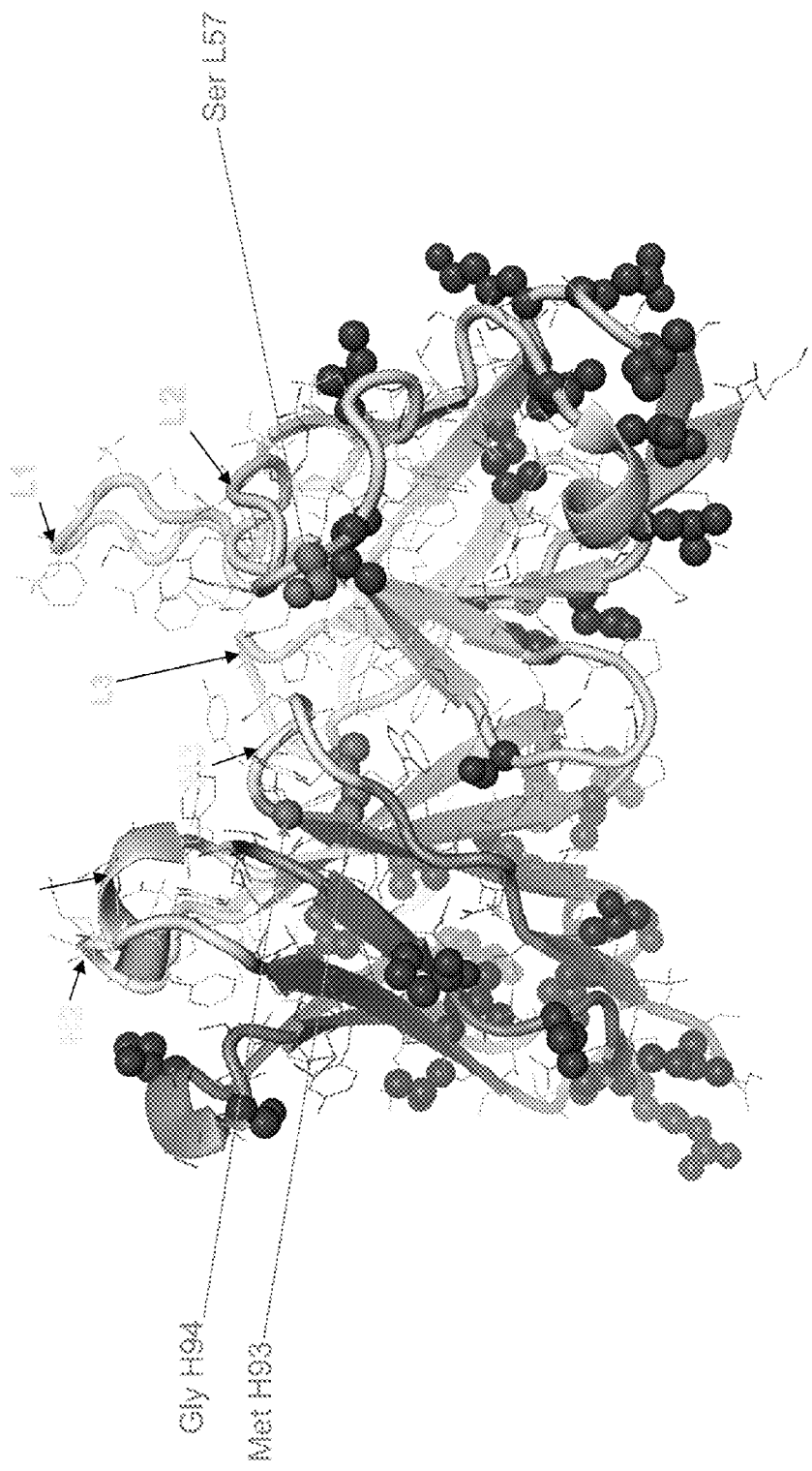
FIG. 18A is a schematic illustrating the structure of the 3D3 antibody model.
Figure 18B:
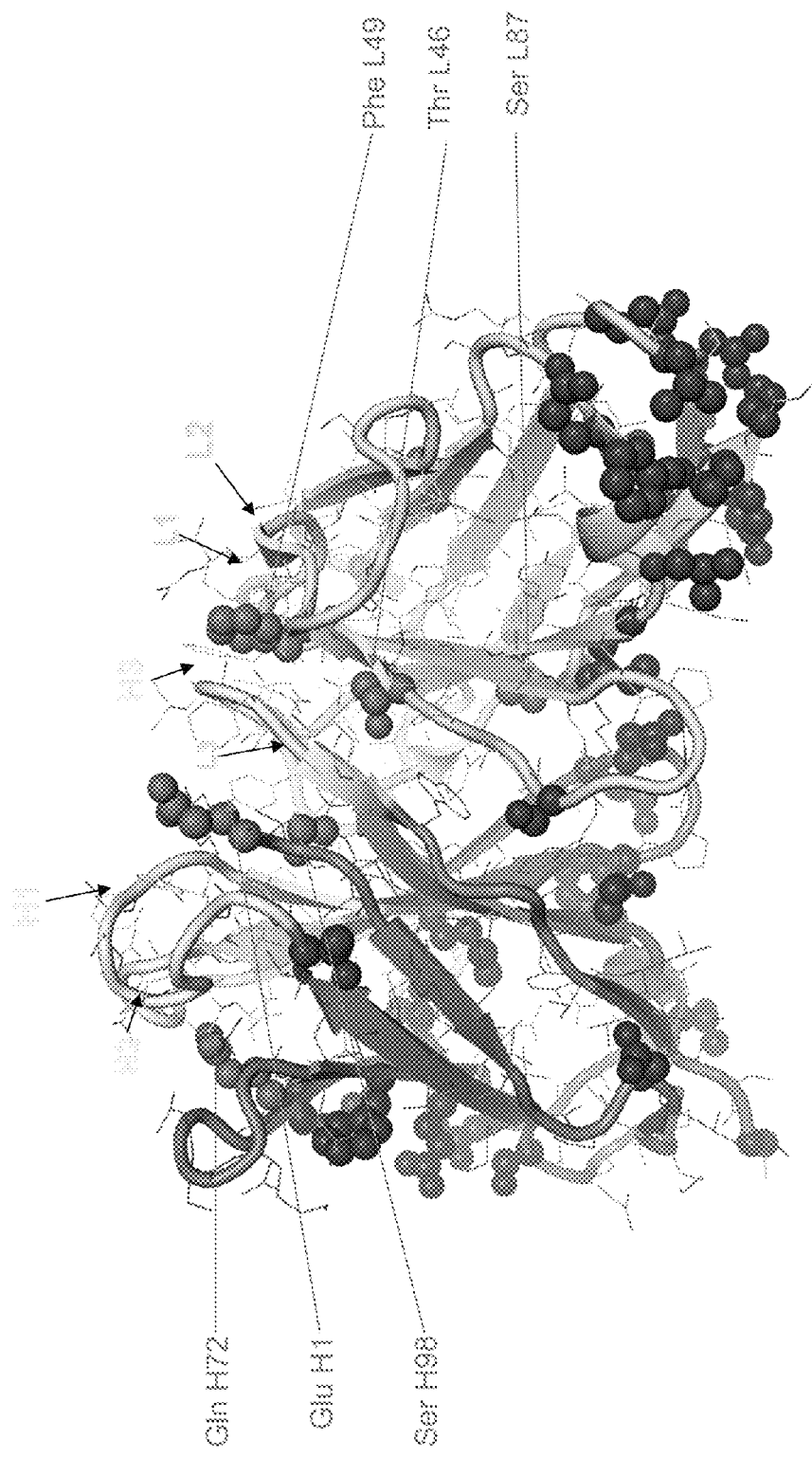
FIG. 18B is a schematic illustrating the structure of the 3C4 antibody model.

On the basis of both the in vitro and preliminary in vivo results, two mouse anti-KAAG1 antibody candidates, designated 3D3 and 3C4, were selected for humanization using in silico modeling using methods familiar to those in the art. In brief, the variable regions of the murine antibodies were modeled in 3D based on available crystal structures of mouse, humanized, and fully human variable regions that displayed high sequence homology and similar CDR loop lengths. The CDRs are the amino acid sequences that contribute to antigen binding; there are 3 CDRs on each antibody chain. Additionally, the framework regions, the amino acid sequences that intervene between the CDRs, were modified by standard homology comparison between mouse and human antibody sequences resulting in the 'best-fit' human sequence. These modifications ensured that the proper positioning of the CDR loops was maintained to ensure maximum antigen binding in the humanized structure as well as preserving the potential N- and O-linked glycosylation sites. The sequence of both the heavy and light chain variable regions in the humanized (h) 3D3 and 3G4 resulted in 96% and 94% humanization, respectively. The structure of the 3D3 and 3C4 models for each antibody is shown in FIGS. 18A and 18B, respectively. As illustrated in these structures, the 3D3 required the maintenance of 3 unusual amino acids (FIG. 18A, Met93 and Gly94 on the heavy chain and Ser57 on the light chain) because of their proximity to the CDRs. Modeling predicted that replacement of these mouse amino acids with human equivalents might compromise binding of the antibody with the KAAG1 antigen. In the case of 3C4, 6 amino acids were considered unusual (FIG. 18B, Glu1, Gln72 and Ser98 on the heavy chain and Thr46, Phe49 and Ser87 on the light chain). In both figures, the light chain CDRs are indicated by L1, L2, and L3 for CDR1, CDR2, and CDR3, respectively, whereas the heavy chain CDRs are indicated by H1, H2, and H3 for CDR1, CDR2, and CDR3, respectively.

The sequences that encode the complete anti-KAAG1 3D3 immunoglobulin light and heavy chains are shown in SEQ ID NO.:176 and 177, respectively. The variable region of the humanized 3D3 light chain is contained between amino acids 21-133 of SEQ ID NO.:176 and is shown in SEQ ID NO.:178. The variable region of the humanized 3D3 heavy chain is contained between amino acids 20-132 of SEQ ID NO.:177 and is shown in SEQ ID NO.:179. The sequences that encode the complete anti-KAAG1 3C4 immunoglobulin light and heavy chains are shown in SEQ ID NO.:180 and 181, respectively. The variable region of the humanized 3C4 light chain is contained between amino acids 21-127 of SEQ ID NO.:180 and is shown in SEQ ID NO.:182. The variable region of the humanized 3C4 heavy chain is contained between amino acids 19-136 of SEQ ID NO.:181 and is shown in SEQ ID NO.:183.

Figure 19A:
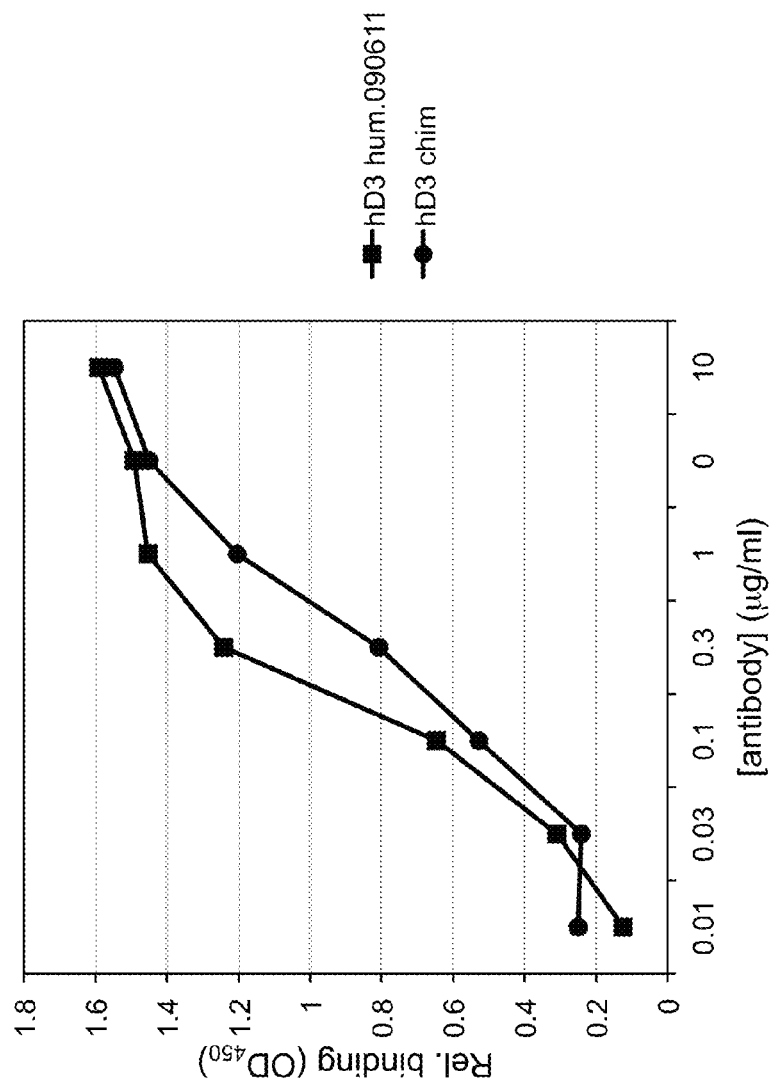
FIG. 19A is a graph illustrating the binding of increasing concentration of the humanized 3D3 antibody in comparison with the chimeric 3D3 antibody to recombinant KAAG1.

Following assembly of expression vectors and production of the h3D3 in transfected mammalian cells (see Example 5), several assays were performed to demonstrate the bio-equivalence of the humanization process. Since an antibody harboring effector functions was required, the h3D3 was assembled as a human $IgG_1$. ELISA-based assays were performed to directly compare the ability of the h3D3 to recombinant KAAG1. The methods used to perform these tests were as described in Example 3 using recombinant Fc-KAAG1. As shown in FIG. 19A, the binding activity of the h3D3 was identical to that of the chimeric 3D3.

More precise measurements were conducted using Surface Plasmon Resonance (SPR) in a Biacore instrument. Kinetic analysis was used to compare the affinity of the chimeric 3D3 with the h3D3 as well as with hybrid antibodies encompassing different permutations of the light and heavy chains (see FIG. 19B). Briefly, anti-human Fc was immobilized on the Biacore sensor chip and chimeric or h3D3 was captured on the chip. Different concentrations of monomeric recombinant KAAG1 were injected and the data were globally fitted to a simple 1:1 model to determine the kinetic parameters of the interaction. The kinetic parameters of the chimeric 3D3 were tabulated in FIG. 19B (m3D3). The average $K_D$ of the chimeric 3D3 was $2.35 \times 10^{-10}$ M. In comparison, all permutations of the chimeric(C)/humanized(H) displayed very similar kinetic parameters. The average $K_D$ of the chimeric light chain expressed with the chimeric heavy chain (indicated as 'CC' in FIG. 19B) was $2.71 \times 10^{-10}$ M, the average $K_D$ of the humanized light chain expressed with the chimeric heavy chain (indicated as 'HC' in FIG. 19B) was $3.09 \times 10^{-10}$ M, the average $K_D$ of the chimeric light chain expressed with the humanized heavy chain (indicated as 'CH' in FIG. 19B) was $5.05 \times 10^{-10}$ M, and the average $K_D$ of the humanized light chain expressed with the humanized heavy chain (indicated as 'HH' in FIG. 19B) was $4.39 \times 10^{-10}$ M. The analyses indicated that the humanization of 3D3 conserved the binding activity of the original mouse antibody.

Figure 19C:
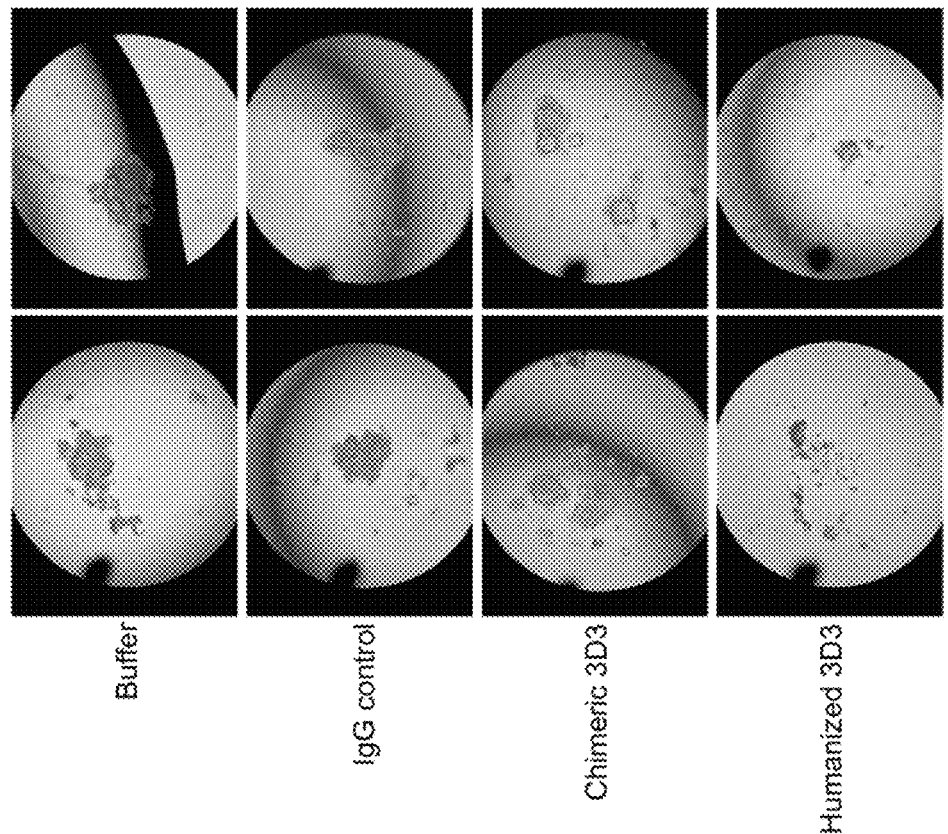
FIG. 19C illustrates spheroid formation of SKOV-3 ovarian cancer cells in the presence of the humanized 3D3 antibody, chimeric 3D3 antibody or in the presence of a buffer or a control IgG.

The biological function of the h3D3 was evaluated in the spheroid culture assay (see Example 6). SKOV-3 ovarian cancer cells were cultured in the presence of 5% FBS in the presence of h3D3 or a non-KAAG1 binding isotype control antibody. The results (shown in FIG. 19C), indicated that treatment with either the buffer or the non-related IgG did not inhibit the formation of the compact 3-D structures. In contrast, both the chimeric 3D3 and the humanized 3D3 prevented the spheroids from forming. The results are shown in duplicate (left and right panels). These results indicate that the biological activity of the chimeric 3D3 was conserved in the humanized 3D3 and suggests that the h3D3 will behave in an identical manner.

CITED REFERENCES

Jemal A, Murray T, Ward E, Samuels A, Tiwari R C, Ghafoor A, Feuer E J and Thun M J. Cancer statistics, 2005. CA Cancer J Clin 2005; 55: 10-30.

Menon U, Skates S J, Lewis S, Rosenthal A N, Rufford B, Sibley K, Macdonald N, Dawnay A, Jeyarajah A, Bast R C Jr, Oram D and Jacobs I J. Prospective study using the risk of ovarian cancer algorithm to screen for ovarian cancer. J Clin Oncol. 2005; 23(31):7919-26.

Bonome T, Lee J Y, Park D C, Radonovich M, Pise-Masison C, Brady J, Gardner G J, Hao K, Wong W H, Barrett J C, Lu K H, Sood A K, Gershenson D M, Mok S C and Birrer M J. Expression profiling of serous low malignancy potential, low grade, and high-grade tumors of the ovary. Cancer Res 2005; 65: 10602-10612.

Chambers, A and Vanderhyden, B. Ovarian Cancer Biomarkers in Urine. Clin Cancer Res 2006; 12(2): 323-327.

Berek et al. Cancer Medicine. 5th ed. London: B. C. Decker, Inc.; 2000. pp. 1687-1720.

Bristow R. E. Surgical standards in the management of ovarian cancer. Curr Opin Oncol 2000; 12: 474-480.

Brown E, Stewart M, Rye T, Al-Nafussi A, Williams A R, Bradburn M, Smyth J and Gabra H. Carcinosarcoma of the ovary: 19 years of prospective data from a single center. Cancer 2004; 100: 2148-2153.

Shih L-M and Kurman R J. Molecular Pathogenesis of Ovarian Borderline Tumors: New Insights and Old Challenges. Clin Cancer Res 2005; 11(20): 7273-7279.

Seidman J D, Russell P, Kurman R J. Surface epithelial tumors of the ovary. In: Kurman R J, editor. Blaustein's pathology of the female genital tract. 5th ed. New York: Springer-Verlag; 2002. pp. 791-904.

Cannistra S A and McGuire W P. Progress in the management of gynecologic cancer. J. Clin. Oncol. 2007; 25(20): 2865-2866.

Oei A L, Sweep F C, Thomas C M, Boerman O C, Massuger L F. The use of monoclonal antibodies for the treatment of epithelial ovarian cancer. Int. J. Oncol. 2008; 32(6): 1145-1157.

Nicodemus C F and Berek J S. Monoclonal antibody therapy of ovarian cancer. Expert Rev. Anticancer Ther. 2005; 5(1): 87-96.

Burger R A. Experience with bevacizumab in the management of epithelial ovarian cancer. J. Clin. Oncol. 2007; 25(20): 2902-2908.

Simon I, Zhuo S, Corral L, Diamandis E P, Sarno M J, Wolfert R L, Kim N W. B7-H4 is a novel membrane-bound protein and a candidate serum and tissue biomarker for ovarian cancer. Cancer Res. 2006; 66(3): 1570-1575.

Ebel W, Routhier E L, Foley B, Jacob S, McDonough J M, Patel R K, Turchin H A, Chao Q, Kline J B, Old L J, Phillips M D, Nicolaides N C, Sass P M, Grasso L. Preclinical evaluation of MORab-003, a humanized monoclonal antibody antagonizing folate receptor-alpha. Cancer Immun. 2007; 7: 6-13.

Van den Eynde B J, Gaugler B, Probst-Kepper M, Michaux L, Devuyst O, Lorge F, Weynants P, Boon T. A new antigen recognized by cytotoxic T lymphocytes on a human kidney tumor results from reverse strand transcription. J. Exp. Med. 1999; 190(12): 1793-1799.

Sooknanan R, Tremblay G B, Filion M. Polynucleotides and polypeptide sequences involved in cancer. 2007; PCT/CA2007/001134.

Schumacher J, Anthoni H, Dandouh F, König I R, Hillmer A M, Kluck N, Manthey M, Plume E, Warnke A, Remschmidt H, Hülsmann J, Cichon S, Lindgren C M, Propping P, Zucchelli M, Ziegler A, Peyrard-Janvid M, Schulte-Körne G, Nöthen M M, Kere J. Strong genetic evidence of DCDC2 as a susceptibility gene for dyslexia. Am. J. Hum. Genet. 2006; 78: 52-62.

Cope N, Harold D, Hill G, Moskvina V, Stevenson J, Holmans P, Owen M J, O'Donovan M C, Williams J. Strong evidence that KIAA0319 on chromosome 6p is a susceptibility gene for developmental dyslexia. Am. J. Hum. Genet. 2005; 76: 581-591.

Mor G, Visintin I, Lai Y, Zhao H, Schwartz P, Rutherford T, Yue L, Bray-Ward P and Ward D C Serum protein markers for early detection of ovarian cancer. PNAS 2005; 102: 7677-7682.

Kozak K R, Amneus M W, Pusey S M, Su F, Luong M N, Luong S A, Reddy S T and Farias-Eisner R. Identification of biomarkers for ovarian cancer using strong anion-exchange ProteinChips: potential use in diagnosis and prognosis. PNAS 2003; 100: 12343-12348.

Benoît M H, Hudson T J, Maire G, Squire J A, Arcand S L, Provencher D, Mes-Masson A M, Tonin P N. Global analysis of chromosome X gene expression in primary cultures of normal ovarian surface epithelial cells and epithelial ovarian cancer cell lines. Int. J. Oncol. 2007; 30(1): 5-17.

Cody N A, Zietarska M, Filali-Mouhim A, Provencher D M, Mes-Masson A M, Tonin P N. Influence of monolayer, spheroid, and tumor growth conditions on chromosome 3 gene expression in tumorigenic epithelial ovarian cancer cell lines. BMC Med. Genomics 2008; 1(1):34.

Buechler J, Valkirs G, Gray J. Polyvalent display libraries. 2000; U.S. Pat. No. 6,057,098.

Durocher Y, Kamen A, Perret S, Pham P L. Enhanced production of recombinant proteins by transient transfection of suspension-growing mammalian cells. 2002; Canadian patent application No. CA 2446185.

Durocher Y. Expression vectors for enhanced transient gene expression and mammalian cells expressing them. 2004; U.S. patent application No. 60/662,392.

The invention claimed is:

1. A method of treating ovarian cancer comprising cells expressing Kidney associated antigen 1 (KAAG1; SEQ ID NO.:2) in a subject, the method comprising administering an isolated antibody or antigen binding fragment thereof capable of binding to KAAG1 to the subject wherein the antibody or antigen binding fragment thereof is selected from the group consisting of antibodies and antigen binding fragment thereof comprising:
   a. A heavy chain variable region comprising a CDRH3 having the sequence of SEQ ID NO.: 32, a CDRH1 having the sequence of SEQ ID NO.: 30 and a CDRH2 having the sequence of SEQ ID NO.:31 and a light chain variable region comprising a CDRL3 having the sequence of SEQ ID NO.:29, a CDRL1 having the sequence of SEQ ID NO.:27 and a CDRL2 having the sequence of SEQ ID NO.:28;
   b. A heavy chain variable region comprising the sequence set forth in SEQ ID NO.:18 and a light chain variable region comprising the sequence set forth in SEQ ID NO.:16;
   c. A heavy chain comprising the sequence set forth in SEQ ID NO.:6 and a light chain comprising the sequence set forth in SEQ ID NO.:4;
   d. A heavy chain variable region comprising the sequence set forth in SEQ ID NO.:179 and a light chain variable region comprising the sequence set forth in SEQ ID NO.:178;
   e. A heavy chain comprising the sequence set forth in SEQ ID NO.:177 and a light chain comprising the sequence set forth in SEQ ID NO.:176;
   f. A heavy chain variable region comprising a CDRH3 having the sequence of SEQ ID NO.: 38, a CDRH1 having the sequence of SEQ ID NO.: 36 and a CDRH2 having the sequence of SEQ ID NO.:37 and a light chain variable region comprising a CDRL3 having the sequence of SEQ ID NO.:35, a CDRL1 having the sequence of SEQ ID NO.:33 and a CDRL2 having the sequence of SEQ ID NO.:34;
   g. A heavy chain variable region comprising the sequence set forth in SEQ ID NO.:22 and a light chain variable region comprising the sequence set forth in SEQ ID NO.:20; and;
   h. A heavy chain comprising the sequence as set forth in SEQ ID NO.:10 and a light chain comprising the sequence as set forth in SEQ ID NO.:8.

2. The method of claim 1 a. or f., wherein the antibody or antigen binding fragment thereof comprises framework amino acids of a human antibody.

3. The method of claim 1, wherein the ovarian cancer is recurrent ovarian cancer.

4. The method of claim 1, wherein the ovarian cancer is metastatic.

5. A method for reducing metastasis of ovarian tumor cells expressing Kidney associated antigen 1 (KAAG1; SEQ ID NO.:2) in a subject, the method comprising administering a monoclonal antibody or antigen binding fragment thereof capable of specific binding to an epitope located between amino acids 36 to 60 of KAAG1 to the subject.

6. The method of claim 5, wherein the ovarian cancer is recurrent ovarian cancer.

7. The method of claim 5, wherein the ovarian cancer is metastatic.

8. The method of claim 7, wherein the antibody or antigen binding fragment thereof binds to KAAG1 at a surface of tumor cells, induces lysis of tumor cells, reduces spreading of tumor cells, decreases formation of tumor or decreases metastasis of tumor cells.

9. The method of claim 1, wherein the antibody or antigen binding fragment thereof comprises a heavy chain variable region comprising the sequence set forth in SEQ ID NO.:179 and a light chain variable region comprising the sequence set forth in SEQ ID NO.:178.

10. The method of claim 1, wherein the antibody or antigen binding fragment thereof comprises a heavy chain variable region as defined in SEQ ID NO.:18 and a light chain variable region as defined in SEQ ID NO.: 16.

11. The method of claim 1, wherein the antibody or antigen binding fragment thereof is conjugated with a cytotoxic moiety.

12. The method of claim 5, wherein the antibody or antigen binding fragment thereof is conjugated with a cytotoxic moiety.

13. The method of claim 10, wherein the antibody or antigen binding fragment thereof is conjugated with a cytotoxic moiety.

14. The method of claim 9, wherein the antibody or antigen binding fragment thereof is conjugated with a cytotoxic moiety.

15. The method of claim 5, wherein the monoclonal antibody or antigen binding fragment thereof is a chimeric antibody, a humanized antibody, a human antibody or an antigen binding fragment thereof.

16. The method of claim 12, wherein the monoclonal antibody or antigen binding fragment thereof is a chimeric antibody, a humanized antibody, a human antibody or an antigen binding fragment thereof.

17. A method of treating ovarian cancer comprising cells expressing Kidney associated protein 1 (KAAG1: SEQ ID NO.:2) in a subject, the method comprising administering a monoclonal antibody or an antigen binding fragment thereof, that is capable of specific binding to at least 10 contiguous amino acids of amino acid residues 36 to 60 of SEQ ID NO.:2 to the subject.

18. The method of claim 17, wherein the monoclonal antibody or antigen binding fragment thereof is a chimeric antibody, a humanized antibody, a human antibody or an antigen binding fragment thereof.

19. The method of claim 17, wherein the monoclonal antibody or antigen binding fragment thereof is conjugated with a cytotoxic moiety.

20. The method of claim 18, wherein the antibody or antigen binding fragment thereof is conjugated with a cytotoxic moiety.

* * * * *